United States Patent
Makarov et al.

(10) Patent No.: US 11,203,781 B2
(45) Date of Patent: *Dec. 21, 2021

(54) METHODS FOR MULTIPLEX PCR

(71) Applicant: Swift Biosciences, Inc., Ann Arbor, MI (US)

(72) Inventors: Vladimir Makarov, Ann Arbor, MI (US); Julie Laliberte, Ypsilanti, MI (US)

(73) Assignee: SWIFT BIOSCIENCES, INC., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/238,016

(22) Filed: Apr. 22, 2021

(65) Prior Publication Data
US 2021/0238657 A1 Aug. 5, 2021

Related U.S. Application Data

(60) Continuation of application No. 16/389,243, filed on Apr. 19, 2019, which is a division of application No. 15/252,397, filed on Aug. 31, 2016, now Pat. No. 10,316,359, which is a continuation of application No. 15/223,792, filed on Jul. 29, 2016, now Pat. No.

(Continued)

(51) Int. Cl.
| | |
|---|---|
| *C12P 19/34* | (2006.01) |
| *C12Q 1/686* | (2018.01) |
| *C12N 15/66* | (2006.01) |
| *C12Q 1/6869* | (2018.01) |
| *C12Q 1/6886* | (2018.01) |
| *C12Q 1/6855* | (2018.01) |
| *C12Q 1/6874* | (2018.01) |

(52) U.S. Cl.
CPC .......... *C12Q 1/686* (2013.01); *C12N 15/66* (2013.01); *C12Q 1/6855* (2013.01); *C12Q 1/6869* (2013.01); *C12Q 1/6874* (2013.01); *C12Q 1/6886* (2013.01); *C12Q 2521/501* (2013.01); *C12Q 2521/525* (2013.01); *C12Q 2521/531* (2013.01); *C12Q 2525/186* (2013.01); *C12Q 2525/191* (2013.01)

(58) Field of Classification Search
CPC .................................................... C12Q 1/686
See application file for complete search history.

(56) References Cited

U.S. PATENT DOCUMENTS

| | | |
|---|---|---|
| 5,888,737 A | 3/1999 | DuBridge et al. |
| 6,287,825 B1 | 9/2001 | Weissman et al. |

(Continued)

FOREIGN PATENT DOCUMENTS

| | | |
|---|---|---|
| EP | 0923650 | 3/2007 |
| WO | 9746704 A1 | 12/1997 |

(Continued)

OTHER PUBLICATIONS

Notice of First Office Action cited in corresponding Chinese Patent Application No. 2015-80017244.3 dated Sep. 25, 2018.

(Continued)

*Primary Examiner* — Kenneth R Horlick
(74) *Attorney, Agent, or Firm* — Barnes & Thornburg LLP; Ryan P. Cox; Matthew S. Gibson

(57) ABSTRACT

Methods for performing multiplex PCR-based enrichment of a target substrate are provided. Systems and methods for generating a sequencing library are also provided.

20 Claims, 59 Drawing Sheets

Specification includes a Sequence Listing.

Related U.S. Application Data 10,316,357, which is a continuation of application No. PCT/US2015/013994, filed on Jan. 30, 2015.

(60) Provisional application No. 61/934,515, filed on Jan. 31, 2014, provisional application No. 62/078,309, filed on Nov. 11, 2014, provisional application No. 62/078,313, filed on Nov. 11, 2014.

(56) References Cited

U.S. PATENT DOCUMENTS

| | | | |
|---|---|---|---|
| 6,958,225 | B2 | 10/2005 | Dong |
| 9,023,769 | B2 | 5/2015 | Drmanac et al. |
| 10,011,869 | B2 | 7/2018 | Wang et al. |
| 10,316,359 | B2 | 6/2019 | Makarov et al. |
| 2002/0058250 | A1 | 5/2002 | Firth |
| 2009/0069190 | A1 | 3/2009 | Dinauer |
| 2009/0291475 | A1 | 11/2009 | Lao et al. |
| 2010/0129874 | A1 | 5/2010 | Mitra et al. |
| 2011/0003701 | A1 | 1/2011 | Ferreri et al. |
| 2011/0189677 | A1 | 8/2011 | Adli et al. |
| 2011/0212490 | A1 | 9/2011 | Fredriksson |
| 2012/0077716 | A1 | 3/2012 | Godwin et al. |
| 2012/0238738 | A1 | 9/2012 | Hendrickson |
| 2013/0011881 | A1 | 1/2013 | Leamon et al. |
| 2013/0231253 | A1 | 9/2013 | Amorese et al. |
| 2013/0261027 | A1 | 10/2013 | Li et al. |
| 2014/0200146 | A1 | 7/2014 | Xie et al. |
| 2016/0257994 | A1 | 9/2016 | Wang et al. |
| 2017/0088887 | A1 | 3/2017 | Makarov et al. |
| 2017/0107561 | A1 | 4/2017 | Wang et al. |

FOREIGN PATENT DOCUMENTS

| | | | |
|---|---|---|---|
| WO | 9808970 | A1 | 3/1998 |
| WO | 2007018601 | A1 | 2/2007 |
| WO | 2007052006 | A1 | 5/2007 |
| WO | 2007087291 | A2 | 8/2007 |
| WO | 2008033442 | A2 | 3/2008 |
| WO | 2009133466 | A1 | 11/2009 |
| WO | 2012012037 | A1 | 1/2012 |
| WO | 2012112582 | | 8/2012 |
| WO | 2012149154 | | 11/2012 |
| WO | 2013081755 | A1 | 6/2013 |
| WO | 2013081864 | A1 | 6/2013 |
| WO | 2013181170 | A1 | 12/2013 |
| WO | 2015074017 | | 5/2015 |
| WO | 2015117040 | | 8/2015 |
| WO | 2015120177 | A1 | 8/2015 |
| WO | 2015134552 | | 9/2015 |
| WO | 2016037389 | A1 | 3/2016 |
| WO | 2016144619 | A1 | 9/2016 |

OTHER PUBLICATIONS

Extended European Search Report cited in corresponding European Patent Application No. 18165783.4 dated Aug. 16, 2018.
Schenk Desiree et al: "Amplification of overlapping DNA amplicons in a single-tube multiplex PCR for targeted next-generation sequencing of BRCA1 and BRCA2", PLOS One 2017, vol. 12, No. 7.
Chen et al., "A cost-effective method for Illumina small RNA-Seq library preparation using T4 RNA ligase 1 adenylated adapters." Plant Methods, 2012, vol. 8, Iss. 41, pp. 1-5.
Brownie, et al., "The elimination of primer-dimer accumulation in PCR", Nucleic Acids Research, 1997, vol. 25, No. 16, pp. 3235-3241.
Notification of Reasons for Refusal cited in corresponding Japanese Application No. 2016-567462 dated Mar. 25, J019.
Zhang et al., "Universal Primer-Multiplex-Polymerase Chain Reaction (UP-M-PCR) and Capillary Electrophoresis—aser Induced Fluorescence Analysis for the Simultaneous Detection of Six Genetically Modified Maize Line", Journal of Agricultural and Food Chemistry, 2011, vol. 59, p. 5188-5194.
Wen et al., "Universal Multiplex PCR: a novel method of simultaneous amplification of multiple DNA fragments", Plant Methods, 2012, vol. 8, No. 32, p. 1-9.
Xu et al., "A Novel Universal Primer-Multiplex-PCR Method with Sequencing Gel Electrophoresis Analysis", PLoS One, 2012, vol. 7, issue 1, e22900.
Bai et al., "A novel common primer multiplex PCR (CP-M-PCR) method for the simultaneous detection of meat species", Food Control, 2009, vol. 20, p. 366-370.
Petition for Inter Partes Review of U.S. Pat. No. 10,316,359, filed Jan. 7, 2021, IPR2021-00401, Paper 2.
Declaration of Yun Bao, Ph.D., IPR2021-00401, Exhibit 1002, (2021).
Summary of Qualifications of Yun Bao, Ph.D., Head of R&D, Avida Biomed, Fremont, CA, IPR2021-00401, Exhibit 1003, (2021).
Samantha Fowler, et al., "Concepts of Biology," OpenStax (2013, as reprint in 2014, 2017), https://openstax.org/details/books/concepts-biology.
Todd C. Lorenz, "Polymerase Chain Reaction: Basic Protocol Plus Troubleshooting and Optimization Strategies," J Vis Exp. (63):e3998 (2012).
Jeffrey S. Chamberlain, et al., "Deletion screening of the Duchenne muscular dystrophy locus via multiplex DNA amplification," Nucleic Acids Res. 16(23):11141-56 (1988).
P. Markoulatos, et al., "Multiplex Polymerase Chain Reaction: A Practical Approach," J Clin Lab Anal. 16:47-51 (2002).
National Research Council & Institute of Medicine, "Bio Watch PCR Assays: Building Confidence, Ensuring Reliability: Abbreviated Version," The National Academies Press (2015).
Lilit Garibyan & Nidhi Avashia, "Research Techniques Made Simple: Polymerase Chain Reaction (PCR)," J Invest Dermatol. 133(3):e6 (2013).
Xiaohan Yang, et al., "Recent developments in primer design for DNA polymorphism and mRNA profiling in higher plants," Plant Methods 2:4 (2006).
Shirley Kwok, et al., "A Guide to the Design and Use of Mismatched and Degenerate Primers," PCR Methods Appl. 3:539-547 (1994).
Chenghang Zong, et al., "Genome-Wide Detection of Single-Nucleotide and Copy-Number Variations of a Single Human Cell," Science 338(6114):1622-1626 (2012).
Jannine Brownie, et al., "The elimination of primer-dimer accumulation in PCR," Nucleic Acids Res. 25(16):3235-3241 (1997).
Mary C. Edwards & Richard A. Gibbs, "Multiplex PCR: Advantages, Development, and Applications," PCR Methods Appl. 3:S65-S75 (1994).
Shea N. Gardner, et al., "Multiplex Degenerate Primer Design for Targeted Whole Genome Amplification of Many Viral Genomes," Adv Bioinformatics. 2014(101894):1-8 (2014).
Improved methods for processing DNA substrates, U.S. Appl. No. 61/934,515, filed Jan. 31, 2014.
Shea N. Gardner, et al., "Multiplex Degenerate Primer Design for Targeted Whole Genome Amplification of Many Viral Genomes," Adv Bioinformatics. 2014(101894):1-8 (2014), Supplementary Information.
O. Henegariu, et al., "Multiplex PCR: Critical Parameters and Step-by-Step Protocol," Biotechniques. 23(3):504-511 (1997).
Håkan Telenius, et al., "Degenerate Oligonucleotide-Primed PCR: General Amplification of Target DNA by a Single Degenerate Primer," Genomics 13:718-725 (1992).
Schenk D, Song G, Ke Y, Wang Z (2017) Amplification of overlapping DNA amplicons in a single-tube multiplex PCR for targeted next-generation sequencing of BRCA1 and BRCA2. PLoS One 12(7): e0181062, available at https://doi.org/10.1371/journal.pone.0181062.
Patent Owner's Preliminary Response, IPR2021-00401, Paper 6, filed Apr. 22, 2021.

FIG. 1
Fill-in adapter
Y-adapter
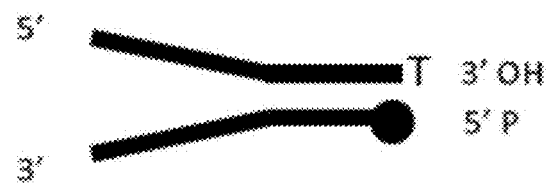
Stem-loop adapters
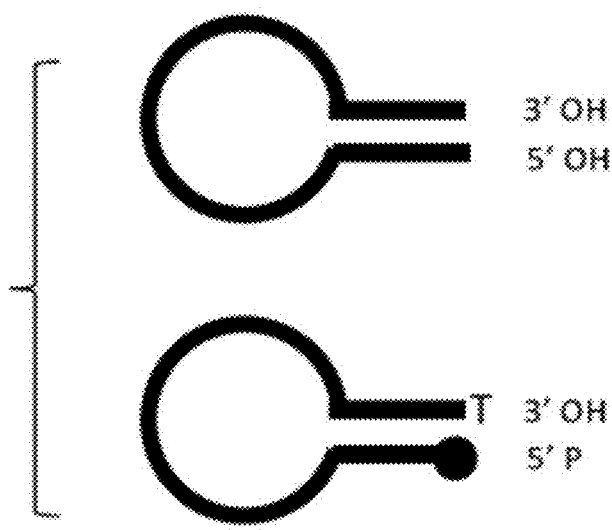

FAM only,
15% denaturing gel

FIG. 24

| Lane | 1 | 2 |
|---|---|---|
| FAM oligonucleotide substrate (pmoles) | 30 | 30 |
| 5' adapter oligonucleotide for displacement-cleavage (pmoles) | 45 | 45 |
| Oligonucleotide template (pmoles) | 45 | 45 |
| E. coli DNA ligase | | + |
| Taq DNA polymerase | | + |

Ligation product → 69 bases

FAM oligonucleotide substrate →
FAM oligonucleotide substrate nick translation product →

| Lane | 1 | 2 |
|---|---|---|
| FAM oligonucleotide substrate (pmoles) | 30 | 30 |
| 5' adapter oligonucleotide for displacement-cleavage (pmoles) | 45 | 45 |
| Oligonucleotide template (pmoles) | 45 | 45 |
| Taq DNA ligase | | + |
| Taq DNA polymerase | | + |

Ligation product → 69 bases

FAM oligonucleotide substrate →
FAM oligonucleotide substrate nick translation product →

FAM only, 15% denaturing gel

Position in read (bp)

FIG. 30

Fill-in adapter

```
                                                                  12-900
AATGATACGGCGACCACCGAGATCTACACTCTTTCCCTACACGACGCTCTTCCGATCT -OH 3'
                                     /ƐↃdSƐ/ƃⱯ⊥Ↄ⊥ƃↃ⊥ↃↃⱯƃⱯⱯƃↃↃ⊥ⱯƃⱯ -OH-5'
                                                                  13-426
```

3' Adapter with a blocking 3' deoxythymidine base

```
            13-340
/5PHOS/AGATCGGAAGAGCGTCGTGTAGGGAAAGAGTGTAGATCTCGGTGGTCGCCGTATCATT/3SpC3/
       ⊥⊥ⱯↃ⊥Ʉ⊥ƃↃↃƃↃ⊥Ↄƃƃ⊥ƃƃↃ⊥Ʉƃ⊥Ʉƃ⊥ƃ⊥ƃⱯƃⱯⱯƃƃƃ⊥Ʉ⊥ƃ⊥ƃↃ⊥ƃↃƃⱯƃⱯⱯƃƃↃ⊥ⱯƃⱯ
            13-559
```

3' Adapter with a 3' phosphate group

```
            13-340
/5PHOS/AGATCGGAAGAGCGTCGTGTAGGGAAAGAGTGTAGATCTCGGTGGTCGCCGTATCATT/3SpC3/
/SOHdƐ/⊥Ↄ⊥ⱯↃↃ⊥⊥Ↄ⊥ƃↃↃⱯƃↃⱯↃⱯ
            13-558
```

FIG. 31

FAM substrate A

13-562

/5Phos/TGTACCTCACTTCTCATCACTGCT/3Fam/
3'HO-ACATGGAGTGAAGAGTAGTGACGA 13-563

FAM substrate B

13-561

/5Phos/TGTACCTCACTTCTCATCACTGCT
3'HO-ACATGGAGTGAAGAGTAGTGACGA/5Fam/

13-564

FAM substrate C

13-560

5'OH-TGTACCTCACTTCTCATCACTGCT
3'HO-ACATGGAGTGAAGAGTAGTGACGA/5Fam/

Fill-in adapter

```
                                                              13-489
/5SpC3/A*A*TGATACGGCGACCACCGAGATCTACACTCTTTCCCTACACGACGCTCTTCCGATCT
                                    /ƐɔdSƐ/ƆVLƆLƆƆLƆƆƆVƆVVƆƆƆLVƆV 5'
                                                              13-426
```

3'Adapter

```
            13-340
/5PHOS/AGATCGGAAGAGCGTCGTGTAGGGAAAGAGTGTAGATCTCGGTGGTCGCCGTATCATT/3SpC3/
       LPPƆLVƆƆƆLLƆLƆƆƆVƆVƆV 5'
           13-559
```

FIG. 37

"P7 adapter"

3' Adapter; 1st oligonucleotide 13-501

/5PHOS/AGATCGGAAGAGCACACGTCTGAACTCCAGTCACATCACGATCTCGTATGCCGTCTTCTGCT*T*G/3SpC3/

3' Adapter; 2nd oligonucleotide 13-712

"P5 adapters"

5' adapter oligonucleotide for nick-translation (13-489)

/5SpC3/A*A*TGATACGGCGACCACCGAGATCTACACTCTTTCCCTACACGACGCTCTTCCGATCT

5' adapter oligonucleotide for displacement-cleavage (13-595)

/5SpC3/A*A*TGATACGGCGACCACCGAGATCTACACTCTTTCCCTACACGACGCTCTTCCGATCT

FIG. 38

"P7 adapter"

3' Adapter; 1st oligonucleotide 13-510

/5Phos/AGATCGGAAGAGCACACGTCTGAACTCCAGTCACGCCAATATCTCGTATGCCGTCTTCTGCT*T*G/3spC3/
                                                                 AGCAAGACCAGAGATGAGCAGGACTAGCA
                                                                                           5'
3' Adapter; 2nd oligonucleotide 13-712

"P5 adapters"

5' adapter oligonucleotide for nick-translation (13-489)

/5SpC3/A*A*TGATACGGCGACCACCGAGATCTACACTCTTTCCCTACACGACGCTCTTCCGATCT

FIG. 39

3-step Amplicon library synthesis

Multiplex PCR using target-specific primers with universal sequence at the 5' end (2 PCR cycles or more)

Purification or Exo I treatment (optional)

PCR with primer comprising universal sequence with cleavable bases

Purification 1-step attachment of NGS adapters

Purification

2-step Amplicon library synthesis

Multiplex PCR using target-specific primers with universal sequence at the 5' end and primer comprising universal sequence with cleavable bases

Purification 1-step attachment of NGS adapters

Purification

SEQUENCE LISTING

```
<160> NUMBER OF SEQ ID NOS: 127

<210> SEQ ID NO 1
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 1
aatgatacgg cgaccaccga gatctacact ctttccctac acgacgctct tccgatct      58

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(22)
<223> OTHER INFORMATION: 3' C3 spacer (IDT)

<400> SEQUENCE: 2
agatcggaag agcgtcgtgt ag                                              22

<210> SEQ ID NO 3
<211> LENGTH: 58
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Phosphorylation (IDT)
<220> FEATURE:
<221> NAME/KEY: misc_feature
<222> LOCATION: (58)..(58)
<223> OTHER INFORMATION: 3' C3 spacer (IDT)

<400> SEQUENCE: 3
```
agatcggaag agcgtcgtgt agggaaagag tgtagatctc ggtggtcgcc gtatcatt        58

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: 3'- Dideoxythymidine (TriLink)

<400> SEQUENCE: 4
acacgacgct cttccgatc        19

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: 3' Phosphorylation (IDT)

<400> SEQUENCE: 5
acacgacgct cttccgatct        20

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Phosphorylation (IDT)

<400> SEQUENCE: 6
tgtacctcac ttctcatcac tgct        24

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
agcagtgatg agaagtgagg taca        24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Phosphorylation (IDT)

<400> SEQUENCE: 8
tgtacctcac ttctcatcac tgct        24

```
<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' 6-carboxyfluorescein (IDT)

<400> SEQUENCE: 9
agcagtgatg agaagtgagg taca                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
tgtacctcac ttctcatcac tgct                                              24

<210> SEQ ID NO 11
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 11
gtgactggag ttcagacgtg tgctcttccg atct                                   34

<210> SEQ ID NO 12
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)..(34)
<223> OTHER INFORMATION: 3' 6-carboxyfluorescein (IDT)

<400> SEQUENCE: 12
tgtacctcac ttctcatcac tgctgtcatc cgat                                   34

<210> SEQ ID NO 13
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (46)..(46)
<223> OTHER INFORMATION: 3' C3 spacer (IDT)

<400> SEQUENCE: 13
agcagtgatg agaagtgagg tacaagatcg gaagagcgtc gtgtag                      46

<210> SEQ ID NO 14
<211> LENGTH: 33
<212> TYPE: DNA
<213> ORGANISM: Artificial Sequence
<220> FEATURE:
<223> OTHER INFORMATION: Synthetic oligonucleotide
```

```
<400> SEQUENCE: 14
gactggagtt cagacgtgtg ctcttccgat ctt                                     33

<210> SEQ ID NO 15
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 15
caagcagaag acggcatacg agatcgtgat gtgactggag ttcagacgtg tgctcttccg       60
atctt                                                                   65

<210> SEQ ID NO 16
<211> LENGTH: 65
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' C3 spacer (IDT)
<220> FEATURE:
<221> NAME/KEY: misc_feature
<222> LOCATION: (1)..(1)
<223> OTHER INFORMATION: Phosphorothioated base
<220> FEATURE:
<221> NAME/KEY: misc_feature
<222> LOCATION: (2)..(2)
<223> OTHER INFORMATION: Phosphorothioated base
<220> FEATURE:
<221> NAME/KEY: misc_feature
<222> LOCATION: (65)..(65)
<223> OTHER INFORMATION: n is a, c, g, or t

<400> SEQUENCE: 16
caagcagaag acggcatacg agatcgtgat gtgactggag ttcagacgtg tgctcttccg       60 atctn                                                                   65

<210> SEQ ID NO 17
<211> LENGTH: 64
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Phosphorylation (IDT)
<220> FEATURE:
<221> NAME/KEY: misc_feature
<222> LOCATION: (62)..(62)
<223> OTHER INFORMATION: Phosphorothioated base
<220> FEATURE:
<221> NAME/KEY: misc_feature
<222> LOCATION: (63)..(63)
<223> OTHER INFORMATION: Phosphorothioated base
<220> FEATURE:
<221> NAME/KEY: misc_feature
<222> LOCATION: (64)..(64)
<223> OTHER INFORMATION: 3' C3 spacer (IDT)

<400> SEQUENCE: 17
agatcggaag agcacacgtc tgaactccag tcacatcacg atctcgtatg ccgtcttctg       60
cttg                                                                    64
```

```
<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: 2', 3'- Dideoxythymidine (TriLink)

<400> SEQUENCE: 18
agacgugugc ucutccgatc                                               20

<210> SEQ ID NO 19
<211> LENGTH: 58
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' C3 spacer (IDT)
<220> FEATURE:
<221> NAME/KEY: misc_feature
<222> LOCATION: (1)..(1)
<223> OTHER INFORMATION: Phosphorothioated base
<220> FEATURE:
<221> NAME/KEY: misc_feature
<222> LOCATION: (2)..(2)
<223> OTHER INFORMATION: Phosphorothioated base

<400> SEQUENCE: 19
aatgatacgg cgaccaccga gatctacact ctttccctac acgacgctct tccgatct      58

<210> SEQ ID NO 20
<211> LENGTH: 59
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' C3 spacer (IDT)
<220> FEATURE:
<221> NAME/KEY: misc_feature
<222> LOCATION: (1)..(1)
<223> OTHER INFORMATION: Phosphorothioated base
<220> FEATURE:
<221> NAME/KEY: misc_feature
<222> LOCATION: (2)..(2)
<223> OTHER INFORMATION: Phosphorothioated base
<220> FEATURE:
<221> NAME/KEY: misc_feature
<222> LOCATION: (59)..(59)
<223> OTHER INFORMATION: n is a, c, g, or t

<400> SEQUENCE: 20
aatgatacgg cgaccaccga gatctacact ctttccctac acgacgctct tccgatctn     59

<210> SEQ ID NO 21
<211> LENGTH: 64
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Phosphorylation (IDT)
```

<220> FEATURE:
<221> NAME/KEY: misc_feature
<222> LOCATION: (62)..(62)
<223> OTHER INFORMATION: Phosphorothioated base
<220> FEATURE:
<221> NAME/KEY: misc_feature
<222> LOCATION: (63)..(63)
<223> OTHER INFORMATION: Phosphorothioated base
<220> FEATURE:
<221> NAME/KEY: misc_feature
<222> LOCATION: (64)..(64)
<223> OTHER INFORMATION: 3' C3 spacer (IDT)

<400> SEQUENCE: 21
agatcggaag agcacacgtc tgaactccag tcacgccaat atctcgtatg ccgtcttctg    60
cttg                                                                64

<210> SEQ ID NO 22

<400> SEQUENCE: 22

000

<210> SEQ ID NO 23
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 23
tcagacgtgt gctcttccga tctcctgccc ttccaatgga tc                      42

<210> SEQ ID NO 24
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (39)..(39)
<223> OTHER INFORMATION: Phosphorothioated DNA bases (IDT)
<220> FEATURE:
<221> NAME/KEY: misc_feature
<222> LOCATION: (40)..(40)
<223> OTHER INFORMATION: Phosphorothioated DNA bases (IDT)

<400> SEQUENCE: 24
tcagacgtgt gctcttccga tctcccctag cagagacctg t                       41

<210> SEQ ID NO 25
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 25
tcagacgtgt gctcttccga tctgcccaac ccttgtcctt ac         42

<210> SEQ ID NO 26
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 26
tcagacgtgt gctcttccga tctctgactg ctcttttcac ccat       44

<210> SEQ ID NO 27
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 27
tcagacgtgt gctcttccga tctgagcagc ctctggcatt ctg        43

<210> SEQ ID NO 28
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 28
tcagacgtgt gctcttccga tcttgaagac ccaggtccag atga       44

<210> SEQ ID NO 29
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:

```
<221> NAME/KEY: misc_feature
<222> LOCATION: (43)..(43)
<223> OTHER INFORMATION: Phosphorothioated DNA bases (IDT)

<400> SEQUENCE: 29
tcagacgtgt gctcttccga tctgctgccc tggtaggttt tctg            44

<210> SEQ ID NO 30
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 30
tcagacgtgt gctcttccga tctctggccc ctgtcatctt ctg             43

<210> SEQ ID NO 31
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 31
tcagacgtgt gctcttccga tctcaggcat tgaagtctca tgga            44

<210> SEQ ID NO 32
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 32
tcagacgtgt gctcttccga tcttcctccc tgcttctgtc tc              42

<210> SEQ ID NO 33
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
```

```
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 33
tcagacgtgt gctcttccga tctctgtcag tggggaacaa gaag            44

<210> SEQ ID NO 34
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 34
tcagacgtgt gctcttccga tctgtgctgt gactgcttgt aga             43

<210> SEQ ID NO 35
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 35
tcagacgtgt gctcttccga tctctctgtc tccttcctct tcctac          46

<210> SEQ ID NO 36
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 36
tcagacgtgt gctcttccga tctctgtgca gctgtgggtt ga              42

<210> SEQ ID NO 37
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
```

<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 37
tcagacgtgt gctcttccga tctgctcacc atcgctatct gag       43

<210> SEQ ID NO 38
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 38
tcagacgtgt gctcttccga tctcatgacg gaggttgtga gg        42

<210> SEQ ID NO 39
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 39
tcagacgtgt gctcttccga tctagcaatc agtgaggaat cagag     45

<210> SEQ ID NO 40
<211> LENGTH: 40
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (38)..(38)
<223> OTHER INFORMATION: Phosphorothioated DNA bases (IDT)
<220> FEATURE:
<221> NAME/KEY: misc_feature
<222> LOCATION: (39)..(39)
<223> OTHER INFORMATION: Phosphorothioated DNA bases (IDT)

<400> SEQUENCE: 40
tcagacgtgt gctcttccga tctagctggg gctggagaga          40

<210> SEQ ID NO 41
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature -continued

```
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 41
tcagacgtgt gctcttccga tctgtcatcc aaatactcca cacgca          46

<210> SEQ ID NO 42
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 42
tcagacgtgt gctcttccga tctgcatctt atccgagtgg aagg            44

<210> SEQ ID NO 43
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 43
tcagacgtgt gctcttccga tctcactgac aaccaccctt aacc            44

<210> SEQ ID NO 44
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 44
tcagacgtgt gctcttccga tctcaggtag gacctgattt ccttac          46

<210> SEQ ID NO 45
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 45
tcagacgtgt gctcttccga tctttcttgc ggagattctc ttcc           44

<210> SEQ ID NO 46
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 46
tcagacgtgt gctcttccga tcttgggacg aacagctttg ag             43

<210> SEQ ID NO 47
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (39)..(39)
<223> OTHER INFORMATION: Phosphorothioated DNA bases (IDT)
<220> FEATURE:
<221> NAME/KEY: misc_feature
<222> LOCATION: (40)..(40)
<223> OTHER INFORMATION: Phosphorothioated DNA bases (IDT)

<400> SEQUENCE: 47
tcagacgtgt gctcttccga tctccaccgc ttcttgtcct g              41

<210> SEQ ID NO 48
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 48
tcagacgtgt gctcttccga tctgggtgca gttatgcctc ag             42

<210> SEQ ID NO 49
<211> LENGTH: 45
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 49
tcagacgtgt gctcttccga tctagactta gtacctgaag ggtga            45

<210> SEQ ID NO 50
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 50
tcagacgtgt gctcttccga tcttagcact gcccaacaac acc              43

<210> SEQ ID NO 51
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 51
tcagacgtgt gctcttccga tctcggcatt ttgagtgtta gactgg           46

<210> SEQ ID NO 52
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 52
tcagacgtgt gctcttccga tctcctggtt gtagctaact aacttc           46

<210> SEQ ID NO 53
<211> LENGTH: 46
<212> TYPE: DNA
<213> ORGANISM: Artificial Sequence
<220> FEATURE:
```

<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 53
tcagacgtgt gctcttccga tctaccatcg taagtcaagt agcatc                46

<210> SEQ ID NO 54
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 54
tcagacgtgt gctcttccga tctatggttc tatgactttg cctga                 45

<210> SEQ ID NO 55
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 55
tcagacgtgt gctcttccga tctagcaggc taggctaagc tatg                  44

<210> SEQ ID NO 56
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (50)..(50)
<223> OTHER INFORMATION: Phosphorothioated DNA bases (IDT)
<220> FEATURE:
<221> NAME/KEY: misc_feature
<222> LOCATION: (51)..(51)
<223> OTHER INFORMATION: Phosphorothioated DNA bases (IDT)

<400> SEQUENCE: 56
tcagacgtgt gctcttccga tctcctgctg aaaatgactg aatataaact tg         52

<210> SEQ ID NO 57
<211> LENGTH: 44
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 57
tcagacgtgt gctcttccga tctggtcctg caccagtaat atgc            44

<210> SEQ ID NO 58
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (45)..(45)
<223> OTHER INFORMATION: Phosphorothioated DNA bases (IDT)
<220> FEATURE:
<221> NAME/KEY: misc_feature
<222> LOCATION: (46)..(46)
<223> OTHER INFORMATION: Phosphorothioated DNA bases (IDT)

<400> SEQUENCE: 58
tcagacgtgt gctcttccga tcttgcttgc tctgatagga aaatgag         47

<210> SEQ ID NO 59
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (45)..(45)
<223> OTHER INFORMATION: Phosphorothioated DNA bases (IDT)
<220> FEATURE:
<221> NAME/KEY: misc_feature
<222> LOCATION: (46)..(46)
<223> OTHER INFORMATION: Phosphorothioated DNA bases (IDT)

<400> SEQUENCE: 59
tcagacgtgt gctcttccga tctggatcca gacaactgtt caaactg         47

<210> SEQ ID NO 60
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 60
tcagacgtgt gctcttccga tctccagaaa ctgcctcttg acc             43

<210> SEQ ID NO 61
<211> LENGTH: 43
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 61
tcagacgtgt gctcttccga tctgatgtaa gggacaagca gcc            43

<210> SEQ ID NO 62
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 62
tcagacgtgt gctcttccga tctgaaccaa tggatcgatc tgcc           44

<210> SEQ ID NO 63
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 63
tcagacgtgt gctcttccga tctggggaac tgatgtgact tacc           44

<210> SEQ ID NO 64
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 64
tcagacgtgt gctcttccga tctctgagca agaggctttg gag            43

<210> SEQ ID NO 65
<211> LENGTH: 43
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 65
tcagacgtgt gctcttccga tctaacagtg cagtgtggaa tcc          43

<210> SEQ ID NO 66
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (45)..(45)
<223> OTHER INFORMATION: Phosphorothioated DNA bases (IDT)
<220> FEATURE:
<221> NAME/KEY: misc_feature
<222> LOCATION: (46)..(46)
<223> OTHER INFORMATION: Phosphorothioated DNA bases (IDT)

<400> SEQUENCE: 66
tcagacgtgt gctcttccga tctccacaga aacccatgta tgaagta          47

<210> SEQ ID NO 67
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 67
tcagacgtgt gctcttccga tctgtaccca aaaaggtgac atgga          45

<210> SEQ ID NO 68
<211> LENGTH: 49
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (47)..(47)
<223> OTHER INFORMATION: Phosphorothioated DNA bases (IDT)
<220> FEATURE:
<221> NAME/KEY: misc_feature
<222> LOCATION: (48)..(48)
<223> OTHER INFORMATION: Phosphorothioated DNA bases (IDT)

<400> SEQUENCE: 68
tcagacgtgt gctcttccga tcttttcagt gttacttacc tgtcttgtc          49

<210> SEQ ID NO 69
```

```
<211> LENGTH: 48
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (46)..(46)
<223> OTHER INFORMATION: Phosphorothioated DNA bases (IDT)
<220> FEATURE:
<221> NAME/KEY: misc_feature
<222> LOCATION: (47)..(47)
<223> OTHER INFORMATION: Phosphorothioated DNA bases (IDT)

<400> SEQUENCE: 69
tcagacgtgt gctcttccga tctggactct gaagatgtac ctatggtc                48

<210> SEQ ID NO 70
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 70
tcagacgtgt gctcttccga tctctcacca tgtcctgact gtg                     43

<210> SEQ ID NO 71
<211> LENGTH: 40
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (38)..(38)
<223> OTHER INFORMATION: Phosphorothioated DNA bases (IDT)
<220> FEATURE:
<221> NAME/KEY: misc_feature
<222> LOCATION: (39)..(39)
<223> OTHER INFORMATION: Phosphorothioated DNA bases (IDT)

<400> SEQUENCE: 71
tcagacgtgt gctcttccga tctgtggcac tctggaagca                         40

<210> SEQ ID NO 72
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 72
tcagacgtgt gctcttccga tctgttactg aaagctcagg gatag                   45
```

```
<210> SEQ ID NO 73
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 73
tcagacgtgt gctcttccga tctccacact tacacatcac tttgc              45

<210> SEQ ID NO 74
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 74
tcagacgtgt gctcttccga tcttagtctt tctttgaagc agcaag             46

<210> SEQ ID NO 75
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 75
tcagacgtgt gctcttccga tctctagctg tgatcctgaa actgaa             46

<210> SEQ ID NO 76
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 76
tcagacgtgt gctcttccga tcttcctcct gcaggattcc tac                43
```

```
<210> SEQ ID NO 77
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 77
tcagacgtgt gctcttccga tcttggtgga tgtcctcaaa agac                44

<210> SEQ ID NO 78
<211> LENGTH: 49
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (47)..(47)
<223> OTHER INFORMATION: Phosphorothioated DNA bases (IDT)
<220> FEATURE:
<221> NAME/KEY: misc_feature
<222> LOCATION: (48)..(48)
<223> OTHER INFORMATION: Phosphorothioated DNA bases (IDT)

<400> SEQUENCE: 78
tcagacgtgt gctcttccga tctcaggatt cttacagaaa acaagtggt           49

<210> SEQ ID NO 79
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 79
tcagacgtgt gctcttccga tcttgatggc aaatacacag aggaag              46

<210> SEQ ID NO 80
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 80
tcagacgtgt gctcttccga tctgacgggt agagtgtgcg tg                  42
```

<210> SEQ ID NO 81
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 81
tcagacgtgt gctcttccga tctcgccaca gagaagttgt tgag        44

<210> SEQ ID NO 82
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (39)..(39)
<223> OTHER INFORMATION: Phosphorothioated DNA bases (IDT)
<220> FEATURE:
<221> NAME/KEY: misc_feature
<222> LOCATION: (40)..(40)
<223> OTHER INFORMATION: Phosphorothioated DNA bases (IDT)

<400> SEQUENCE: 82
tcagacgtgt gctcttccga tctcgcactg gcctcatctt g           41

<210> SEQ ID NO 83
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 83
tcagacgtgt gctcttccga tctcttccag tgtgatgatg gtgag       45

<210> SEQ ID NO 84
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 84
tcagacgtgt gctcttccga tctcatgtgt aacagttcct gcatg        45

<210> SEQ ID NO 85
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (39)..(39)
<223> OTHER INFORMATION: Phosphorothioated DNA bases (IDT)
<220> FEATURE:
<221> NAME/KEY: misc_feature
<222> LOCATION: (40)..(40)
<223> OTHER INFORMATION: Phosphorothioated DNA bases (IDT)

<400> SEQUENCE: 85
tcagacgtgt gctcttccga tctggtcaga ggcaagcaga g        41

<210> SEQ ID NO 86
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 86
tcagacgtgt gctcttccga tctttacttc tcccctcct ctg        43

<210> SEQ ID NO 87
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (39)..(39)
<223> OTHER INFORMATION: Phosphorothioated DNA bases (IDT)
<220> FEATURE:
<221> NAME/KEY: misc_feature
<222> LOCATION: (40)..(40)
<223> OTHER INFORMATION: Phosphorothioated DNA bases (IDT)

<400> SEQUENCE: 87
tcagacgtgt gctcttccga tctcttccca gcctgggcat c        41

<210> SEQ ID NO 88
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 88
tcagacgtgt gctcttccga tctgctgaat gaggccttgg aac    43

<210> SEQ ID NO 89
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 89
tcagacgtgt gctcttccga tctctttcca acctaggaag gcag    44

<210> SEQ ID NO 90
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (45)..(45)
<223> OTHER INFORMATION: Phosphorothioated DNA bases (IDT)
<220> FEATURE:
<221> NAME/KEY: misc_feature
<222> LOCATION: (46)..(46)
<223> OTHER INFORMATION: Phosphorothioated DNA bases (IDT)

<400> SEQUENCE: 90
tcagacgtgt gctcttccga tctgcactgt aataatccag actgtgt    47

<210> SEQ ID NO 91
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 91
tcagacgtgt gctcttccga tctcatgtac tggtccctca ttgc    44

<210> SEQ ID NO 92
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 92
tcagacgtgt gctcttccga tctcctttca ggatggtgga tgtg                            44

<210> SEQ ID NO 93
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (39)..(39)
<223> OTHER INFORMATION: Phosphorothioated DNA bases (IDT)
<220> FEATURE:
<221> NAME/KEY: misc_feature
<222> LOCATION: (40)..(40)
<223> OTHER INFORMATION: Phosphorothioated DNA bases (IDT)

<400> SEQUENCE: 93
tcagacgtgt gctcttccga tctcgactcc accaggactt g                               41

<210> SEQ ID NO 94
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 94
tcagacgtgt gctcttccga tctgttaacc ttgcagaatg gtcgat                          46

<210> SEQ ID NO 95
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (45)..(45)
<223> OTHER INFORMATION: Phosphorothioated DNA bases (IDT)
<220> FEATURE:
<221> NAME/KEY: misc_feature
<222> LOCATION: (46)..(46)
<223> OTHER INFORMATION: Phosphorothioated DNA bases (IDT)

<400> SEQUENCE: 95
tcagacgtgt gctcttccga tctccacgag aacttgatca tattcac                         47

<210> SEQ ID NO 96
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 96
tcagacgtgt gctcttccga tctcaacagg ttcttgctgg tgtg         44

<210> SEQ ID NO 97
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (45)..(45)
<223> OTHER INFORMATION: Phosphorothioated DNA bases (IDT)
<220> FEATURE:
<221> NAME/KEY: misc_feature
<222> LOCATION: (46)..(46)
<223> OTHER INFORMATION: Phosphorothioated DNA bases (IDT)

<400> SEQUENCE: 97
tcagacgtgt gctcttccga tctatggtgg gatcatattc atctaca      47

<210> SEQ ID NO 98
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 98
tcagacgtgt gctcttccga tctagcttgt ggagcctctt aca          43

<210> SEQ ID NO 99
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 99
tcagacgtgt gctcttccga tctgggacct taccttatac accgt        45

<210> SEQ ID NO 100
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)

<223> OTHER INFORMATION: Phosphorothioated DNA bases (IDT)

<400> SEQUENCE: 100
tcagacgtgt gctcttccga tctcaccatc tcacaattgc cagt                                44

<210> SEQ ID NO 101
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 101
tcagacgtgt gctcttccga tctgctttcg gagatgttgc ttctc                               45

<210> SEQ ID NO 102
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 102
tcagacgtgt gctcttccga tctgatccca gaaggtgaga aagtt                               45

<210> SEQ ID NO 103
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 103
tcagacgtgt gctcttccga tcttgaggtt cagagccatg ga                                  42

<210> SEQ ID NO 104
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 104
tcagacgtgt gctcttccga tctctccagg aagcctacgt ga        42

<210> SEQ ID NO 105
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 105
tcagacgtgt gctcttccga tctggacata gtccaggagg ca        42

<210> SEQ ID NO 106
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 106
tcagacgtgt gctcttccga tctcaccgca gcatgtcaag atc        43

<210> SEQ ID NO 107
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 107
tcagacgtgt gctcttccga tctgacctaa agccacctcc ttac        44

<210> SEQ ID NO 108
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:

```
<221> NAME/KEY: misc_feature
<222> LOCATION: (45)..(45)
<223> OTHER INFORMATION: Phosphorothioated DNA bases (IDT)

<400> SEQUENCE: 108
tcagacgtgt gctcttccga tcttccacta tactgacgtc tccaac          46

<210> SEQ ID NO 109
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 109
tcagacgtgt gctcttccga tctacacacg caaaatactc cttcag          46

<210> SEQ ID NO 110
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 110
tcagacgtgt gctcttccga tctctgtcct cacagagttc aagc            44

<210> SEQ ID NO 111
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 111
tcagacgtgt gctcttccga tctgttttg cagatgatgg gctcc            45

<210> SEQ ID NO 112
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (39)..(39)
<223> OTHER INFORMATION: Phosphorothioated DNA bases (IDT)
```

```
<220> FEATURE:
<221> NAME/KEY: misc_feature
<222> LOCATION: (40)..(40)
<223> OTHER INFORMATION: Phosphorothioated DNA bases (IDT)

<400> SEQUENCE: 112
tcagacgtgt gctcttccga tctctggacc aagcccatca c                    41

<210> SEQ ID NO 113
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 113
tcagacgtgt gctcttccga tcttgtggcc ttgtactgca ga                   42

<210> SEQ ID NO 114
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 114
tcagacgtgt gctcttccga tctcagtgtg ttcacagaga cctg                 44

<210> SEQ ID NO 115
<211> LENGTH: 45
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (43)..(43)
<223> OTHER INFORMATION: Phosphorothioated DNA bases (IDT)
<220> FEATURE:
<221> NAME/KEY: misc_feature
<222> LOCATION: (44)..(44)
<223> OTHER INFORMATION: Phosphorothioated DNA bases (IDT)

<400> SEQUENCE: 115
tcagacgtgt gctcttccga tctgtaggaa atagcagcct cacat                45

<210> SEQ ID NO 116
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
```

<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 116
tcagacgtgt gctcttccga tcttgttcct gatctcctta gacaac                    46

<210> SEQ ID NO 117
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 117
tcagacgtgt gctcttccga tctcttgctg cacttctcac acc                       43

<210> SEQ ID NO 118
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (42)..(42)
<223> OTHER INFORMATION: Phosphorothioated DNA bases (IDT)
<220> FEATURE:
<221> NAME/KEY: misc_feature
<222> LOCATION: (43)..(43)
<223> OTHER INFORMATION: Phosphorothioated DNA bases (IDT)

<400> SEQUENCE: 118
tcagacgtgt gctcttccga tcttgaaaat tccagtggcc atca                      44

<210> SEQ ID NO 119
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 119
tcagacgtgt gctcttccga tctcaatgaa gagagaccag agc                       43

<210> SEQ ID NO 120
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature

```
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 120
tcagacgtgt gctcttccga tctcccatac cctctcagcg tac        43

<210> SEQ ID NO 121
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (40)..(40)
<223> OTHER INFORMATION: Phosphorothioated DNA bases (IDT)
<220> FEATURE:
<221> NAME/KEY: misc_feature
<222> LOCATION: (41)..(41)
<223> OTHER INFORMATION: Phosphorothioated DNA bases (IDT)

<400> SEQUENCE: 121
tcagacgtgt gctcttccga tctgtggatg tcaggcagat gc         42

<210> SEQ ID NO 122
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (41)..(41)
<223> OTHER INFORMATION: Phosphorothioated DNA bases (IDT)
<220> FEATURE:
<221> NAME/KEY: misc_feature
<222> LOCATION: (42)..(42)
<223> OTHER INFORMATION: Phosphorothioated DNA bases (IDT)

<400> SEQUENCE: 122
tcagacgtgt gctcttccga tctccctccc agaaggtcta cat        43

<210> SEQ ID NO 123
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: Phosphorothioated DNA bases (IDT)
<220> FEATURE:
<221> NAME/KEY: misc_feature
<222> LOCATION: (45)..(45)
<223> OTHER INFORMATION: Phosphorothioated DNA bases (IDT)

<400> SEQUENCE: 123
tcagacgtgt gctcttccga tcttttttgac atggttggga ctcttg    46

<210> SEQ ID NO 124
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (21)..(21)
<223> OTHER INFORMATION: Phosphorothioated DNA bases (IDT)
<220> FEATURE:
<221> NAME/KEY: misc_feature
<222> LOCATION: (22)..(22)
<223> OTHER INFORMATION: Phosphorothioated DNA bases (IDT)

<400> SEQUENCE: 124
tcagacgugu gcucuuccga ucu                                               23

<210> SEQ ID NO 125
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: 3' Phosphorylation (IDT)

<400> SEQUENCE: 125
gtgactggag ttcagacgtg t                                                 21

<210> SEQ ID NO 126
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (44)..(44)
<223> OTHER INFORMATION: 3' Phosphorylation (IDT)

<400> SEQUENCE: 126
aactccagtc actaatgcgc atctcgtatg ccgtcttctg cttg                        44

<210> SEQ ID NO 127
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 127
aatgatacgg cgaccaccga gatctacaca ggcgaagaca ctctttccct acacgacgct       60
cttccgatct                                                              70
```

METHODS FOR MULTIPLEX PCR

CROSS REFERENCE TO RELATED APPLICATIONS

The present application is a continuation application of U.S. patent application Ser. No. 16/389,243 filed Apr. 19, 2019, which is a divisional application of U.S. patent application Ser. No. 15/252,397 filed Aug. 31, 2016, now U.S. Pat. No. 10,316,359, which is a continuation of U.S. patent application Ser. No. 15/223,792 filed on Jul. 29, 2016, now U.S. Pat. No. 10,316,357, which is a continuation application of International Application No. PCT/US15/13994, filed Jan. 30, 2015, which claims priority benefits under 35 U.S.C. § 119 (e) of Provisional U.S. Patent Application No. 61/934,515, filed Jan. 31, 2014, Provisional U.S. Patent Application No. 62/078,309, filed Nov. 11, 2014, and Provisional U.S. Patent Application No. 62/078,313, filed Nov. 11, 2014, the disclosure of each of which is incorporated herein by reference in its entirety.

INCORPORATION BY REFERENCE OF MATERIALS SUBMITTED ELECTRONICALLY

This application contains, as a separate part of disclosure, a Sequence Listing in computer readable form (Filename: 47999A_Seqlisting.txt; created Jan. 29, 2015; 47,035 bytes), which is incorporated herein by reference in its entirety.

INTRODUCTION

All commercially available next-generation sequencing (NGS) technologies require library preparation, whereby a pair of specific adapter sequences are ligated to the ends of DNA fragments in order to enable sequencing by the instrument. Most NGS adapters comprise three functional domains: (1) unique PCR primer annealing sequences for library and clonal amplification, (2) unique sequencing primer annealing sequences and (3) unique sample indexing sequences. Currently, most platforms utilize clonal amplification to make hundreds of copies of each individual DNA library molecule. This is achieved by bridge amplification or emulsion PCR for the purpose of amplifying the signal generated for the particular mode of sequence detection for each library molecule (e.g., fluorescence or pH). For sequencing by synthesis, annealing domains for sequencing primers are juxtaposed to the adapter-insert junctions; to enable paired-end sequencing, each adapter possesses a unique sequence for primer annealing. Sample index sequences are comprised of short unique sequences, typically 6-8 bases, that when sequenced, identify the sample source of a particular sequence read, enabling samples to be multiplexed or co-sequenced. There are existing and emerging single molecule sequencing technologies that do not rely on clonal amplification for signal detection but still require the attachment of adapter sequences to their termini for other purposes, such as adding a terminal hairpin-loop to DNA duplexes to enable sequencing of both strands as a single molecule or introducing a leader sequence for nanopore entry.

Targeted next generation sequencing is encompassed by two leading technologies: amplicon sequencing and hybridization-capture enrichment of targets from whole genome libraries. Amplicon sequencing is the method of choice for rapid turnaround time given the reduced number of steps, for when panels of target loci significantly smaller than whole exomes are desired, and for significant overall cost savings in both preparative reagents and sequencing depth. Amplicon sequencing is represented by a variety of available techniques. Examples of these include 1. Multiplex PCR using degradable target-specific primers to eliminate primer dimers, followed by polishing and NGS adapter ligation, where overlapping targets are divided into separate tubes (Ion Torrent AmpliSeq); 2. Multiplex extension-ligation reactions that incorporate NGS adapters at the termini of each target-specific oligonucleotide pair, followed by NGS adapter mediated PCR amplification, which avoids multiplex PCR altogether; however, ligation-mediated PCR requires higher input DNA quantity (Illumina TSCA); 3. Multiplex PCR on microfluidic cells that separate primer pairs to avoid primer dimer formation and enable overlapping target loci; separate reactions require higher input DNA quantity (Fluidigm access array); 4. Multiplex PCR by digital droplet PCR that also separates primer pairs to avoid primer dimer formation and enable overlapping target loci; also has higher input DNA quantity requirement (Raindance). Each technology is designed to eliminate primer dimers or avoid their formation during the multiplexed amplification process, as to avoid having these artifacts dominate the resulting NGS amplicon library. Drawbacks to existing methods are: A. the high cost of microfluidic or digital droplet instrumentation and consumables, B. higher input quantity requirements; and C. the necessity to separate multiplex reactions where overlapping or contiguous coverage is desired, thus further increasing input quantity requirements. An alternative to these options when contiguous coverage is desired is to perform long-range PCR. However, long range PCR is difficult to multiplex and the subsequent fragmentation required for most sequencing platforms followed by separate NGS library preparation is both time consuming and more costly. What is needed in the art is a simple method of amplicon generation that enables low inputs of approximately 10 nanograms (ng) DNA, does not require instrumentation other than a thermocycler, and is independent of whether targets are separate hotspot loci or whether targets are overlapping regions of the genome when contiguous coverage is required. The compositions and methods disclosed herein provides a solution to this need.

Typically, preparation of an NGS DNA library involves 5 steps: (1) DNA fragmentation, (2) polishing, (3) adapter ligation, (4) size selection, and (5) library amplification (See FIGS. 1 and 2).

(1) Fragmentation: Fragmentation of DNA can be achieved by enzymatic digestion or physical methods such as sonication, nebulization or hydrodynamic shearing. Each fragmentation method has its advantages and limitations. Enzymatic digestion produces DNA ends that can be efficiently polished and ligated to adapter sequences. However, it is difficult to control the enzymatic reaction and produce fragments of predictable length. In addition, enzymatic fragmentation is frequently base-specific thus introducing representation bias into the sequence analysis. Physical methods to fragment DNA are more random and DNA size distribution can be more easily controlled, but DNA ends produced by physical fragmentation are damaged and the conventional polishing reaction is insufficient to generate ample ligation-compatible ends.

(2) Polishing: Typical polishing mixtures contain T4 DNA polymerase and T4 polynucleotide kinase (PNK). The 5'-3' polymerase and the 3'-5' exonuclease activities of T4 DNA polymerase excise 3' overhangs and fill-in 3' recessed ends, which results in excision of damaged 3' bases as well as polishing (creation of blunt) DNA ends. The T4 polynucleotide kinase in the polishing mix adds a phosphate to the 5' ends of DNA fragments that can be lacking such, thus making them ligation-compatible to NGS adapters.

What has remained unknown in the art is that a significant number of 5' ends produced by physical fragmentation are damaged in an unidentified manner and do not get phosphorylated by PNK. There is no enzyme in a conventional polishing mix that can trim a damaged 5' terminal base. As a result, a substantial fraction of DNA fragments in the preparation do not get converted into NGS library molecules because they remain ligation incompatible at their 5' termini to NGS adapters. Although it is known in the art that adapter ligation is inefficient, ligation is typically performed on both strands simultaneously so it has remained unknown which strand is limiting. We separated the reactions into strand-specific ligation to test the efficiency of each, respectively. Through this analysis, we were able to pinpoint the rate limiting step in the overall process to the 5' termini which, for a significant fraction of the DNA fragments, are poor substrates for PNK and as a result, adapter ligation.

(3) Adapter Ligation: Another factor that contributes to low NGS library yield apart from a lack of 5' phosphate groups is the ligation reaction itself. Prior to ligation, adenylation of repaired DNA using a DNA polymerase which lacks 3'-5' exonuclease activity is often performed in order to minimize chimera formation and adapter-adapter (dimer) ligation products. In these methods, single 3' A-overhang DNA fragments are ligated to single 5' T-overhang adapters, whereas A-overhang fragments and T-overhang adapters have incompatible cohesive ends for self-ligation. However, the adenylation reaction is incomplete and generates non-specific side products, further reducing the number of available molecules for ligation which reduces library yield. A more efficient, alternative approach to minimize concatamer formation is presented herein.

(4) Size Selection: The size selection process also impacts library yield. During size selection, fragments of undesired size are eliminated from the library using gel or bead-based selection in order to optimize the library insert size for the desired sequencing read length. This maximizes sequence data output by minimizing overlap of paired end sequencing that occurs from short DNA library inserts. In the case of samples with extremely limited input quantities, this step can be skipped, and in exchange for a higher degree of paired-end overlap, more rare fragments are sequenced.

(5) Amplification: The problem of low library yield results in the necessity to amplify libraries by PCR prior to NGS analysis, which leads to loss of library complexity and introduction of base composition bias. The only current solution to avoid this problem is higher quantities of input DNA for library prep, but up to 20% of clinical samples submitted for NGS analysis have insufficient DNA quantity, so instead, additional PCR cycles are applied to overcome the insufficient DNA input. This results in reduced sequence data from the presence of an unacceptable percentage of PCR duplicates.

SUMMARY OF THE INVENTION

To address some of the existing problems described above which cause low yields for NGS library construction, an enhanced adapter ligation method is provided. This novel method overcomes the necessity to add a phosphate group to the 5' ends of DNA fragments (which is required for conventional adapter ligation; see FIGS. 1 and 2). Instead, the 5' terminal bases that are damaged as a result of physical fragmentation of the DNA, are removed. By removal of the damaged base, a ligation compatible base with a 5' phosphate is exposed and adapter ligation efficiency is restored, leading to a significant increase in library yield and the ability to construct libraries from reduced input DNA quantities. In addition, an alternative to adenylation/TA ligation for the prevention of chimeric library inserts (concatamer formation during ligation) and formation of adapter dimer ligation products is introduced, which also contributes to higher library preparation yields. In any embodiment of a method described herein, the processing comprises converting the 5' and/or 3' terminus of a substrate molecule to one that is ligation-compatible.

This method, in its exemplary form, is comprised of four separate incubations (see FIGS. 3, 4 and 5) to generate a processed substrate molecule. In the first incubation, double-stranded fragmented DNA is combined with a phosphatase enzyme and under appropriate reaction conditions, the enzyme removes phosphate groups from the termini of the DNA fragments. This prevents chimeric library inserts from being generated by preventing DNA fragment concatamer formation in the subsequent ligation reactions.

In the second incubation, the de-phosphorylated DNA fragments are combined with a polymerase or a cocktail of polymerases that possess 3'-5' exonuclease activity. Under appropriate reaction conditions and in the presence of dNTPs, damaged 3' bases are trimmed and polishing of the double-stranded DNA fragments is achieved by excision of 3' overhangs and filling in of 3' recessed ends that were generated during physical fragmentation. At the completion of this step, the DNA fragments possess blunt ends with ligation compatible 3' termini and 5' termini which lack phosphate groups, therefore rendering the DNA fragments incapable of self-ligation.

In the third incubation, the blunt ended, double-stranded DNA fragments are combined with a DNA ligase and a first double-stranded blunt ended NGS adapter (3' adapter) that comprises a 5' phosphate and which is capable of ligating to the 3' ends of the DNA fragments (see FIG. 3). The special feature of this 3' adapter is that the adapter DNA strand that would typically simultaneously ligate to the 5' end of the DNA fragments has a 3' end modification that prevents ligation, and therefore a nick remains at the junction of the 5' terminus of each DNA fragment and the 3' end of the 3' adapter following the ligation reaction even in the presence of the 5' phosphate. The same 3' modification that prevents ligation to the 5' termini of the DNA fragments also prevents adapter-adapter ligation products from forming, albeit they would be comprised of a single adapter sequence which would not be a functional adapter dimer (functional dimers are comprised of both adapters). The product of this step is double-stranded DNA fragments with a single NGS adapter ligated to only one strand on both 3' termini.

In the fourth incubation, the strand of the 3' adapter that remains unligated to the DNA fragments (due to the 3' modification) is also displaceable or degradable due to the incorporation of degradable bases during oligo synthesis. In the presence of an optional, appropriate enzyme during the fourth incubation, the 3' adapter strand is degraded or is displaced by a new single-stranded adapter comprising the second NGS adapter sequence that is also present in the reaction (5' adapter, see FIG. 3), and through a complementary sequence to the 3' adapter at the junction of the adapter-insert, the single-stranded 5' adapter anneals to the complementary portion of the 3' adapter that is ligated to the 3' ends of the double-stranded DNA fragments, resulting in the restoration of a nick or gap. Additionally in the reaction is a DNA polymerase that possesses 5'-3' exonuclease activity, and in the presence of dNTPs, a ligase and the appropriate reaction conditions, nick translation is initiated at the nick or gap residing at the junction of the 5' adapter and the 5' termini of the DNA fragments. Nick translation results in replacement of the damaged 5' terminal base (and an additional one or more bases internal to the 5' terminus) and exposes a ligation-compatible 5' terminal phosphate group. Subsequently, efficient ligation of the 5' adapter to the DNA substrate molecule occurs when ligase seals the nick that is translated one or more bases (see FIG. 4). At the completion of this novel adapter ligation process, both ends of each double-stranded DNA fragment are flanked by two different, single-stranded NGS adapters that share a short complementary adapter sequence at the adapter-insert junction.

Alternatively, removal of the 5' terminal base and 5' adapter ligation can be achieved without polymerization, by annealing the single-stranded 5' adapter with one or more additional random bases at its 3' terminus which overlaps with the damaged 5' base(s) of the substrate molecule, and in the absence of dNTPs, cleavage of the displaced base at the 5' terminus of DNA substrate molecules by a 5' flap-specific nuclease occurs following displacement, which results in efficient ligation of the second NGS adapter to the exposed 5' phosphate on the termini of the cleaved DNA substrate molecules (see FIG. 5).

In another alternative, 5' terminal base removal and 5' adapter ligation can be achieved by a single dideoxy base extension from the degradable or displaceable strand of the 3' adapter that is followed by cleavage of the 5' terminal base of the DNA fragments by the 5' flap endonuclease activity of the polymerase. The strand is then degraded or displaced by the 5' adapter, and in the presence of a ligase, the 5' adapter efficiently ligates to the exposed 5' phosphate on the DNA fragments. Alternative embodiments of this step and preceding steps are presented below.

Accordingly, in one aspect the disclosure provides a method of producing a processed substrate molecule, the method comprising (i) ligating a first polynucleotide to a 3' terminus of a substrate molecule that is at least partially double stranded; (ii) annealing a second polynucleotide to the first polynucleotide under conditions that promote the annealing; (iii) excising at least one nucleotide from the 5' terminus of the substrate molecule; and then (iv) ligating the second polynucleotide to the 5' terminus of the double stranded substrate molecule to produce the processed substrate molecule. In one embodiment, the method further comprises the step, prior to step (i), of contacting the substrate molecule with a phosphatase enzyme. In another embodiment, the method further comprises the step of making the substrate molecule blunt-ended by contacting the substrate molecule with a polymerase enzyme possessing 3'-5' exonuclease activity. In yet another embodiment, the method further comprises the step of contacting the substrate molecule with a template-independent polymerase to adenylate the 3' end of the substrate molecule.

In any of the methods disclosed herein, it is contemplated that the substrate molecule is naturally occurring or the substrate molecule is synthetic. In one embodiment, the substrate molecule is naturally occurring. In another embodiment, the substrate molecule is genomic DNA, and in further embodiments the genomic DNA is eukaryotic or prokaryotic. In embodiments in which the substrate molecule is genomic DNA, the disclosure contemplates that the genomic DNA is fragmented in vitro or in vivo. In some embodiments, the in vitro fragmenting is performed by a process selected from the group consisting of shearing, cleaving with an endonuclease, sonication, heating, irradiation using an alpha, beta, or gamma source, chemical cleavage in the presence of metal ions, radical cleavage, and a combination thereof. In some embodiments, the in vivo fragmenting occurs by a process selected from the group consisting of apoptosis, radiation, and exposure to asbestos.

The disclosure also contemplates embodiments in which the substrate molecule is synthetic and is selected from the group consisting of cDNA, DNA produced by whole genome amplification, primer extension products comprising at least one double-stranded terminus, and a PCR amplicon.

In any of the aspects or embodiments of the disclosure, it is contemplated that the first polynucleotide is at least partially double stranded and comprises oligonucleotide 1 and oligonucleotide 2. In some embodiments, the second polynucleotide anneals to oligonucleotide 1, and in further embodiments, the annealing results in a nick, a gap, or an overlapping base between the second polynucleotide and the substrate molecule. In some embodiments, the annealing results in dehybridization of oligonucleotide 1 and oligonucleotide 2.

The second polynucleotide, in various embodiments, is contacted with a polymerase, resulting in degradation of oligonucleotide 2.

Also contemplated by the disclosure are embodiments wherein oligonucleotide 2 comprises a base that is susceptible to degradation, and the disclosure also provides embodiments wherein oligonucleotide 2 comprises a blocking group at its 3' end that prevents ligation. In some embodiments, the second polynucleotide comprises a modified base.

In further embodiments, a method of the disclosure further comprises (i) ligating a third polynucleotide to a 3' terminus of an additional substrate molecule that is at least partially double stranded; (ii) annealing a fourth polynucleotide to the third polynucleotide under conditions that promote the annealing; (iii) excising at least one nucleotide from the 5' terminus of the additional substrate molecule; and then (iv) ligating the fourth polynucleotide to the 5' terminus of the double stranded additional substrate molecule to produce a processed additional substrate molecule. In some embodiments, the first polynucleotide and the third polynucleotide are the same. In some embodiments, the second polynucleotide and the fourth polynucleotide are the same.

The method of targeted amplicon NGS library construction comprises two separate steps: multiplex PCR target enrichment followed by an NGS adapter ligation step (see FIG. 39). Two separate workflow options are possible: a two-step PCR followed by adapter ligation or a one-step PCR followed by ligation.

In the multiplex PCR step using either method, pairs of target-specific primers are designed to desired target loci and comprise a universal truncated NGS adapter sequence at their 5' termini (see FIGS. 40 and 41, Table 2). The first PCR cycles have elongated cycling times to allow the high complexity of primer pairs, each of which is at a low concentration, to create universal NGS adapter tagged amplicons from their target sequences. These primers optionally possess unique degenerate sequence tags to identify individual amplicons (UI=unique identifier), where each UI is located between the universal NGS adapter sequence at the 5' terminus and the target-specific portion at the 3' terminus of each primer (and represented as a stretch of NNNN bases, FIGS. 40, 41). If UI sequences are used, the elongated multiplex PCR cycles are limited to 2 in order to avoid incorporation of additional UI sequences into copies of previously generated amplicons; if UI sequences are not used, the elongated multiplex PCR cycles can be performed for more than 2 cycles. The more limited the target-specific cycle number performed, the fewer primer dimer products that accumulate, so the minimum number of multiplexed cycles feasible for the input sample quantity should be performed. Following the multiplex cycles (2 or more), PCR is continued with shorter elongation times for a second phase of amplification using a single, universal primer that corresponds to the universal truncated NGS adapter flanking each target amplicon. The universal primer is used at a relatively high concentration compared to the target-specific primers, where the total number of cycles is determined by the desired library yield. The concentration of target-specific primers are not sufficient to amplify the targets, so the universal primer which cannot self-interact, takes over the amplification reaction with the absence of additional primer dimer formation. Additionally, the primer dimers that accumulate during the limited multiplexed cycles will be shorter in length than the desired amplicons and will be subject to stable secondary structure which results in less efficient amplification by the single universal primer. If UI sequences are used, a purification step or exonuclease I digestion of multiplex primers is required prior to addition of the universal primer, in order to prevent additional UI sequences labeling subsequent copies of previously generated amplicons. If UI sequences are not used, the universal primer can be added at the beginning of the reaction with the multiplex primers and will become functional once universal adapter tagged amplicons are generated.

An additional feature of the universal primer is that it optionally comprises cleavable bases to enable downstream adapter ligation. Without limitation, the cleavable bases can be comprised of deoxyuridine, RNA or deoxyinosine. Alternatively, the universal primer does not comprise cleavable bases and this sequence is later excised using a 5' exonuclease to enable adapter ligation (see FIG. 42). In addition, both target-specific primers and the universal primer optionally comprise nuclease-resistant modifications at their 3' termini; these include phosphorothioate linkages, 2'O-Methyl or methylphosphonate modifications. These enable more specific and efficient priming when using a proofreading polymerase that possesses 3' to 5' exonuclease activity. It also limits 5' exonuclease digestion if this enzyme is used to remove the universal adapter sequence from amplicons prior to adapter ligation. Following PCR, a purification step is required to remove the unused reagents and polymerase.

For the final step of adapter ligation (see FIG. 42), the portion of each amplicon derived from the universal primer is digested due to incorporation of degradable bases into the primer and use of modification-specific endonuclease. Alternatively, for primers containing nuclease-resistant bases at their 3' end, the 5' portion of each amplicon can be trimmed by 5' exonuclease digestion. In this case, exonuclease digestion of the 5' termini of amplicons will be terminated at the position of the nuclease-resistant base. The primer digestion reaction creates a single stranded 3' overhang on both termini of each amplicon. Also present in the reaction is a full-length, single-stranded adapter B comprising a second NGS adapter sequence, and through a complementary sequence to the universal adapter at the junction of the adapter-target, the single-stranded second adapter B anneals to the complementary portion of the universal adapter that is located at the 3' overhangs of each amplicon, where the adapter annealing results in the formation of a nick or gap. Additionally in the reaction is a DNA polymerase that possesses 5'-3' exonuclease activity, and in the presence of dNTPs, a ligase and the appropriate reaction conditions, nick translation is initiated at the nick or gap residing at the junction of adapter B and the 5' termini of the amplicons. Nick translation results in replacement of one or more bases internal to the 5' terminus and exposes a ligation-compatible 5' terminal phosphate group. Subsequently, efficient ligation of adapter B to the DNA substrate amplicon occurs when ligase seals the nick that is translated one or more bases. Alternatively, ligation of adapter B is accomplished by a displacement-cleavage reaction using a polymerase with flap endonuclease activity and additionally a ligase. In this case, dNTPs are not required, only a several base overlap between the 3' terminus of Adapter B and the 5' terminus of the universal adapter portion remaining on each amplicon. To complete the adapter ligation process, a linker-mediated ligation is simultaneously performed to complete the 1" adapter (A) on the remaining universal adapter sequence at the 3' end of each amplicon. The linker oligonucleotide is complementary to the 3' terminus of the remaining universal adapter on each amplicon and complementary to the oligonucleotide comprising the remainder of the 1" adapter. Through its complementarity to both sequences, the linker oligonucleotide hybridizes to both the 3' remainder of the 1" adapter and the remaining universal adapter present on each amplicon, enabling ligation to occur. At the completion of this novel adapter ligation process, both ends of each amplicon are flanked by two different, single-stranded NGS adapters (A and B) that share a short complementary adapter sequence at the adapter-target junction. A final purification step prior to library quantification and sequencing is then performed.

An additional feature of the disclosed method is the choice of DNA polymerase used in the multiplexed PCR amplification reaction. The error rate during amplification can be improved when using high fidelity Pfu DNA polymerase, Phusion DNA polymerase, KAPA HiFi DNA polymerase, Q5 DNA polymerase or their derivatives and analogs. Additionally, given that the universal primer used in the second phase of the amplification reaction optionally comprises cleavable bases, a high fidelity DNA polymerase that is tolerant of uracil, RNA or inosine bases is also desirable. This includes but is not limited to KAPA HiFi U+ polymerase, Themo Phusion U and Enzymatics VeraSeq ULtra polymerases, all engineered to tolerate uracil containing substrates. Given the use of high fidelity enzymes that possess 3' to 5' exonuclease activity in the amplification reaction, all target-specific primers as well as the universal primer comprise nuclease resistant linkages at their 3' termini to increase the fidelity and efficiency of primer extension. This includes but is not limited to a phosphorothioate linkage or other nuclease resistant moiety.

Additionally, as previously mentioned, methods for multiplexed PCR for targeted NGS libraries that are capable of amplifying overlapping targets for contiguous coverage in a single tube format is desired. The method disclosed herein is capable of achieving this effect (FIGS. 43 and 44). In the case of two primer pairs that have overlapping target regions, 4 possible amplicons can be generated: an amplicon specific to each of the two primer pairs, a maxi-amplicon resulting from amplification of the two distal primers and a mini-amplicon resulting from amplification of the two proximal primers. To avoid having the mini-amplicon dominate the multiplexed PCR reaction (short amplicons such as this and primer dimers often dominate amplification reactions due to their short length and ease of amplification), most methods separate overlapping primer pairs into two tubes, which is effective but doubles the workload and required DNA input quantity. The method disclosed herein enables overlapping amplicons to be created in a single tube, because due to the presence of the universal sequence at each terminus, the short mini-amplicon will be subject to stable secondary structure which results in less efficient amplification by the single universal primer. Therefore, even if the mini-amplicon is produced during the initial target-specific PCR cycles, it will not be efficiently amplified. As a result, using methods disclosed herein, only the amplicons specific to each primer pair and the maxi-amplicon are produced from high quality, high molecular weight DNA input. When cross-linked FFPE DNA or fragmented DNA (particularly circulating cell-free DNA that is in the 165 bp range) is used, formation of the maxi-amplicon is suppressed since template length or integrity cannot support an amplicon of this size, and only the amplicons specific to each primer pair are produced.

In any of the methods disclosed herein, it is contemplated that the sample DNA input is naturally occurring. In one embodiment, the input DNA is genomic DNA, either intact high molecular weight DNA or fragmented circulating cell-free DNA, and in further embodiments, the genomic DNA is eukaryotic, prokaryotic, mitochondrial or viral in origin. In other embodiments, the input DNA is single-stranded or double-stranded or is synthetic and is the result of a prior whole genome amplification or the result of a random or otherwise primed reverse transcription of RNA.

In further aspects of the disclosure, a composition is provided comprising a ligase and a first polynucleotide that is at least partially double stranded and comprises oligonucleotide 1 and oligonucleotide 2; wherein oligonucleotide 1 comprises a 5' phosphate and a blocking group at its 3' terminus; and wherein oligonucleotide 2 (i) comprises a base that is susceptible to degradation and/or (ii) can be displaced by non-denaturing heat condition and further comprises a blocking group at its 3' end, said blocking group prevents ligation of the 3' end but enables ligation of the 5' end of oligonucleotide 1.

In some embodiments, the 3' blocking group of oligonucleotide 2 is 3' deoxythymidine, 3' deoxyadenine, 3' deoxyguanine, 3' deoxycytosine or a dideoxy nucleotide. In further embodiments, the base that is susceptible to degradation is deoxyuridine, a ribonucleotide, deoxyinosine, or inosine. The non-denaturing heat condition, in various embodiments, is from about 50° C. to about 85° C.

In some embodiments, oligonucleotide 2 comprises a base modification that reduces the binding stability of oligonucleotide 2, wherein the base modification is deoxyinosine, inosine or a universal base.

The disclosure also provides, in some aspects, a composition comprising a ligation product resulting from incubation of a double stranded substrate with a composition of the disclosure; a ligase, a DNA polymerase having nick translation activity, an endonuclease that recognizes a base that is susceptible to degradation, and a second polynucleotide that is single stranded and comprises a 3' domain that is sufficiently complementary to the 5' portion of oligonucleotide 1 of polynucleotide 2 to anneal under appropriate conditions when oligonucleotide 2 of polynucleotide 1 is either degraded or displaced.

In some embodiments, the second polynucleotide is of a sufficient length to displace oligonucleotide 2 of the first polynucleotide or the second polynucleotide comprises a base modification that increases its binding stability. In further embodiments, the endonuclease is selected from the group consisting of UDG plus endonuclease VIII, RNase HI, RNase H2 and Endonuclease V. In still further embodiments, the ligase is *E. coli* DNA ligase or T4 DNA ligase. The base modification that increases its binding stability is, in various embodiments, a locked nucleic acid (LNA).

In further aspects of the disclosure, a composition is provided comprising a ligation product resulting from incubation of a double stranded substrate with a composition of the disclosure; a ligase; a flap endonuclease; an endonuclease that recognizes a base that is susceptible to degradation; a second polynucleotide comprising a single stranded oligonucleotide comprising a 3' domain that is sufficiently complementary to the 5' portion of oligonucleotide 1 of polynucleotide 2 to anneal under appropriate conditions when oligonucleotide 2 of polynucleotide 1 is either degraded or displaced, wherein the second polynucleotide is of a sufficient length to displace oligonucleotide 2 of the first polynucleotide or the second polynucleotide comprises a base modification that increases its binding stability, and wherein the second polynucleotide further comprises a 3' terminal degenerate base.

In another aspect, the disclosure provides a method of producing a processed substrate molecule, the method comprising: (i) ligating a first polynucleotide to a 3' terminus of a substrate molecule that is at least partially double stranded; (ii) annealing a second polynucleotide to the first polynucleotide under conditions that promote the annealing; (iii) excising at least one nucleotide from the 5' terminus of the substrate molecule; and then (iv) ligating the second polynucleotide to the 5' terminus of the double stranded substrate molecule to produce the processed substrate molecule. In some embodiments, the method further comprises a step, prior to step (i), of contacting the substrate molecule with a phosphatase enzyme.

In some embodiments, the phosphatase enzyme is calf intestinal phosphatase or shrimp phosphatase.

In further embodiments, the method further comprises a step of making the substrate molecule blunt-ended by contacting the substrate molecule with a polymerase enzyme possessing 3'-5' exonuclease activity.

In some embodiments, the polymerase enzyme is selected from the group consisting of T4 DNA ligase, Klenow fragment, T7 polymerase, and a combination thereof. In still further embodiments, the method further comprises a step of contacting the substrate molecule with a template-independent polymerase to adenylate the 3' end of the substrate molecule.

In various embodiments, the substrate molecule is naturally occurring or the substrate molecule is synthetic. Thus, in some embodiments, the substrate molecule is naturally occurring. In further embodiments, the substrate molecule is genomic DNA. In still further embodiments, the genomic DNA is eukaryotic or prokaryotic, and in yet additional embodiments, the genomic DNA is fragmented in vitro or in vivo. In some embodiments, the substrate molecule is circulating cell-free DNA.

In some embodiments, the method further comprises, prior to step (i), adjusting temperature to between about 50° C. to about 85° C. In some embodiments, the temperature is 65° C.

In additional embodiments, the in vitro fragmenting is performed by a process selected from the group consisting of shearing, cleaving with an endonuclease, sonication, heating, irradiation using an alpha, beta, or gamma source, chemical cleavage in the presence of metal ions, radical cleavage, and a combination thereof. In further embodiments, the in vivo fragmenting occurs by a process selected from the group consisting of apoptosis, radiation, and exposure to asbestos.

The substrate molecule, in further embodiments, is synthetic and is selected from the group consisting of cDNA, DNA produced by whole genome amplification, primer extension products comprising at least one double-stranded terminus, and a PCR amplicon.

In some embodiments, the first polynucleotide is at least partially double stranded and comprises oligonucleotide 1 and oligonucleotide 2. In various embodiments, the second polynucleotide anneals to oligonucleotide 1. The annealing, in some embodiments, results in a nick, a gap, or an overlapping base between the second polynucleotide and the substrate molecule.

The second polynucleotide, in various embodiments, is contacted with a polymerase, resulting in degradation of oligonucleotide 2.

In some embodiments, oligonucleotide 2 comprises a base that is susceptible to degradation. In further embodiments, the base that is susceptible to degradation is selected from the group consisting of deoxyuridine, RNA, deoxyinosine, and inosine. In still further embodiments, oligonucleotide 2 comprises a blocking group at its 3' end that prevents ligation. the blocking group, in various embodiments, is a 3' deoxynucleotide or a dideoxynucleotide.

In some embodiments, the second polynucleotide comprises a modified base.

In further embodiments, the annealing results in dehybridization of oligonucleotide 1 and oligonucleotide 2.

In still further embodiments, the method further comprises: (i) ligating a third polynucleotide to a 3' terminus of an additional substrate molecule that is at least partially double stranded; (ii) annealing a fourth polynucleotide to the third polynucleotide under conditions that promote the annealing; (iii) excising at least one nucleotide from the 5' terminus of the additional substrate molecule; and then (iv) ligating the fourth polynucleotide to the 5' terminus of the double stranded additional substrate molecule to produce a processed additional substrate molecule.

In some embodiments, the first polynucleotide and the third polynucleotide are the same. In further embodiments, the second polynucleotide and the fourth polynucleotide are the same.

In further aspects, the disclosure provides a composition comprising a universal primer and a plurality of target-specific oligonucleotide primer pairs; wherein each target-specific primer of the plurality of primer pairs comprises a target-specific sequence and a 5' terminal sequence that is not complementary to a target substrate molecule; wherein the universal primer comprises the 5' terminal sequence and a cleavable base or a nuclease resistant modification; wherein each target-specific primer of the plurality of primer pairs and the universal primer each comprise a nuclease resistant modification at their 3' termini; a high fidelity polymerase that is tolerant of the cleavable base incorporated into the universal primer; wherein the target-specific primer pairs and the universal primer anneal to their target substrate molecules at the same temperature; and wherein the molar ratio of target-specific to universal primer is at least about 1:100.

In some embodiments, the cleavable base is deoxyuridine, RNA, deoxyinosine, or inosine. In further embodiments, the nuclease resistant modification is phosphorothioate.

In additional embodiments, at least one target-specific primer further comprises a molecular identification tag between the target-specific sequence and the 5' terminal sequence.

In various embodiments of the disclosure, the molar ratio of target-specific to universal primer is at least about 1:200, or at least about 1:300, or at least about 1:400, or at least about 1:500, or at least about 1:1000, or at least about 1:2000, or at least about 1:3000, or at least about 1:5000, or at least about 1:10,000 or greater.

In various embodiments, the composition further comprises a substrate molecule.

In some aspects, a composition is provided comprising a product of a polymerase chain reaction (PCR) generated by a universal primer, wherein the product comprises at least one cleavable base incorporated via the universal primer; an endonuclease that can cleave the cleavable base; (i) at least one nucleotide and a DNA polymerase possessing nick translation activity, or (ii) an enzyme possessing flap endonuclease activity; a DNA ligase; a 5' adapter comprising (i) a 3' sequence that is complementary to the 5' portion of the reverse complement of the universal primer exposed by endonuclease cleavage of the universal primer and (ii) a 5' portion that is not complementary to the reverse complement of the universal primer; and wherein the 3' portion of the reverse complement of the universal primer anneals to a partially double stranded truncated 3' adapter.

In some embodiments, the endonuclease is selected from the group consisting of UDG+Endonuclease VIII, RNase HI, RNase H2, and Endonuclease V. In further embodiments, the DNA ligase is E. coli DNA ligase or T4 DNA ligase.

In further aspects, the disclosure provides a composition comprising: a product of a polymerase chain reaction (PCR) generated by a universal primer, wherein the product comprises at least one nuclease resistant modification incorporated via the universal primer; a 5' exonuclease that is not able to digest the PCR product beyond the nuclease resistant modification; (i) at least one nucleotide and a DNA polymerase possessing nick translation activity, or (ii) an enzyme possessing flap endonuclease activity; a DNA ligase; 5' adapter comprising (i) a 3' sequence that is complementary to the 5' portion of the reverse complement of the universal primer exposed by endonuclease cleavage of the universal primer and (ii) a 5' portion that is not complementary to the reverse complement of the universal primer; and wherein the 3' portion of the reverse complement of the universal primer anneals to a partially double stranded truncated 3' adapter molecule.

In still further aspects, a method of polymerase chain reaction (PCR) is provided comprising contacting a substrate molecule with: (i) a target-specific primer pair, where each primer comprises a 5' sequence that is not complementary to the substrate molecule and which incorporates a single universal adapter at the termini of the resulting amplicon; and (ii) a single primer that comprises the single universal adapter sequence and additionally comprises a cleavable base or nuclease resistant modification, where under appropriate reaction conditions using a constant annealing temperature for each cycle of PCR but varying the annealing time, in the presence of a high fidelity DNA polymerase and nucleotides, wherein the molar ratio of each target-specific primer:universal primer is at least about 1:100, target-specific amplicons are generated during the first two or more PCR cycles that have annealing times of 5 minutes or more, followed by amplification of the resulting amplicons during the remaining PCR cycles which each comprise annealing times of 1 minute or less, wherein amplification of the target-specific amplicon by the higher concentration single universal primer is achieved.

In additional aspects, a method of multiplexed PCR is provided comprising contacting a substrate molecule with (i) a plurality of target-specific primer pairs, wherein each primer comprises a 5' sequence that is not complementary to the substrate and which incorporates a single universal adapter at the termini of the resulting amplicon, and (ii) a single primer that comprises the single universal adapter sequence and additionally comprises a cleavable base or nuclease resistant modification, where under appropriate reaction conditions using a constant annealing temperature for each PCR cycle but varying the annealing time, in the presence of a high fidelity DNA polymerase and nucleotides, wherein the molar ratio of each target-specific primer: universal primer is at least about 1:100, target-specific amplicons are generated during the first two or more PCR cycles that have annealing times of five minutes or more, followed by amplification of the resulting amplicons during the remaining PCR cycles which each comprise an annealing time of one minute or less, wherein multiplexed amplification of the target-specific amplicons by the higher concentration single universal primer is achieved.

In some aspects, a method of converting a polymerase chain reaction (PCR) product is provided, comprising a single universal adapter sequence at each terminus into a product comprising asymmetric 5' and 3' adapters at each terminus, comprising: (a) digesting the 5' terminus of the PCR product where either a cleavable base or nuclease resistant modification was introduced, followed by (b) annealing and (i) nick-translation ligation or (ii) flap endonuclease cleavage ligation of a 5' adapter that is complementary to the 5' portion of the reverse complement of the universal adapter that was exposed by the digestion, and (c) wherein a partially double stranded truncated 3' adapter anneals and ligates to the 3' portion of the reverse complement of the universal adapter, thereby converting the PCR product into a product comprising asymmetric adapters at each terminus.

In some embodiments, the PCR product is a whole genome amplification (WGA) product.

In any of the methods disclosed herein, it is contemplated that the target loci chosen for multiplexed amplification correspond to any of a variety of applications, including but not limited to oncology specific targets, drug resistance specific targets, targets for inherited disease, targets from infectious pathogens, targets for pathogen hosts, species-specific targets, and any clinically actionable targets.

BRIEF DESCRIPTION OF THE FIGURES

FIG. 1 is exemplary of alternative existing NGS adapter designs including: a fill-in adapter (blunt-ended or with T-overhang) with 3' and 5' hydroxyls; a Y-adapter (with T-overhang) with 3' hydroxyl and 5' phosphate; and a stem-loop adapter (blunt-ended or with T-overhang) with 3' hydroxyl and 5' hydroxyl or phosphate.

In FIG. 9A, during Step 1, 3' adapter attachment occurs leaving a nick at the 3' terminus of oligonucleotide 2 (due to 5' OH on substrate); during Step 2, the 3' terminus of oligonucleotide 2 is extended with a ddNTP; and during Step 3, partial degradation of the 3' adapter oligonucleotide 2 by UDG is followed by 5' adapter annealing and attachment by a DNA ligase. In FIG. 9B, during Step 1, 3' adapter attachment occurs leaving a nick at the 5' terminus of oligonucleotide 2 (due to dideoxy 3' terminus); during Step 2, partial degradation of the 3' adapter oligonucleotide 2 by UDG, annealing of the 5'primer and its extension with ddNTP mix is performed; and during Step 3, degradation of the 5' primer by RNase H, 5' adapter annealing and attachment by a DNA ligase is performed. In FIG. 9C, during Step 1, 3' adapter attachment occurs leaving a nick at the 3' terminus of oligonucleotide 2 (due to 5' OH on substrate); during Step 2, 3' adapter oligonucleotide 2 is extended with a ddNTP mix; and in Step 3, partial degradation of the 3' adapter oligonucleotide 2 by UDG, 5' adapter annealing, single base extension with T7 or T4 DNA Polymerase and dNTP mix and attachment by a ligase is performed. In FIG. 9D, during Step 1, 3' adapter attachment is performed, leaving a nick at the 3' terminus of oligonucleotide 2 due to the dideoxy terminus; during Step 2, partial degradation of the 3' adapter oligonucleotide 2 by UDG, annealing of the 5' primer and its extension with a ddNTP mix is performed; and during Step 3, degradation of the 5' primer by RNase H, 5' adapter annealing, single base extension with T7 or T4 DNA polymerase and dNTP mix and attachment by a DNA ligase is performed.

In FIG. 21 A, the gel electrophoresis depicts Taq polymerase mediated nick translation products when varying the dNTP composition or reaction temperature from 30-50° C. In FIG. 21 B, the gel electrophoresis depicts Taq polymerase mediated nick translation when varying the temperature from 50-60° C.

FIG. 24 provides data related to a coupled displacement-cleavage-ligation reaction, as described in Example 6. The polyacrylamide gel electrophoresis depicts displacement-cleavage-ligation products when using either E. coli DNA ligase (upper panel) or Taq DNA ligase (bottom panel).

FIG. 30 depicts the sequence and structure of exemplary oligonucleotide adapters described in Example 1. The 12-900/13-426 oligonucleotide duplex is the fill-in adapter; the 13-340/13-559 oligonucleotide 1 and 2 duplex is the 3' adapter option 1 with a blocking 3' deoxythymidine base at the 3' terminus of 13-559; and the 13-340/13-558 oligonucleotide 1 and 2 duplex is the 3' adapter option 2 where there is a phosphate group at the 3' terminus of 13-558.

FIG. 31 depicts FAM substrate molecules used in Example 1. The 13-562/13-563 duplex is a substrate where the FAM group labels ligation to the 5' phosphate of the substrate; the 13-561/13-564 duplex is a substrate where the FAM group labels ligation to the 3' OH of the substrate and where the corresponding 5' terminus of the substrate has a phosphate; the 13-560/13-564 duplex is a substrate where the FAM group labels ligation to the 3' OH of the substrate and where the corresponding 5' terminus of the substrate lacks a phosphate.

FIG. 32 depicts the structure of adapters as described in Example 2. The 13-489/13-426 oligonucleotide duplex is a fill-in adapter; the 13-340/13-559 oligonucleotide 1 and 2 duplex is a 3' adapter option 1 containing a blocking 3' deoxythymidine base at the 3' terminus of 13-559.

FIG. 37 depicts the structure of P7 and P5 adapters as described in Example 10, where the P7 adapter is depicted above comprising a 3' adapter where the 1st oligonucleotide is 13-501 annealed to the 2nd oligonucleotide 13-712; and where two P5 adapters are depicted below, the first comprising an oligonucleotide for nick translation (13-489) and the second comprising an oligonucleotide for displacement cleavage with a 3' terminal N base (13-595).

FIG. 38 depicts the structure of P7 and P5 adapters as described in Example 11, where the P7 adapter is depicted above comprising a 3' adapter where the 1st oligonucleotide is 13-501 annealed to the $2^{nd}$ oligonucleotide 13-712; and where a P5 adapter is depicted below, an oligonucleotide for nick translation (13-489).

FIG. 39 depicts two workflows for the amplicon NGS library construction method, where the diagram on the left depicts a 3 step amplicon library synthesis using a two-step PCR followed by a 1 step attachment of NGS adapters; and where the diagram on the right depicts a 2 step amplicon library synthesis using a single step PCR followed by a 1 step attachment of NGS adapters.

DETAILED DESCRIPTION OF THE INVENTION

Figure 2:
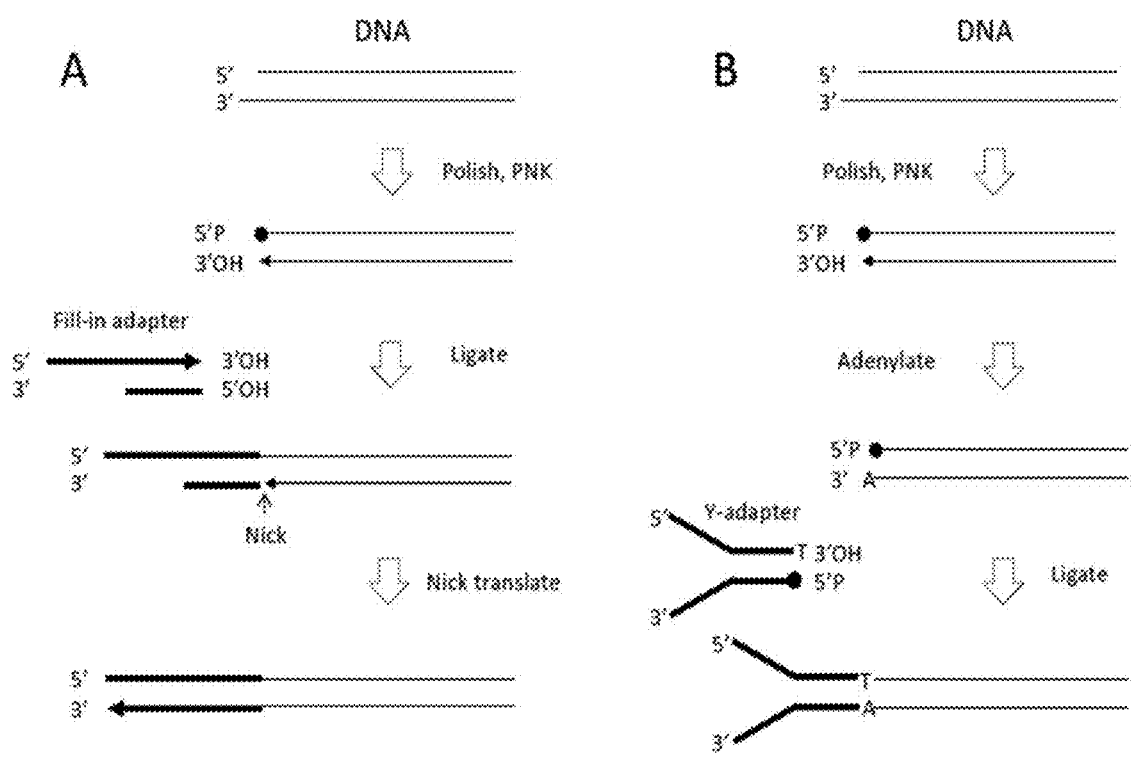
FIG. 2 is exemplary of alternative existing adapter ligation chemistries. Panel A depicts an adaptor ligation chemistry for use with fill-in adaptors while panel B depicts adaptor ligation chemistry for a Y-adaptor.

In one aspect, the invention describes a highly efficient method of adapter ligation to the ends of fragmented double-stranded DNA molecules. Such DNA molecules are referred to herein as "substrate molecules." In one aspect, the method comprises a single incubation that includes (1) annealing of a 5' adapter to a pre-existing 3' overhang on a substrate molecule, preferably a 3' adapter, (2) removal of a damaged base from the 5'-termini of the substrate molecules, which enables (3) efficient ligation of the 5' adapter to the exposed 5'-phosphate of the substrate molecules. In another aspect, the method comprises two incubations, where in the first incubation a 3' adapter is ligated to the substrate molecule, and in the second incubation the 5' adapter is ligated to the substrate molecule, as described above (see FIG. 6). In various embodiments, the disclosure further provides methods that comprise additional steps that occur prior to the one or two ligation steps, including: (i) a dephosphorylation reaction, (ii) a polishing reaction to excise damaged 3' termini and generate a blunt end, and (iii) an adenylation reaction; various combinations of the steps are contemplated by the disclosure, and are discussed in further detail below.

In another aspect, disclosure describes a highly efficient method of multiplex amplicon NGS library preparation. In one aspect, the method allows synthesis and amplification of multiple overlapping amplicons in a single tube. In another aspect, it describes a novel, highly efficient method of adapter ligation to the ends of PCR amplicons that is free of chimeric amplicons and adapter-dimers. In one aspect, it allows incorporation of unique degenerate sequence tags to identify individual amplicons. In another aspect, the method comprises a single incubation that includes degradation of the 5' termini of the amplicons followed by simultaneous ligation of the second adapter B and linker-mediated ligation of the remainder of the 1st adapter A to the substrate amplicons. In various embodiments, the disclosure further provides methods that comprise additional steps that occur prior to the ligation step, including: (i) a multiplexed PCR reaction (ii) a purification step, and (iii) a universal single primer amplification step. Alternatively, additional steps that occur prior to the ligation step include: (i) a combined multiplex PCR reaction with universal single primer amplification, followed by (ii) a purification step. Various options of the steps are contemplated by the disclosure, and are discussed in further detail below.

The term "reaction conditions" or "standard reaction conditions" as used herein means conditions according to manufacturer's instructions. It is understood that all enzymes herein disclosed are used under standard reaction conditions, unless indicated otherwise. The term "first polynucleotide" as used herein is used interchangeably with "3' adapter," "first adapter," or "Adapter A" and the term "second polynucleotide" as used herein is used interchangeably with "5' adapter," "second adapter" or "Adapter B." In certain instances, when Adapter A is used in reference to IonTorrent™ technology, e.g., FIGS. 12-13, it refers to Adapter A as provided by the manufacturer for the IonTorrent™ method, and not "Adapter A" as defined herein.

A "3' adapter" as used herein ligates to a 3' end of a substrate molecule, and a "5' adapter" ligates to a 5' end of a substrate molecule.

As used herein, a "damaged" 5' terminus is one that lacks a 5' phosphate.

As used herein, a "processed" substrate molecule is one to which a 5' adapter has been attached.

As used herein, a "high fidelity polymerase" is one that possesses 3'-5' exonuclease (i.e., proofreading) activity.

The term "tolerant," as used herein, refers to a property of a polymerase that can extend through a template containing a cleavable base (e.g., uracil, inosine, and RNA).

As used herein, the term "asymmetric" refers to a double stranded molecule with both adapters at both termini instead of a single adapter at both termini. Thus, the asymmetry arises from the fact that both adapters are largely non-complementary to each other and have single stranded portions.

As used herein, a "universal primer" is an oligonucleotide used in an amplification reaction to incorporate a universal adapter sequence. A "universal adapter" as used herein is a portion of the amplification product that corresponds to the universal primer sequence and its reverse complement.

It will be understood that a modification that decreases the binding stability of two nucleic acids includes, but is not limited to a nucleotide mismatch, a deoxyinosine, an inosine or a universal base.

It will also be understood that a modification that increases the binding stability of two nucleic acids includes, but is not limited to a locked nucleic acid (LNA), spermine and spermidine or other polyamines, and cytosine methylation.

As used herein, the term "universal base" is one that can base pair with all four naturally occurring bases without hydrogen bonding and is less destabilizing than a mismatch, and includes but is not limited to 5' nitroindole.

A "molecular identification tag" as used herein is anywhere between 4 and 16 bases in length where the optimal length is between 8 and 12 degenerate N bases.

Substrate Molecule

It is contemplated that a substrate molecule is obtained from a naturally occurring source or it can be synthetic. The naturally occurring sources include but are not limited to genomic DNA, cDNA, DNA produced by whole genome amplification, primer extension products comprising at least one double-stranded terminus, and a PCR amplicon. The naturally occurring source is, in various embodiments, a prokaryotic source or a eukaryotic source. For example and without limitation, the source can be a human, mouse, virus, plant or bacteria or a mixture comprising a plurality of genomes.

As used herein, an "amplicon" is understood to mean a portion of a polynucleotide that has been synthesized using amplification techniques.

If the source of the substrate molecule is genomic DNA, it is contemplated that in some embodiments the genomic DNA is fragmented. Fragmenting of genomic DNA is a general procedure known to those of skill in the art and is performed, for example and without limitation in vitro by shearing (nebulizing) the DNA, cleaving the DNA with an endonuclease, sonicating the DNA, by heating the DNA, by irradiation of DNA using alpha, beta, gamma or other radioactive sources, by light, by chemical cleavage of DNA in the presence of metal ions, by radical cleavage and combinations thereof. Fragmenting of genomic DNA can also occur in vivo, for example and without limitation due to apoptosis, radiation and/or exposure to asbestos. According to the methods provided herein, a population of substrate molecules is not required to be of a uniform size. Thus, the methods of the disclosure are effective for use with a population of differently-sized substrate polynucleotide fragments.

The substrate molecule, as disclosed herein, is at least partially double stranded and comprises a 3' overhang (see FIG. 7a), a blunt end, a 3' recessed end, or a free 3' hydroxyl group. The length of an overhang or recessed end of a substrate polynucleotide can be varied. In various aspects, the length of an overhang or recessed end of a substrate molecule is 1, 2, 3, 4, 5, 6, 7, 8, 9, 10, 11, 12, 13, 14, 15, 16, 17, 18, 19, 20 or more nucleotides in length. In further embodiments, the length of an overhang or recessed end of a substrate molecule is at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 nucleotides in length. In still further embodiments, the length of an overhang or recessed end of a substrate molecule is from about 1 to about 5, or from about 1 to about 10, or from about 1 to about 15, or from about 1 to about 20 nucleotides in length. A population of substrate molecules, in various aspects, includes those wherein more than one of the above-mentioned types of substrate molecules are present in a single reaction. The disclosure also contemplates that the substrate molecule is at least partially single stranded. Aspects of the disclosure in which the substrate molecule is single stranded involve the use of a single stranded ligase enzyme.

Some applications of the current invention involve attachment of adapter sequences not to original or native double stranded DNA substrate molecules but to a double stranded DNA produced by primer extension synthesis. One example of such an application is a DNA library produced by (a) attachment of an oligonucleotide comprising a primer-binding sequence to the 3' end of single-stranded or double-stranded DNA to enable primer extension, (b) extension of the primer annealed to the oligonucleotide, and (c) attachment of the 3' and 5' adapters to the double-stranded DNA ends produced by the primer-extension.

The length of either a double-stranded portion or a single-stranded portion of a substrate molecule is contemplated to be between about 3 and about $1\times10^6$ nucleotides. In some aspects, the length of the substrate molecule is between about 10 and about 3000 nucleotides, or between about 40 and about 2000 nucleotides, or between about 50 and about 1000 nucleotides, or between about 100 and about 500 nucleotides, or between about 1000 and about 5000 nucleotides, or between about 10,000 and 50,000 nucleotides, or between about 100,000 and 1×106 nucleotides. In further aspects, the length of the substrate molecule is at least 3 and up to about 50, 100 or 1000 nucleotides; or at least 10 and up to about 50, 100 or 1000 nucleotides; or at least 100 and up to about 1000, 5000 or 10000 nucleotides; or at least 1000 and up to about 10000, 20000 and 50000; or at least 10000 and up to about 20000, 50000 and 100,000 nucleotides; or at least 20000 and up to about 100,000, 200,000 or 500,000 nucleotides; or at least 200,000 and up to about 500,000, 700,000 or 1,000,000 nucleotides. In various aspects, the length of the substrate molecule is about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, 10,000, 15,000, 20,000, 50,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000 or more nucleotides.

Amplicon Molecules

As used herein, an "amplicon" is understood to mean a portion of a polynucleotide that has been synthesized using amplification techniques.

The length of an amplicon is contemplated to be between about 10 bp to 175 bp, where the desired amplicon size is significantly shorter than circulating cell-free DNA fragments (~165 bp) and small enough in size as to not span formalin-induced cross linked DNA from preserved samples, ideally <150 bp in length. It is contemplated the amplicon can be 15 bp, 20 bp, 25 bp, 30 bp, 35 bp, 40 bp, 45 bp, 50 bp, 51 bp, 52 bp, 53 bp, 54 bp, 55 bp, 56 bp, 57 bp, 58 bp, 59 bp, 60 bp, 61 bp, 62 bp, 63 bp, 64 bp, 65 bp, 66 bp, 67 bp, 68 bp, 69 bp, 70 bp, 71 bp, 72 bp, 73 bp, 74 bp, 75 bp, 76 bp, 77 bp, 78 bp, 79 bp, 80 bp, 81 bp, 82 bp, 83 bp, 84 bp, 85 bp, 86 bp, 87 bp, 88 bp, 89 bp, 90 bp, 91 bp, 92 bp, 93 bp, 94 bp, 95 bp, 96 bp, 97 bp, 98 bp, 99 bp, 100 bp, 101 bp, 102 bp, 103 bp, 104 bp, 105 bp, 106 bp, 107 bp, 108 bp, 109 bp, 110 bp, 111 bp, 112 bp, 113 bp, 114 bp, 115 bp, 116 bp, 117 bp, 118 bp, 119 bp, 120 bp, 121 bp, 122 bp, 123 bp, 124 bp, 125 bp, 126 bp, 127 bp, 128 bp, 129 bp, 130 bp, 131 bp, 132 bp, 133 bp, 134 bp, 135 bp, 136 bp, 137 bp, 138 bp, 139 bp, 140 bp, 141 bp, 142 bp, 143 bp, 144 bp, 145 bp, 146 bp, 147 bp, 148 bp, 149 bp, 150 bp, 151 bp, 152 bp, 153 bp, 154 bp, 155 bp, 156 bp, 157 bp, 158 bp, 159 bp, 160 bp, 161 bp, 162 bp, 163 bp, 164 bp, 165 bp, 166 bp, 167 bp, 168 bp, 169 bp, 170 bp, 171 bp, 172 bp, 173 bp, 174 bp, 175 bp or more in length.

Alternatively, for longer reads, particularly for long read sequence technologies capable of providing multi-kilobase reads that provide haplotyping information or span repetitive or other difficult sequences (PacBio), amplicon length is contemplated to be between 150 bp to 150,000 bp or more in length, when high molecular weight DNA is utilized as the input DNA for the amplification reaction. It is contemplated the amplicon can be 150 bp, 200 bp, 300 bp, 400 bp, 500 bp, 600 bp, 700 bp, 800 bp, 900 bp, 1,000 bp, 2,000 bp, 3,000 bp, 4,000 bp, 5,000 bp, 6,000 bp, 7,000 bp, 8,000 bp, 9,000 bp, 10,000 bp, 11,000 bp, 12,000 bp, 13,000 bp, 14,000 bp, 15,000 bp, 16,000 bp, 17,000 bp, 18,000 bp, 19,000 bp, 20,000 bp, 30,000 bp, 40,000 bp, 50,000 bp, 100,000 bp, 150,000 bp or more in length.

In any of the methods disclosed herein, it is contemplated that the target loci chosen for multiplexed amplification correspond to any of a variety of applications, including but not limited to oncology specific targets, drug resistance specific targets, drug metabolism and absorption targets (e.g. CYP2D6), targets for inherited disease (e.g. cystic fibrosis CFTR gene, Lynch syndrome MLH1, MSH2, MSH6, PMS2 and EPCAM genes) targets from infectious pathogens, targets for pathogen host loci, species-specific targets, and any clinically actionable targets. In one aspect, the target loci are chosen from a set of oncology targets including but not limited to BRAF, KRAS, EGFR, KIT, HRAS, NRAS, MET, RET, GNA11, GNAQ, NOTCH1, ALK, PIK3CA, JAK2, AKT1, DNMT3A, IDH2, ERBB2 and TP53. In another aspect, the oncology targets include 400-600 genes, including but not limited to the following subset of genes: ACURL1, AKT1, APC, APEX1, AR, ATM, ATP11B, BAP1, BCL2L1, BCL9, BIRC2, BIRC3, BRCA1, BRCA2, CCND1, CCNE1, CD274, CD44, CDH1, CDK4, CDK6, CDKN2A, CSNK2A1, DCON1D1, EGFR, ERBB2, FBXW7, FGFR1, FGFR2, FGFR3, FGFR4, FLT3, GAS6, GATA3, IGF1R, IL6, KIT, KRAS, MCL1, MDM2, MET, MSH2, MYC, MYCL, MYCN, MYO18A, NF1, NF2, NKX2-1, NKX2-8, NOTCH1, PDCD1LG2, PDGFRA, PIK3CA, PIK3R1, PNP, PPARG, PTCH1, PTEN, RB1, RPS6KB1, SMAD4, SMARCB1, SOX2, STK11, TERT, TET2, TIAF1, TP53, TSC1, TSC2, VHL, WT1 and ZNF217. In further embodiments, the target loci are chosen from a subset of genes known to have clinical relevance in oncology, including but not limited to ABI1, ABL1, ABL2, ACSL3, AF15Q14, AF1Q, AF3p21, AF5q31, AKAP9, AKT1, AKT2, ALDH2, ALK, ALO17, AMER1, APC, ARHGEF12, ARHH, ARID1A, ARID2, ARNT, ASPSCR1, ASXL1, ATF1, ATIC, ATM, ATP1A1, ATP2B3, ATRX, AXIN1, BAP1, BCL10, BCL11A, BCL11B, BCL2, BCL3, BCLS, BCL6, BCL7A, BCL9, BCOR, BCR, BHD, BIRC3, BLM, BMPR1A, BRAF, BRCA1, BRCA2, BRD3, BRD4, BRIP1, BTG1, BUB1B, C12orf9, C15orf21, C15orf55, C16orf75, C2orf44, CACNA1D, CALR, CAMTA1, CANT1, CARD11, CARS, CASP8, CBFA2T1, CBFA2T3, CBFB, CBL, CBLB, CBLC, CCDC6, CCNBHP1, CCND1, CCND2, CCND3, CCNE1, CD273, CD274, CD74, CD79A, CD79B, CDC73, CDH1, CDH11, CDK12, CDK4, CDK6, CDKN2A, CDKN2C, CDKN2a(p14), CDX2, CEBPA, CEP1, CEP89, CHCHD7, CHEK2, CHIC2, CHN1, CIC, CIITA, CLIP1, CLTC, CLTCL1, CMKOR1, CNOT3, COL1A1, COL2A1, COPEB, COX6C, CREB1, CREB3L1, CREB3L2, CREBBP, CRLF2, CRTC3, CSF3R, CTNNB1, CUX1, CYLD, D10S170, DAXX, DCTN1, DDB2, DDIT3, DDX10, DDX5, DDX6, DEK, DICER1, DNM2, DNMT3A, DUX4, EBF1, ECT2L, EGFR, EIF3E, EIF4A2, ELF4, ELK4, ELKS, ELL, ELN, EML4, EP300, EPS15, ERBB2, ERC1, ERCC2, ERCC3, ERCC4, ERCC5, ERG, ETV1, ETV4, ETV5, ETV6, EVI1, EWSR1, EXT1, EXT2, EZH2, EZR, FACL6, FAM46C, FANCA, FANCC, FANCD2, FANCE, FANCF, FANCG, FAS, FBX011, FBXW7, FCGR2B, FEV, FGFR1, FGFR1OP, FGFR2, FGFR3, FH, FHIT, FIP1L1, FLI1, FLJ27352, FLT3, FNBP1, FOXA1, FOXL2, FOXO1A, FOXO3A, FOXO4, FOXP1, FSTL3, FUBP1, FUS, FVT1, GAS7, GATA1, GATA2, GATA3, GMPS, GNA11, GNAQ, GNAS, GOLGA5, GOPC, GPC3, GPHN, GRAF, H3F3A, H3F3B, HCMOGT-1, HEAB, HERPUD1, HEY1, HIP1, HIST1H3B, HIST1H4I, HLA-A, HLF, HLXB9, HMGA1, HMGA2, HNRNPA2B1, HOOK3, HOXA11, HOXA13, HOXA9, HOXC11, HOXC13, HOXD11, HOXD13, HRAS, HSPCA, HSPCB, IDH1, IDH2, IGH\, IGK, IGL, IKZF1, IL2, IL21R, IL6ST, IL7R, IRF4, IRTA1, ITK, JAKL JAK2, JAK3, JAZFL JUN, KCNJ5, KDM5A, KDM5C, KDM6A, KDR, KIAA1549, KIAA1598, KIF5B, KIT, KLF4, KLK2, KMT2D, KRAS, KTN1, LAF4, LASP1, LCK, LCP1, LCX, LHFP, LIFR, LMNA, LMO1, LMO2, LPP, LRIG3, LSM14A, LYL1, MAF, MAFB, MALAT1, MALT1, MAML2, MAP2K1, MAP2K2, MAP2K4, MAX, MDM2, MDM4, MDS1, MDS2, MECT1, MED12, MEN1, MET, MITF, MKL1, MLF1, MLH1, MLL, MLL3, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYD88, MYH11, MYH9, MYO5A, MYST4, NAB2, NACA, NBS1, NCOA1, NCOA2, NCOA4, NDRG1, NF1, NF2, NFATC2, NFE2L2, NFIB, NFKB2, NIN, NKX2-1, NONO, NOTCH1, NOTCH2, NPM1, NR4A3, NRAS, NRG1, NSD1, NT5C2, NTRK1, NTRK3, NUMA1, NUP214, NUP98, NUTM2A, NUTM2B, OLIG2, OMD, P2RY8, PAFAH1B2, PALB2, PAX3, PAX5, PAX7, PAX8, PBRM1, PBX1, PCM1, PCSK7, PDE4DIP, PDGFB, PDGFRA, PDGFRB, PER1, PHF6, PHOX2B, PICALM, PIK3CA, PIK3R1, PIM1, PLAG1, PLCG1, PML, PMS1, PMS2, PMX1, PNUTL1, POT1, POU2AF1, POU5F1, PPARG, PPFIBP1, PPP2R1A, PRCC, PRDM1, PRDM16, PRF1, PRKAR1A, PSIP1, PTCH1, PTEN, PTPN11, PTPRB, PTPRC, PTPRK, PWWP2A, RAB5EP, RAC1, RAD21, RAD51L1, RAF1, RALGDS, RANBP17, RAP1GD51, RARA, RB1, RBM15, RECQL4, REL, RET, RNF43, ROS1, RPL10, RPL22, RPL5, RPN1, RSPO2, RSPO3, RUNDC2A, RUNX1, RUNXBP2, SBDS, SDC4, SDH5, SDHB, SDHC, SDHD, 42253, SET, SETBP1, SETD2, SF3B1, SFPQ, SFRS3, SH2B3, SH3GL1, SIL, SLC34A2, SLC45A3, SMAD4, SMARCA4, SMARCB1, SMARCE1, SMO, SOCS1, SOX2, SRGAP3, SRSF2, SS18, SS18L1, SSX1, SSX2, SSX4, STAG2, STAT3, STATSB, STAT6, STK11, STL, SUFU, SUZ12, SYK, TAF15, TAL1, TAL2, TBL1XR1, TCEA1, TCF1, TCF12, TCF3, TCF7L2, TCL1A, TCL6, TERT, TET2, TFE3, TFEB, TFG, TFPT, TFRC, THRAP3, TIF1, TLX1, TLX3, TMPRSS2, TNFAIP3, TNFRSF14, TNFRSF17, TOP1, TP53, TPM3, TPM4, TPR, TRA, TRAF7, TRB, TRD, TRIM27, TRIM33, TRIP11, TRRAP, TSC1, TSC2, TSHR, TTL, U2AF1, UBRS, USP6, VHL, VTI1A, WAS, WHSC1, WHSC1L1, WIF1, WRN, WT1, WWTR1, XPA, XPC, XPO1, YWHAE, ZCCHC8, ZNF145, ZNF198, ZNF278, ZNF331, ZNF384, ZNF521, ZNF9 and ZRSR2.

In another aspect, the targets are specific to drug resistance loci, including loci conferring resistance to tyrosine kinase inhibitors used as targeted anti-tumor agents, other targeted loci related to targeted anti-tumor agents, antibiotic resistance loci, and anti-viral resistance loci.

In another aspect, detection of enteric, blood-borne, CNS, respiratory, sexually transmitted, and urinary tract pathogens including bacteria, fungi, yeasts, viruses, or parasites can be performed. Pathogens causing infections of the ear, dermis, or eyes could also be detected. Differentiation between pathovars of bacteria or viruses could be conducted as well as genes promoting antibiotic resistance or encoding toxins.

The types of genetic lesions that can be detected from sequence analysis of the resulting amplicons include SNV (single nucleotide variants), point mutations, transitions, transversions, nonsense mutations, missense mutations, single base insertions and deletions, larger insertions and deletions that map between a primer pair, known chromosomal rearrangements such as translocations, gene fusions, deletions, insertions where primer pairs are designed to flank the breakpoint of such known rearrangements; copy number variations that include amplification events, deletions and loss of heterozygosity (LOH), aneuploidy, uniparental disomies, and other inherited or acquired chromosomal abnormalities. In addition, if bisulfite conversion is performed prior to multiplexed PCR and primers are designed to bisulfite converted DNA and optionally do not overlap with CpG dinucleotides which can result in various modified sequence states making primer design more difficult, methylation changes can also be detected using the disclosed method.

For amplification of the target loci, the optimal length of the 3' target-specific portion of the primer is between 15 and 30 bases but not limited to this range, where the target-specific portion of the primer is 5 to 50 bases or 10 to 40 bases or any length in between. The desired Tm defined at 2.5 mM Mg$^{2+}$, 50 mM NaCl and 0.25 µM of oligonucleotides is 63° C., where variation in Tm among multiplexed primers is not more than ±2.5° C. to ensure even amplification under fixed reaction conditions. Desired GC content of the target-specific portion of the primers is ideally 50% but can vary between 30% and 70%. The target-specific primers are designed to avoid overlap with repetitive, non-unique sequences or common SNP polymorphisms or known mutations for the condition being assayed, in order to ensure specific, unbiased amplification from DNA samples from diverse genetic backgrounds. Additionally, target-specific targets and complementary primer designs should not be subject to secondary structure formation which would reduce performance.

The universal primer comprises cleavable bases including but not limited to deoxyuridine, deoxyinosine or RNA, and can contain one, two, three, four, five or more cleavable bases. Additionally, the target-specific primers and the universal primer comprise 1, 2, 3, 4 or more nuclease resistant moieties at their 3' termini.

Adapter Molecule

Figure 3:
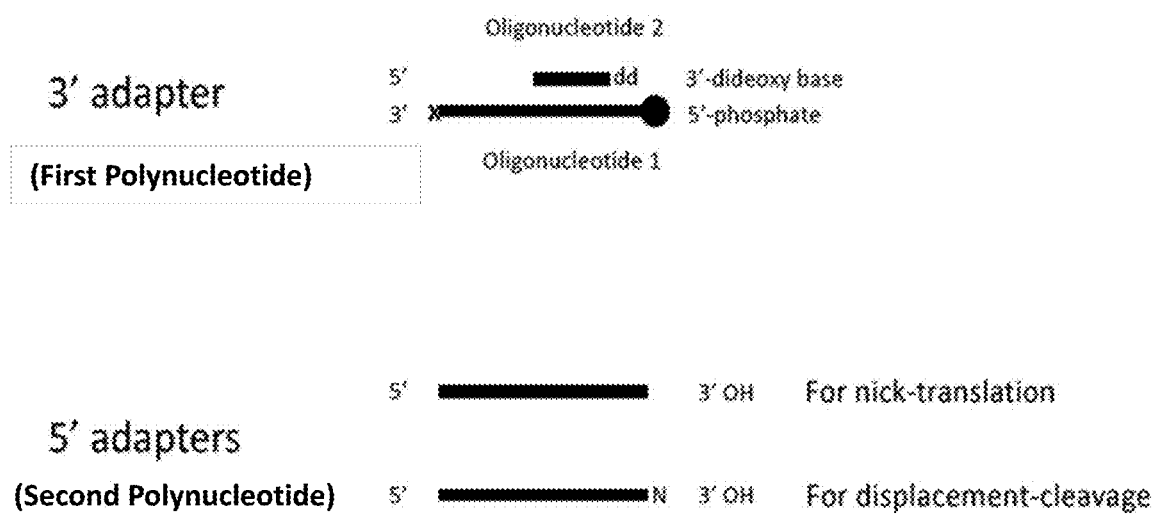
FIG. 3 depicts the structural features of the 3' and 5' adapters of the present application.

The disclosure contemplates the use of a 5' adapter and a 3' adapter (see FIG. 3). According to the disclosure, a 3' adapter is optionally double stranded, comprising an "oligonucleotide 1" and an "oligonucleotide 2." For such a double stranded substrate molecule, any length of oligonucleotide 1 and oligonucleotide 2 is contemplated as long as the two oligonucleotides are capable of annealing to each other under standard reaction conditions. Thus, the complementarity between oligonucleotide 1 and oligonucleotide 2 is such that they can anneal to each other. In various embodiments, the complementarity is from about 70%, 75%, 80%, 85%, 90%, 95% to about 100%, or from about 70%, 75%, 80%, 85%, 90%, to about 95%, or from about 70%, 75%, 80%, 85% to about 90%. In specific embodiments, the degree of complementarity between oligonucleotide 1 and oligonucleotide 2 is 70%, 75%, 80%, 85%, 90%, 95%, 99% or 100%. In further embodiments, oligonucleotide 2 comprises a nucleotide that is susceptible to degradation/removal such as an abasic nucleotide or a ribonucleotide. In certain embodiments, oligonucleotide 1 and oligonucleotide 2 are different lengths and oligonucleotide 1 hybridizes anywhere along the length of oligonucleotide 2.

In further embodiments, the 5' adapter is single stranded. In embodiments wherein the 5' adapter hybridizes to oligonucleotide 1 of the 3' adapter, it is contemplated in further embodiments that such annealing results in either a nick, gap or in an overlapping base or bases between the 5' adapter and the substrate molecule (see FIG. 8). In various embodiments, the gap or the number of overlapping bases is 1, 2, 3, 4, 5, 6, 7, 8, 9, 10, 15, 20, 25, 30, 35, 40, 45, 50, 55, 60, 65, 70, 75, 80, 85, 90, 95 or 100 bases in length. In another embodiment wherein the 3' adapter is double stranded, following annealing of the 5' adapter to the 3' adapter, an enzyme is added to catalyze the "chewing forward" of the 5' adapter via nick translation to remove oligonucleotide 2. In some embodiments, the 5' adapter additionally comprises a random single, double or more N bases at its 3' terminus that are not complementary to oligonucleotide 1 and which can anneal to the first base(s) of the substrate molecule if its 5' bases are displaced. In other embodiments, the 5' adapter is a modified polynucleotide. Modified oligonucleotides contemplated for use are disclosed in United States Patent Application Publication Number 2011/0129832, incorporated by reference in its entirety. In a specific embodiment, the 5' adapter comprises a base modification selected from the group consisting of a locked nucleic acid (LNA) and a peptide nucleic acid (PNA). In certain embodiments, the 5'-adapter oligonucleotide is pre-annealed to the 3'-adapter (see FIG. 8).

The disclosure also contemplates the use of a universal adapter incorporated by PCR, a single stranded 5' adapter and the remainder of a 3' adapter that is ligated to one strand of the universal adapter on partially processed amplicon substrates. According to the disclosure, ligation of the remainder of the 3' adapter is mediated by a linker. For the linker molecule, any length complementary to the universal adapter and the remainder of the 3' adapter is contemplated as long as the three oligonucleotides are capable of annealing to each other under standard reaction conditions. Thus, the complementarity is such that they can anneal to each other. In various embodiments, the complementarity is from about 70%, 75%, 80%, 85%, 90%, 95% to about 100%, or from about 70%, 75%, 80%, 85%, 90%, to about 95%, or from about 70%, 75%, 80%, 85% to about 90%.

In further embodiments, the 5' adapter is single stranded. In embodiments wherein the 5' adapter hybridizes to the 3' overhang of the universal adapter on the amplicon termini, it is contemplated in further embodiments that such annealing results in either a nick or gap between the 5' adapter and the amplicon substrate. In embodiments, the gap is 1, 2, 3, 4, 5, 6, 7, 8, 9, 10, 15, 20, 25, 30, 35, 40, 45, 50, 55, 60, 65, 70, 75, 80, 85, 90, 95 or 100 bases in length.

The length of either a universal adapter, 5' adapter B or remainder of the 3' adapter A is contemplated to be between about 5 and about 200 nucleotides. In some aspects, the length of the universal adapter, 5' adapter or the 3' adapter is between about 5 and about 200 nucleotides, or between about 5 and about 150 nucleotides, or between about 5 and about 100 nucleotides, or between about 5 and about 50 nucleotides, or between about 5 and about 25 nucleotides, or between about 10 and 200 nucleotides, or between about 10 and 100 nucleotides. In further aspects, the length of the 5' adapter or the 3' adapter is at least 5 and up to about 50, 100 or 200 nucleotides; or at least 10 and up to about 50, 100 or 200 nucleotides; or at least 15 and up to about 50, 100, or 200 nucleotides; or at least 20 and up to about 50, 100 or 200 nucleotides; or at least 30 and up to about 50, 100 or 200 nucleotides; or at least 40 and up to about 50, 100 or 200 nucleotides. In various aspects, the length of the substrate molecule is about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 300, about 400, about 500, about 600, about 700, about 800, about 900, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, about 5100, about 5200, about 5300, about 5400, about 5500, about 5600, about 5700, about 5800, about 5900, about 6000, about 6100, about 6200, about 6300, about 6400, about 6500, about 6600, about 6700, about 6800, about 6900, about 7000, about 7100, about 7200, about 7300, about 7400, about 7500, about 7600, about 7700, about 7800, about 7900, about 8000, about 8100, about 8200, about 8300, about 8400, about 8500, about 8600, about 8700, about 8800, about 8900, about 9000, about 9100, about 9200, about 9300, about 9400, about 9500, about 9600, about 9700, about 9800, about 9900, about 10000, about 10500, about 11000, about 11500, about 12000, about 12500, about 13000, about 13500, about 14000, about 14500, about 15000, about 15500, about 16000, about 16500, about 17000, about 17500, about 18000, about 18500, about 19000, about 19500, about 20000, about 20500, about 21000, about 21500, about 22000, about 22500, about 23000, about 23500, about 24000, about 24500, about 25000, about 25500, about 26000, about 26500, about 27000, about 27500, about 28000, about 28500, about 29000, about 29500, about 30000, about 30500, about 31000, about 31500, about 32000, about 32500, about 33000, about 33500, about 34000, about 34500, about 35000, about 35500, about 36000, about 36500, about 37000, about 37500, about 38000, about 38500, about 39000, about 39500, about 40000, about 40500, about 41000, about 41500, about 42000, about 42500, about 43000, about 43500, about 44000, about 44500, about 45000, about 45500, about 46000, about 46500, about 47000, about 47500, about 48000, about 48500, about 49000, about 49500, about 50000, about 60000, about 70000, about 80000, about 90000, about 100000 or more nucleotides in length.

To complete NGS adapter ligation, the universal adapter primer additionally comprises modified bases and/or linkages that can be destroyed enzymatically, chemically or physically. Modifications include but are not limited to dU-bases, deoxyinosine and RNA bases. Annealing of the single-stranded 5' adapter to the 3' overhang of the amplicons occurs as result of degradation of one strand of the universal adapter that corresponds to the incorporated universal primer with cleavable bases. In some embodiments, degradation is achieved enzymatically, more specifically, by using uracil-DNA glycosylase (UDG), or a combination of UDG and apurinic/apyrimidinic endonuclease if the oligonucleotide contains deoxyuracil bases, or by endonuclease V if the oligonucleotide contains deoxyinosine bases. Degradation can also be performed by incubation with RNase H1 or RNase H2 if the incorporated primer contains RNA bases. In some applications, degradation of the incorporated primer can be performed chemically or physically, for example, by light. Alternatively, the 3' overhang of the amplicon can be produced by limited exonuclease digestion of the 5' end of the amplicon. Such limited digestion can be achieved enzymatically, more specifically, by using T7 Gene 6 exonuclease or lambda 5'→3'exonuclease if the primer oligonucleotide contains nuclease-resistant base(s) at the 3' end, specifically, a base(s) with phosphorothioate linkage. In this case, the exonuclease reaction stops at the modified base and produces a 3' overhang.

Method—Steps

The first three incubations of the method are pre-ligation steps, and include (i) dephosphorylation, (ii) polishing and (iii) optional adenylation. The remaining 2 incubations of the method include (1) 3' adapter ligation, and (2) 5' adapter ligation which comprises (a) 5' adapter annealing (b) removal of the 5' base from the substrate molecule and (c) 5' adapter ligation (see FIGS. 4-6). In this aspect, the method has up to 3 pre-ligation steps and 2 ligation steps. In another aspect, the method has a single ligation step of the 5' adapter if the substrate molecule comprises a pre-existing 3' overhang, preferably serving as a 3' adapter (see FIG. 7a).

Within the amplification reaction, the number of multiplexed cycles is limited to a minimum of 2 or can be performed as 3 cycles, 4 cycles, 5 cycles or more, up to N cycles prior to switching to the non-multiplexed universal adapter single primer amplification. The number of universal cycles can be varied from 1 cycle to 40 or more cycles, depending on the DNA input and desired library yield. Following multiplex PCR amplification, a purification step is performed, then the simultaneous adapter ligation step is performed.

Pre-Ligation Steps

(I) Dephosphorylation

Prior to adapter ligation, the DNA ends are optionally processed to improve efficiency of the adapter ligation reaction. DNA end processing in existing methods typically uses two enzymatic reactions: (a) incubation with a proofreading DNA polymerase(s) to polish DNA ends by removing the 3'-overhangs and filling-in the recessed 3' ends and (b) incubation with a polynucleotide kinase to add a phosphate group to the 5' termini. When processing DNA ends some methods also adenylate blunt-ended DNA at the 3' termini by incubation of polished DNA with a non-proofreading DNA polymerase. Adenylation helps to prevent DNA self-ligation and formation of chimeric products. It also minimizes formation of adapter-dimers due to the presence of dT at the 3' end of corresponding adapters. The current invention addresses these issues in a completely different way. Rather than adding a phosphate group to the 5' ends of the DNA fragments, the method of the invention implements an optional complete removal of the phosphate group from the 5' ends of the DNA fragments. Dephosphorylation of DNA ends is achieved by incubation of DNA fragments with an enzyme capable of removing a phosphate from a DNA terminus. Examples of enzymes useful in the methods of the disclosure to remove a 5' or a 3' phosphate include, but are not limited to, any phosphatase enzyme, such as calf intestinal alkaline phosphatase, bacterial alkaline phosphatase, shrimp alkaline phosphatase, Antarctic phosphatase, and placental alkaline phosphatase, each used according to standard conditions.

(ii) Polishing

After removal of the alkaline phosphatase or its inactivation by heat, DNA substrate molecules are optionally subjected to incubation with a proofreading DNA polymerase in the presence of dNTPs to create blunt ends. The reactions are performed according to standard conditions. Dephosphorylated and polished DNA fragments are good substrates for attachment of the 3' adapter but they are poor substrates for DNA fragment concatamer ligation and chimera formation. They are also poor substrates for ligation of a conventional adapter.

In some applications of the current invention, 5' end dephosphorylation by a phosphatase enzyme can be omitted but the addition of an enzyme such as T4 polynucleotide kinase to the DNA polishing mix is preferable in this case to assure removal of the phosphate group from the 3' termini prior to DNA polishing. Alternatively, the first two pre-ligation reactions described above, dephosphorylation and polishing, can be executed in any order and result in blunt-ended, double-stranded DNA lacking 5' phosphate groups at their termini.

(iii) Adenylation

The current invention also contemplates the use of adenylation of the 3' terminus of the blunt-end DNA fragments using DNA polymerases with non-template polymerase activity including but not limited to (exo-) Klenow fragment of DNA polymerase I, and Taq DNA polymerase. Both alkaline phosphatase treatment and adenylation reduce the propensity of DNA fragment self-ligation and formation of chimeric library molecules. In the case of including an adenylation step, the 3' adapter used in the subsequent step would require a single T overhang.

Ligation Steps

(1) 3' Adapter Ligation, or, Generation of a Single-Stranded 3' Overhang on DNA Substrates The options are depicted in FIG. 7

Figure 7A:
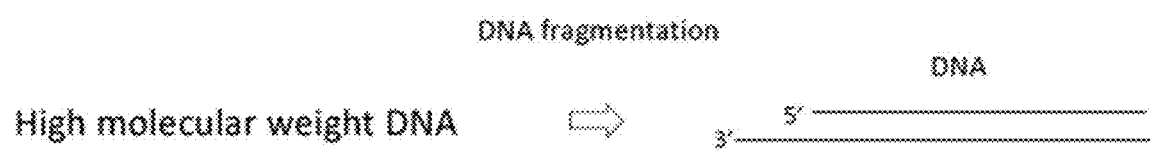
FIG. 7A provides for an initial fragmentation step resulting in generation of a single-stranded 3' overhang.

Option 1a: 3' Blocked Oligonucleotide 2 as Part of a Double Stranded 3' Adapter (FIG. 7a)

Existing NGS library preparation protocols rely on ligation between the 3'OH group of the adapter and the 5' phosphate group at the termini of the DNA fragments. For this reason, adapters used in conventional methods typically have one functional double-stranded end with a 3' hydroxyl group and optional 5' phosphate group (see FIGS. 1 and 2). In contrast, the current invention uses a ligation reaction between the 5' phosphate group of the 3' adapter and the 3'OH group of DNA fragments while leaving a nick between the 3' terminus of the 3' adapter and the 5' terminus of the DNA fragments (see FIG. 3). The 3' adapter has a functional double-stranded end with a 5'-phosphate group and in this option, a 3' nucleotide that is not competent for ligation (for example comprised of a sugar modified base analogs such as 2',3' dideoxy base or a 3'-deoxy base). The 3' adapter is formed by annealing two oligonucleotides: oligonucleotide 1 that has a phosphate group at the 5' end and a blocking group (such as a C3 spacer) at the 3' end, and oligonucleotide 2 that lacks a phosphate group at the 5' end and comprises a non-ligatable base at the 3' end. Oligonucleotide 2 additionally comprises modified bases and/or linkages that can be destroyed enzymatically, chemically or physically. In most applications, the end of the 3' adapter that is involved in ligation with the substrate molecule is a blunt end. In applications that involve adenylation of DNA fragments, the ligatable end of the 3' adapter has a 3' overhang containing a 2',3' dideoxythymidine or 3'-deoxythymidine base (or other modifications of the thymine base that block its ability to form a covalent linkage with the adjacent base). In other applications, the functional end of the 3' adapter could have either a 3' or 5' overhang containing multiple bases. During incubation with a DNA ligase, the 5' phosphate of the 3' adapter becomes ligated to the 3' terminus of the DNA substrate molecules while leaving a nick between the 3' terminus of the 3' adapter and the 5' terminus of the DNA substrate molecules. After the reaction is completed, ligated DNA is subjected to purification by spin-column or SPRI bead-based purification to remove excess adapters and other components of the ligation reaction.

Option 1b: 3' Hydroxyl Oligonucleotide 2 as Part of a Double Stranded 3' Adapter (FIG. 7a)

In an alternative method, a 3'-adapter that is lacking a blocked, unligatable base at the 3' terminus of oligonucleotide 2 can be used. Ligation of a non-blocked oligonucleotide 2 to the substrate molecule will still be prevented by the lack of 5' phosphate on the substrate molecule as a result of the dephosphorylation reaction. The advantage of using a non-blocked oligonucleotide 2 is that the 3' end of oligonucleotide 2 can be extended by a single base using a dideoxy nucleotide mix and a DNA polymerase capable nick-translation DNA synthesis. This enables an alternate method to perform 5' base excision from the substrate molecule, see subsequent steps described below. The disadvantage of using a non-blocked 3'-adapter is the creation of adapter-dimers during the ligation reaction which reduces adapter concentration and as a result, may decrease adapter ligation efficiency. Also for this option, oligonucleotide 2 additionally comprises modified bases and/or linkages that can be destroyed enzymatically, chemically or physically.

Option 2: Single Stranded 3' Adapter (FIG. 7a)

In the presence of a ligase (DNA or RNA) capable of covalently attaching a single stranded adapter to a double stranded (or single stranded) substrate molecule, oligonucleotide 2 can be omitted from the reaction.

Option 3: Homopolymer 3' Adapter (FIG. 7a)

In the presence of a template independent polymerase such as terminal deoxynucleotidyl transferase (TdT), poly (A) polymerase, poly(U) polymerase or DNA polymerases that lack 3'-exonuclease proofreading activity and comprising a nucleotide, a homopolymer or other tail can be incorporated on the 3' termini of the substrate molecules that can serve as a 3' adapter sequence.

Option 4: Controlled Tailing and Simultaneous 3' Adapter Ligation (FIG. 7a)

In the presence of a template independent polymerase such as TdT, nucleotides, and additionally comprising a ligase and an attenuator-adapter molecule, a synthetic tail and defined 3' adapter sequence can be incorporated on the 3' termini of the substrate molecules. See International patent application number PCT/US13/31104, filed Mar. 13, 2013, incorporated herein by reference in its entirety.

Figure 7B:
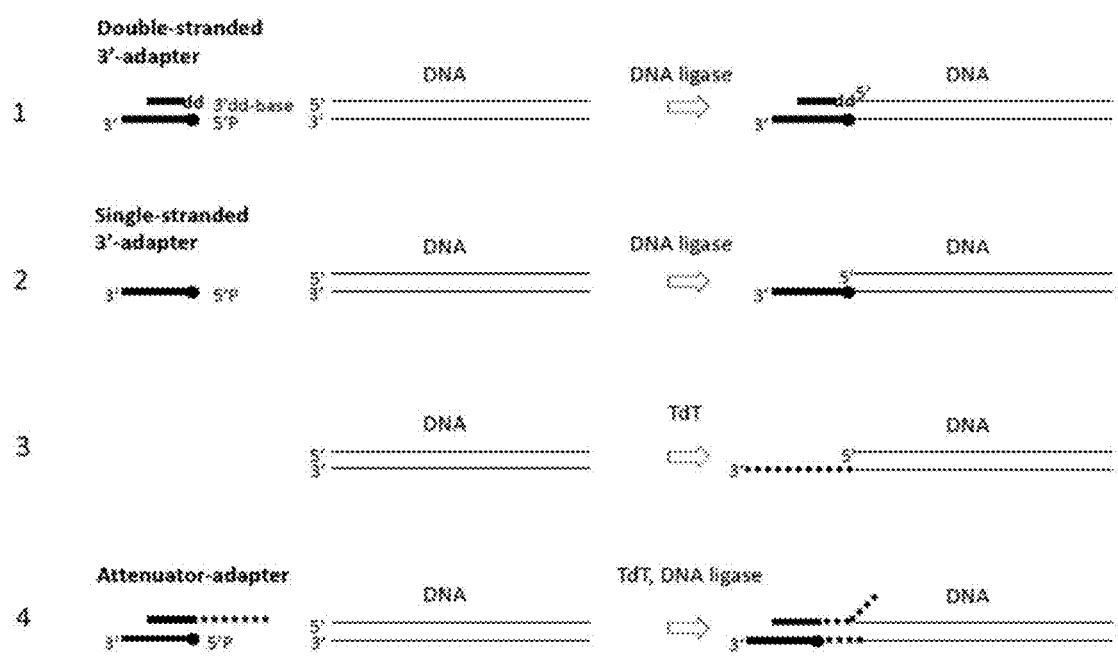
FIG. 7B provides four alternative approaches for enzymatically adding a 3'-adapter overhang sequence: 1—conventional ligation using T4 DNA ligase; 2—single-strand DNA (RNA) ligase; 3—conventional homopolymer tailing with terminal transferase; and 4—controlled tailing and simultaneous adapter ligation using terminal transferase, DNA ligase and attenuator-adapter molecule. See International patent application number PCT/US13/31104, filed Mar. 13, 2013, incorporated by reference in its entirety. Alternatively, DNA fragmentation or other processing can result in pre-existing DNA ends with 3'-overhangs sufficient for 5' adapter annealing.

Option 5: Omit 3' Adapter Ligation Step (FIG. 7b)

In the case of substrate molecules that comprise a pre-existing 3' overhang that is naturally occurring or resulting from a previous enzymatic or other treatment, either as a defined or random sequence, a separate 3' adapter ligation step is not required and can be omitted, wherein the pre-existing 3' overhang can serve as the 3' adapter.

In an alternative embodiment, a phosphatase enzyme with Zinc and other reaction components can be added to the 3' adapter ligation reaction at its completion. Performing a phosphatase reaction following 3' adapter ligation is a means of rendering any non-ligated 3' adapter molecules incapable of subsequent ligation, which prevents adapter dimers from forming in subsequent steps when the 5' adapter is present.

(2) 5' Adapter Ligation, which is Comprised of Three Steps that Occur in a Single Incubation (I) Annealing of the 5' Adapter In the case of single stranded 3' adapter ligation (option 2), homopolymer addition (option 3) or use of pre-existing 3' overhang as 3' adapter (option 5), annealing of the 5' adapter can be performed directly without other consideration as there is no oligonucleotide 2 to degrade or displace.

Figure 8A:
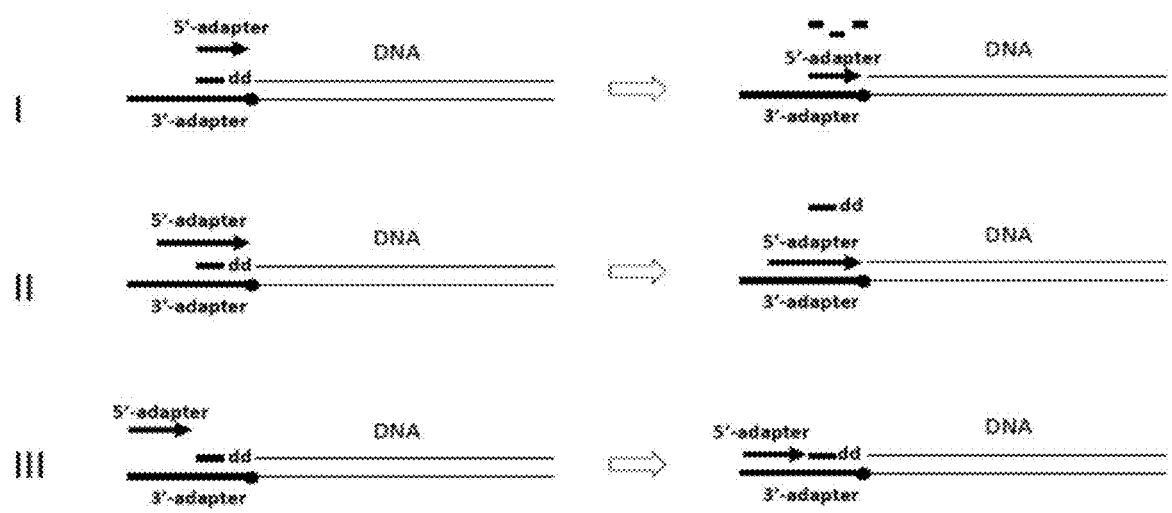
FIG. 8A depicts steps (I)-(III) for annealing a 5' adaptor to a nucleic acid substrate. The steps include: I—binding after degradation of the second oligonucleotide that was previously annealed to the 3'-adapter; II—competitive displacement of the second oligonucleotide that was previously annealed to the 3'-adapter; and III—binding to the upstream region of the 3'-adapter (followed by limited nick-translation and degradation of the second oligonucleotide that was previously annealed to the 3'-adapter).
Figure 8B:
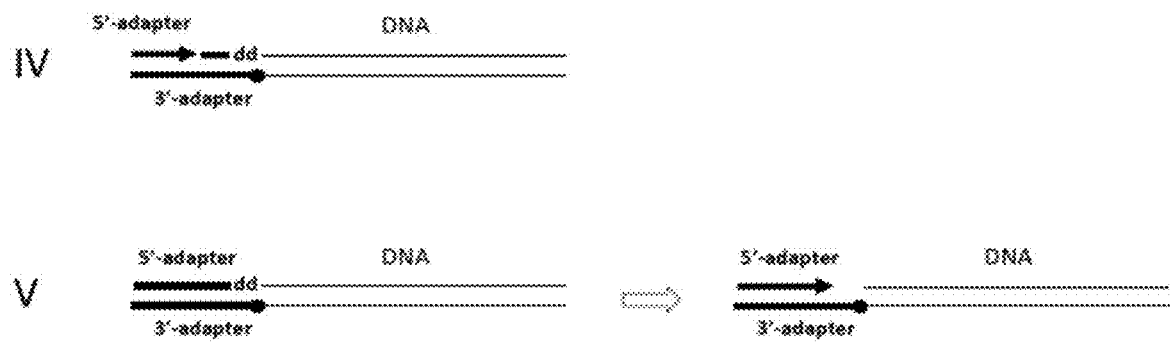
FIG. 8B depicts additional steps (IV)-(V) of the annealing method shown in FIG. 8A. The steps include: IV—having the 5'-adapter pre-annealed to the upstream region of the 3'-adapter (followed by limited nick-translation and degradation of the second oligonucleotide that was previously annealed to the 3'-adapter); and V—having 3' blocked 5'-adapter instead of the 2nd oligonucleotide that is activated by cleavage.
Figure 9A:
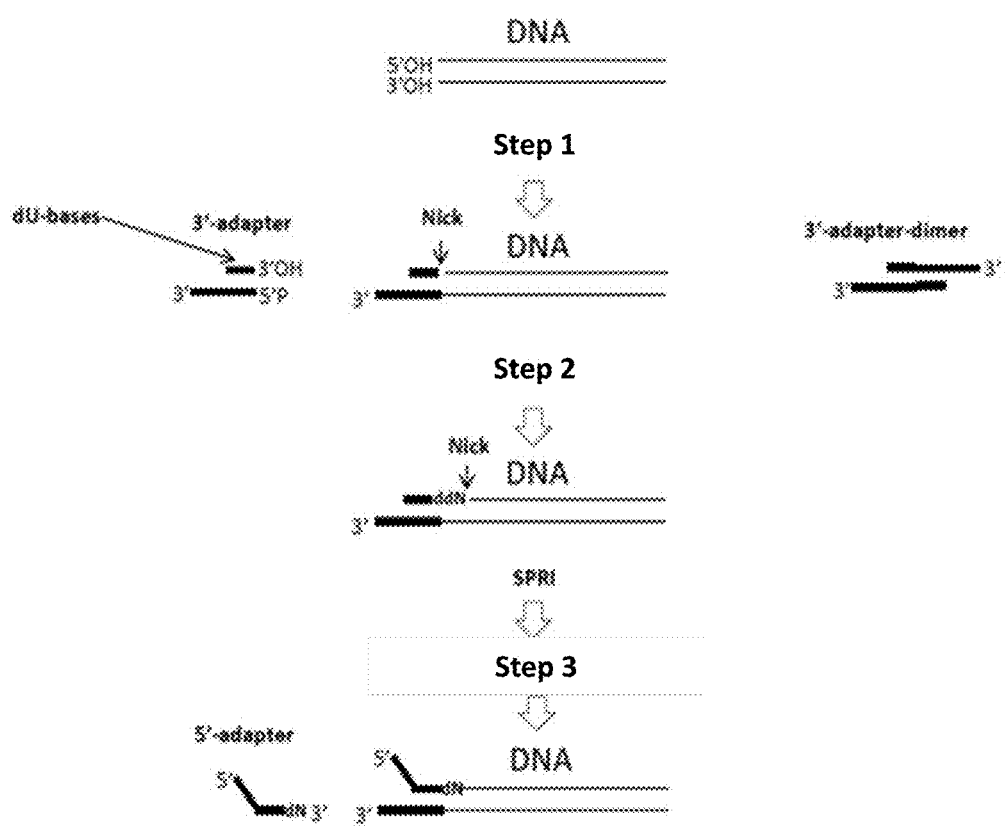
FIGS. 9A, 9B, 9C, and 9D depict various embodiments for ligation of the 5' adapter using single base extension.
Figure 9B:
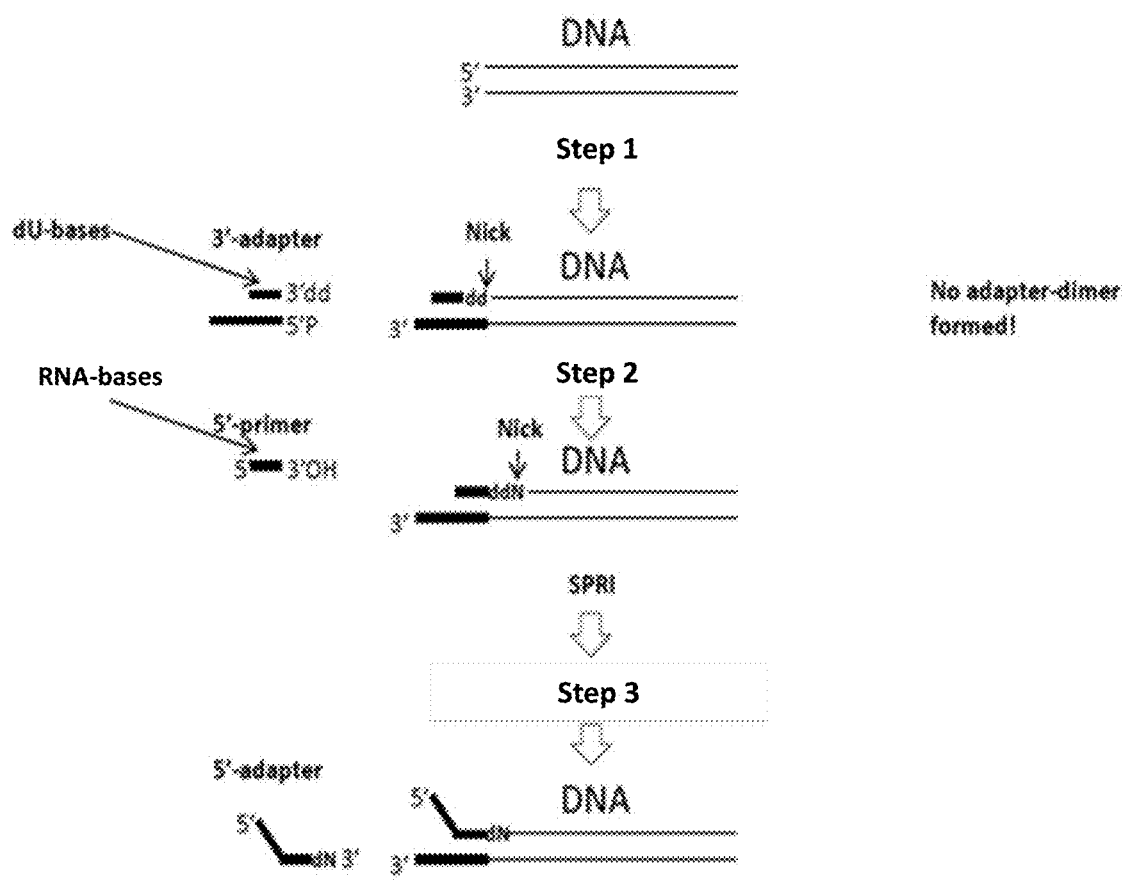
Figure 9C:
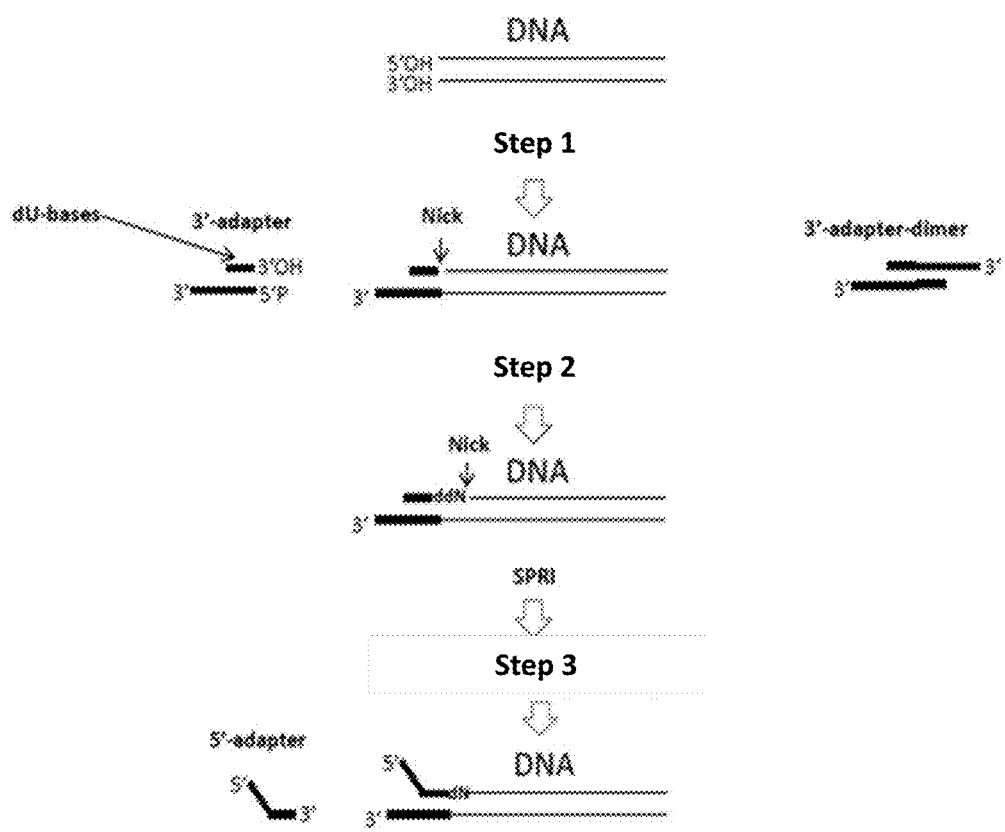
Figure 9D:
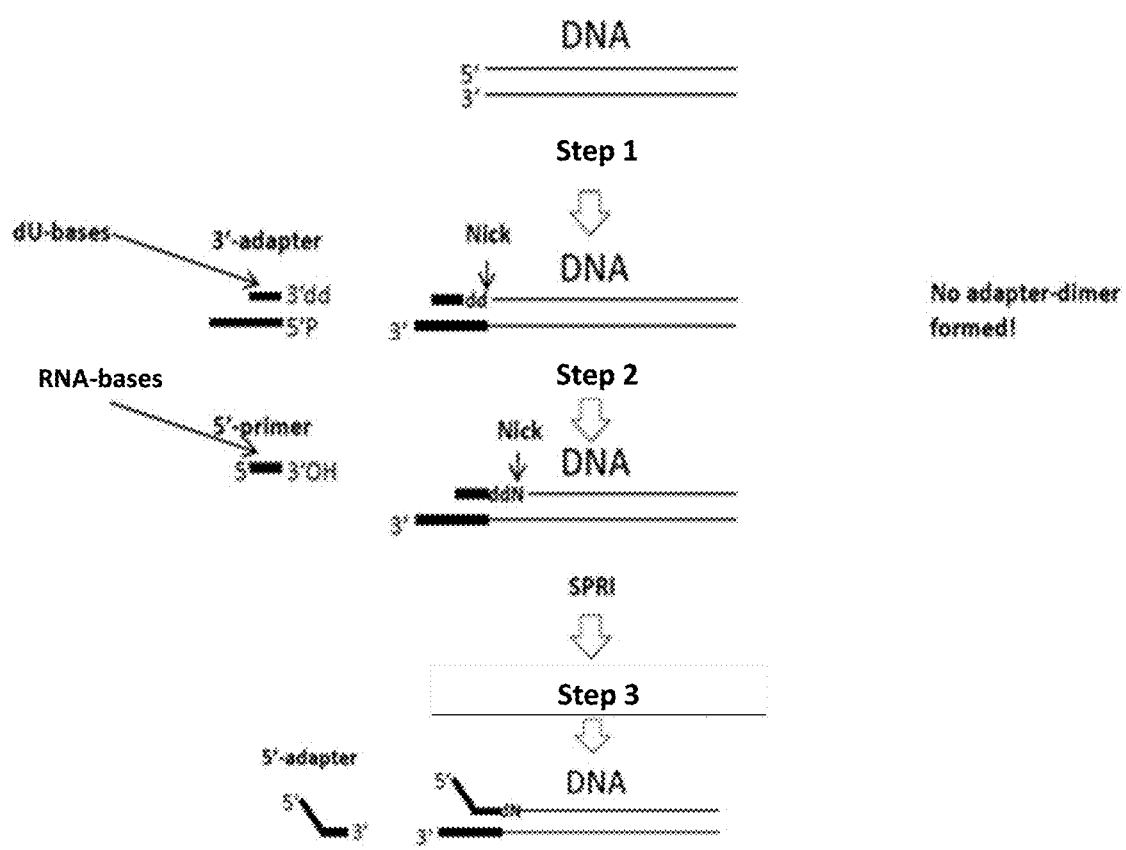

When ligation of a double-stranded 3'-adapter is used to create a single-stranded 3' overhang at the ends of double-stranded DNA (options 1a, 1b and 4 above), the 5'-adapter can be annealed to the 3'-adapter using any of five different options, each of which is discussed below and depicted in FIG. 8:
  i) following degradation of oligonucleotide 2 that was annealed to the 3' adapter
  ii) by competitive displacement of oligonucleotide 2 that was annealed to the 3'-adapter
  iii) by annealing the 5' adapter further 3' on oligonucleotide 1 relative to the annealing site of oligonucleotide 2, followed by nick-translation and degradation of oligonucleotide 2
  iv) by having the 5' adapter pre-annealed to the 3' region of oligonucleotide 1 of the 3' adapter, followed by nick-translation and degradation of oligonucleotide 2
  v) by having the 5' adapter with a 3' blocking group pre-annealed to the 5' region of oligonucleotide 1 of the 3' adapter (instead of oligonucleotide 2), followed by enzymatic excision of the 3' blocking group Option i Oligonucleotide 2 of the 3' adapter additionally comprises modified bases and/or linkages that can be destroyed enzymatically, chemically or physically. Modifications include but are not limited to dU-bases, deoxyinosine and RNA bases. Annealing of the single-stranded 5' adapter to the 5' portion of oligonucleotide 1 of the 3' adapter occurs as result of partial degradation of the 3' adapter, specifically, of oligonucleotide 2. In some embodiments, degradation of oligonucleotide 2 is achieved enzymatically, more specifically, by using uracil-DNA glycosylase (UDG), or a combination of UDG and apurinic/apyrimidinic endonuclease if the second oligonucleotide contains deoxyuracil bases, or by endonuclease V if the second oligonucleotide contains deoxyinosine bases. Degradation of oligonucleotide 2 can also be performed by incubation with RNase H1 or RNase H2 if the second oligonucleotide contains RNA bases. In some applications, degradation of the second oligonucleotide can be done chemically or physically, for example, by light.

Option ii

In some applications, annealing of the 5' adapter to oligonucleotide 1 of the 3'adapter occurs without degradation of oligonucleotide 2. In this case, replacement of oligonucleotide 2 with the single-stranded 5' adapter can be facilitated by higher affinity of the 5' adapter over that of oligonucleotide 2 either due to increased complementarity between oligonucleotide 1 and the 5' adapter sequence or due to base modifications within the 5' adapter that increase its melting temperature (for example, LNA bases). Depending on the design of the 5' adapter, annealing to oligonucleotide 1 of the 3' adapter could either result in a nick or gap between the 3' end of the 5' adapter and the 5' end of the DNA substrate molecule, or in overlap of the 3' and 5' bases of the 5' adapter and DNA substrate molecule, correspondingly.

Option iii

In this case, neither degradable modifications or competitive displacement of oligonucleotide 2 is used. Instead, the 5' adapter replaces oligonucleotide 2 by annealing to the 3' adapter further 3' on oligonucleotide 1 relative to the annealing site of oligonucleotide 2, followed by limited nick-translation "chewing forward" which results in degradation or partial degradation of oligonucleotide 2.

Options iv and v

In these cases, the 5' adapter constitutes a part of the 3' adapter and it is present during ligation of the 3' adapter to the DNA substrate. In option iv, the 5' adapter is pre-annealed to the 3' adapter further 3' on oligonucleotide 1 relative to the annealing site of oligonucleotide 2 (similar to option iii). In option v, the 5' adapter has a blocking group at the 3' end and it is pre-annealed the 3' adapter instead of oligonucleotide 2. After ligation of the 3' adapter, the blocking group at the 3' end of the 5' adapter is removed enzymatically to allow its extension by a DNA polymerase.

(II) 5'-Base Removal from the Substrate Molecule Resulting in Exposure of a 5' Phosphate In this step, creation of a ligation-compatible 5' terminal phosphate group on the substrate molecule is achieved by removal of the damaged 5' terminal base of the DNA substrate molecules either by nick-translation of the 5' adapter oligonucleotide using a DNA polymerase and nucleotides (option i), by a displacement-cleavage reaction using the 5' adapter and a 5'-flap endonuclease in the absence of nucleotides (option ii), or by single dideoxy base extension from oligonucleotide 2 followed by displacement-cleavage using a 5'-flap endonuclease in the absence of nucleotides (option iii). For the third option, 5' base excision of the substrate molecule occurs prior to 5' adapter annealing, because it is alternately performed using the annealed oligonucleotide 2 instead of the 5' adapter, but is included in this section to simplify description of the method (see FIG. 9).

Option i

Figure 4:
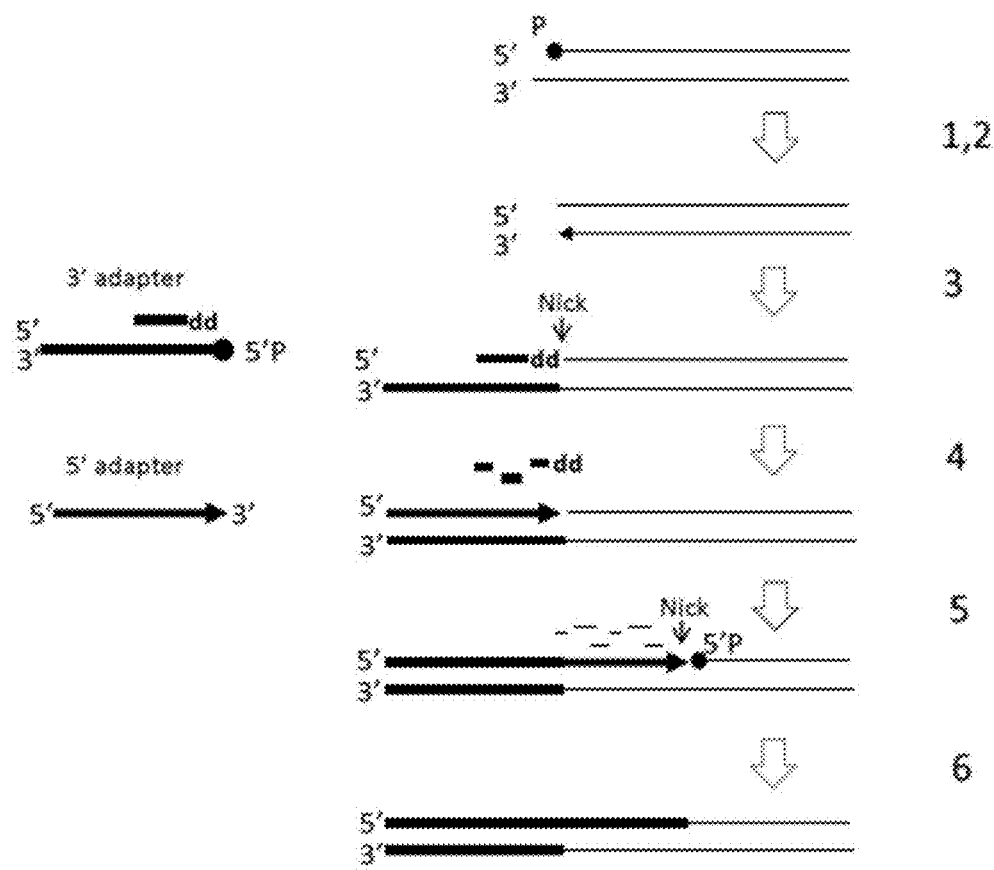
FIG. 4 depicts one embodiment of the present methods for ligation of the 3' adapter and the 5' adaptor by nick-translation. The steps include: 1—substrate molecule dephosphorylation; 2—substrate molecule polishing/blunt end generation; 3—3' adapter ligation; 4—partial degradation of the 3' adapter and annealing of the 5' adapter; 5—polymerase extension of the 5' adapter by nick-translation; and 6—ligation of the extended 5' adapter to the exposed 5' phosphate of the DNA substrate.
Figure 6A:
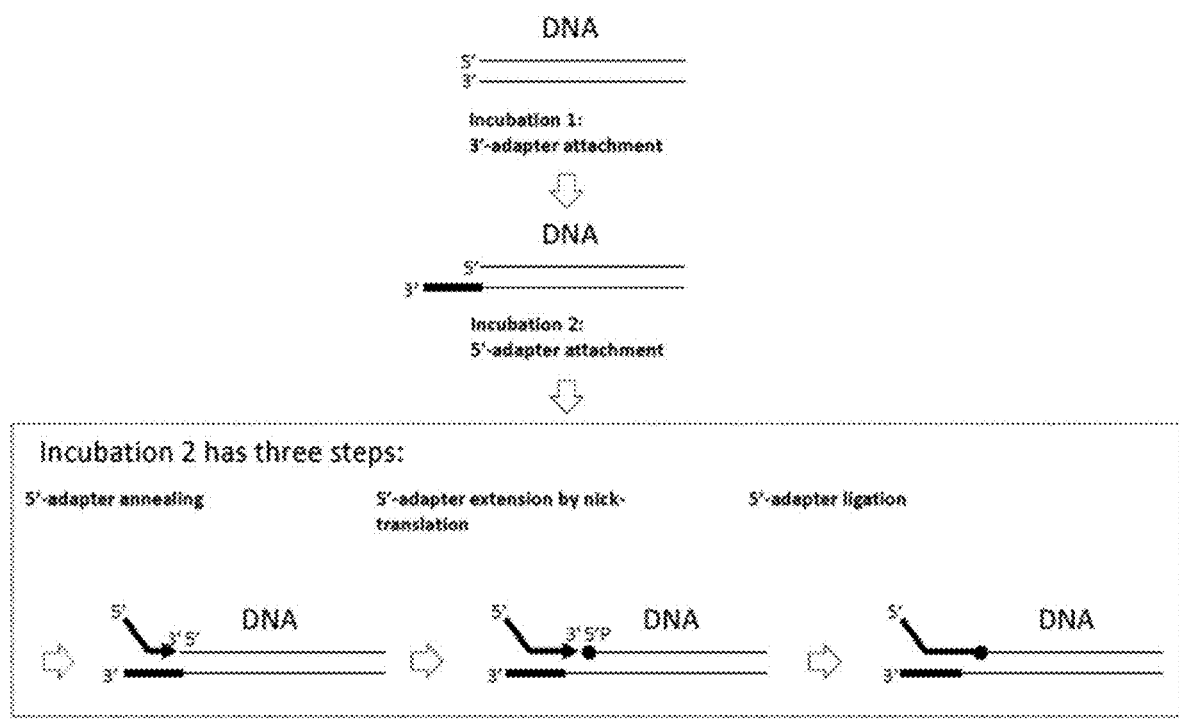
FIG. 6A depicts 5'-adapter attachment by coupled annealing-nick-translation-ligation. This is achieved in two incubations where the first incubation is a 3'-adapter attachment, and the second incubation combines three reactions that occur sequentially: annealing of the 5'-adapter; 5'-adapter extension by DNA polymerase with nick-translation activity (excision of damaged 5' terminus of substrate DNA); and ligation of the 5'-adapter to the exposed 5'-phosphate of the substrate DNA.

Nick-translation DNA synthesis is initiated at the nick or gap between the 3' end of the 5' adapter oligonucleotide and the 5' end of the DNA substrate molecules and stops when the ligation reaction seals the nick (see FIGS. 4 and 6a). The nick-translation reaction can be performed by but is not limited to DNA polymerases such as DNA polymerase I (holoenzyme), Taq DNA polymerase, Tth DNA polymerase, and Bst DNA polymerase (holoenzyme). Additional enzymes contemplated for use include, without limitation, DNA polymerases with 5'-3' exonuclease activity, 5' flap endonuclease, and a combination of a strand displacement polymerase and a 5' flap endonuclease.

The reaction conditions contemplated for this step include those where (i) both a polymerase with endogenous 5' exonuclease activity and a ligase are active; (ii) a strand displacement polymerase and flap endonuclease polymerase and ligase are active; (iii) a flap endonuclease and a ligase are active, (iv) simultaneous activity of both a thermostable enzyme and a thermolabile enzyme occur; or (v) where activity of only thermostable or only thermolabile enzymes can occur. In some embodiments, conditions (i) and (ii) are each performed with dNTPs for nick translation. In a specific embodiment, Taq polymerase and E. coli ligase are used at a reaction temperature of 40° C. In various embodiments, however, a range of reaction temperatures from 10° C. to 75° C. are contemplated.

The nick-translation reaction results in removal of one, two or more bases from the 5' end of the DNA substrate molecules prior to the ligation reaction which occurs between the 5' adapter extension product and the DNA substrate molecule. Nick-translation synthesis can occur in the presence of all four nucleotides dGTP, dCTP, dTTP and dATP or their restricted combinations. Restricted combinations include but are not limited to three-nucleotide combinations such as dGTP, dCTP and dATP, or dGTP, dCTP and dTTP, or dGTP, dATP and dTTP, or dCTP, dATP and dTTP, two-nucleotide combination such as dGTP and dCTP, or dGTP and dATP, or dGTP and dTTP, or dCTP and dATP, or dCTP and dTTP, or dATP and dTTP or just one nucleotide such as dGTP, or dCTP, or dATP, or dTTP.

Option ii

Figure 5:
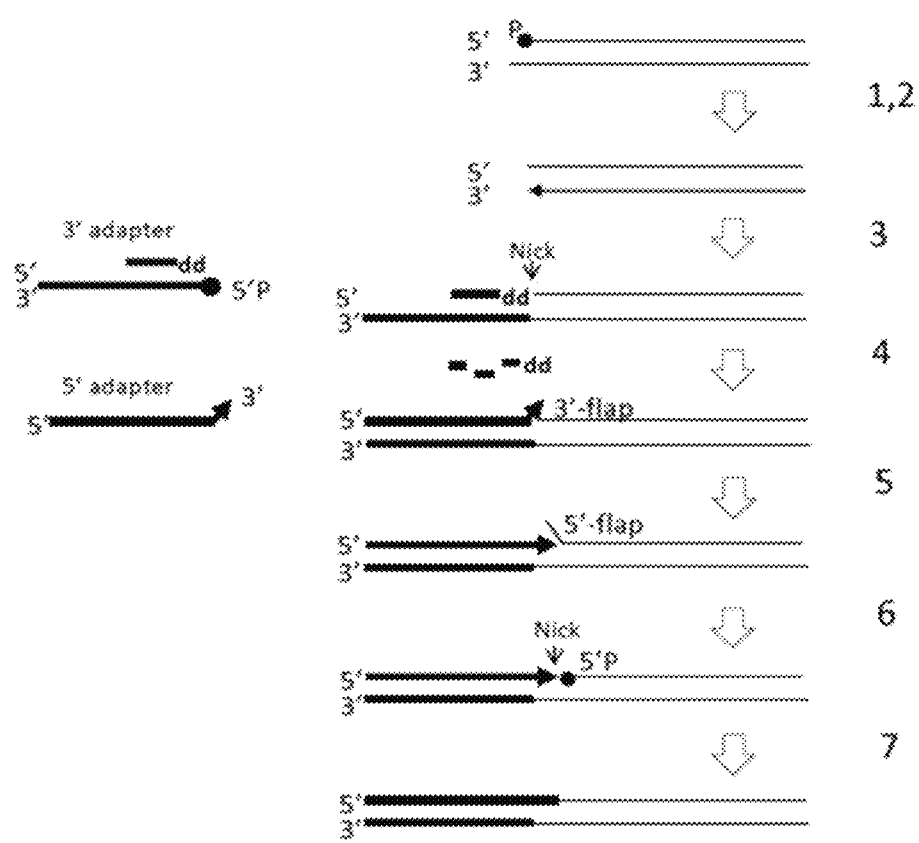
FIG. 5 depicts another embodiment of the present methods for ligation of the 3' adaptor and the 5' adapter by displacement-cleavage. The steps include: 1—substrate molecule dephosphorylation; 2—substrate molecule end polishing/blunt end generation; 3—3' adapter ligation; 4—partial degradation of the 3' adapter and annealing of the 5' adapter; 5—displacement of the 5' base(s) of the DNA fragment and annealing of the 3' base(s) of the 5' adapter; 6—cleavage of the displaced 5' base(s) of DNA by a 5'-flap endonuclease; and 7—ligation of the 3' end of the 5' adapter to the exposed 5' phosphate of the substrate DNA.
Figure 6B:
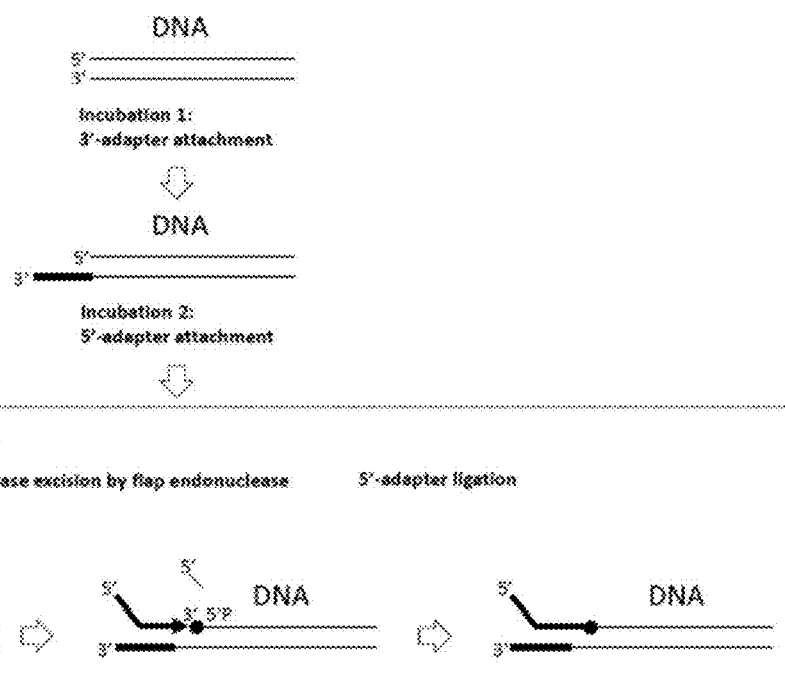
FIG. 6B depicts 5'-adapter attachment by coupled annealing-base excision-ligation. This is achieved in two incubations where the first incubation is a 3'-adapter attachment, and the second incubation combines three reactions that occur sequentially: annealing of the 5'-adapter with one or several random bases at the 3'-end and displacement of one or several terminal 5'-bases of substrate DNA; cleavage of displaced 5-bases by 5'-flap endonuclease (excision of damaged 5' terminus of substrate DNA); and ligation of the 5'-adapter to the exposed 5'-phosphate of the substrate DNA.

The displacement-cleavage reaction does not require dNTPs but requires that the 5' adapter sequence comprises one, two or more random bases at the 3' terminus to create an overlap with the substrate molecule, and which comprises a plurality of 5' adapters in the reaction (see FIGS. 5 and 6b). The displacement-cleavage reaction is initiated by annealing of the 5' adapters, displacement of the 5' DNA bases of the DNA substrate molecule that overlap with the 3' bases of the 5' adapters, and cleavage of the displaced bases by a 5'-flap endonuclease. In some embodiments, the 5' adapter has one random base dN at the 3' end. In this case the overlap involves one base and only a single 5' base would be removed from the 5' end of DNA substrate molecules and replaced with a similar base from the 5' adapter sequence. Efficiency of the displacement-cleavage reaction is increased by cycling the temperature of the reaction between 40° C. and 65° C. to allow 5' adapters to dissociate and re-anneal if its terminal 3' base is mismatched to the 5' base of the DNA substrate molecule.

Option iii

An alternative embodiment to the 5' adapter participating in the 5' base excision of the substrate molecules is to instead, in a previous step, have oligonucleotide 2 of the 3' adapter participate in the 5' base excision of the substrate molecules (see FIG. 9).

In one approach (FIGS. 9a and c), oligonucleotide 2 of the 3' adapter comprises an extendable 3' terminus and in the presence of a dideoxy nucleotide mixture and a polymerase under appropriate conditions, a single dideoxy base addition occurs which leads to a single base overlap with the 5' terminus of the substrate molecules, which induces single base displacement-cleavage by an appropriate flap endonuclease or polymerase that possesses 5' flap endonuclease activity. Subsequently, a 5' adapter with a random dN base at its 3' terminus is used (FIG. 9a), where a nick is formed after binding to the 3'-adapter attached to the end of double stranded DNA. The nick can be sealed by a DNA ligase resulting in covalent attachment of the 5'adapter to the 5' terminus of the DNA substrate molecule.

Alternatively, a 5'adapter oligonucleotide that lacks a random dN base at its 3' terminus can be used (FIG. 9c), which forms a single base gap after binding to the 3'-adapter attached to the end of double stranded DNA substrate molecule. The gap can be filled in by a DNA polymerase lacking strand-displacement activity (for example T7 or T4 DNA polymerase) to create a nick that can be in turn sealed by a DNA ligase resulting in covalent attachment of the 5'adapter to the 5' end of DNA substrate molecule.

In another alternative (see FIGS. 9b and d), oligonucleotide 2 that comprises a blocked 3' terminus is partially degraded or displaced by a primer oligonucleotide that becomes extended with a single dideoxy-base by a DNA polymerase with 5' flap endonuclease activity resulting in excision of a single base from the 5' terminus of DNA. The primer oligonucleotide, in turn, becomes degraded or displaced by the 5' adapter with a random dN base at its 3' terminus to create a nick that can be sealed by a DNA ligase.

(III) Ligation of the 5' Adapter

Covalent attachment of the 5' adapter to the substrate molecule involves ligation between the 5' adapter or its extension product and the exposed 5' phosphate of the substrate molecules. When excision of the 5' base(s) of DNA substrate molecules is achieved by a nick-translation reaction, the ligation reaction seals the nick between the polymerase-extended 5' adapter and the excised 5' end of the DNA substrate molecule. When excision of the 5' base of DNA substrate molecules is achieved through the displacement-cleavage reaction, the ligation occurs between the original 5' adapter oligonucleotide and the excised 5' end of the DNA substrate molecule. The standard conditions with respect to the ligation reaction in this step comprise, in various embodiments, use of any DNA ligase that is capable of sealing nicks or gaps in DNA. In one embodiment, the ligase is E. coli DNA ligase and the reaction occurs in the temperature interval between 10° C. and 50° C. In some embodiments, the ligase is a thermostable DNA ligase such as Taq DNA ligase, or AmplLigase, and the reaction occurs in the temperature interval between 30° C. and 75° C.

In various aspects of the current invention, the three steps (I), (II) and (III) of the 5' adapter ligation step are performed simultaneously in a single incubation by mixing and incubating the 3'-adapted substrate DNA with (i) an optional degradation endonuclease (e.g., UDG, endonuclease V, RNase H, or their combination); (ii) a nick-translation DNA polymerase or a 5'-flap endonuclease; and (iii) a DNA ligase (see FIG. 6). The incubation is carried out at a constant temperature or using temperature cycling conditions in the interval 10° C.-75° C. In other applications, 3' adapter partial degradation is performed separately from the downstream reactions.

Construction of NGS Libraries

Figure 10A:
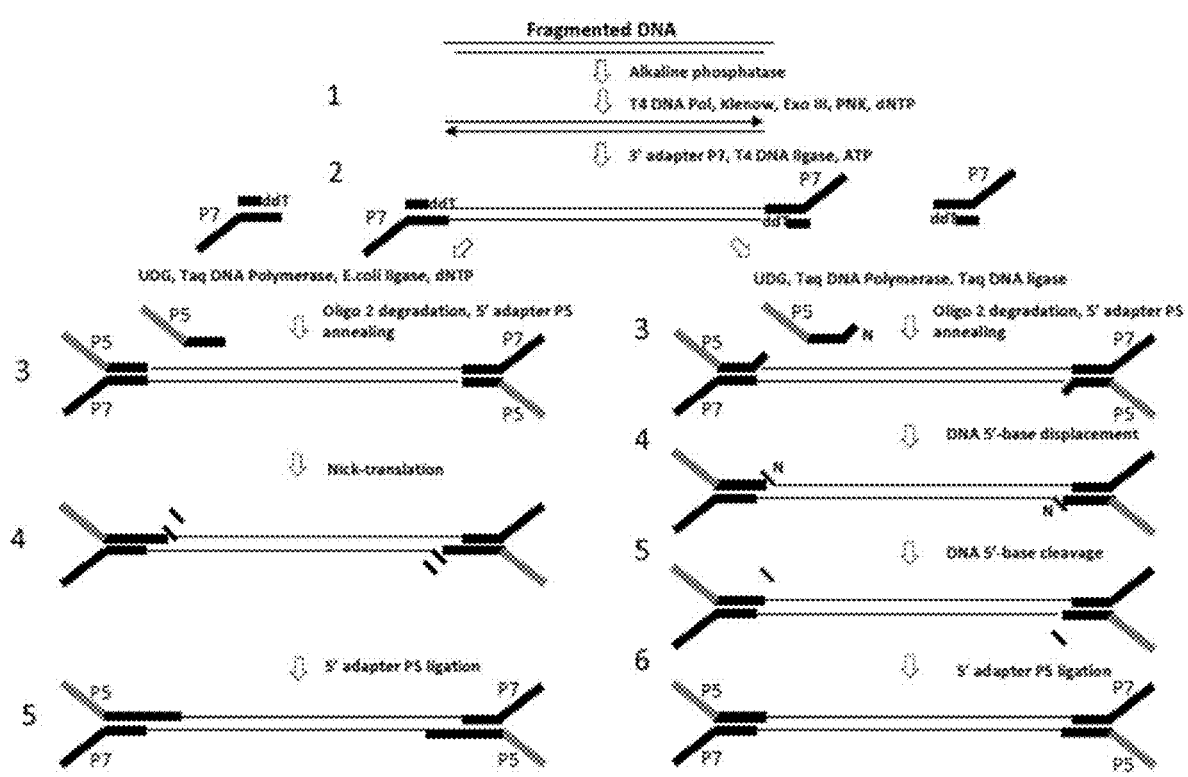
FIG. 10A depicts a method of synthesizing an Illumina NGS library I using either a nick translation ligation approach (3-5 on left) or a flap endonuclease approach (3-6 on right). The steps for either approach include: 1—substrate molecule dephosphorylation and polishing; 2—ligation of the 3' adapter with Illumina sequence P7; and 3—partial degradation of the 3' adapter and annealing of the complementary 5' adapter with Illumina sequence P5. For the nick translation approach, the steps further include: 4—polymerase extension of the 5' adapter by nick-translation; and 5—ligation of the 3' end of the 5' adapter to the exposed 5' phosphate of the DNA substrate. For the flap endonuclease approach, the steps further include: 4—displacement of the 5' base(s) of the DNA substrate and annealing of the 3' base(s) of the 5' adapter; 5—cleavage of the displaced 5' base(s) of the DNA substrate by a 5'-flap endonuclease; and 6—ligation of the 3' end of the 5' adapter to the exposed 5' phosphate of the DNA substrate. The library is then amplified by PCR using primers P5 and P7'.
Figure 10B:
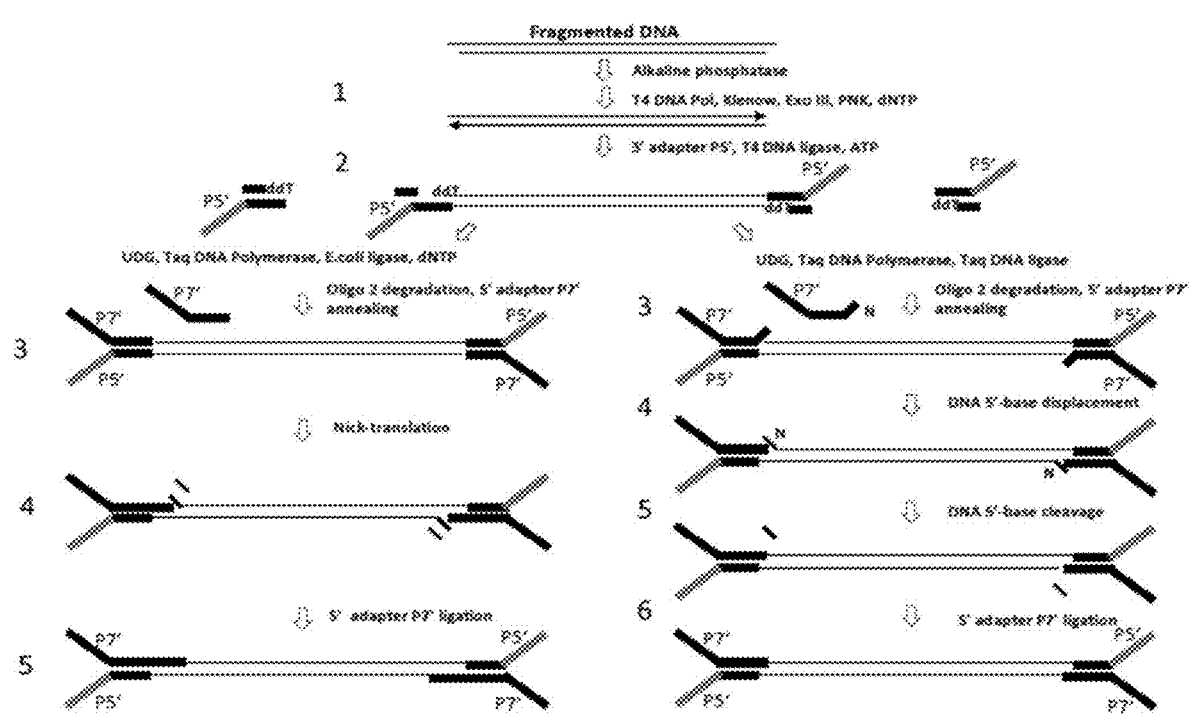
FIG. 10B depicts an alternative method of synthesizing an Illumina NGS library I using either a nick translation ligation approach (3-5 on left) or a flap endonuclease approach (3-6 on right). The steps for either approach include: 1—substrate molecule dephosphorylation and polishing; 2—ligation of the 3' adapter with Illumina sequence P5'; and 3—partial degradation of the 3' adapter and annealing of the complementary 5' adapter with Illumina sequence P7'. For the nick translation approach, the steps further include: 4—polymerase extension of the 5' adapter by nick-translation; and 5—ligation of the 3' end of the 5' adapter to the exposed 5' phosphate of the DNA substrate. For the flap endonuclease approach, the steps further include: 4—displacement of the 5' base(s) of the DNA substrate and annealing of the 3' base(s) of the 5' adapter; 5—cleavage of the displaced 5' base(s) of the DNA substrate by a 5'-flap endonuclease; and 6—ligation of the 3' end of the 5' adapter to the exposed 5' phosphate of the DNA substrate. The library is then amplified by PCR using primers P5 and P7'.
Figure 11:
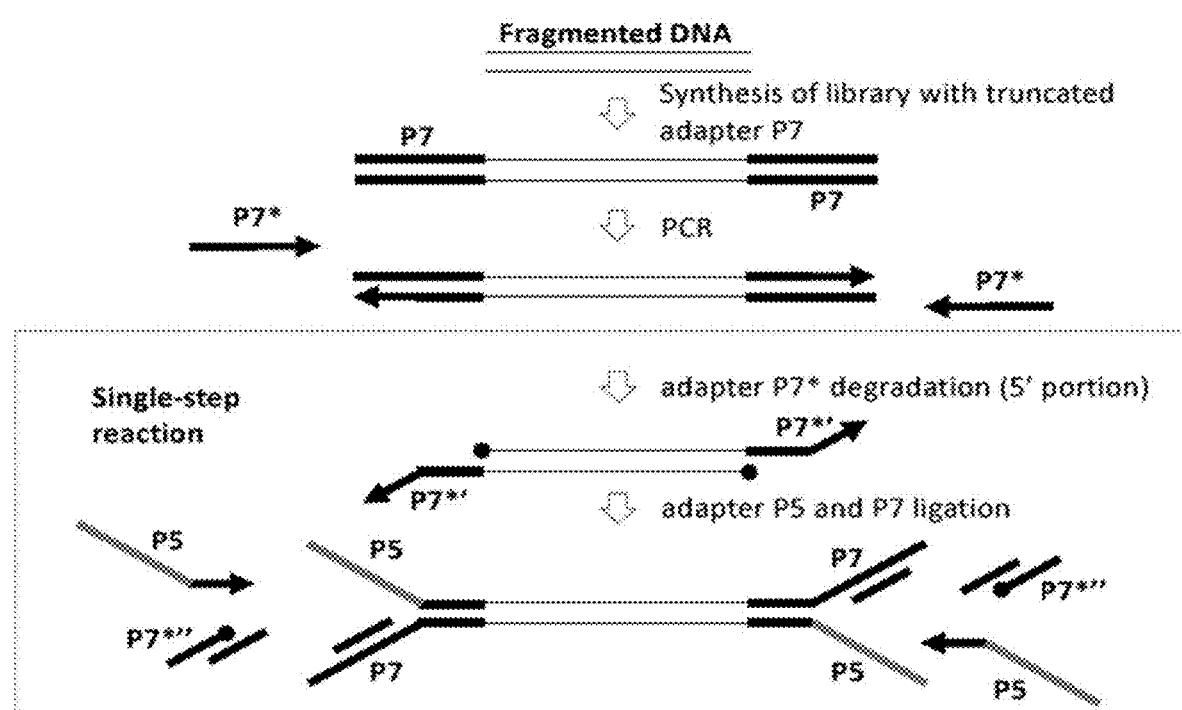
FIG. 11 depicts synthesis of an Illumina NGS library II using the following steps: synthesis of NGS library with truncated adapter P7 by one of two methods described in FIGS. 6A and 6B; library amplification with truncated or full length degradable primer P7*; degradation of the incorporated P7* primer followed by annealing and ligation of the 5' adapter P5; and if a truncated degradable primer P7* was used, a bridge-ligation of the P7*''' adapter to the truncated adapter P7*' is performed to complete full-length adapter P7.

Synthesis of an Illumina NGS library can be performed using the disclosed methods. As shown in FIG. 10, an Illumina library can be constructed using either the nick translation ligation method (left side) or the displacement cleavage ligation method (right side). The order of attachment of the two Illumina adapters is flexible, where in FIG. 10a, Illumina adapter P7 is a 3' adapter and Illumina adapter P5 is a 5' adapter, whereas in FIG. 10b, Illumina adapter P5 is a 3' adapter and Illumina adapter P7 is a 5' adapter. The libraries depicted in FIG. 10 can be constructed PCR-free or can be PCR amplified, depending on the amount of input substrate DNA. Alternatively, synthesis of Illumina NGS libraries can be performed using the disclosed methods where PCR amplification is required, because the method uses truncated adapter sequences (see FIG. 11). In this case, either P5 or P7 is introduced as a truncated adapter (only P7 shown), and following amplification using a PCR primer that introduces the full-length adapter sequence as well as comprises degradable bases at its 5' terminus, following degradation of the 5' portions of the resulting amplicons, either P7 or P5 can be introduced by annealing and ligation. If alternatively a truncated degradable primer is used for the PCR amplification, a bridge-ligation of the remainder of the adapter can be performed to complete the full-length sequence.

Figure 12A:
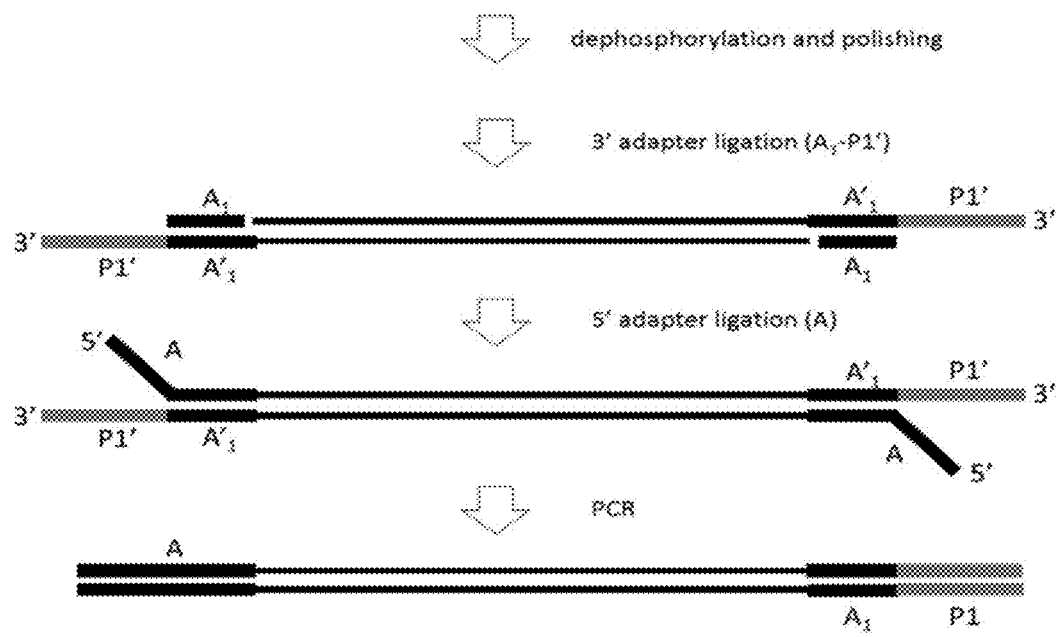
FIG. 12A depicts a synthesis method for an Ion Torrent library performed by the following steps: DNA substrate dephosphorylation and polishing; ligation of the 3' adapter with sequence A1'-P1'; nick-translation ligation or base cleavage ligation of the 3' end of the 5' adapter with sequence A to the 5' end of trimmed DNA; and library amplification by PCR using primers A and P1.
Figure 12B:
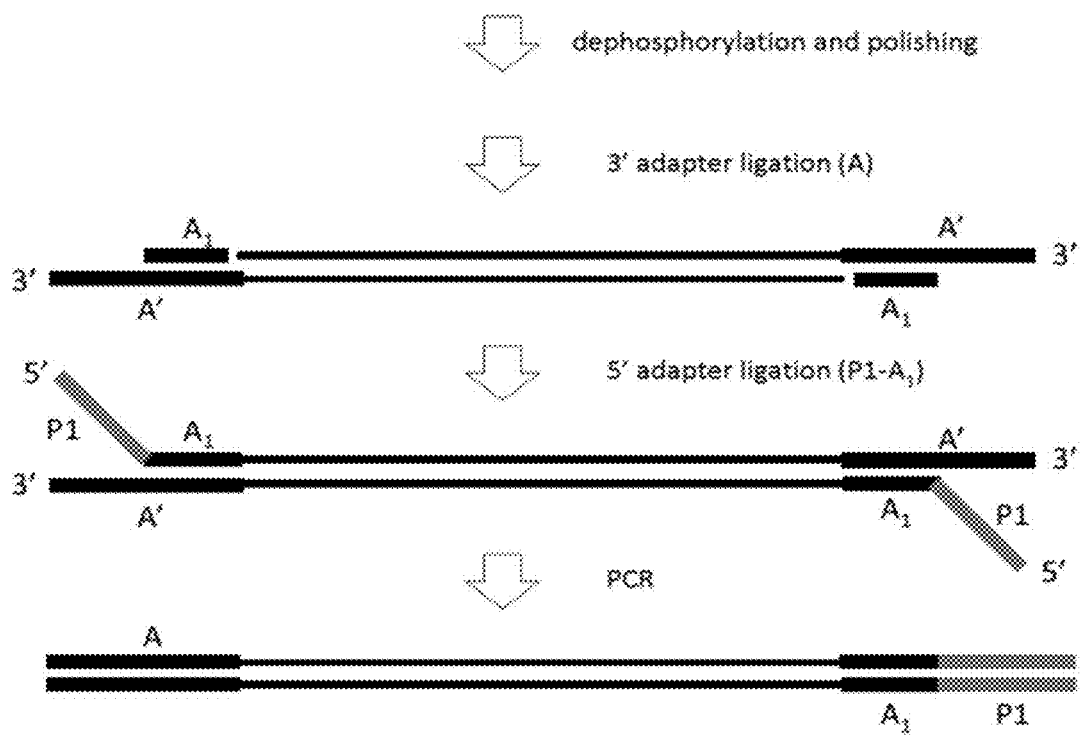
FIG. 12B depicts an alternative synthesis method for an Ion Torrent library performed by the following steps: DNA substrate dephosphorylation and polishing; ligation of the 3' adapter with sequence A'; nick-translation ligation or base cleavage ligation of the 3' end of the 5' adapter with sequence P1-A1 to the 5' end of trimmed DNA; and library amplification by PCR using primers A and P1.
Figure 13A:
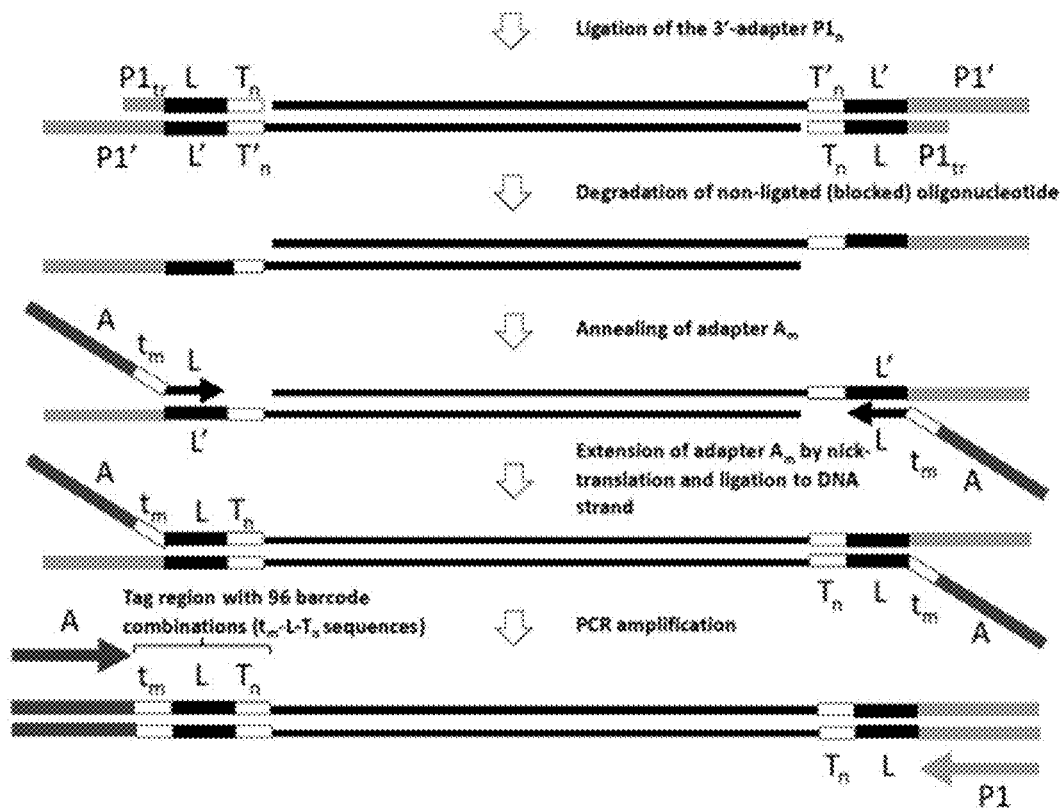
FIG. 13A depicts another synthesis method for an Ion Torrent library with 96 combinatorial barcode sequences using only 20 adapter sequences. The steps include: DNA end dephosphorylation and polishing (not shown); ligation of the (blunt) 3'-adapter $P1_n$ with sequence $T'_n$-L'-P1' and 5' phosphate group and 3'-blocked complementary oligonucleotide with sequence $P1_{tr}$-L-$T_n$; degradation of the 3'-blocked complementary oligonucleotide $P1_{tr}$-L-$T_n$; annealing of the 5'-adapter $A_m$ with sequence A-$t_m$-L to the linker region L'; extension of the 5'-adapter $A_m$ by nick-translation polymerization and ligation of the 3' end of the extended 5'-adapter $A_m$ to the 5' end of DNA; and library amplification by PCR using primers A and P1.
Figure 13B:
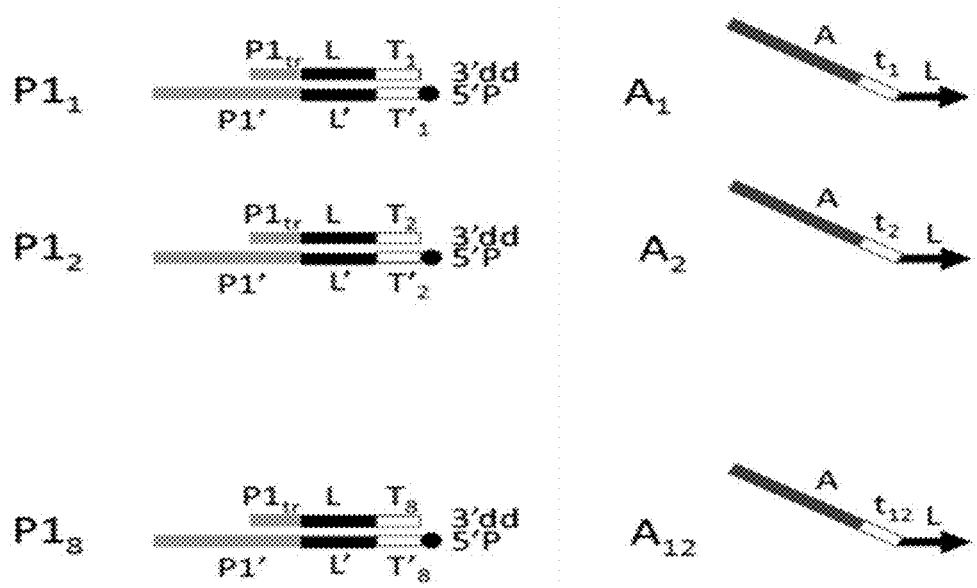
FIG. 13B depicts various adapters with combinatorial barcodes include eight adapters $P1_n$ containing barcode sequences $T_1, T_2, \ldots, T_8$ and twelve adapters $A_m$ containing barcode sequences $t_1, t_2, \ldots, t_{12}$ providing a library having a combinatorial barcode sequence $t_m$-L-$T_n$ with up to 96 barcode combinations.

The disclosed methods can be used to construct NGS libraries for a variety of sequencing platforms, and another example is presented in FIGS. 12 and 13 where Ion Torrent library construction is depicted. As shown in FIG. 12, by introducing a partial duplication of the A adapter sequence on the P1 adapter at the insert junction site, subsequent annealing of a 5' adapter after 3' adapter ligation can occur. The order of ligation is flexible, where adapter P1 with a partial duplication of adapter A can be introduced as a 3' adapter followed by ligation of adapter A as a 5' adapter using either nick translation or displacement cleavage (FIG. 12a). Alternatively, adapter A can be introduced as a 3' adapter and adapter P1 with a partial duplication of adapter A can be a 5' adapter (FIG. 12b). Since Ion Torrent sequencing is performed as a single read from the A adapter, due to the length of the partial duplication of adapter A on the P1 adapter, it will not interfere with sequencing primer annealing or other adapter functions.

Alternatively in FIG. 13, combinatorial barcoding can be introduced to Ion Torrent libraries using the disclosed method. During the 3' adapter ligation step, the first portion of the dual combinatorial barcode is introduced, adjacent to a linker region L that is common to all 20 barcodes. After degradation of the 3' blocked strand that does not ligate to the DNA substrate, a 5' adapter anneals to the common linker region L which incorporates the second portion of the dual barcode 5' adjacent to the linker region L. Following nick translation ligation, the resulting library can be amplified with standard Ion Torrent PCR primers, and when library molecules are sequenced from the A adapter side, the sample identification of each Ion sphere will be read at the beginning of the read, where 96 possible combinations can be achieved.

Applications for Target Selected NGS Libraries

The disclosed methods can be used to construct NGS libraries where specific targets can be selected and enriched, as a way to reduce complexity and sequencing requirements relative to whole genome sequencing. An example of such an application would be attachment of the 3' adapter and 5' adapter to randomly fragmented, denatured and primer-extended DNA substrates, where the primer or plurality of primers anneal to known targeted DNA regions. In this case, only the targeted loci would comprise a double stranded terminus, where non-selected loci would remain single stranded and adapter ligation would not occur on their termini.

Figure 14:
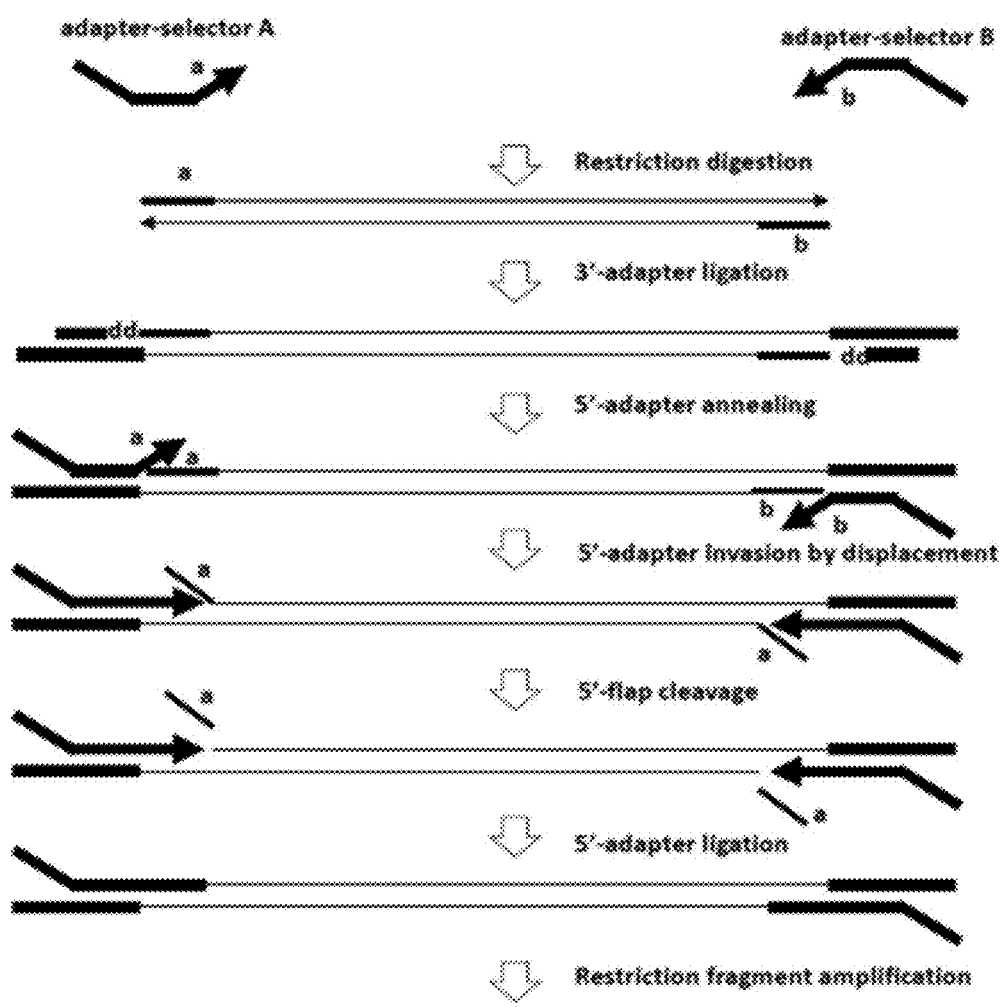
FIG. 14 depicts a method for enrichment of selected restriction fragments by 5' adapter ligation. A restriction DNA fragment is selected by 5'-adapter ligation followed by PCR amplification. Selection occurs by two 5'-adapter-selectors A and B containing sequences a and b that are identical to the 5' terminal sequences of the restriction fragment. The method of enrichment involves: DNA digestion with restriction endonuclease; ligation of the 3'-adapter; partial degradation of the 3'-adapter and annealing of the 5'-adapter-selectors; invasion of the 5'-adapter-selectors into terminal sequences a and b of the restriction fragment; cleavage of the displaced terminal sequences a and b by a 5'-flap endonuclease; ligation of the 5'-adapter-selectors to the ends of the restriction fragment; and amplification of the selected restriction fragment by PCR. The initial digestion and ligation of the 3' adaptor and annealing of the 5'-adaptor selectors can be combined into a single incubation reaction with the subsequent steps in single incubation reaction as well.

In other applications, the 5' adapter of the current invention can be used to select and enrich a small fraction of DNA fragments with known terminal sequences. Pre-selected DNA sequences could contain one, two, three or more terminal DNA bases. To achieve such selection the 5' adapter sequence should contain selected invasion bases or base combinations at the 3' end. As a result, only DNA fragments with selected terminal sequences will be ligated to the 5' adapter and amplified. As shown in FIG. 14, use of 5' adapters with 3' termini complementary to the terminal sequences of selected restriction fragments can be used to select restriction fragment targets from a plurality of restriction fragments. In another embodiment, use of 5' adapters with 3' termini comprising CpG dinucleotides would enrich for fragments originating from CpG islands.

Figure 15A:
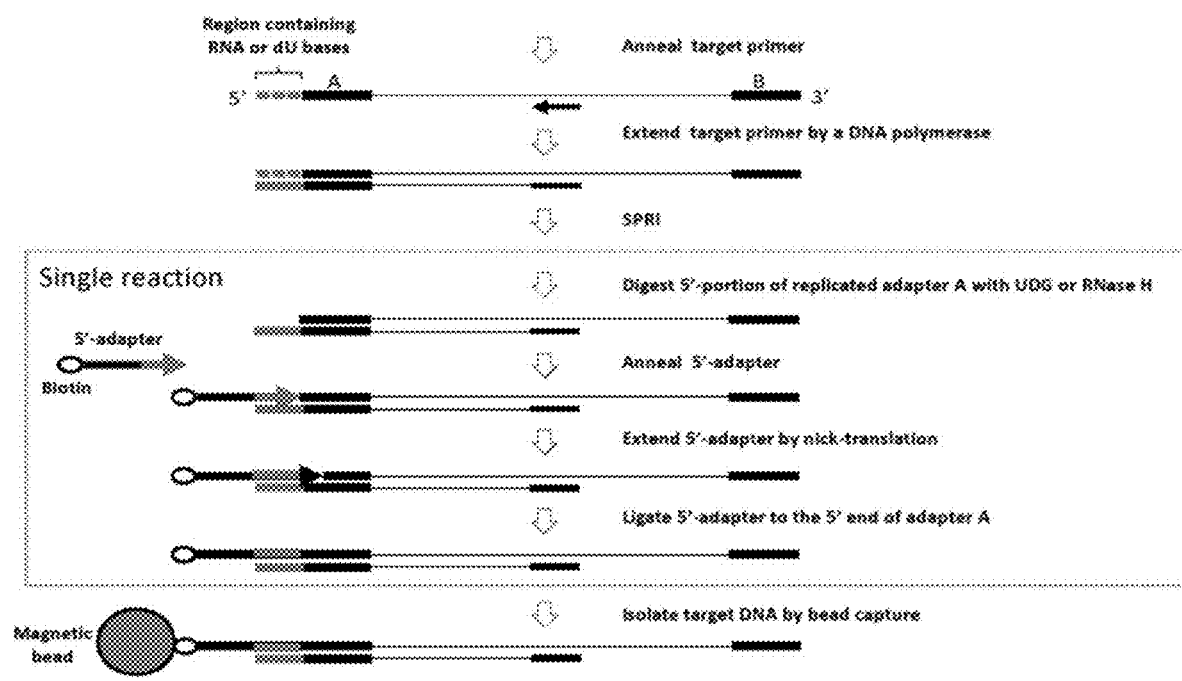
FIG. 15A depicts a method for target enrichment by primer extension. Enrichment is performed by 5' adapter attachment where the 3' overhang is created by extension of a primer complementary to a target DNA region on a library with adapters A and B and partial digestion of the 5' domain of adapter A. Biotinylated 5'-adapter is annealed to the 3'-overhang of adapter A and then ligated to the 5' end of adapter A after trimming by limited nick-translation. Library fragments containing target DNA region are then isolated by affinity capture using streptavidin magnetic beads, amplified by PCR and analyzed by sequencing.
Figure 15B:
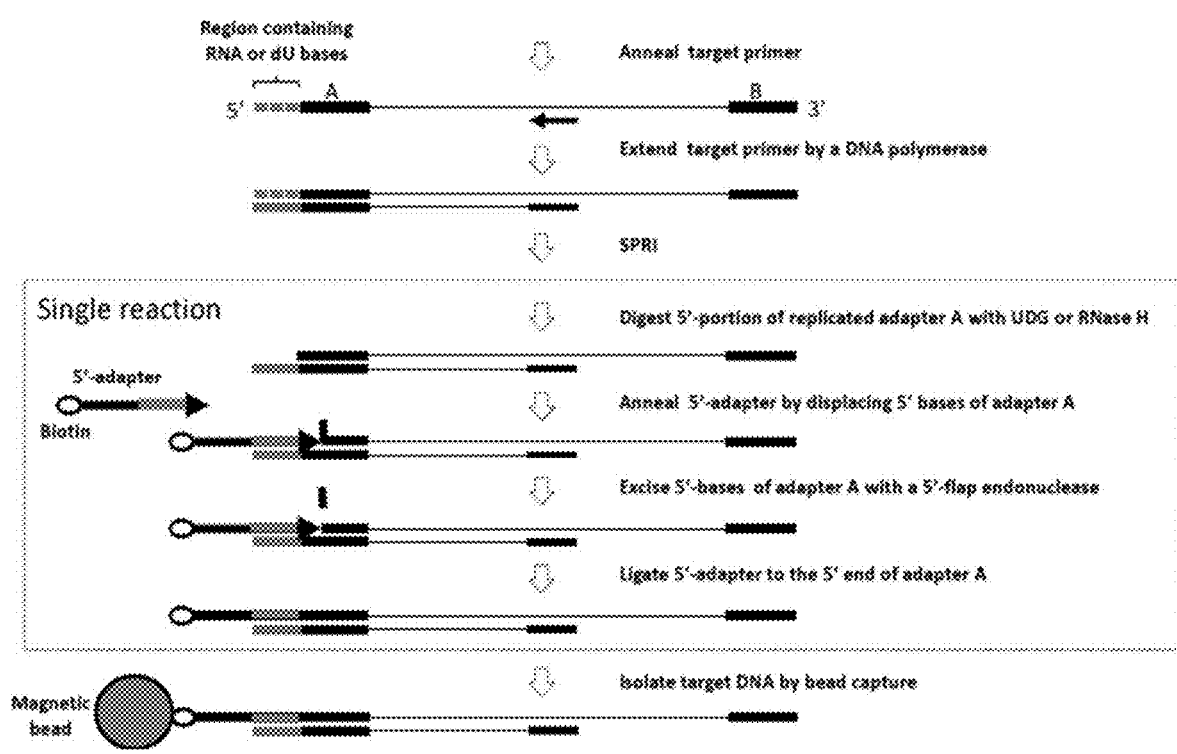
FIG. 15B depicts a method for target enrichment by primer extension. Enrichment is performed by 5' adapter attachment where the 3' overhang is created by extension of a primer complementary to a target DNA region on a library with adapters A and B and partial digestion of the 5' domain of adapter A. Biotinylated 5'-adapter is annealed to the 3'-overhang of adapter A and then ligated to the 5' end of adapter A either after trimming by invasion-cleavage reaction. Library fragments containing target DNA region are then isolated by affinity capture using streptavidin magnetic beads, amplified by PCR and analyzed by sequencing.

Alternatively, target selection can be performed following library construction using the methods disclosed within (see FIG. 15). If such a library is constructed where one adapter comprises degradable bases at its 5' terminus, following target-specific primer extension and partial digestion of the degradable portion of the adapter, a biotinylated 5' adapter can be annealed to the resulting 3' overhang and using either nick translation ligation (FIG. 15a) or displacement cleavage ligation (FIG. 15b), the biotinylated 5' adapter is covalently attached to only targeted DNA substrates and can be subsequently captured using streptavidin magnetic beads and then PCR amplified to generate sufficient material for sequencing.

Alternative Adapter Designs and Applications

Figure 16:
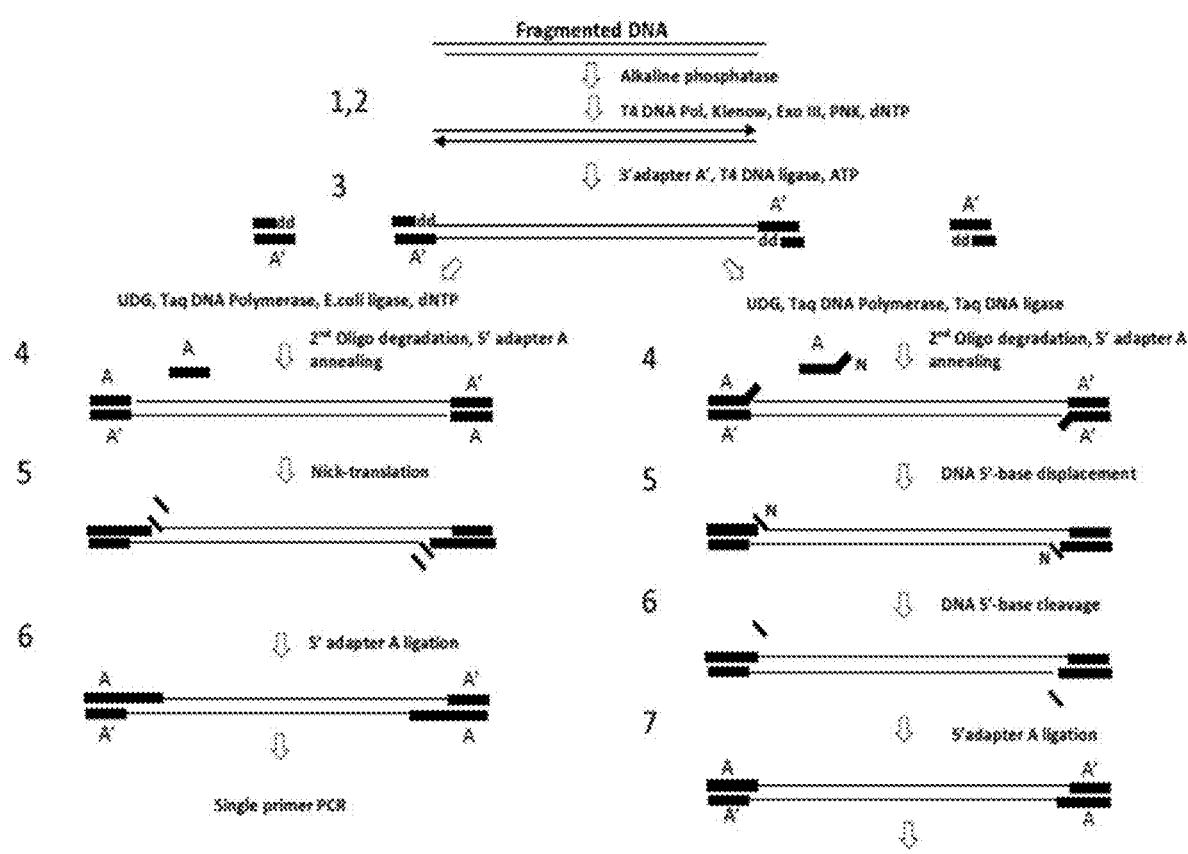
FIG. 16 depicts an alternative method of synthesizing a NGS library using either a nick translation ligation approach (4-6 on left) or a flap endonuclease approach (4-7 right). The steps for either approach include: 1—substrate molecule dephosphorylation; 2—substrate molecule end polishing/blunt end generation; 3—ligation of the 3' adapter with sequence A'; and 4—partial degradation of the 3' adapter and annealing of the complementary 5' adapter with sequence A. The steps for the nick translation approach further include: 5—polymerase extension of the 5' adapter by nick-translation; and 6—ligation of the 3' end of the 5' adapter to the exposed 5' phosphate of the DNA substrate. The steps for the flap endonuclease approach further include: 5—displacement of the 5' base(s) of DNA and annealing of the 3' base(s) of the 5' adapter; 6—cleavage of the displaced 5' base(s) of DNA by a 5'-flap endonuclease; and 7—ligation of the 3' end of the 5' adapter to the exposed 5' phosphate of the DNA substrate. The library can be amplified by PCR using single primer A.

Several alternative adapter designs and ligation methods using the disclosed methods are also presented. In FIG. 16, a library is constructed using a single adapter sequence instead of a pair of adapter sequences. In this example, the same steps are used for substrate processing prior to ligation and both 3' adapter ligation and either nick translation ligation or displacement cleavage ligation of the 5' adapter, and the resulting library can be PCR amplified using a single primer.

Figure 17:
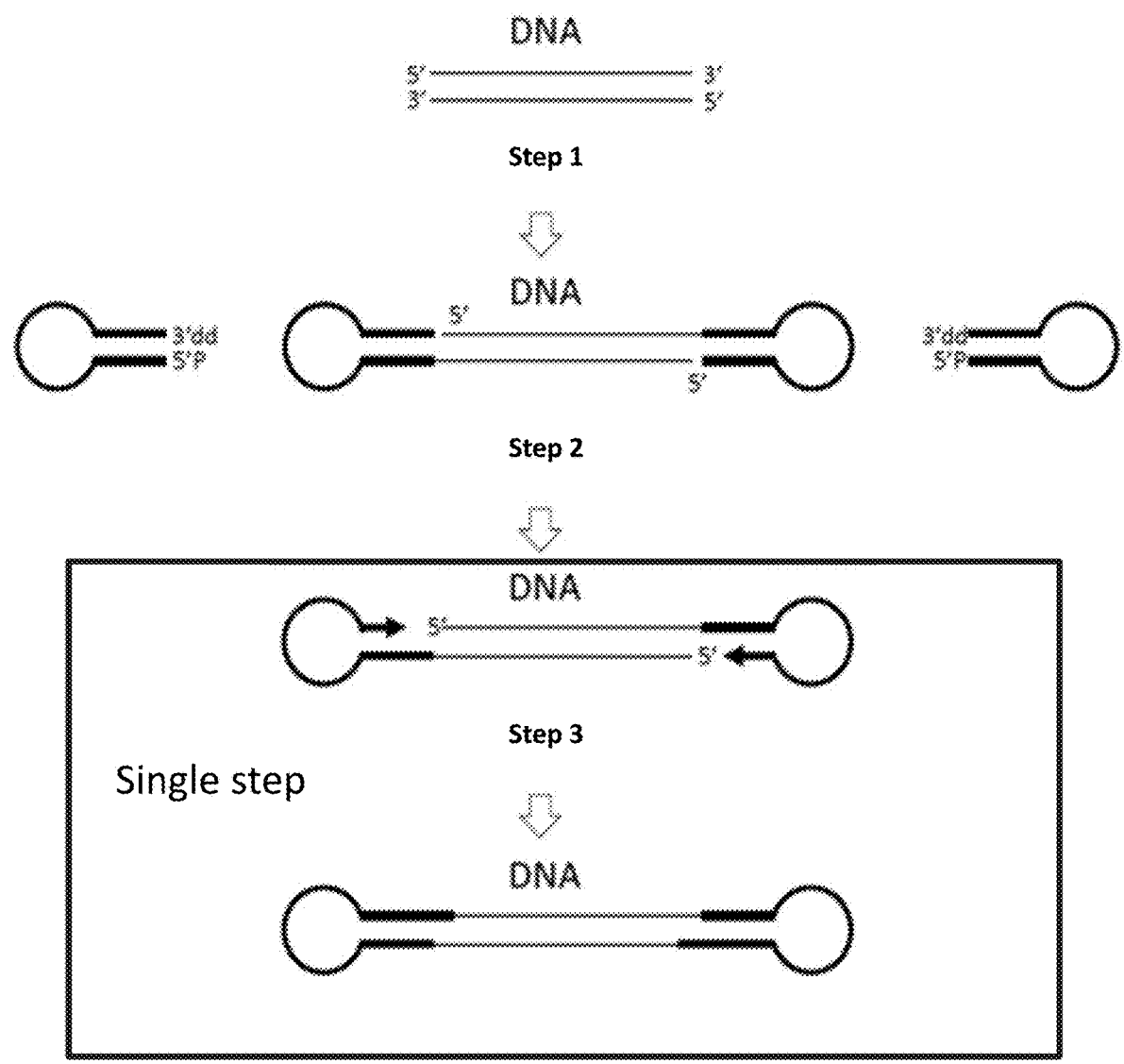
FIG. 17 depicts an alternative method of synthesizing a NGS library. Adapter attachment can create a library of double-stranded DNA fragments with covalently linked 3' and 5' DNA ends. Library construction is performed by the following method following the initial steps of substrate molecule dephosphorylation (not shown) and substrate molecule end polishing/blunt end generation (not shown): Step 1—ligation of the hairpin blunt adapter with phosphorylated 5' end and blocked (optionally) 3' end; Step 2—partial degradation of the hairpin adapter to create an extendable 3' end; and Step 3—nick-translation of the 3' end of the hairpin adapter and its ligation to the exposed 5' phosphate of the DNA substrate.

In FIG. 17, a method for ligation of single oligonucleotide hairpin adapters is presented, wherein the 5' terminus of the hairpin adapter is used to perform 3' adapter ligation to the substrate molecule, and following degradation of the blocked 3' terminus of the hairpin adapter, the truncated 3' terminus of the hairpin adapter is used for nick translation ligation to the exposed 5' phosphate of the substrate molecule.

Figure 18:
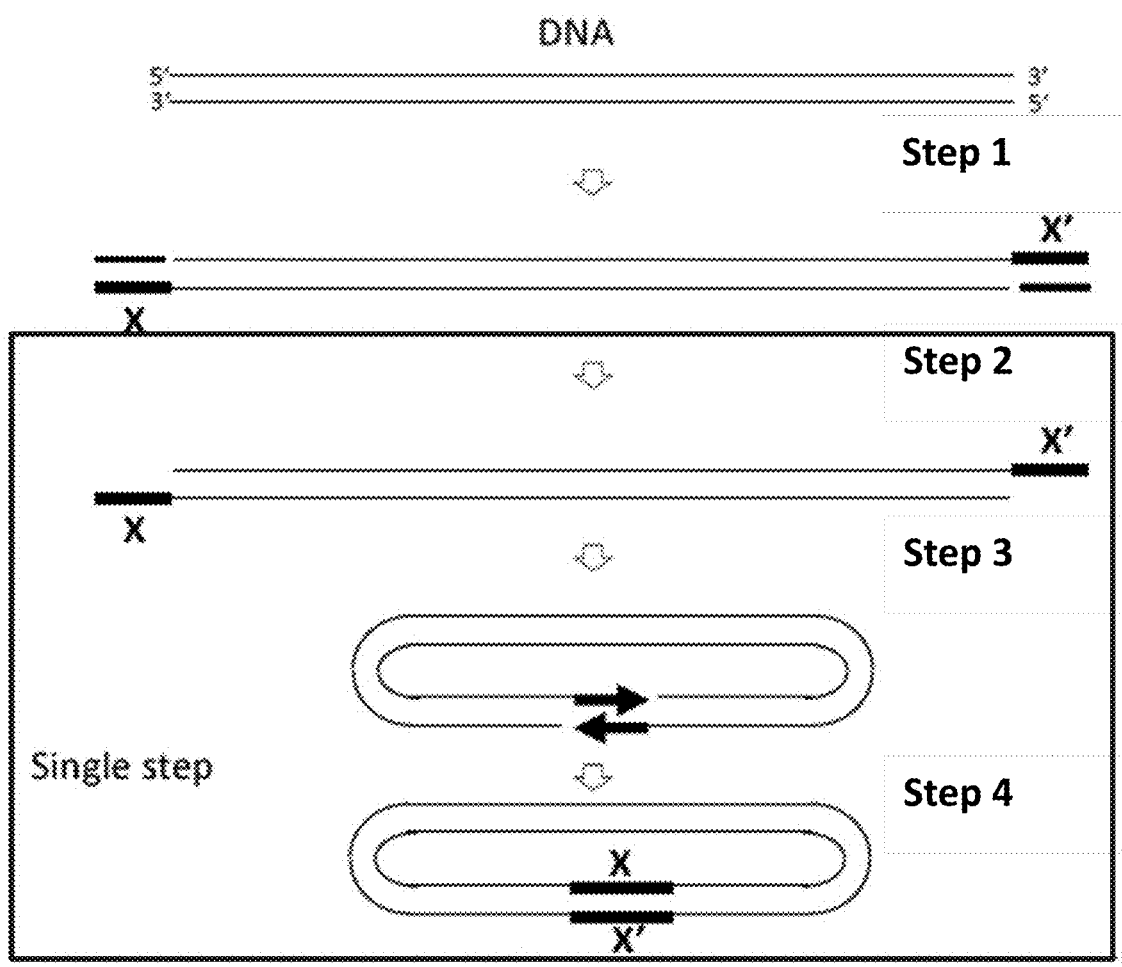
FIG. 18 depicts a method of synthesizing a circularized NGS library. The method includes the initial steps of substrate molecule dephosphorylation (not shown) and substrate molecule end polishing/blunt end generation (not shown) followed by the following steps: Step 1—ligation of adapters with a phosphorylated 5' end and blocked (optionally) 3' end and mutually complementary sequences X and X'; Step 2—degradation of the non-ligated adapter strands to create single-stranded 3' overhangs; Step 3—non-covalent circularization of DNA by annealing of terminal sequences X and X' (performed at low DNA concentration); and Step 4—covalent circularization of DNA by nick-translation ligation reaction.

Sometimes it is useful to generate circular DNA libraries, such as an intermediate structure for the construction of mate-pair NGS libraries. As shown in FIG. 18, such a library can be constructed using methods of the disclosure. In the first step, 3' adapter ligation is performed using mutually complementary adapters X and X'. Following degradation of the non-ligated strand, non-covalent DNA circularization can occur by means of complementarity of the 3' overhangs X and X' on each substrate molecule. To favor unimolecular annealing and reduce concatamer formation, this annealing reaction is performed at an appropriately low DNA concentration. Following 3' overhang annealing, nick translation ligation can be performed.

Enzymes

Ligases that may be used according to standard reaction conditions to practice the methods of the disclosure include but are not limited to T4 DNA ligase, T4 RNA ligase, T3 DNA ligase or T7 DNA ligase, Taq DNA ligase, Ampligase, E. coli DNA ligase and E. coli RNA ligase. The disclosure contemplates, in various embodiments, reaction conditions appropriate for a blunt end or a cohesive ("sticky") end ligation. The cohesive end, in some embodiments, comprises either a 5' overhang or a 3' overhang.

Examples of enzymes useful in the methods of the disclosure to remove a 5' or a 3' phosphate include, but are not limited to, any phosphatase enzyme, such as calf intestinal alkaline phosphatase, bacterial alkaline phosphatase, shrimp alkaline phosphatase, Antarctic phosphatase, and placental alkaline phosphatase, each used according to standard conditions. Additionally, the phosphatase activity of T4 polynucleotide kinase can be used to remove 3' phosphate groups.

The polymerase enzymes useful in the practice of the invention include but are not limited to a DNA polymerase (which can include a thermostable DNA polymerase, e.g., a Taq DNA polymerase), RNA polymerase, DNA polymerase I and reverse transcriptase. Non-limiting examples of enzymes that may be used to practice the present invention include but are not limited to KAPA HiFi and KAPA HiFi Uracil+, VeraSeq Ultra DNA Polymerase, VeraSeq 2.0 High Fidelity DNA Polymerase, Takara PrimeSTAR DNA Polymerase, Agilent Pfu Turbo CX Polymerase, Phusion U DNA Polymerase, Deep VentR™ DNA Polymerase, LongAmp™ Taq DNA Polymerase, Phusion™ High-Fidelity DNA Polymerase, Phusion™ Hot Start High-Fidelity DNA Polymerase, Kapa High-Fidelity DNA Polymerase, Q5 High-Fidelity DNA Polymerase, Platinum Pfx High-Fidelity Polymerase, Pfu High-Fidelity DNA Polymerase, Pfu Ultra High-Fidelity DNA Polymerase, KOD High-Fidelity DNA Polymerase, iProof High-Fidelity Polymerase, High-Fidelity 2 DNA Polymerase, Velocity High-Fidelity DNA Polymerase, ProofStart High-Fidelity DNA Polymerase, Tigo High-Fidelity DNA Polymerase, Accuzyme High-Fidelity DNA Polymerase, VentR® DNA Polymerase, DyNAzyme™ II Hot Start DNA Polymerase, Phire™ Hot Start DNA Polymerase, Phusion™ Hot Start High-Fidelity DNA Polymerase, Crimson LongAmp™ Taq DNA Polymerase, DyNAzyme™ EXT DNA Polymerase, LongAmp™ Taq DNA Polymerase, Phusion™ High-Fidelity DNA Polymerase, Taq DNA Polymerase with Standard Taq (Mg-free) Buffer, Taq DNA Polymerase with Standard Taq Buffer, Taq DNA Polymerase with ThermoPol II (Mg-free) Buffer, Taq DNA Polymerase with ThermoPol Buffer, Crimson Taq™ DNA Polymerase, Crimson Taq™ DNA Polymerase with (Mg-free) Buffer, Phire™ Hot Start DNA Polymerase, VentR® (exo-) DNA Polymerase, Hemo KlenTaq™, Deep VentR™ (exo-) DNA Polymerase, Deep VentR™ DNA Polymerase, DyNAzyme™ EXT DNA Polymerase, Hemo KlenTaq™, LongAmp™ Taq DNA Polymerase, ProtoScript® AMV First Strand cDNA Synthesis Kit, ProtoScript® M-MuLV First Strand cDNA Synthesis Kit, Bst DNA Polymerase, Full Length, Bst DNA Polymerase, Large Fragment, 9° Nm DNA Polymerase, DyNAzyme™ II Hot Start DNA Polymerase, Hemo KlenTaq™, Sulfolobus DNA Polymerase IV, Therminator™ y DNA Polymerase, Therminator™ DNA Polymerase, Therminator™ II DNA Polymerase, Therminator™ III DNA Polymerase, Bsu DNA Polymerase, Large Fragment, DNA Polymerase I (E. coli), DNA Polymerase I, Large (Klenow) Fragment, Klenow Fragment (3'→5' exo-), phi29 DNA Polymerase, T4 DNA Polymerase, T7 DNA Polymerase (unmodified), Terminal Transferase, Reverse Transcriptases and RNA Polymerases, E. coli Poly(A) Polymerase, AMV Reverse Transcriptase, M-MuLV Reverse Transcriptase, phi6 RNA Polymerase (RdRP), Poly(U) Polymerase, SP6 RNA Polymerase, and T7 RNA Polymerase.

The enzymes possessing flap endonuclease activity that are useful in the disclosure include but are not limited to flap endonuclease 1 (FEN1), T5 exonuclease, Taq DNA polymerase, Bst polymerase, Tth polymerase, DNA polymerase I and their derivatives.

EXAMPLES

Example 1

Comparison of Conventional Adapter Ligation to 3' Adapter Ligation with FAM-Labeled Oligonucleotides Rationale: Using a FAM-labeled oligonucleotide system, blunt ligation using fill-in adapters (FIG. 2A) or 3' adapters (FIG. 3) was tested at different molar ratios of substrate to adapter to examine the effect on ligation efficiency and chimera formation.

Materials:
Fill-in adapter contains oligonucleotides 12-900 and 13-426 (Table 1)
3'Adapter; $1^{st}$ oligonucleotide 13-340 (Table 1)
3'Adapter; $2^{nd}$ oligonucleotide option 1 (with a blocking 3' deoxythymidine base at the 3' terminus) 13-559 (Table 1)
3'Adapter; $2^{nd}$ oligonucleotide option 2 (a phosphate group at the 3' terminus) 13-558 (Table 1)
FAM substrate A composed of oligonucleotides 13-562 and 13-563, where the FAM group labels ligation to the 5' Phosphate of the substrate (Table 1)
FAM substrate B composed of oligonucleotides 13-561 and 13-564, where the FAM group labels ligation to the 3' OH of the substrate and where the corresponding 5' terminus of the substrate has a phosphate (Table 1)
FAM substrate C composed of oligonucleotides 13-560 and 13-564, where the FAM group labels ligation to the 3' OH of the substrate and where the corresponding 5' terminus of the substrate lacks a phosphate (Table 1)
T4 DNA Ligase (Rapid) (Enzymatics, Cat #L6030-HC-L)
10×T4 DNA Ligase Buffer (Enzymatics, Cat #B6030)
Method Conventional adapter ligation reactions were assembled in a total volume of 10 μl, comprising 1×T4 DNA Ligase Buffer, 10 pmoles of FAM substrate A, 20 or 200 pmoles of Fill-in adapter, 600 units T4 DNA Ligase (Rapid) or no ligase.

3' adapter ligation reactions were assembled in a total volume of 10 μl, containing 1×T4 DNA Ligase Buffer, 10 pmoles of FAM substrate B or 10 pmoles of FAM substrate C, 20 or 200 pmoles of 3'Adapter option 1 or 20 or 200 pmoles of 3'Adapter option 2 and 600 units T4 DNA Ligase (Rapid) or no T4 DNA ligase.

All ligation reactions were performed at 25° C. for 30 minutes. The total ligation reaction volume (10 μl) was mixed with 10 μl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat #S11494) in an oven at 65° C., visualized on a Dark reader light box (Clare Chemical Research) and photographed using a digital camera. Subsequently the gel was stained SYBR® Gold nucleic acid gel stain (Invitrogen, Cat #S11494) (not shown).

Results

Figure 19:
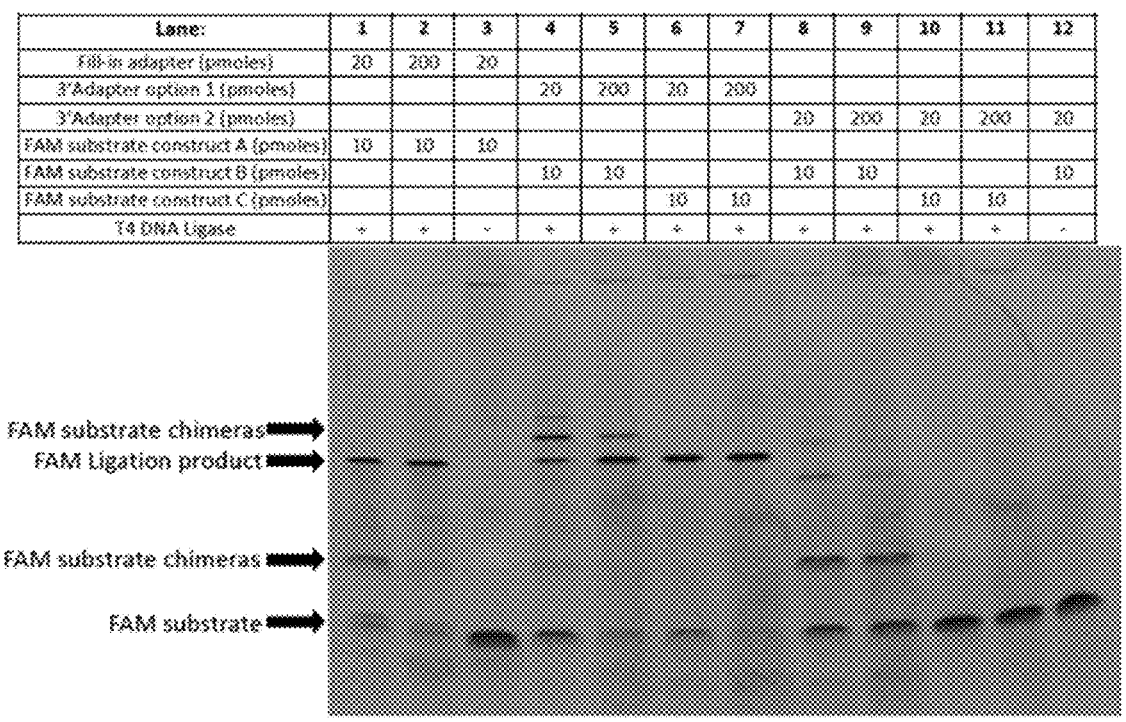
FIG. 19 provides a comparison of conventional adapter ligation to 3' adapter ligation using FAM-labeled oligonucleotide substrates by polyacrylamide gel electrophoresis as described in Example 1. Lanes 1-2 demonstrate ligation products of a fill-in adapter to a FAM-labeled substrate, Lanes 4-11 demonstrate ligation products of 3' adapters with a FAM-labeled substrate; Lanes 3 and 12 are no ligase controls.

FAM substrate A was converted into ligation product in the presence of the fill-in adapter and T4 DNA ligase (FIG. 19, lanes 1-2). This conventional adapter ligation showed some FAM substrate A chimera formation when a ratio of only 2:1 adapter:substate (FIG. 19, lane 1) was used compared to a ratio of 20:1 (lane 2). No ligation product was observed in absence of T4 DNA ligase (FIG. 19, lane 3).

Different scenarios of 3' adapter ligation were tested in lanes 4 to 12 (FIG. 19). Lanes 4 and 5 show ligation reactions between FAM substrate B and 3' Adapter option 1. At 2:1 (lane 4) or 20:1 (lane 5) adapter:substate ratio, chimeric products of higher molecular weight formed which may or not involve the 3' Adapter. However, the ligation product was more abundant and its formation favored at a ratio of 20:1 adapter:substate (lane 5). Lanes 6 and 7 show ligation reactions between FAM substrate C and 3' Adapter option 1. The reaction was favored at a ratio of 20:1 adapter:substate (lane 7) and no chimeric products were observed. Lanes 8 and 9 show ligation reactions between FAM substrate B and 3' Adapter option 2. No ligation product was observed, however chimeric products were detected. Lanes 10 and 11 show ligation reactions between FAM substrate C and 3' Adapter option 2. No ligation product was observed. No ligation product was observed in absence of T4 DNA ligase (lane 12).

Conclusion

Conventional adapter ligation required a 5'-phosphate on the FAM substrate which led to the formation of chimeras if the fill-in adapters were not in excess. Ligation of the 3' Adapter was more efficient and with fewer chimeras when the FAM substrate had a 5'hydroxy group and the 3' Adapter had a blocking 3-deoxythymidine base (option 1) which prevented ligation between adapter molecules and favored the ligation between substrate and adapter. In both cases, the ratio of adapter:substate of 20:1 was favored for ligation product formation.

Example 2

Comparison of Conventional Adapter Ligation to 3' Adapter Ligation with Sheared, Size-Selected Genomic DNA Rationale: This experiment was performed to test the effect of polishing of physically sheared genomic DNA on the efficiency of conventional or 3' adapter ligation Materials:
Fill-in adapter contains oligonucleotides 13-489 and 13-426 (Table 1)
3'Adapter; 1st oligonucleotide 13-340 (Table 1) and 2nd oligonucleotide option 1 (containing a blocking 3' deoxythymidine base at the 3' terminus) 13-559 (Table 1)
NEBuffer 2 (New England Biolabs, cat #B7002S)
100 mM 2'-deoxynucleoside 5'-triphosphate (dNTP) Set, PCR Grade (Invitrogen (Life technologies), cat #10297-018)
Adenosine 5'-Triphosphate (ATP) (New England Biolabs, cat #P0756S)
DNA Polymerase I, Large (Klenow) Fragment (New England Biolabs, cat #M0210S)
T4 DNA polymerase (New England Biolabs, cat #M0203S)
T4 Polynucleotide Kinase (New England Biolabs, cat #M0201S)

Exonuclease III (*E. coli*) (New England Biolabs, cat #M0293S)
Antarctic Phosphatase (New England Biolabs, cat #M0289S)
Antarctic Phosphatase reaction buffer (New England Biolabs, cat #B0289S)
T4 DNA Ligase (Rapid) (Enzymatics, cat #L6030-HC-L)
10×T4 DNA Ligase Buffer (Enzymatics, cat #B6030)
*E. coli* genomic DNA ATCC 11303 strain (Affymetrix, cat #14380)
M220 Focused-ultrasonicator, (Covaris, cat #PN 500295)
Pippin Prep (Sage Science)
CDF2010 2% agarose, dye free w/internal standards (Sage Science)
DNA Clean & Concentrator-5 (Zymo research, cat #D4004)
25 bp ladder DNA size marker (Invitrogen (Life technologies), cat #10488-022)

Method

*E. coli* genomic (gDNA) was resuspended in DNA suspension buffer (Teknova, cat #T0227) at a concentration of 100 ng/ul. The DNA was fragmented with the M220 Focused-ultrasonicator to 150 base pairs average size. A tight size distribution of fragmented DNA from approximately 150 bp to approximately 185 bp was subsequently isolated on a 2% agarose gel using Pippin Prep.

200 ng of the size-selected DNA was subjected to the activity of different enzymes. The reactions were assembled in a total volume of 30 µl, comprising a final concentration of 1×NEBuffer 2, 100 µM of each dNTP, 3 units T4 DNA polymerase or 5 units DNA Polymerase I, Large (Klenow) Fragment or 3 units T4 DNA polymerase and 5 units DNA Polymerase I, Large (Klenow) Fragment or 3 units T4 DNA polymerase and 5 units DNA Polymerase I, Large (Klenow) Fragment and 1 unit of Exonuclease III. Another reaction was assembled in a total volume of 30 µl comprising a final concentration 1×NEBuffer 2, 1 mM ATP, 10 units of T4 Polynucleotide Kinase. Another reaction was assembled in a total volume of 30 µl comprising a final concentration 1× Antarctic Phosphatase reaction buffer and 5 units of Antarctic phosphatase. A control reaction was assembled with 200 ng of the size-selected DNA with 1×NEBuffer 2. All reactions were incubated at 37° C. for 30 minutes and the DNA purified using the DNA Clean & Concentrator-5 columns. DNA was eluted in 30 µl of DNA suspension buffer and divided into 2 tubes of 15 µl for subsequent conventional adapter ligation or 3' adapter ligation. The conventional adapter ligations were assembled in a total volume of 30 µl comprising 1×T4 DNA Ligase Buffer, Fill-in adapter containing oligonucleotides 13-489 (220 pmoles) and 13-426 (440 pmoles), and 1200 units of T4 DNA Ligase (Rapid). The 3' adapter ligation reactions were assembled in a total volume of 30 µl, containing 1×T4 DNA Ligase Buffer, 220 pmoles of 3' Adapter 1st oligonucleotide, 440 pmoles of 3'Adapter 2nd oligonucleotide and 1200 units T4 DNA Ligase (Rapid). All reactions were purified using DNA Clean & Concentrator-5-columns. The DNA was resuspended in 10 µl of DNA suspension buffer and was mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 6% polyacrylamide gel, TBE-Urea (Invitrogen, Cat #S11494) in an oven at 65° C. The gel was stained SYBR® Gold nucleic acid gel stain (Invitrogen, Cat #S11494) and visualized on a Dark reader light box (Clare Chemical Research) and photographed using a digital camera.

Results

Figure 20:
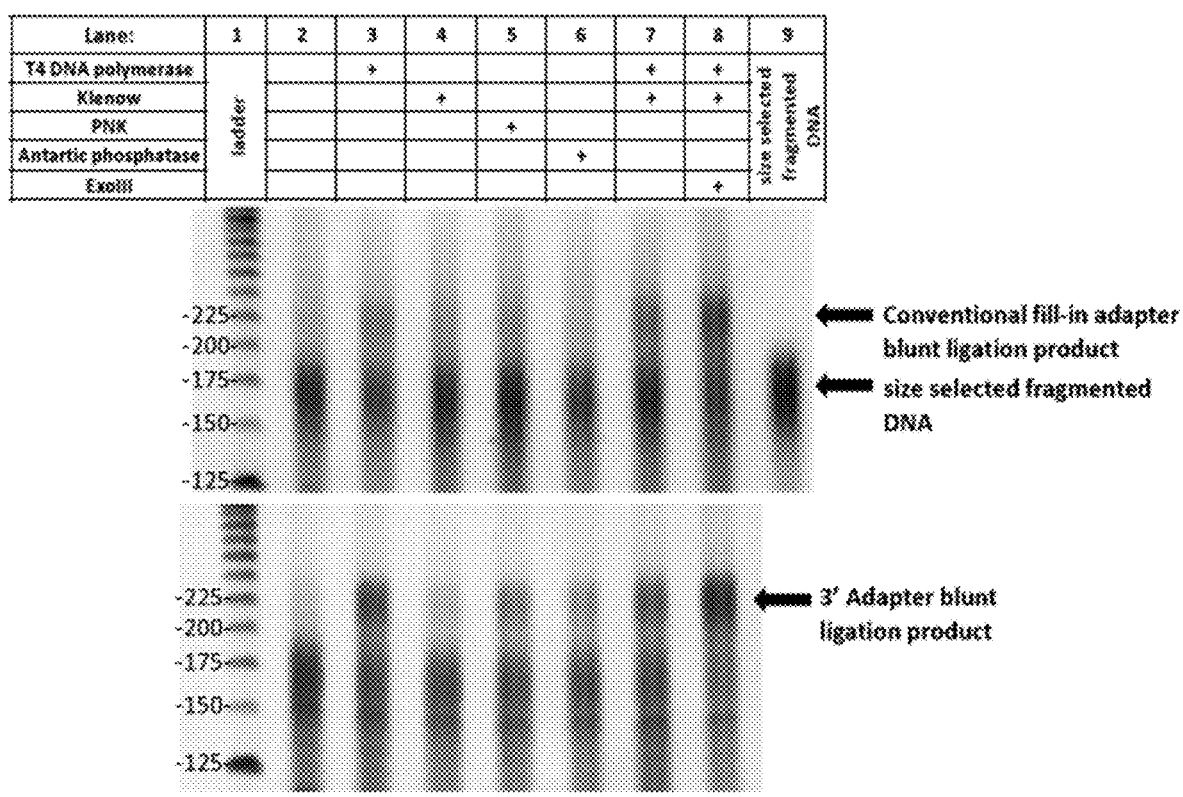
FIG. 20 provides a comparison of conventional adapter ligation to 3' adapter ligation using sheared, ~150 base pair size-selected genomic DNA substrate by polyacrylamide gel electrophoresis, as described in Example 2. Each lane tests the effect of different polishing enzymes on the efficiency of conventional (fill-in adapter) ligation or 3' adapter ligation.

The conventional adapter ligation reactions (FIG. 20, upper panel) which require a 5' phosphate on the sheared DNA substrate showed a lower efficiency than the 3' adapter ligation which does not (FIG. 20, lower panel). The ligation reactions were more efficient after treating DNA with T4 DNA polymerase alone (lane 3) or in combination with Klenow (lane 7) or Klenow plus Exonuclease III (lane 8) for both types of ligations. Treatment with Klenow, T4 Polynucleotide Kinase or Antarctic phosphatase alone (lanes 4, 5 and 6, respectively) only moderately enhanced blunt ligation compared to the non-treated DNA (lane 2). The tight range distribution fragmented DNA was loaded on lane 9.

Conclusion

Ligation of blunt adapters to sheared DNA highly depends on the polishing of this DNA. DNA polymerases like T4 DNA polymerase which present a strong 5' to 3' exonuclease activity and a 5' to 3' polymerase activity are well suited for this purpose. The conventional adapter ligation reaction depends on the presence of an intact 5' phosphate on the substrate's blunt end. However, ligation of the 3' adapter does not, since the ligation occurs at the 3' hydroxyl terminus of the fragmented DNA. Since the 5' termini of sheared DNA are not enzymatic substrates for T4 DNA polymerase, this explains why the 3' adapter was more successfully ligated than the fill-in adapter (lane 3). The combination of T4 DNA Polymerase plus Klenow and Exonuclease III significantly enhanced the blunt ligation. Exonuclease III activity produced blunt ends required for ligation of blunt adapters by removing 3' hydroxyl termini which could be damaged at the 3' terminus of DNA. Exonuclease III also possesses a 3' phosphatase activity, which makes the 3' terminus accessible to DNA polymerase polishing activity.

Example 3

Temperature Optimization for 5' Adapter Ligation Using a FAM-Labeled Oligonucleotide Substrate Rationale: This experiment assessed the temperature dependence and dNTP composition on nick translation mediated 5' adapter ligation.

Materials:

5' adapter oligonucleotide for nick-translation (13-144) (Table 1)
FAM oligonucleotide substrate (13-581) (Table 1)
Oligonucleotide template (13-582) (Table 1)
100 mM 2'-deoxynucleoside 5'-triphosphate (dNTP) Set, PCR Grade (Invitrogen (Life technologies), cat #10297-018)
*E. coli* DNA ligase (New England BioLabs, cat #M0205S)
10× *E. coli* DNA Ligase Reaction Buffer (New England BioLabs)
Taq DNA polymerase, concentrated 25 U/ul (Genscript, cat #E00012)
25 bp ladder DNA size marker (Invitrogen (Life technologies), cat #10488-022)

Method

A first set of nick translation reactions was assembled in a total volume of 30 µl, comprising a final concentration of 1× *E. coli* DNA ligase Buffer, 30 pmoles of FAM oligonucleotide substrate, 45 pmoles of 5' adapter oligonucleotide for nick-translation and 45 pmoles of oligonucleotide template, 200 µM of dTTP or a mix of 200 uM of each dTTP/dGTP or 200 uM of each dATP/dTTP/dGTP and 2.5 units of Taq DNA polymerase or no Taq DNA polymerase. The reactions were incubated at 30° C., 40° C. or 50° C. for 30 minutes.

A second set of nick translation reactions followed by ligations were assembled in 30 ul comprising a final concentration of 1× E. coli DNA ligase Buffer, 30 pmoles of FAM oligonucleotide substrate, 45 pmoles of 5' adapter oligonucleotide for nick-translation and 45 pmoles of oligonucleotide template, 200 uM of each dATP/dTTP/dGTP, and 2.5 units of Taq DNA polymerase. The reactions were incubated at 50° C., 53° C., 56° C. or 60° C. for 30 minutes. 10 µl of those reactions were taken for gel analysis. 10 units of E. coli ligase were added to the 20 µl left and incubated at 25° C. for 15 minutes. An additional control reaction was assembled in 30 ul comprising a final concentration of 1× E. coli DNA ligase Buffer, and 30 pmoles of FAM oligonucleotide substrate. 10 µl of those reactions were mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, cat #S11494) in an oven at 65° C., visualized on a Dark reader light box (Clare Chemical Research) and photographed using a digital camera.

Results

Figure 21A:
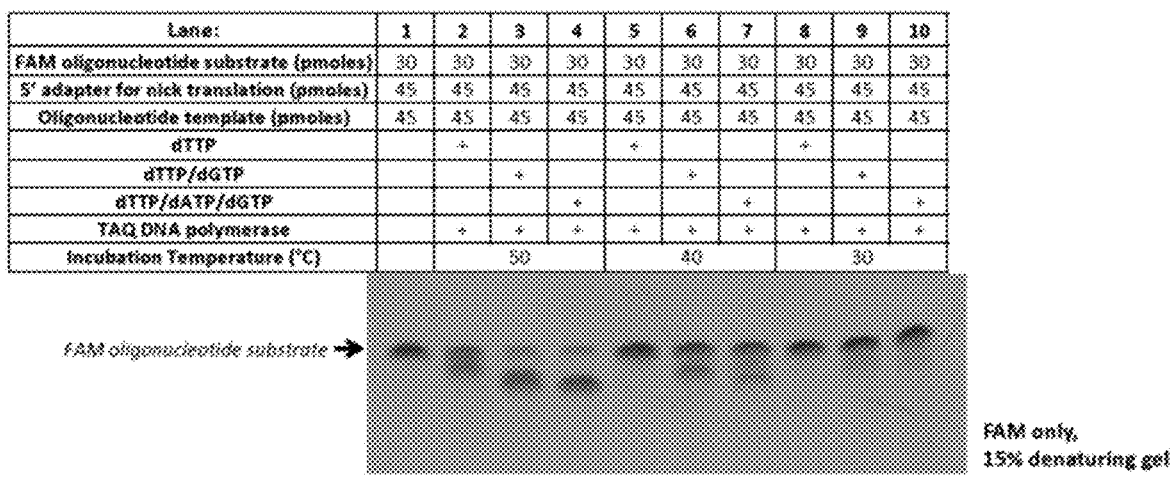
FIG. 21A and FIG. 21B depicts optimization for 5' adapter ligation using a FAM-labeled oligonucleotide substrate, as described in Example 3.
Figure 21B:
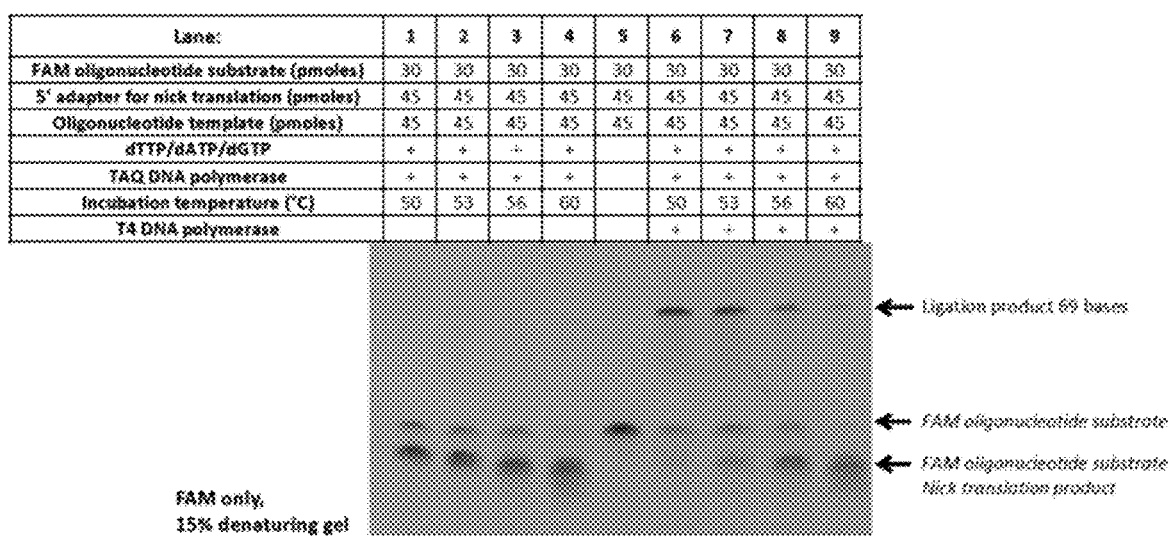

As shown in FIG. 21, panel A, Taq DNA polymerase elongated the 3' hydroxyl terminus of the 5' adapter oligonucleotide for nick-translation, removing nucleotides on the FAM oligonucleotide substrate by its 5' flap endonuclease activity. Adding dTTP only (FIG. 21, lanes 2, 5, 8, panel A) allowed only the addition of one base at the 3' terminus of the 5' adapter oligonucleotide for nick-translation, adding dTTP/dGTP (FIG. 21, lanes 3, 6, 9, panel A) allowed the addition of three bases and adding dTTP/dGTP/dATP (FIG. 21, lanes 4, 7, 10, panel A) allowed the addition of four bases which was proportional to the number of bases cleaved from the FAM oligonucleotide substrate (FIG. 21, panel A). The number of bases cleaved from the FAM oligonucleotide substrate also depended on the temperature in which the reactions take place. At 50° C. (FIG. 21, lanes 2 to 4, panel A), the amount of bases cleaved from the FAM oligonucleotide substrate was greater than those cleaved at 40° C. or 30° C. The efficiency of the nick translation and the amount of FAM oligonucleotide substrate cleaved was also highly dependent on the temperature of the reaction. At 40° C. or 30° C., adding dTTP only (FIG. 21, lanes 5, 8, panel A), did not allow any cleavage of the FAM oligonucleotide substrate, as observed at 50° C. (FIG. 21, lane 2, panel A). Adding dTTP/dGTP or dTTP/dGTP/dATP allowed some cleavage at 40° C. (lanes 6 and 7) or 30° C. (lanes 9 and 10) at a lower efficacy than at 50° C. (lanes 3 and 4). Lane 1 (FIG. 21, panel A) shows FAM oligonucleotide substrate in the absence of Taq DNA polymerase.

The efficiency of nick translation and the amount of FAM oligonucleotide substrate cleaved was highly dependent on the temperature of the reaction. At 60° C., the FAM oligonucleotide substrate was almost entirely processed to smaller species (FIG. 21, lane 4, panel B). The FAM oligonucleotide substrate cleavage product size also decreased as the temperature of the reaction increased (FIG. 21, lanes 1 to 4, panel B). Lane 5 (FIG. 21, panel B) shows the FAM oligonucleotide substrate in the absence of Taq DNA polymerase. During the nick translation reaction, Taq DNA polymerase cleaves the 5' terminus of the FAM oligonucleotide substrate and generates a terminal 5' phosphate that is essential for E. coli ligase to covalently attach the 3' terminus of the 5' adapter oligonucleotide to the 5' terminus of the FAM oligonucleotide substrate. The ligation efficiency was also dependent on the temperature at which the reaction took place. The ligation product was more abundant at 50° C. (lane 6) and almost absent at 60° C. (lane 9), and an intermediate amount of ligation product was generated at 53° C. and 56° C.

Conclusion

During nick translation, the number of bases cleaved from the FAM oligonucleotide substrate depended on the complementary dNTPs introduced in the reaction and the temperature at which the reactions took place. During the nick translation reaction, Taq DNA polymerase cleaves the 5' terminus of the FAM oligonucleotide substrate and generates a terminal 5' phosphate that is essential for E. coli ligase to ligate two fragments. FAM oligonucleotide substrates cleaved by nick translation at higher temperatures were poor substrates for ligation by E. coli ligase because of a potential gap formed between the 3' terminus of the 5' adapter oligonucleotide and the 5' terminus of the FAM oligonucleotide substrate.

Example 4

Analysis of dNTP Composition Effects on 5' Adapter Ligation

Rationale: This experiment was performed to assess the degree of nick-translation that occurs in the presence of varied dNTP composition and the effect on the coupled ligation reaction.

Materials:
5' adapter oligonucleotide for nick-translation (13-144) (Table 1)
FAM oligonucleotide substrate (13-581) (Table 1)
Oligonucleotide template (13-582) (Table 1)
100 mM 2'-deoxynucleoside 5'-triphosphate (dNTP) Set, PCR Grade (Invitrogen (Life technologies), cat #10297-018)
25 bp ladder DNA size marker (Invitrogen (Life technologies), cat #10488-022)
E. coli DNA ligase (Enzymatics, cat #L6090L)
10× E. coli DNA ligase Buffer (Enzymatics, cat #B6090)
Taq-B DNA polymerase (Enzymatics, cat #P7250L)

Method

The reactions were assembled in a total volume of 30 µl, comprising a final concentration of 1× E. coli DNA ligase Buffer, 30 pmoles of FAM oligonucleotide substrate, 45 pmoles of 5' adapter oligonucleotide for nick-translation and 45 pmoles of oligonucleotide template, 200 µM of each 4 dNTP or a mix of 200 µM of each: dCTP, dTTP, dGTP or dATP, dTTP, dGTP or dATP, dCTP, dGTP or dATP, dTTP, dCTP or no dNTP, 10 units of E. coli ligase and 10 units of Taq-B DNA polymerase. All reactions were incubated at 40° C. for 30 minutes. 10 µl of those reaction were mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat #S11494) in an oven at 65° C., visualized on a Dark reader light box (Clare Chemical Research) and photographed using a digital camera (lower panel). Subsequently the gel was stained SYBR® Gold nucleic acid gel stain (Invitrogen, Cat #S11494), visualized on a Dark reader light box (Clare Chemical Research) and photographed using a digital camera (upper panel).

Results

Figure 22:
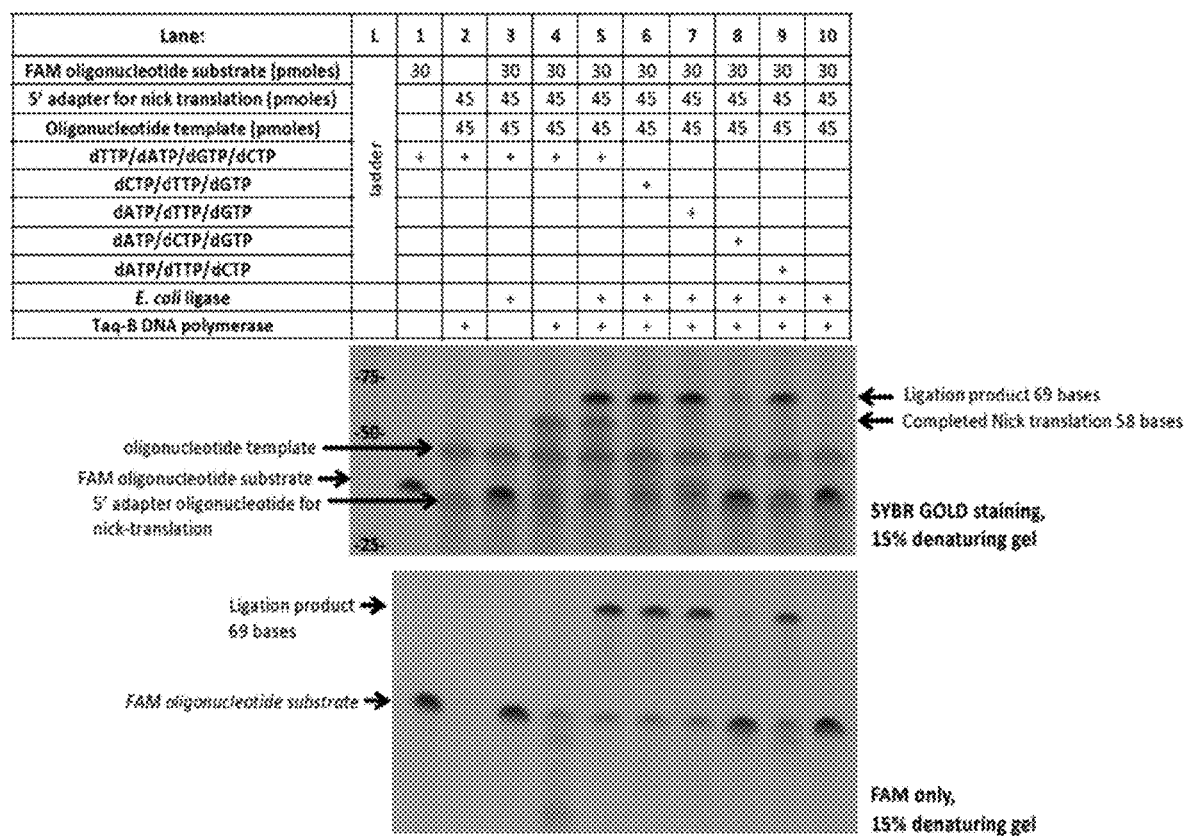
FIG. 22 provides analysis of dNTP composition and ligase effects on 5' adapter nick translation and ligation, as described in Example 4. The polyacrylamide gel electrophoresis depicts nick translation and ligation products produced from varying the dNTP composition from combinations of 3 to 4 nucleotides.

The first two lanes of FIG. 22 show control oligonucleotide. In the absence of Taq-B DNA polymerase, E. coli ligase alone cannot ligate the 5' adapter oligonucleotide to the FAM oligonucleotide substrate because the FAM substrate lacks a 5' phosphate modification (FIG. 22, lane 3). In the presence of Taq-B DNA polymerase and the 4 dNTPs, the 5' adapter oligonucleotide was extended, forming a new product of 58 bases and the FAM oligonucleotide substrate was displaced and degraded by the 5' flap endonuclease activity of Taq-B DNA polymerase (FIG. 22, lane 4). In the presence of E. coli ligase, Taq-B DNA polymerase and dATP/dTTP/dGTP (FIG. 22, lane 7) or dCTP/dTTP/dGTP (FIG. 22, lane 6) or dATP/dTTP/dCTP (FIG. 22, lane 9), nick translation was limited to the addition of four, three or one bases, respectively. With the extension of the 5' adapter, a flap was formed at the 5' terminus of the FAM oligonucleotide substrate. This flap becomes a substrate for the Taq-B 5' flap endonuclease activity creating a required 5' phosphate for ligation. The 5' adapter was ligated to the FAM oligonucleotide substrate forming a product of 69 bases. A flap of three or four bases (FIG. 22, lane 6 and 7) supported the ligation more efficiently than the one base flap (FIG. 22, lane 9). In the presence of E. coli ligase, Taq-B DNA polymerase and dATP/dCTP/dGTP (FIG. 22, lane 8), a faint band corresponding to the ligation product was observed. A weak ligation activity may come from the incorporation of an "unmatched" base (A C or G instead of T), leading to formation of the flap on some FAM oligonucleotide substrates. In the presence of E. coli ligase, Taq-B DNA polymerase and no dNTP, no ligation product was observed. In the presence of E. coli ligase, Taq-B DNA polymerase and the 4 dNTPs, the 5' adapter was ligated to the FAM oligonucleotide substrate forming a product of 69 bases (FIG. 22, lane 5). Since the 5' adapter and the oligonucleotide template were in excess compared to the FAM oligonucleotide substrate, a nick translation product was also observed at 58 bases (FIG. 22, lane 5, upper panel). However, the same amount of ligation product was observed. The 25 bp ladder DNA size marker was loaded on lane M.

Conclusion

Phosphorylation of the 5' terminus of the FAM oligonucleotide substrate is required for ligation. The polymerase activity of Taq DNA polymerase in the presence of dNTPs is required to perform the extension of the 5' adapter, which creates a flap at the 5' terminus of the FAM oligonucleotide substrate. This flap is a good substrate for the 5' flap endonuclease activity of Taq DNA polymerase, generating a perfect 5' phosphate substrate for ligation by E. coli ligase. The ligation occurs even if the flap is only formed by one base. The ligation also occurs when all four dNTPs are present which does not restrict the length of the flap or the extent of nick translation, suggesting that the ligation occurs immediately after a 5' phosphate is created at the 5' terminus of the FAM oligonucleotide substrate.

Example 5

Coupled Nick Translation-Ligation Reaction with Thermo Stable Enzymes

Rationale: This experiment was performed to assess the effect of reaction temperature and number of units of Taq DNA Polymerase enzyme in the coupled reaction.

Materials:
5' adapter oligonucleotide for nick-translation (13-144) (Table 1)
FAM oligonucleotide substrate (13-581) (Table 1)
Oligonucleotide template (13-582) (Table 1)
100 mM 2'-deoxynucleoside 5'-triphosphate (dNTP) Set, PCR Grade (Invitrogen (Life technologies), cat #10297-018)
Taq DNA ligase (New England BioLabs, cat #M0208S)
10×Taq DNA ligase Reaction Buffer (New England BioLabs)
Taq DNA polymerase, concentrated 25 U/ul (Genscript, cat #E00012)

Method

The reactions were assembled in a total volume of 30 µl, comprising a final concentration of 1× Taq DNA ligase reaction Buffer, 30 pmoles of FAM oligonucleotide substrate, 45 pmoles of 5' adapter oligonucleotide for nick-translation and 45 pmoles of oligonucleotide template, 200 µM of each: dATP, dTTP, dGTP or dTTP, 40 units of Taq DNA ligase, or 80 units Taq DNA ligase, or 120 units Taq DNA ligase and 10 units of Taq DNA polymerase. Reactions were incubated at 45° C., 50° C., 55° C., or 60° C., for 30 minutes. 10 µl of those reactions were mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat #S11494) in an oven at 65° C., visualized on a Dark reader light box (Clare Chemical Research) and photographed using a digital camera.

Results

Figure 23A:
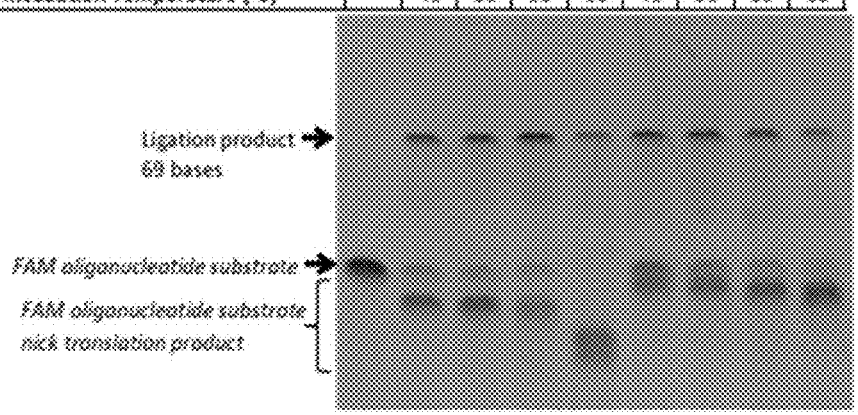
FIG. 23A provides data related to a coupled nick translation-ligation reaction with thermo stable enzymes, as described in Example 5. The polyacrylamide gel electrophoresis depicts nick translation ligation products produced from varying the dNTP composition from combinations of 1-3 nucleotides and varying the reaction temperature when using thermostable polymerase and ligase.
Figure 23B:
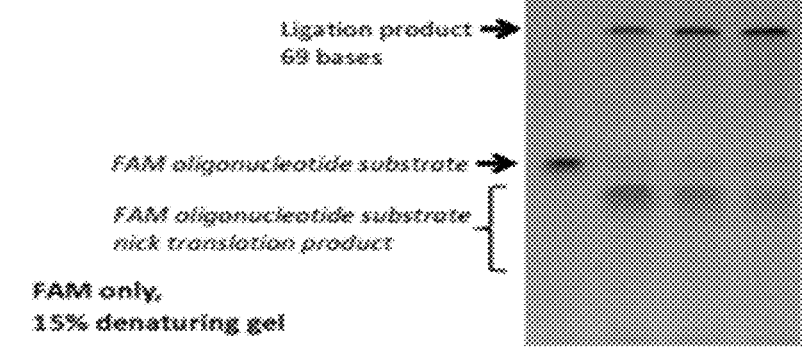
FIG. 23B provides data related to a coupled nick translation-ligation reaction with thermo stable enzymes, as described in Example 5. The polyacrylamide gel electrophoresis depicts nick translation ligation products produced from varying the number of units of thermostable ligase in the reaction.

Taq DNA polymerase elongated the 3' hydroxyl terminus of the 5' adapter oligonucleotide, removing nucleotides on the FAM oligonucleotide substrate by its 5' flap endonuclease activity. Adding dTTP/dGTP/dATP (FIG. 23, lanes 2 to 5, panel A) or dTTP (FIG. 23, lanes 6 to 9, panel A) allowed the addition of four and one bases, respectively, at the 3' terminus of the 5' adapter oligonucleotide and the subsequent cleavage of the 5' terminus of the FAM oligonucleotide substrate. At 60° C. the ligation was impaired (FIG. 23, lanes 5 and 9, panel A). The efficiency of ligation was not affected by adding dTTP/dGTP/dATP (FIG. 23, lanes 2 to 5, panel A) or dTTP (FIG. 23, lanes 6 to 9, panel A). The ligation efficiency was dependent on the amount of Taq DNA ligase present in the reaction. The ligation product was more abundant when 120 units of Taq DNA ligase (FIG. 23, lane 4, panel B) were added to the reaction compared to 40 or 80 units (FIG. 23, lane 2 and 3, panel B, respectively). Lane 1, panel A and lane 1, panel B show control oligonucleotides without enzymes.

Conclusion

During the nick translation reaction, Taq DNA polymerase cleaves the 5' terminus of the FAM oligonucleotide substrate and generates a 5' phosphate terminus essential for Taq DNA ligase between 45° C. and 60° C. to perform ligation. The ligation was reduced at 60° C. The concentration of Taq DNA ligase in the reaction also affected the efficiency of the ligation, as more product was observed in the presence of 120 U enzyme compared to 80 U and 40 U.

Example 6

Coupled Displacement-Cleavage-Ligation Reaction

Rationale: This experiment was performed to demonstrate that either thermostable Taq DNA ligase or thermolabile E. coli ligase can be combined with Taq DNA Polymerase in the coupled displacement-cleavage ligation reaction.

Materials:
5' adapter oligonucleotide for displacement-cleavage (13-156) (Table 1)
FAM oligonucleotide substrate (13-581) (Table 1)
Oligonucleotide template (13-582) (Table 1)
Taq DNA ligase (New England BioLabs, cat #M0208S)
10×Taq DNA ligase Reaction Buffer (New England BioLabs)
Taq DNA polymerase, concentrated 25 U/ul (Genscript, cat #E00012)
E. coli DNA ligase (New England BioLabs, cat #M0205S)
10× E. coli DNA Ligase Reaction Buffer (New England BioLabs)

Method

The reactions were assembled in a total volume of 30 µl, comprising a final concentration of 1× E. coli DNA ligase reaction Buffer or 1×Taq DNA ligase reaction Buffer, 30 pmoles of FAM oligonucleotide substrate, 45 pmoles of 5' adapter oligonucleotide for displacement-cleavage and 45 pmoles of oligonucleotide template, 10 units of E. coli DNA ligase or 40 units Taq DNA ligase, and 10 units of Taq DNA polymerase. Reactions were incubated at 40° C. or 45° C. for 30 minutes. 10 µl of those reactions were mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat #511494) in an oven at 65° C., visualized on a Dark reader light box (Clare Chemical Research) and photographed using a digital camera.

Results

The 5' adapter oligonucleotide for displacement-cleavage has an extra matching base "T" at is 3' terminus, which overlaps with the 5' terminus of the FAM oligonucleotide substrate. When the 3' terminus of the 5' adapter oligonucleotide displaces the 5' terminus of the FAM oligonucleotide substrate, the 5' flap endonuclease activity of Taq DNA polymerase cleaves the 5' terminus of the FAM oligonucleotide substrate to create a 5' phosphate which is essential for the ligation with E. coli ligase (FIG. 24, lane 2, panel A) or Taq DNA ligase (FIG. 24, lane 2, panel B). Lane 1 for panels A and B show oligonucleotide controls without enzymes.

Conclusion

In the absence of dNTPs, no extension of the 5' adapter occurs. However, Taq DNA polymerase can cleave the 5' terminus of the FAM oligonucleotide substrate and generates a terminal 5' phosphate that is essential for E. coli DNA ligase or Taq DNA ligase to perform ligation.

Example 7

Coupled Displacement-Cleavage-Ligation Reaction with Either "N" Universal/Degenerate or "T" Substrate-Specific 5' Adapter 3' Overhang Rationale: This experiment demonstrates that 5' adapter ligation using a flap endonuclease can be performed if either the 5' adapter 3' terminal overhang is a sequence-specific match or if it is composed of a degenerate non sequence-specific 'N'.

Materials:
5' adapter oligonucleotide for displacement-cleavage "T" (13-607) (Table 1)
5' adapter oligonucleotide for displacement-cleavage "N" (13-596) (Table 1)
FAM oligonucleotide substrate (13-581) (Table 1)
Oligonucleotide template (13-582) (Table 1)
Taq DNA ligase (New England BioLabs, cat #M0208S)
10×Taq DNA ligase Reaction Buffer (New England BioLabs)
Taq DNA polymerase, concentrated 25 U/ul (Genscript, cat #E00012)
E. coli DNA ligase (New England BioLabs, cat #M0205S)
10× E. coli DNA Ligase Reaction Buffer (New England BioLabs)

Method

The reactions were assembled in a total volume of 30 µl, comprising a final concentration of 1×Taq DNA ligase reaction buffer, 30 pmoles of FAM oligonucleotide substrate, 45 pmoles of 5' adapter oligonucleotide "T" or 45 pmoles of 5' adapter oligonucleotide "N" 1 or 180 pmoles of 5' adapter oligonucleotide "N" or 450 pmoles of 5' adapter oligonucleotide "N" and 45 pmoles of oligonucleotide template, 40 units Taq DNA ligase, and 10 units of Taq DNA polymerase. Reactions were incubated at 45° C. or 50° C. or 55° C. for 30 minutes or cycling 8 times between 45° C. for 3 minutes, 65° C. for 15 seconds. 10 µl of those reactions were mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat #S11494) in an oven at 65° C., visualized on a Dark reader light box (Clare Chemical Research) and photographed using a digital camera.

Results

Figure 25:
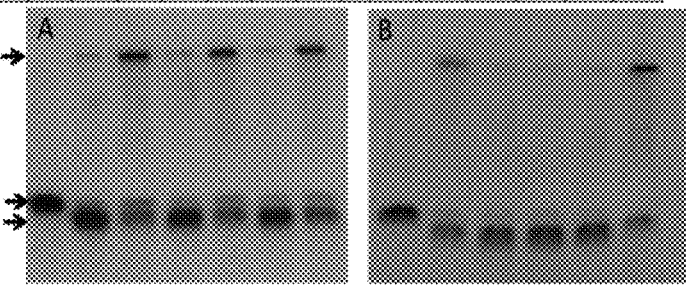
FIG. 25 provides data related to a coupled displacement-cleavage-ligation reaction with either "N" universal/degenerate or "T" substrate-specific 5' adapter 3' overhang, as described in Example 7. The polyacrylamide gel electrophoresis depicts the effect on 5' flap endonuclease cleavage mediated ligation when the 5' adapter 3' terminal overhang is a sequence specific match "T" or if it is composed of a degenerate non-sequence-specific "N", under varying temperature conditions (panel A), or when the concentration of 5' adapter "N" is varied (panel B).

When the 5' adapter oligonucleotide for displacement-cleavage has a "T" at its 3' terminus matching the oligonucleotide template (FIG. 25, lanes 3, 5, 7, panel A), (which overlaps with the 5' terminus of the FAM oligonucleotide substrate), ligation occurred at a higher rate than when the 5' adapter oligonucleotide had a degenerate "N" base, where during oligo synthesis, all four nucleotides were present at this position (FIG. 25, lanes 2, 4, 6, panel A), which is only a perfect match to the oligonucleotide template one fourth of the time. Different reaction temperatures (45° C., 50° C. and 55° C.), were tested without improving the ligation using the 5' adapter oligonucleotide "N" (FIG. 25, lanes 2, 4, 6, panel A). Also, different amounts of 5' adapter oligonucleotide "N" (45 pmoles, 180 pmoles and 450 pmoles), were tested without improving the ligation reaction (FIG. 25, lanes 3 to 5, panel B). However, temperature cycling of the reaction between 45° C. and 65° C. allowed the ligation to occur at the highest rate which was comparable to the "T" matching base 5' adapter oligonucleotide (FIG. 25, lane 6, panel B). Lane 1 for panels A and B show oligonucleotide controls without enzymes.

Conclusion

To allow efficient 5' adapter ligation coupled to displacement-cleavage using the 5' adapter oligonucleotide "N", cycling between a first temperature for Taq DNA ligase to operate and a second temperature where the duplex between the oligonucleotide template and the 5' adapter oligonucleotide "N" could dissociate was critical. The cycling conditions permitted multiple associations between the 5' adapter oligonucleotide "N" and the oligonucleotide template where the displacement-cleavage reaction occurred only if the 3' terminal base of the 5' adapter oligonucleotide is a perfect match to the template and can displace the 5' terminus of the FAM oligonucleotide substrate.

Example 8

Coupled Nick-Translation-Ligation Reaction Using DNA Polymerase I

Rationale: This experiment demonstrates that a DNA polymerase I, which possesses 5'-3' exonuclease activity, can also participate in the nick translation coupled adapter ligation method.

Materials:
  5' adapter oligonucleotide for nick-translation (13-144) (Table 1)
  FAM oligonucleotide substrate (13-581) (Table 1)
  Oligonucleotide template (13-582) (Table 1)
  100 mM 2'-deoxynucleoside 5'-triphosphate (dNTP) Set, PCR Grade (Invitrogen (Life technologies), cat #10297-018)
  25 bp ladder DNA size marker (Invitrogen (Life technologies), cat #10488-022)
  E. coli DNA ligase (Enzymatics, cat #L6090L)
  10× E. coli DNA ligase Buffer (Enzymatics, cat #B6090)
  Taq-B DNA polymerase (Enzymatics, cat #P7250L)
  DNA polymerase I (New England Biolabs, cat #M0209S)

Method

The reactions were assembled in a total volume of 30 comprising a final concentration of 1× E. coli DNA ligase Buffer, 30 pmoles of FAM oligonucleotide substrate, 45 pmoles of 5' adapter oligonucleotide for nick-translation and 45 pmoles of oligonucleotide template, 200 µM of each 4 dNTPs, 10 units of E. coli ligase and 10 units of Taq-B DNA polymerase or 5 units of DNA polymerase I or 1 unit of DNA polymerase I. Reactions were incubated at 40° C., 18° C., 16° C. or 14° C. for 30 minutes. 10 µl of each reaction was mixed with 10 µl of 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat #S11494) in an oven at 65° C., visualized on a Dark reader light box (Clare Chemical Research) with an without SYBR gold (upper panel and lower panel, respectively), and photographed using a digital camera.

Results

Figure 26:
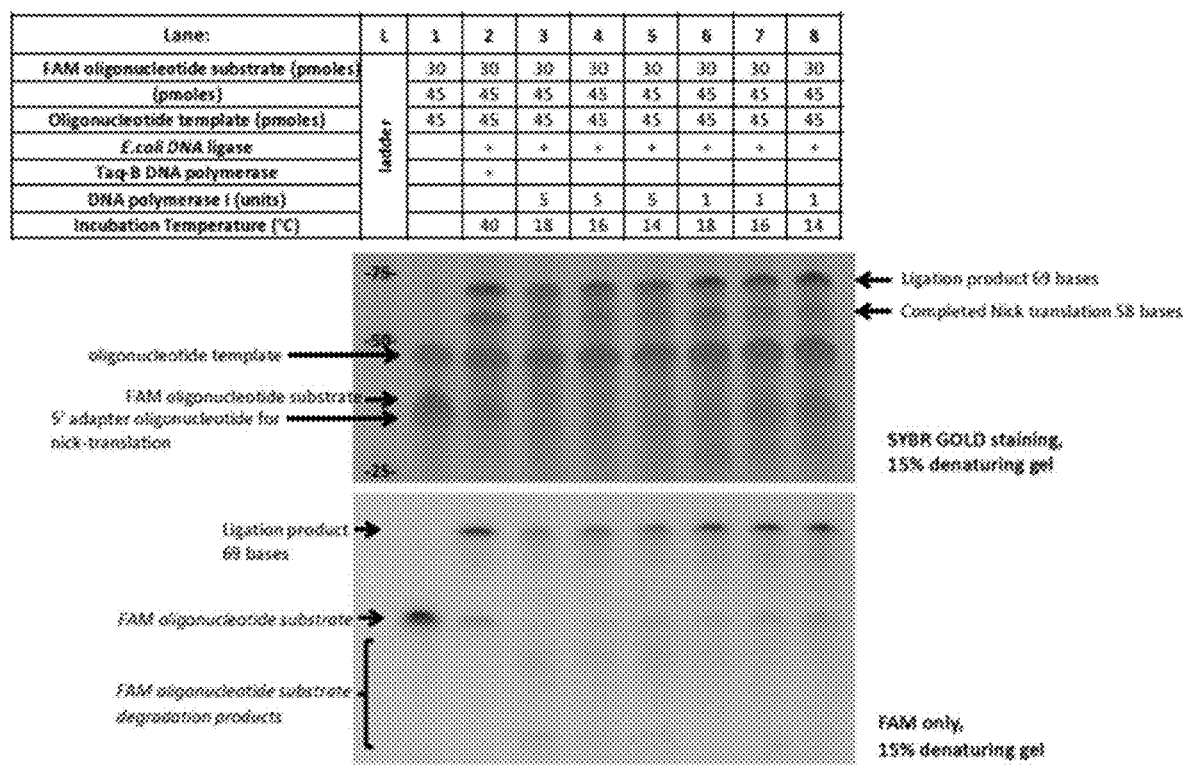
FIG. 26 provides data related to a coupled nick-translation-ligation reaction using DNA polymerase I, as described in Example 8. The polyacrylamide gel electrophoresis depicts nick translation mediated ligation products when using either Taq DNA polymerase at 40° C. or DNA Polymerase I at 14-18° C. with 1-5 enzyme units.

The first lane of FIG. 26 shows the no enzyme control. In the presence of Taq-B DNA polymerase and E. coli ligase (FIG. 26, lane 2), the 5' adapter oligonucleotide was either ligated to the FAM oligonucleotide substrate producing a 69 base product (FIG. 26, lane 2, upper and lower panels) or completely extended forming a new product of 58 bases (FIG. 26, lane 2, upper panel). The 69 base product was from extension by Taq-B DNA polymerase and formation of a flap at the 5' end of the FAM oligonucleotide substrate. The Taq-B 5' flap endonuclease activity cut the flap and generated a 5' phosphate that was used by the E. coli ligase to complete the ligation. The 58 base product was obtained when the FAM oligonucleotide substrate was completely displaced during extension and degraded by the 5' flap endonuclease activity of Taq-B DNA polymerase. These two types of products were also formed when Taq-B DNA polymerase was replaced by DNA polymerase I (FIG. 26, lanes 3 to 8) which has a 5'→3' exonuclease activity that removes nucleotides ahead of a growing DNA chain one by one and allows nick translation to occur. The reaction was performed with either 5 units of DNA polymerase I (FIG. 26, lanes 3 to 5) or 1 unit of DNA polymerase I (FIG. 26, lanes 6 to 8). The reaction with the thermophilic Taq-B DNA polymerase was performed at 40° C. (FIG. 26, lane 2) while the reactions performed with the mesophilic DNA polymerase I were at 18° C. (FIG. 26, lanes 3 and 6), 16° C. (FIG. 26, lanes 4 and 7) or 14° C. (FIG. 26, lanes 5 and 8). The 69 base ligation product was obtained in all cases but the addition of only 1 unit of DNA polymerase I (FIG. 26, lanes 6 to 8) was more efficient than with 5 units (FIG. 26, lanes 3 to 5). This is explained by the very strong 5'→3' exonuclease activity of DNA polymerase that causes the rapid partial degradation of the FAM oligonucleotide substrate before it can be ligated. Degradation products were observed in the bottom part of the lower panel (FIG. 26, lanes 3 to 5). The 25 bp ladder DNA size marker was loaded on lane M.

Conclusion

Taq-B DNA polymerase (thermophilic polymerase) and DNA polymerase I (mesophilic polymerase) can both be used to perform the nick translation mediated ligation but they require different conditions to be fully active. They both generated a 69 base product which was the result of excision of the 5' end followed by ligation but they use different mechanisms. While Taq-B created a flap that was cut to produce the required 5' phosphorylated end for the ligation by E. coli ligase, DNA polymerase I removed nucleotides one by one in front of the growing strand and generated the 5' phosphorylated nucleotide which was the perfect substrate for E. coli ligase to join the two fragments. DNA polymerase I can be used to perform 5' adapter ligation mediated by nick translation.

Example 9

Polishing is Required for Blunt Ligation of Physically Sheared DNA and Dephosphorylation Prevents the Formation of Chimeric Ligation Products Rationale: This experiment demonstrates the importance of end polishing and dephosphorylation for blunt ligation of adapters to physically sheared DNA substrates.

Materials:
  Blue Buffer (Enzymatics, cat #B0110)
  T4 DNA Ligase (Rapid) (Enzymatics, cat #L6030-HC-L)
  10×T4 DNA Ligase Buffer (Enzymatics, cat #B6030)
  100 mM 2'-deoxynucleoside 5'-triphosphate (dNTP) Set, PCR Grade (Invitrogen (Life technologies), cat #10297-018)
  Adenosine 5'-Triphosphate (ATP) (New England Biolabs, cat #P0756S)
  DNA Polymerase I, Large (Klenow) Fragment (New England Biolabs, cat #M0210S)
  T4 DNA polymerase (New England Biolabs, cat #M0203S)
  T4 Polynucleotide Kinase (New England Biolabs, cat #M0201S)
  Shrimp alkaline phosphatase (Affymetrix, cat #78390)
  T4 DNA Ligase (Rapid) (Enzymatics, cat #L6030-HC-L)
  10×T4 DNA Ligase Buffer (Enzymatics, cat #B6030)
  E. coli genomic DNA ATCC 11303 strain (Affymetrix, cat #14380)
  M220 Focused-ultrasonicator, (Covaris, cat #PN 500295)
  Pippin Prep (Sage Science)
  DNA Clean & Concentrator-5—(Zymo research, cat #D4004)
  CDF2010 2% agarose, dye free w/internal stds (Sage Science)

Method

E. coli gDNA was resuspended in DNA suspension buffer (Teknova, cat #T0227) at a concentration of 100 ng/ul. The DNA was fragmented with the M220 Focused-ultrasonicator to 150 base pairs average size. A tight distribution of fragmented DNA from ~150 bp to ~185 bp was subsequently size-selected from a 2% agarose gel using pippin prep.

In a set of reactions A, 100 ng or 500 ng of the size-selected DNA was subjected to the activity of polishing enzymes. The reactions were assembled in a total volume of 30 µl, comprising a final concentration of 1× Blue buffer, 100 µM of each dNTP, 3 units T4 DNA Polymerase, 5 units DNA Polymerase I, Large (Klenow) Fragment, 1 mM ATP, 10 units of T4 Polynucleotide Kinase. The reactions were incubated at 30° C., for 20 minutes. The DNA was purified using the DNA Clean & Concentrator-5 columns. The DNA was eluted in 15 µl of DNA suspension buffer and a subsequent dephosphorylation reactions B was followed by adapter ligation or were placed directly into the ligation reaction without dephosphorylation. The dephosphorylation reactions were assembled in a 30 µl final volume, including the processed DNA, 1× Blue buffer, and 1 unit of shrimp alkaline phosphatase. The reactions were incubated at 37° C., for 10 minutes. The DNA was purified using the DNA Clean & Concentrator-5 columns and eluted in 15 µl of DNA suspension buffer.

In a set of reactions C, 100 ng of the size-selected DNA was subjected to dephosphorylation followed by polishing or directly to polishing in a set of reaction D. The dephosphorylation reactions were assembled in a 30 µl final volume, including the processed DNA, 1× Blue buffer, and 1 unit of shrimp alkaline phosphatase. The reactions were incubated at 37° C., for 10 minutes. The DNA was purified using the DNA Clean & Concentrator-5 columns and eluted in 15 µl of DNA suspension buffer. The polishing reactions D were assembled in a total volume of 30 µl, comprising a final concentration of 1× Blue buffer, 100 µ4 of each dNTP, 3 units T4 DNA polymerase, 5 units DNA Polymerase I, Large (Klenow) Fragment, (lanes 6 to 7). The DNA was purified using the DNA Clean & Concentrator-5 columns and eluted in 15 µl of DNA suspension buffer.

Figure 27:
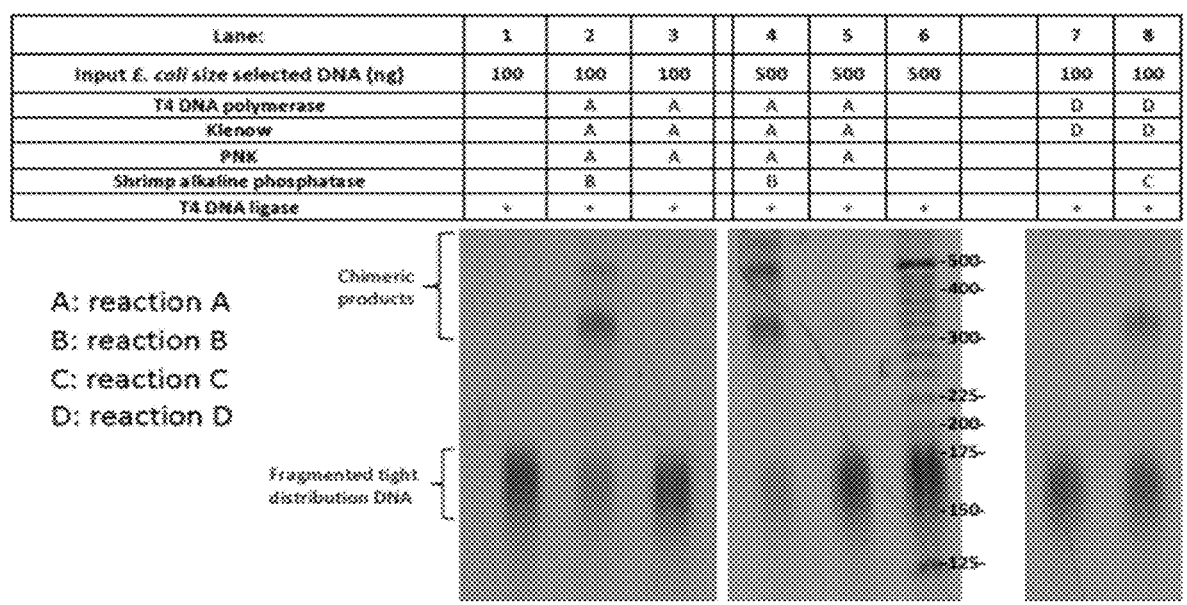
FIG. 27 demonstrates polishing is required for blunt ligation of physically sheared DNA and dephosphorylation prevents the formation of chimeric ligation products, as described in Example 9. The polyacrylamide gel electrophoresis depicts the ligation products following treatment with reactions A-D on size-selected sheared DNA, wherein reactions A and D contain polishing enzymes, and reactions B and C contain a phosphatase.

After purification, all the previous reactions were subject to ligation reactions. Reactions were assembled in a final volume of 30 µl, comprising the processed DNA, 1×T4 DNA ligase reaction buffer and 1200 units of T4 DNA ligase. The reactions were incubated at 25° C., for 15 minutes. 33 ng of DNA from each ligation was mixed with 2× formamide loading buffer (97% formamide, 10 mM EDTA, 0.01% bromophenol blue and 0.01% xylene cyanol), heated at 95° C. for 5 minutes and subsequently run on a pre-cast 15% polyacrylamide gel, TBE-Urea (Invitrogen, Cat #S11494) in an oven at 65° C., stained with SYBR Gold, visualized on a Dark reader light box (Clare Chemical Research) and photographed using a digital camera.
Results Before polishing, physically sheared DNA was not a suitable substrate for ligation to blunt ended adapters by T4 DNA ligase (FIG. 27, lane 1). After polishing with T4 Polynucleotide Kinase, T4 DNA polymerase and Klenow fragment, the DNA ends were blunt, some 5' termini were phosphorylated and the molecules could concatenate or ligate to each other as well as to the blunt adapters (FIG. 27, lanes 2 and 4). The species at ~325 bases, ~500 bases and over 500 bases correspond to the ligation of 2 molecules, 3 molecules and 4 molecules of ~175 bases together, respectively (FIG. 27, lanes 2 and 4). The concentration of DNA influenced the formation of ligation products. At higher concentration of DNA, the chimeric ligation species of higher molecular weight were more abundant (FIG. 27, lane 4). Treatment of DNA with shrimp alkaline phosphatase after the polishing step impaired concatamer formation between DNA molecules (FIG. 27, lanes 3 and 5). Treatment with shrimp alkaline phosphatase also prevented concatamer formation if it was performed before the polishing of the fragmented DNA (FIG. 27, lane 6). The ligation products observed after polishing with T4 DNA polymerase and Klenow fragment (FIG. 27, lane 7) were not as abundant compared to the polishing with T4 DNA polymerase, Klenow and T4 Polynucleotide Kinase (FIG. 27, lane 2).
Conclusion Blunt ligation efficiency of physically sheared DNA depended on end polishing by DNA polymerases. The ligation was also improved by the addition of T4 Polynucleotide Kinase, which phosphorylated the 5' terminus of the DNA fragments and dephosphorylated the 3' terminus. The concentration of DNA also influenced the amount of ligation and the formation of chimeric products. At higher concentration, DNA is more likely to form chimeric products in the presences of T4 DNA ligase. Alkaline phosphatases remove 5' phosphates (which are required for ligation) and prevent the formation of chimeric ligation products (concatamers).

Example 10

NGS Libraries have Increased Yield when Prepared Using 5' Base Trimming Coupled to Adapter Ligation Reaction Rationale: This experiment demonstrates the utility of the reactions presented in their exemplary application to NGS library construction, particularly the increase in library yield that results from including 5' base trimming coupled to 5' adapter ligation. Libraries were constructed from size-selected sheared DNA so library products could be easily visualized by gel electrophoresis.
Materials:
Blue Buffer (Enzymatics, cat #B0110)
T4 DNA Ligase (Rapid) (Enzymatics, cat #L6030-HC-L)
10×T4 DNA Ligase Buffer (Enzymatics, cat #B6030)
100 mM 2'-deoxynucleoside 5'-triphosphate (dNTP) Set, PCR Grade (Invitrogen (Life technologies), cat #10297-018)
Adenosine 5'-Triphosphate (ATP) (New England Biolabs, cat #P0756S)
Klenow Fragment (Enzymatics, cat #P7060L)
T4 DNA polymerase (Enzymatics, cat #P7080L)
T4 Polynucleotide Kinase (Enzymatics, cat #Y904L)
Shrimp alkaline phosphatase (Affymetrix, cat #78390)
T4 DNA Ligase (Rapid) (Enzymatics, cat #L6030-HC-L)
10×T4 DNA Ligase Buffer (Enzymatics, cat #B6030)
3'Adapter; 1st oligonucleotide 13-501 (Table 1)
3'Adapter; 2nd oligonucleotide 13-712 (Table 1)
E. coli genomic DNA ATCC 11303 strain (Affymetrix, cat #14380)
M220 Focused-ultrasonicator, (Covaris, cat #PN 500295)
E. coli DNA ligase (Enzymatics, cat #L6090L)
E. coli DNA ligase buffer (Enzymatics, cat #B6090)
Uracil-DNA glycosylase (Enzymatics, cat #G50100)
Taq-B DNA polymerase (Enzymatics, cat #P7250L)
5' adapter oligonucleotide for nick-translation (13-489) (Table 1)
5' adapter oligonucleotide for displacement-cleavage (13-595) (Table 1)
Taq DNA ligase (Enzymatics, cat #L6060L)
SPRIselect (Beckman coulter, cat #B23419)

Methods

E. coli genomic DNA was resuspended in DNA suspension buffer (Teknova, cat #T0227) at a concentration of 100 ng/μl. The DNA was fragmented with the M220 Focused-ultrasonicator to 150 base pairs average size. A tight distribution of fragmented DNA from ~150 bp to ~185 bp was subsequently size-selected on a 2% agarose gel using pippin prep.

100 ng of the size-selected *E. coli* genomic DNA was used to prepare a library with the enhanced adapter ligation method. The polishing reaction was assembled in 30 μl, comprising a final concentration of 1× Blue buffer, 100 μM of each dNTP, 3 units T4 DNA polymerase, 5 units DNA Polymerase I, Large (Klenow) Fragment, 10 units of T4 Polynucleotide Kinase. The reaction was incubated at 37° C. for 20 minutes. The DNA was purified using the DNA Clean & Concentrator-5 and eluted in 15 μl with DNA suspension buffer. The 3' Adapter ligation reaction was assembled in 30 μl including, 1×T4 DNA ligase buffer, 220 pmoles of the 3' Adapter 1st oligonucleotide, 440 pmoles of the 3' Adapter 2nd oligonucleotide, the 15 μl of DNA purified and 1200 units of T4 DNA ligase. The reaction was incubated at 25° C. for 15 minutes. The DNA was brought up to a 50 μl volume and purified and size selected using 70 μl SPRIselect beads (ratio 1.4×). DNA was eluted in 15 μl of DNA resuspension buffer. The partial degradation of the 3' adapter, annealing of the 5' adapter, 5'-end trimming and ligation of the 5' adapter all took place in the next reaction which was assembled in a final volume of 30 μl containing 1× *E. coli* DNA ligase buffer or 1×Taq DNA ligase buffer, 200 μM of each dNTPs or 200 μM of each dATP, dTTP, dGTP or no dNTPs, 200 pmoles of 5' adapter oligonucleotide for nick-translation or 5' adapter oligonucleotide for displacement-cleavage, 10 units of *E. coli* ligase or 40 units of Taq DNA ligase, 2 units of uracil-DNA glycosylase, 10 units of Taq-B DNA polymerase and 15 μl of the DNA purified after the 3' Adapter ligation reaction. The reaction was incubated at 40° C. or 45° C. for 10 minutes or with 30 cycles of (45° C. for 45 seconds-65° C. for 5 seconds) (library 5). The DNA was brought up to a 50 μl volume and purified and size selected using 40 μl of SPRIselect beads (ratio 0.8×). The DNA was eluted in 20 μl and quantified by qPCR using the Kapa Library Quantification Kit—Illumina/Universal (cat #KK4824).

Results

Figure 28A:
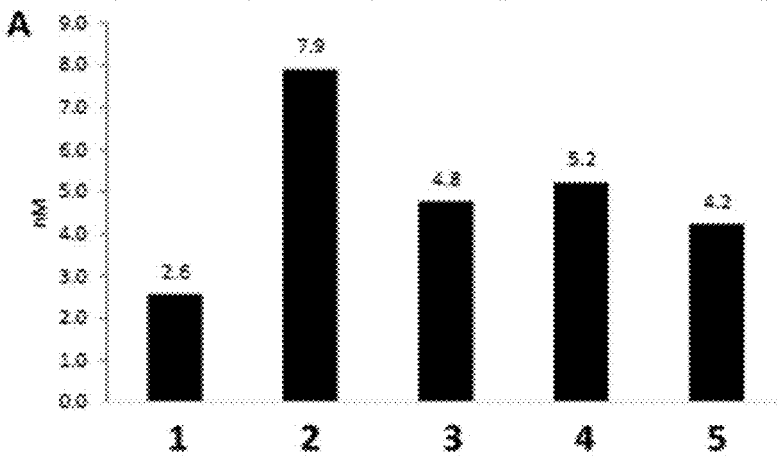
FIG. 28A demonstrates increased NGS Library yield when using 5' base trimming coupled to adapter ligation, as described in Example 10. The quantified library yields obtained from varying library prep conditions as indicated are depicted in the table.
Figure 28B:
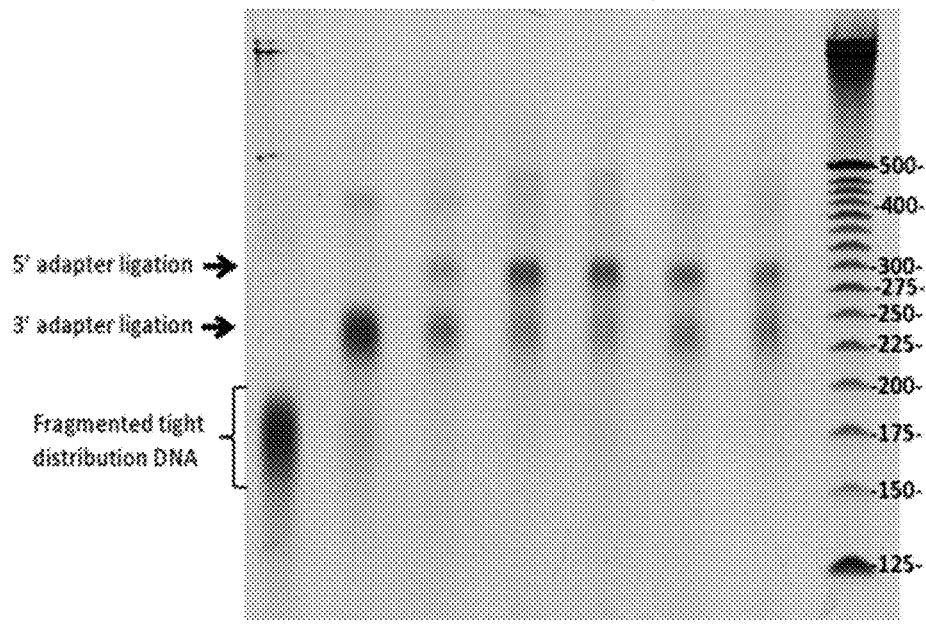
FIG. 28B relates to the libraries constructed in Example 10 which used size-selected sheared DNA so library products could be easily visualized by polyacrylamide gel electrophoresis, as depicted by the 3' and 5' adapter ligation products.

The library concentrations were reported on the plot (FIG. 28, panel A) and the libraries were visualized on a 6% polyacrylamide gel by electrophoresis under denaturing conditions (FIG. 28, panel B). The input DNA migrated between ~150 bases and ~185 bases (FIG. 28, lane I, panel B). An aliquot was taken after the 3' adapter ligation step and loaded on the gel. This product migrated between ~225 to ~250 bases, which corresponds to the addition of the 64 bases of the 3' Adapter (FIG. 28, lane L, panel B). The contribution of Taq-B DNA polymerase in removing one or more bases and exposing a 5'phosphate group at the 5' terminus of the DNA prior to ligation of the 5' adapter was demonstrated in library 1 vs. 2 (FIG. 28, lanes 1 and 2, panels A and B). The concentration of library 1 made without Taq-B (2.6 nM) is three times lower than library 2 made with Taq-B DNA polymerase (7.9 nM). Even after treatment with T4 Polynucleotide Kinase, 75% of the fragmented DNA required processing of their 5' termini in order to be ligation compatible. The finished libraries were also loaded on the gel (FIG. 28, lanes 1 and 2, panel B). These libraries migrated between ~275 bases and ~300 bases which correspond to the addition of the 58 bases of the 5' adapter oligonucleotide for nick-translation or 5' adapter oligonucleotide for displacement-cleavage and the 64 bases of the 3' adapter. Library 1 product was present at a lower intensity than the library 2 bands (FIG. 28, panel B). The libraries 3 and 4 were made with dATP, dTTP, dGTP and *E. coli* ligase or Taq DNA ligase, respectively, during the partial degradation of the 3' adapter, the annealing of the 5' adapter, the 5'-end trimming and the ligation of the 5' adapter step. Library 3 concentration (4.8 nM) was about 60% of library 2 (7.9 nM). This loss of 30% in yield is related to the percent of cytosine "C" in the *E. coli* genome (25%). Every time the 5' terminus of the DNA substrate is a cytosine, the 5' adapter oligonucleotide for nick-translation cannot be extended by Taq and the 5' terminus cannot be trimmed. There is also an extra 6.25% and 1.5% probability to have two and three consecutive cytosines, respectively, at the 5' terminus of the DNA substrate. The ligation at 45° C. with Taq DNA ligase (library 4) gave a similar yield (4.8 nM) when compared with *E. coli* ligase at 40° C. (5.2 nM) (library 3). Library 5, which was made with 5' adapter oligonucleotide for displacement-cleavage, (4.2 nM) was less efficient than library 2 made with the 5' adapter oligonucleotide for nick-translation (7.9 nM).

Conclusion

Libraries were successfully made with the disclosed adapter ligation method. The 5'-end DNA trimming by Taq DNA polymerase allows a three-fold increase in the yield of 5' adapter ligation product when compared to libraries that have no 5' end processing step (libraries 1 vs 2). Both Taq DNA ligase (library 4) and *E. coli* ligase (library 3) efficiently ligated the 5' adapter after the nick-translation. Taq DNA ligase also ligated the 5' adapter after the displacement-cleavage (library 5). Using 4 dNTPs (library 2) instead of 3 (libraries 3 and 4) during the nick-translation may allow the ligation of more DNA substrate to the 5' adapter.

Example 11

Sequence Analysis of NGS Libraries Prepared Using 5' Base Trimming Coupled to Adapter Ligation Rationale: This experiment demonstrates the utility of the reactions presented in their exemplary application to NGS library construction. Libraries were constructed from sheared *E. coli* DNA and then sequenced in order to demonstrate the superior evenness of coverage obtained over a wide base composition of the genome.

Materials:
Blue Buffer (Enzymatics, cat #B0110)
T4 DNA Ligase (Rapid) (Enzymatics, cat #L6030-HC-L)
10×T4 DNA Ligase Buffer (Enzymatics, cat #B6030)
100 mM 2'-deoxynucleoside 5'-triphosphate (dNTP) Set, PCR Grade (Invitrogen (Life technologies), cat #10297-018)
Adenosine 5'-Triphosphate (ATP) (New England Biolabs, cat #P0756S)
Klenow Fragment (Enzymatics, cat #P7060L)
T4 DNA polymerase (Enzymatics, cat #P7080L)
T4 Polynucleotide Kinase (Enzymatics, cat #Y904L)
Shrimp alkaline phosphatase (Affymetrix, cat #78390)
T4 DNA Ligase (Rapid) (Enzymatics, cat #L6030-HC-L)
10×T4 DNA Ligase Buffer (Enzymatics, cat #B6030)
3'Adapter; 1st oligonucleotide 13-510 (Table 1)
3'Adapter; 2nd oligonucleotide 13-712 (Table 1)
*E. coli* genomic DNA ATCC 11303 strain (Affymetrix, cat #14380)

M220 Focused-ultrasonicator, (Covaris, cat #PN 500295)
E. coli DNA ligase (Enzymatics, cat #L6090L)
E. coli DNA ligase buffer (Enzymatics, cat #B6090)
Uracil-DNA glycosylase (Enzymatics, cat #G50100
Taq-B DNA polymerase (Enzymatics, cat #P7250L)
5' adapter oligonucleotide for nick-translation (13-489)
SPRIselect (Beckman coulter, cat #B23419)

Method

E. coli genomic DNA was resuspended in DNA suspension buffer (Teknova, cat #T0227) at a concentration of 100 ng/µl. The DNA was fragmented with the M220 Focused-ultrasonicator to 150 base pairs average size. 100 ng of E. coli covaris genomic DNA was used to prepare a library. A first reaction of dephosphorylation was assembled in a total volume of 15 µl, comprising a final concentration of 1× Blue buffer, 100 ng of fragmented E. coli genomic DNA and 1 unit of shrimp alkaline phosphatase. The reaction was incubated at 37° C. for 10 minutes. The shrimp alkaline phosphatase was inactivated 5 minutes at 65° C. The polishing reaction was assembled in 30 µl, comprising a final concentration of 1× Blue buffer, 100 µM of each dNTP, 3 units T4 DNA polymerase, 5 units DNA Polymerase I, Large (Klenow) Fragment and 15 µl of the dephosphorylation reaction. The reaction was incubated at 20° C. for 30 minutes. The DNA was purified using the DNA Clean & Concentrator-5. The DNA was eluted in 15 µl with DNA suspension buffer. The 3' Adapter ligation reaction was assembled in 30 µl including, 1×T4 DNA ligase buffer, 220 pmoles of the 3' Adapter 1st oligonucleotide, 440 pmoles of the 3' Adapter 2nd oligonucleotide, the 15 µl of DNA purified after polishing and 1200 units of T4 DNA ligase. The reaction was incubated at 25° C. for 15 minutes. After adjusting volume to 50 µl, the DNA was purified and sized selected using 45 µl SPRIselect beads (ratio 0.9×). DNA was eluted in 15 µl of DNA resuspension buffer. The partial degradation of the 3' adapter, annealing of the 5' adapter, 5'-end DNA trimming and ligation of the 5' adapter all took place in the next reaction which was assembled in a final volume of 30 µl containing 1× E. coli DNA ligase, 200 µM of each dNTPs, 200 pmoles of 5' adapter oligonucleotide for nick-translation, 10 units of E. coli ligase, 2 units of uracil-DNA glycosylase, 10 units of Taq-B DNA polymerase and 15 µl of the DNA purified after the 3' Adapter ligation reaction. The reaction was incubated at 40° C. for 10 minutes. After adjusting the volume to 50 µl, the DNA was purified using 70 µl of SPRIselect beads (ratio 1.4×). The DNA was eluted in 20 µl, and quantified by qPCR using the Kapa Library Quantification Kit—Illumina/Universal (cat #KK4824). DNA was denatured 5 minutes with a final concentration of 0.1 mM of sodium hydroxide and 600 µl of 10 pM library was loaded on a MiSeq (Illumina).

Results

Figure 29A:
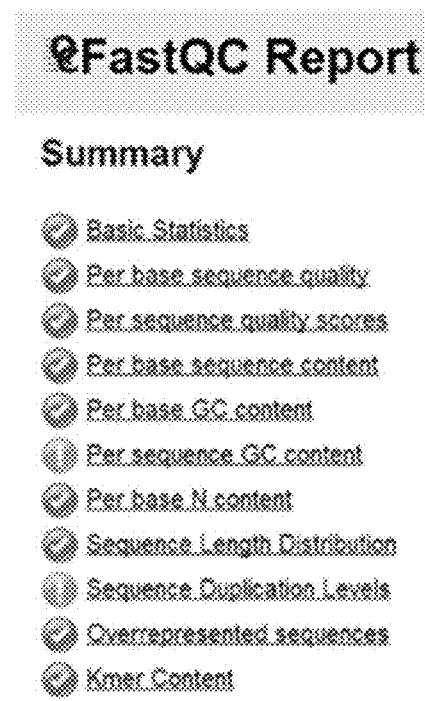
FIG. 29A demonstrates the utility of the reactions presented in their exemplary application to NGS library construction. Libraries were constructed from sheared *E. coli* DNA and sequenced in order to demonstrate the superior evenness of coverage obtained over a wide base composition of the genome. The summary of metrics is listed for the FastQC report of sequence metrics from the Illumina MiSeq run.
Figures 29B, 29C:
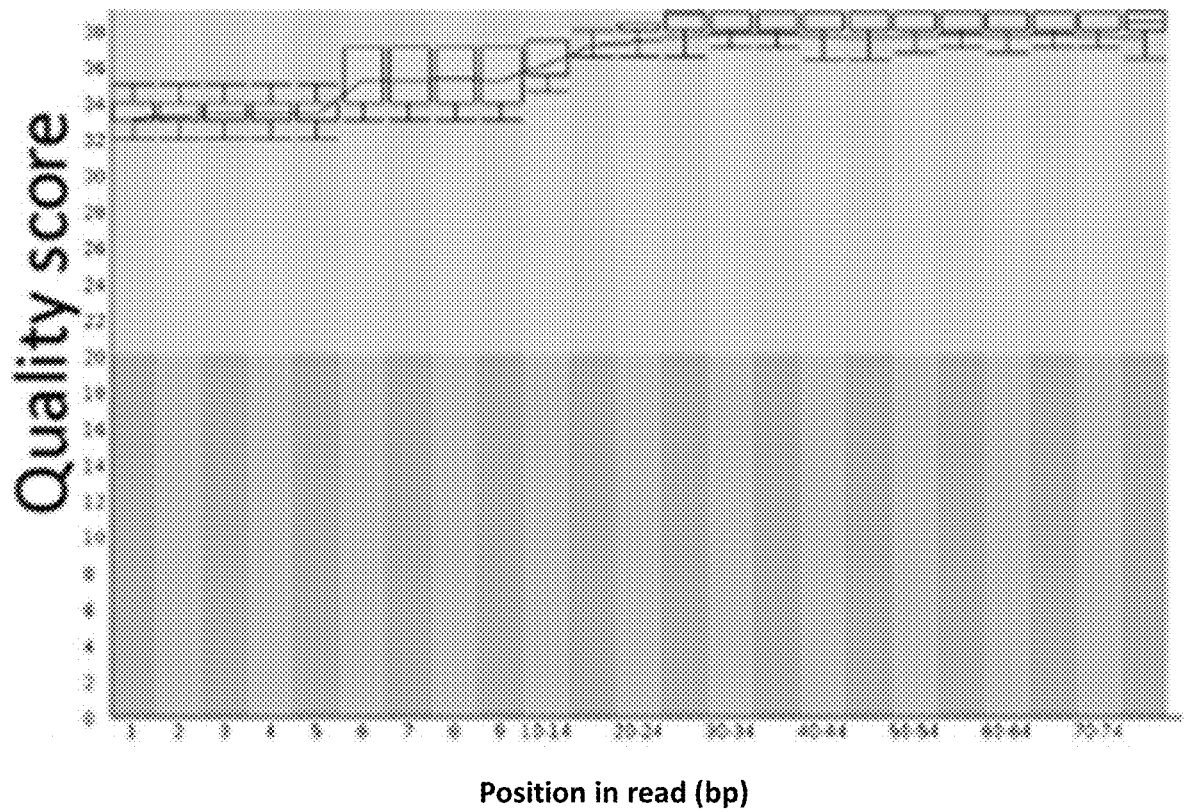
FIG. 29B depicts FastQC basic statistics from the report
FIG. 29C depicts per base sequence quality of the FastQC report
Figure 29D:
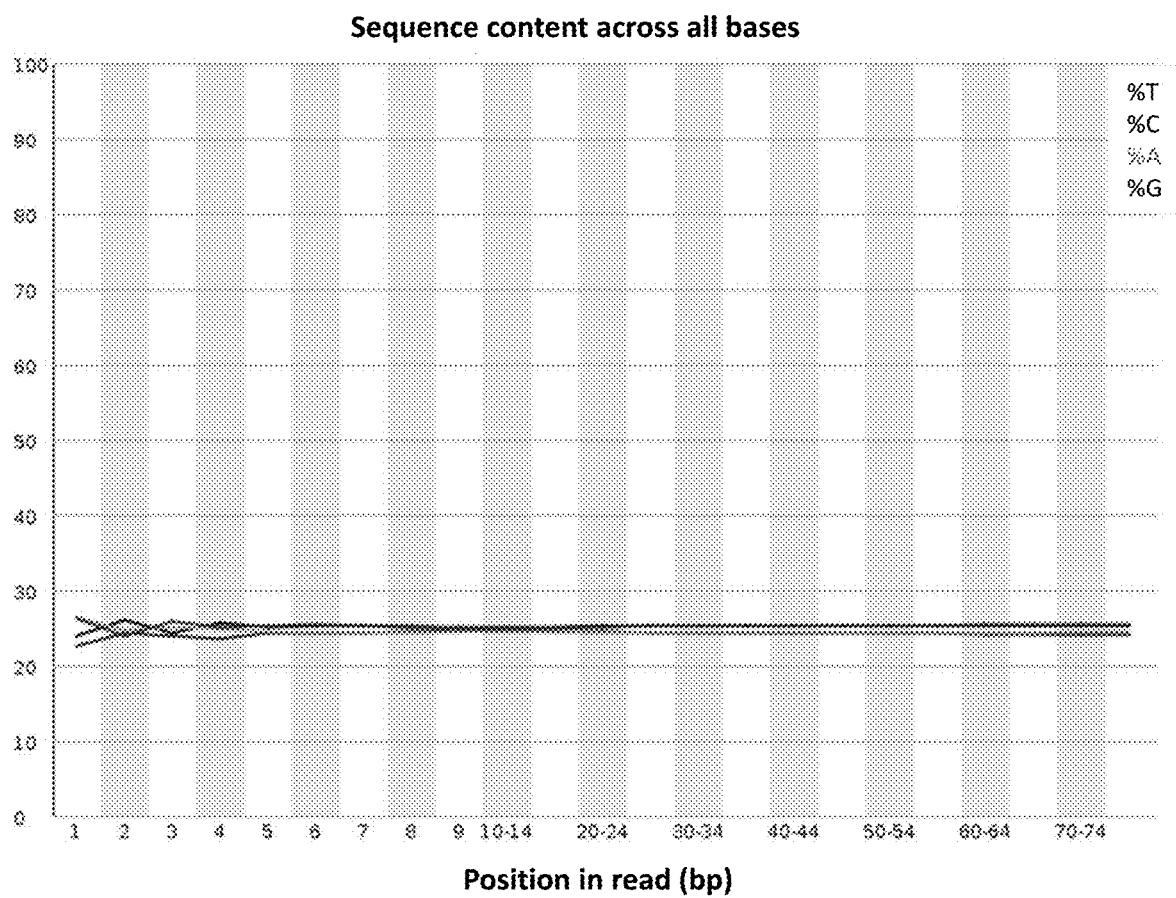
FIG. 29D depicts per base sequence content from the FastQC report
Figure 29E:
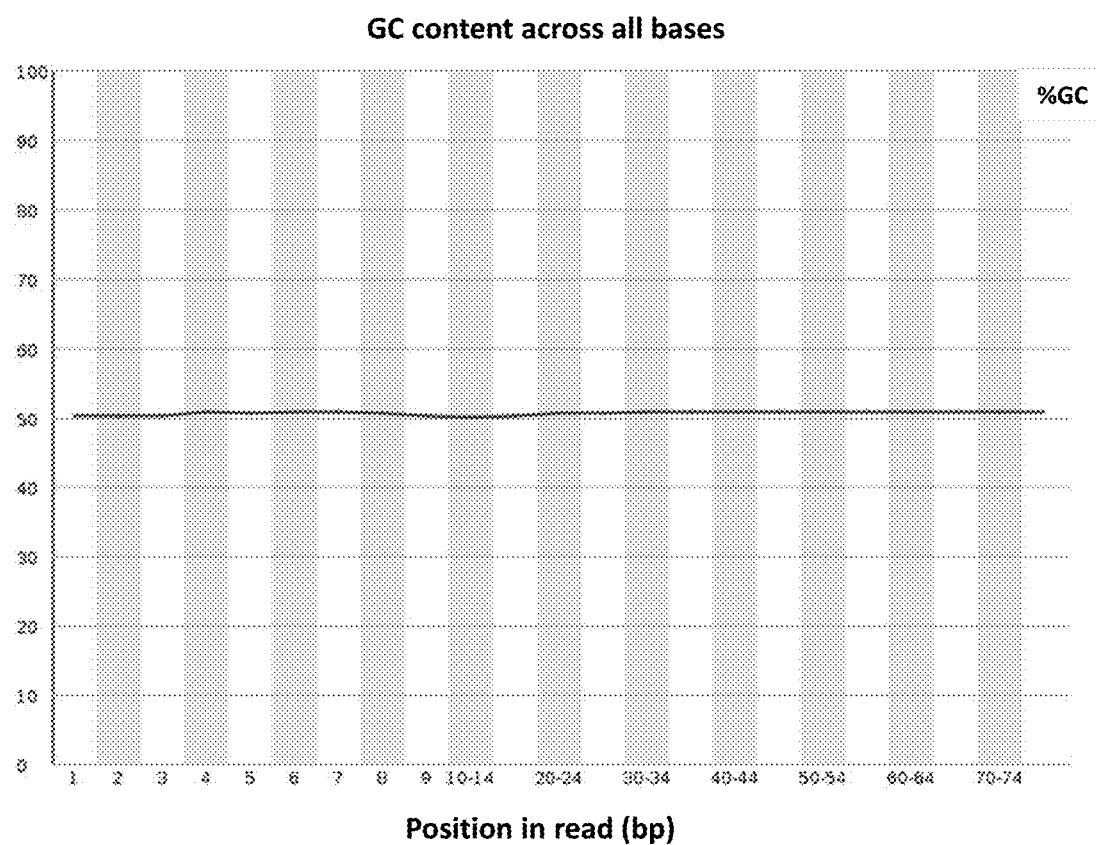
FIG. 29E depicts per base GC content from the FastQC report
Figure 29F:
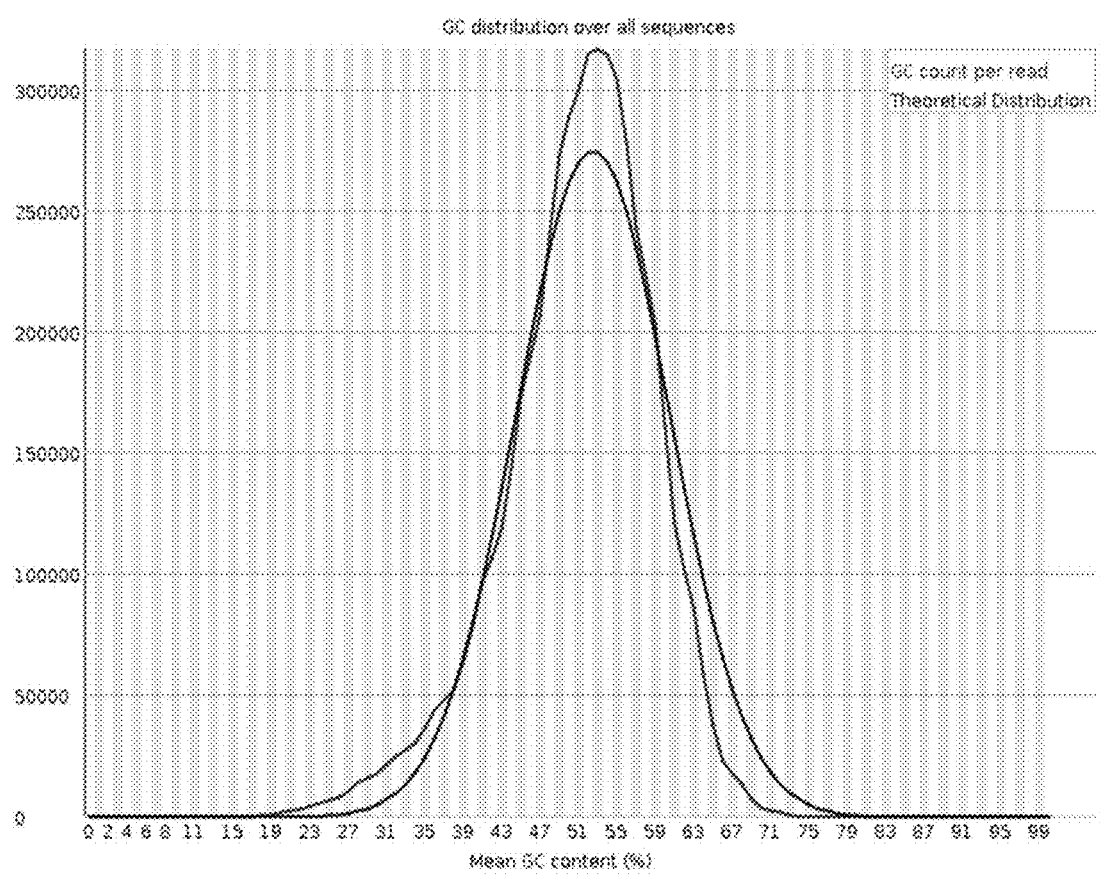
FIG. 29F depicts per sequence GC content from the FastQC report
Figure 29G:
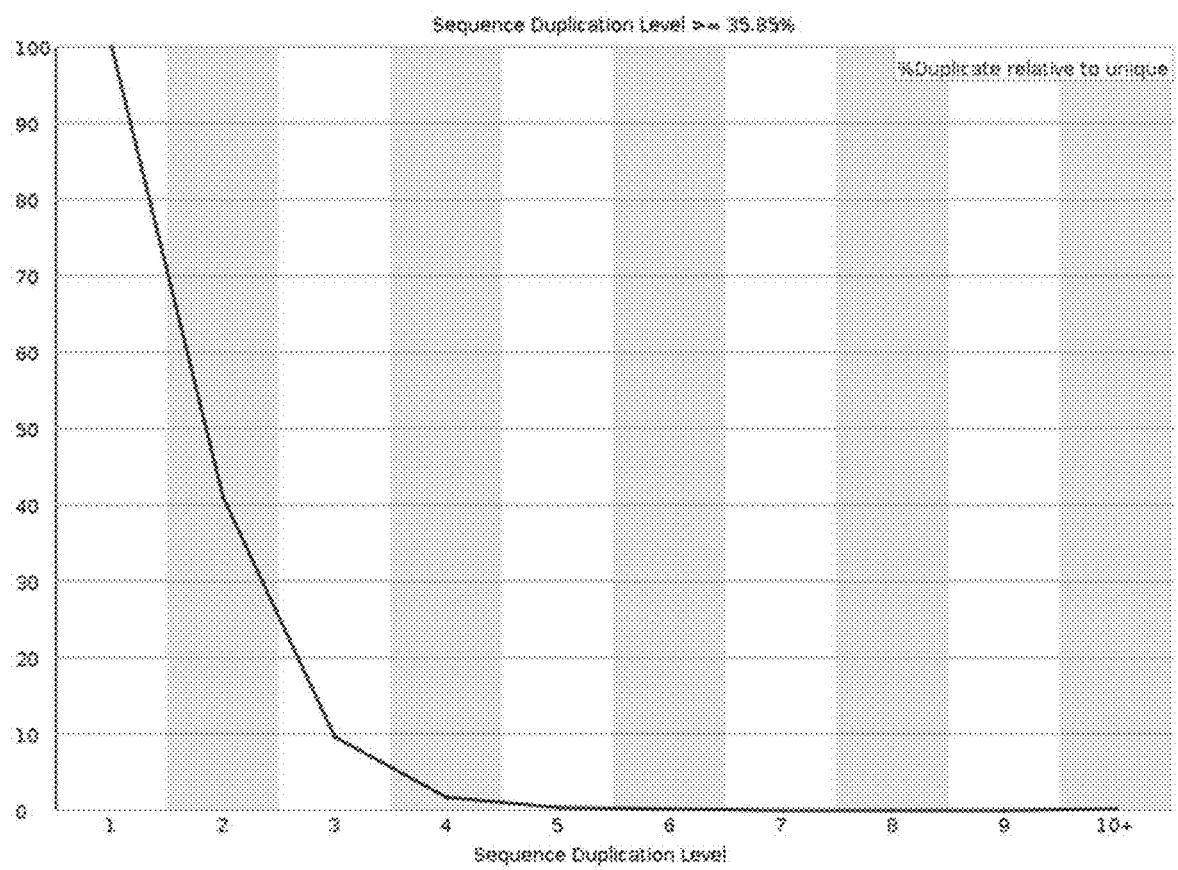
FIG. 29G depicts sequence duplication levels from the FastQC report
Figure 29H:
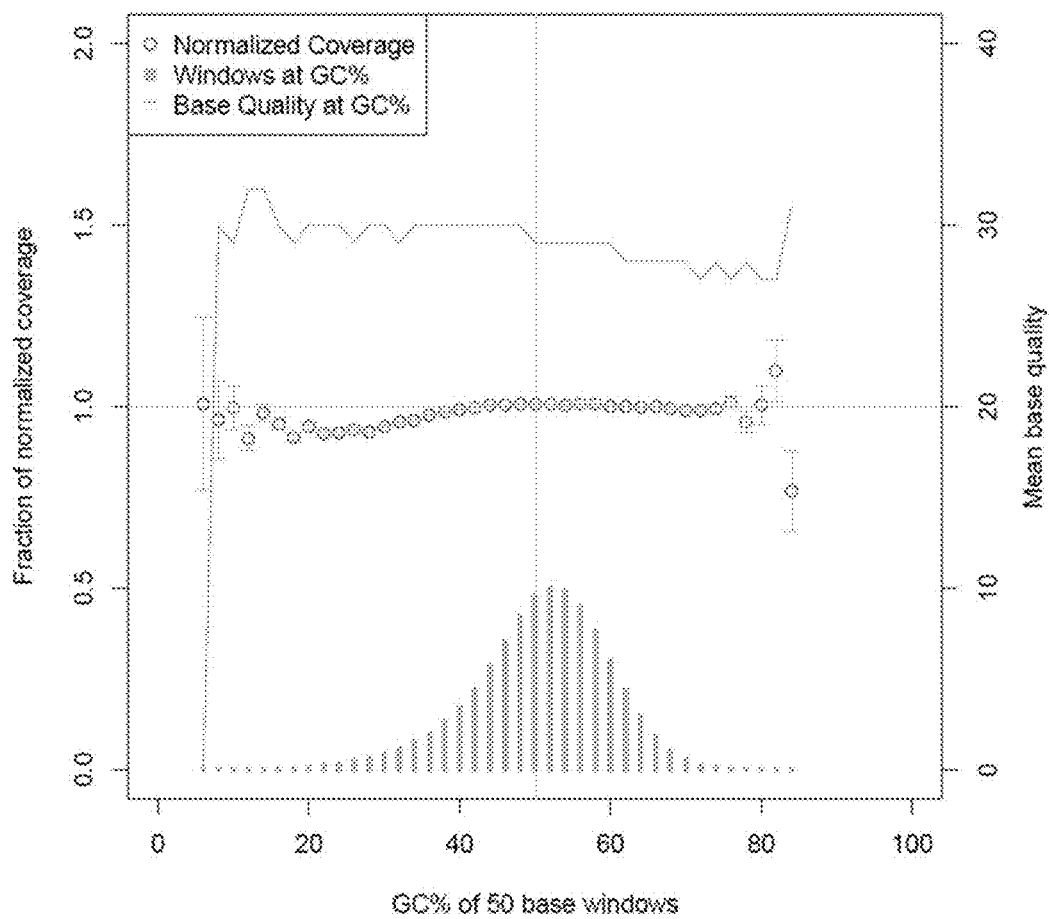
FIG. 29H depicts a Picard CollectGcBiasMetrics plot where the library coverage is plotted relative to the base composition of the *E. coli* genome
Figure 33:
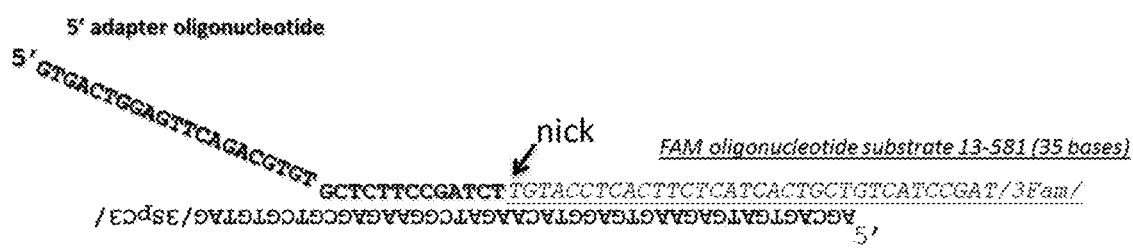
FIG. 33 depicts the oligonucleotide construct system as described in Examples 3, 4, 5, and 8. The 5' adapter oligonucleotide for nick translation is 13-144 (34 bases) in bold type; the FAM oligonucleotide substrate is 13-581 (35 bases) in italics type; the oligonucleotide template is 13-582 (47 bases) in standard type.
Figure 34:
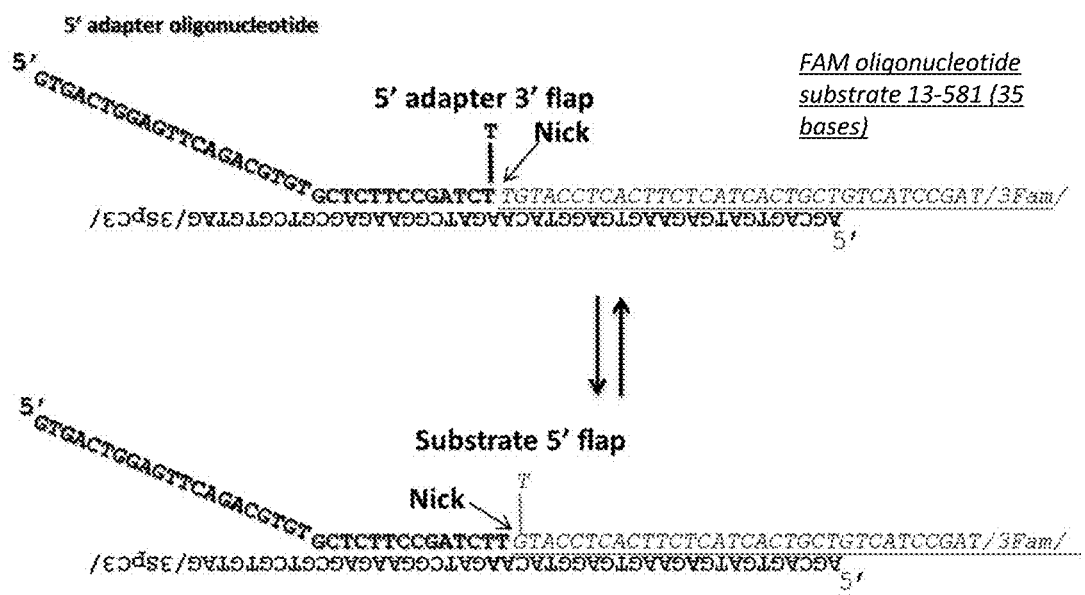
FIG. 34 depicts the oligonucleotide construct system as described in Example 6, where the construct can exist as shown above (5' adapter with 3' flap) or the construct can exist as shown below (substrate with 5' flap). The 5' adapter oligonucleotide for displacement cleavage is 13-156 (35 bases) in bold type; the FAM oligonucleotide substrate is 13-581 (35 bases) in italics type; and the oligonucleotide template is 13-582 (47 bases) in standard type.
Figure 35:
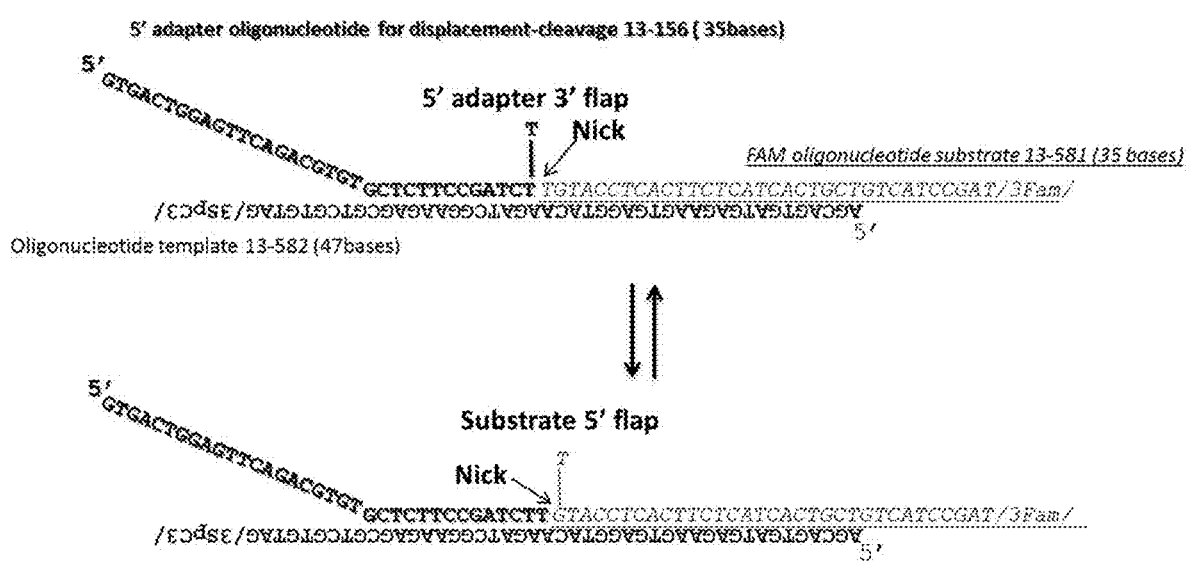
FIG. 35 depicts the oligonucleotide construct system as described in Example 7, where the construct can exist as shown above (5' adapter with 3' flap) or the construct can exist as shown below (substrate with 5' flap). The 5' adapter oligonucleotide for displacement cleavage "T" is 13-607 in bold type; the FAM oligonucleotide substrate is 13-581 (35 bases) in italics type; the oligonucleotide template is 13-582 (47 bases) in standard type.
Figure 36:
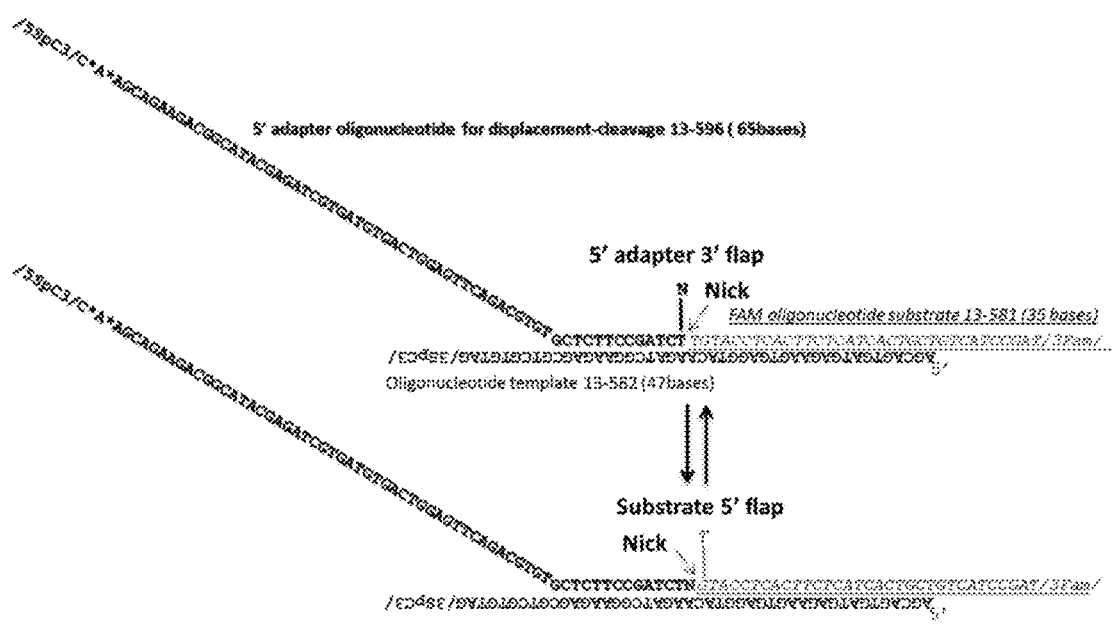
FIG. 36 depicts the oligonucleotide construct system as described in Example 7, where the construct can exist as shown above (5' adapter with 3' flap) or the construct can exist as shown below (substrate with 5' flap). The 5' adapter oligonucleotide for displacement cleavage is 13-596 (65 bases) in bold type; the FAM oligonucleotide substrate is 13-581 (35 bases) in italics type; and the oligonucleotide template is 13-582 (47 bases) in standard type.
Figure 40:
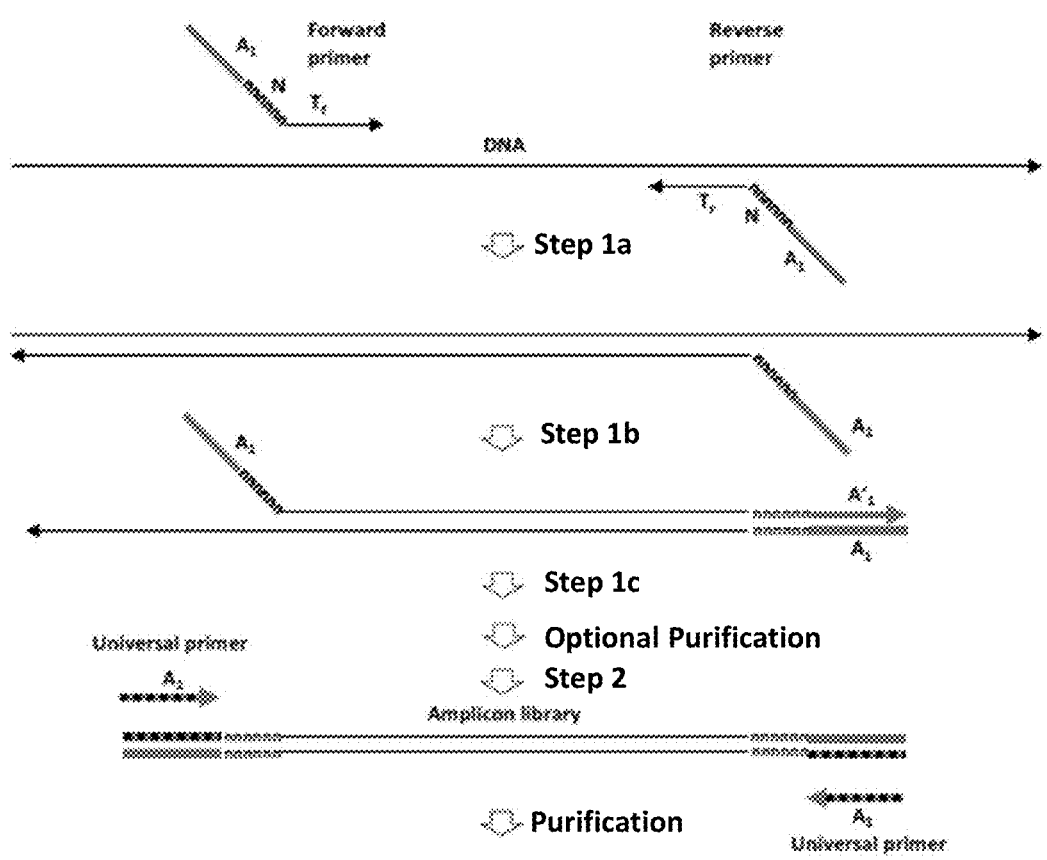
FIG. 40 depicts the first amplicon library workflow where the multiplexed PCR is divided by a purification step. Step 1a is a first PCR cycle: annealing and extension of the reverse primer comprising target-specific sequence T1 at the 3' end, universal sequence A1 at the 5' end, and degenerate sequence N between them (UI). Step 1b is a second PCR cycle: annealing and extension of the forward primer comprising target-specific sequence T1 at the 3' end, universal sequence A1 at the 5' end and degenerate sequence N (UI) between them and creation of an amplicon with universal sequences A1 and A1' at the 5' and 3' end, respectively. Step 1c is optional, where more PCR cycles with reverse and forward primers to increase the number of produced amplicons is performed; Optionally, a purification (SPRI beads or a spin column) or Exonuclease I treatment is performed; During Step 2, multiple PCR cycles are performed with a universal primer comprising universal sequence A1, with cleaveable bases such as deoxyuridine, deoxyinosine or RNA, then a purification step of SPRI beads or a spin column is performed.
Figure 41:
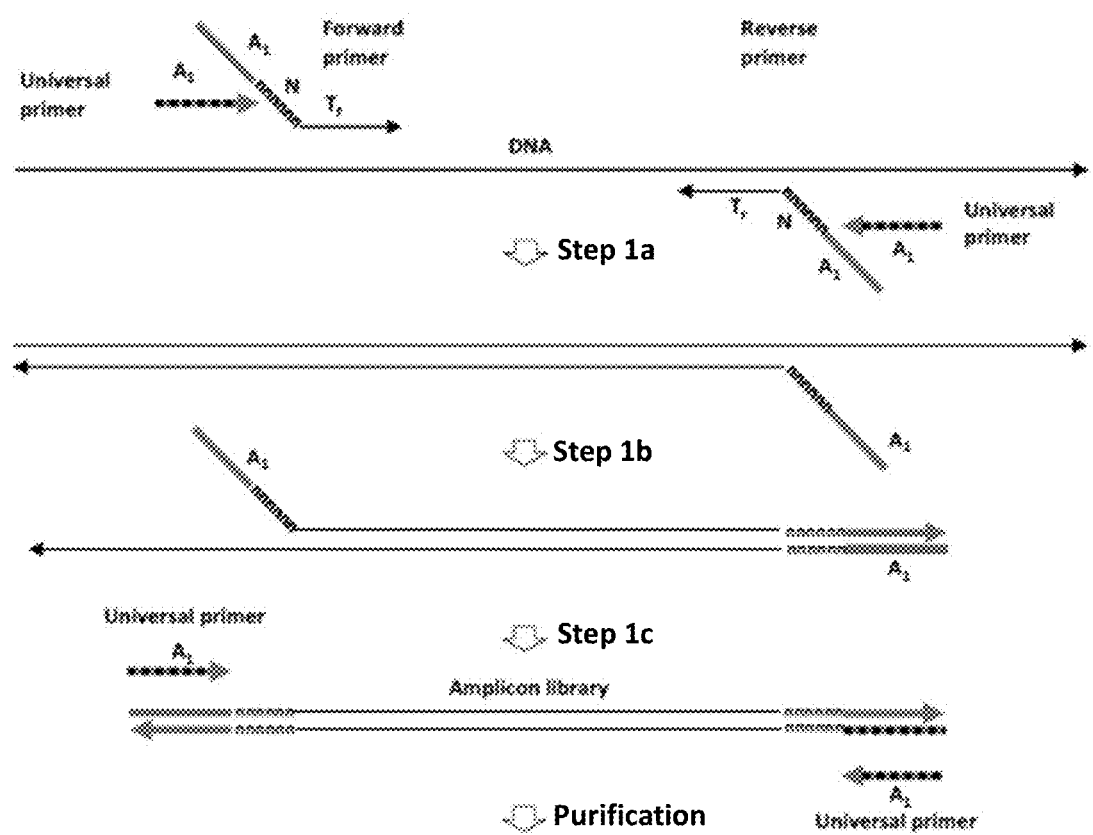
FIG. 41 depicts the second amplicon workflow where the multiplexed PCR is performed as a single step. Step 1a is a first PCR cycle: annealing and extension of the reverse primer comprising target-specific sequence T1 at the 3' end, universal sequence A1 at the 5' end, and degenerate sequence N between them (UI). Step 1b is a second PCR cycle: annealing and extension of the forward primer comprising target-specific sequence T1 at the 3' end, universal sequence A1 at the 5' end and degenerate sequence N (UI) between them and creation of an amplicon with universal sequences A1 and A1' at the 5' and 3' end, respectively; during Step 1c, multiple PCR cycles are performed with a universal primer comprising universal sequence A1, with cleaveable bases such as deoxyuridine, deoxyinosine or RNA, then a purification step of SPRI beads or a spin column is performed.
Figure 42:
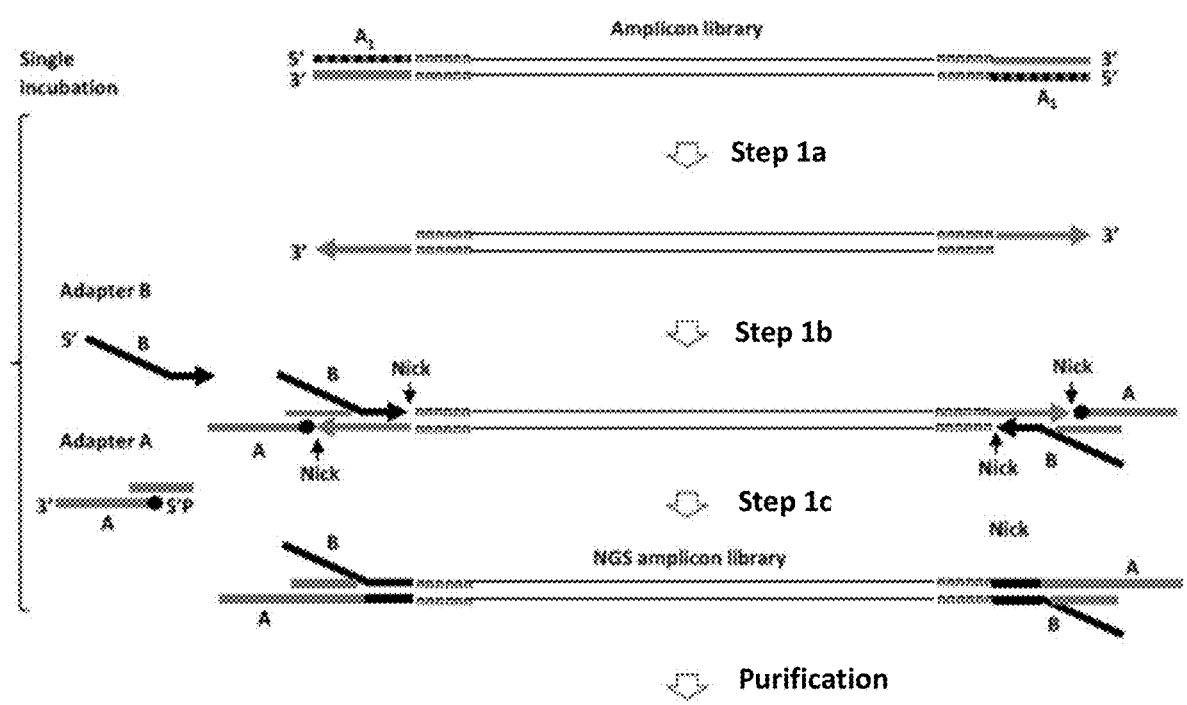
FIG. 42 depicts the final step to amplicon library synthesis: 1-step NGS adapter attachment of adapter A and B to each amplicon, where Adapter B is a 5' adapter and Adapter A is a truncated 3' adapter. In Step 1a, degradation of the universal 5' sequence A1 occurs by UDG, endonuclease V, or RNase H if the cleavable bases within sequence A1 are correspondingly deoxyuridines, deoxyinosines or RNA bases, or by 5' exonuclease if sequence A1 has nuclease-resistant phosphorothioate linkages at the 3' end; during Step 1b, annealing of adapters A and B occur; and during Step 1c, ligation of adapters A and B after limited nick-translation reaction or displacement cleavage reaction and simultaneous linker mediated ligation occur, followed by a purification step by SPRI beads or a spin column.
Figure 43:
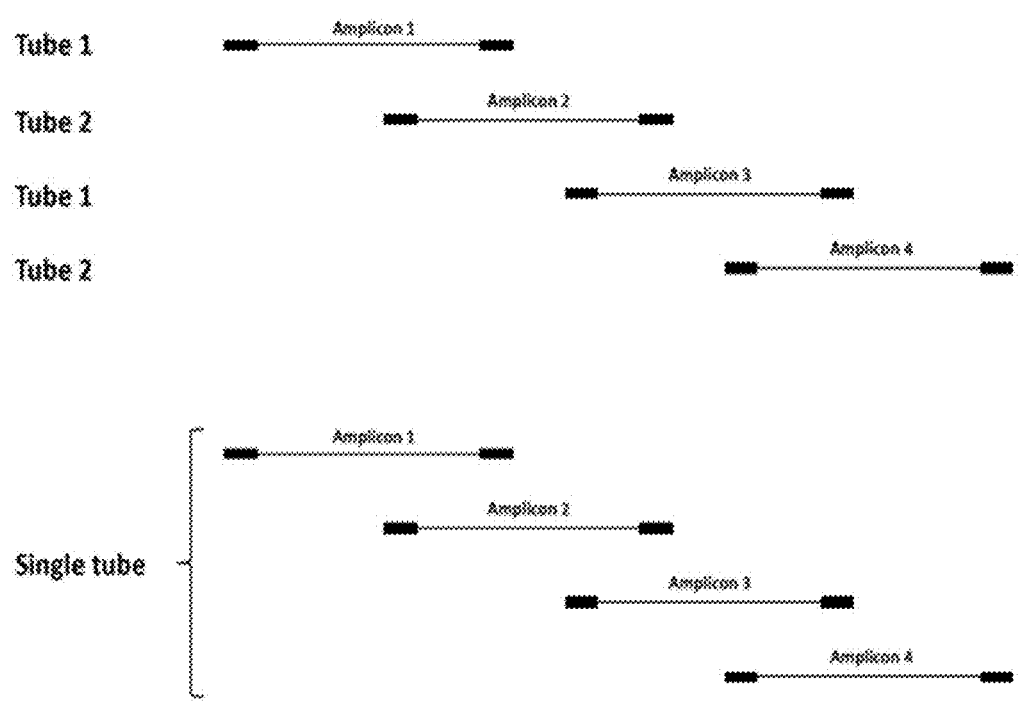
FIG. 43 compares single tube versus two-tube workflow.
Figure 44A:
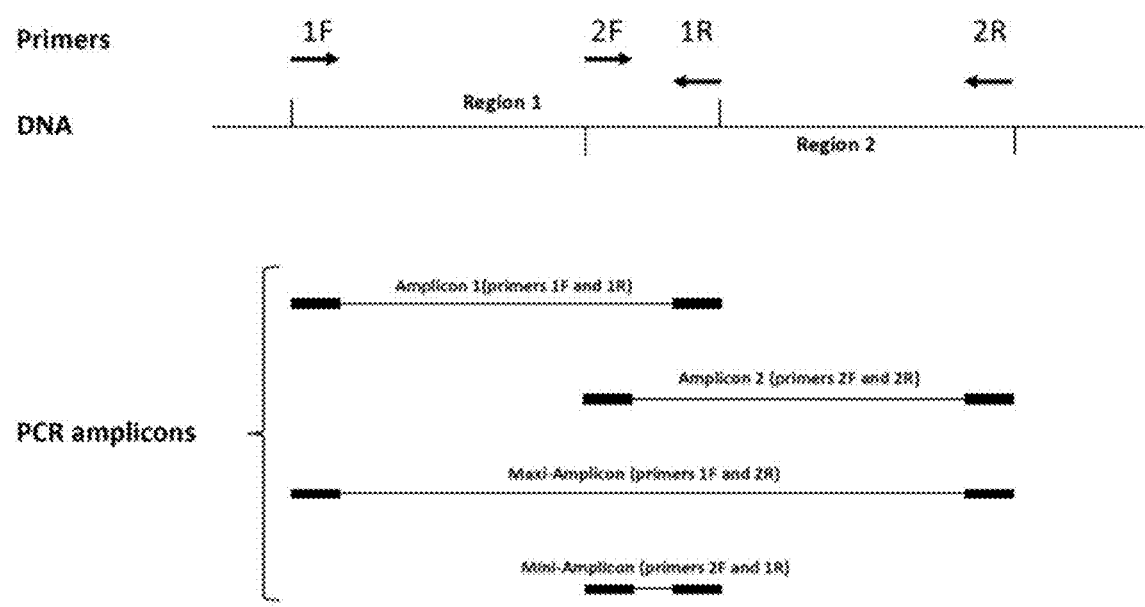
FIG. 44A depict amplicon products generated from overlapping primer pair target regions.
Figure 44B:
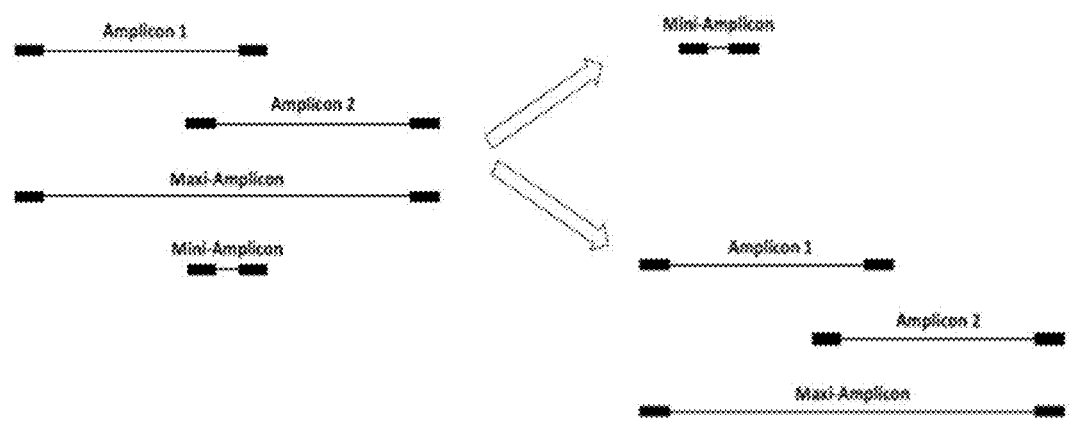
FIG. 44B further depicts amplicon products at earlier cycles on the left panel, where both a maxi-amplicon and a mini-amplicon can form from two overlapping amplicons 1 and 2; where at the end of the amplification on the right panel, where current methods would lead to preferential amplification of the mini-amplicon (top right), the instant invention prevents amplification of the mini-amplicon (bottom right), instead favoring amplification of Amplicon 1, 2 and the maxi-amplicon.

The library concentration as quantified by qPCR was 2.8 nM. Pair end reads of 76 bases were generated by the v2 chemistry of the Illumina MiSeq. 928K/mm² clusters were generated and the Q30 score were 97.8% and 96.9% for the first and second read, respectively. The sequence data quality was assessed using the FastQC report (Babraham Bioinformatics). A summary of the analysis showed 9 green check marks, 2 yellow exclamation points (warning), but no red X (failed) were observed (FIG. 29A). The overall % GC of all bases in all sequences was 50%, as expected for E. coli genome (Green check marks, FIG. 29B). The quality of the sequence was excellent at every read throughout the 76 bases analyzed (Green check mark, FIG. 29C). The percentage of each base was plotted in panel D. The amount of G/C and A/T had <10% difference at any read (Green check mark, FIG. 29D). The GC content was similar throughout the 76 bases analyzed (green check mark, FIG. 29E). The GC content per read across the length of each sequence was compared to a theoretical distribution (yellow exclamation point, FIG. 29F). A warning was raised because the sum of the deviations from the normal distribution was found in more than 15% of the reads (yellow exclamation point, FIG. 29F). No warnings were raised for the Per base N content or the Sequence Length Distribution (summary, FIG. 29 A). The sequence duplication level was 35.85% (FIG. 29G). A yellow warning was raised because non-unique sequences make up more than 20% of the total, due to the high level of coverage 135× (Yellow exclamation point, FIG. 29G). No overrepresented sequences or kmer were reported (summary, FIG. 29A). Virtually, no adapter dimer where observed (0.02%, data not shown). The GC bias was also evaluated using the Picard CollectGcBiasMetrics as shown in FIG. 29H. Evenness of coverage was preserved throughout a broad range of base composition. Deviations in coverage were only observed at lower than 10% GC content or higher than 80%. The base quality was over Q25 which correspond to 99.8% accuracy in the base calling. Again, the lower quality was only observed at extreme low and high GC content.

Conclusion

A library was successfully made using fragmented E. coli genomic DNA. The sequencing demonstrated high quality data and no bias in the coverage throughout the range of GC content.

Example 12

Oncology Hotspot Panel Combined with Comprehensive Coverage of the TP53 Gene

Rationale: A total of 51 amplicons were designed to cover the entire coding region of the TP53 gene as well as 30 hotspot loci representing clinically actionable mutations in oncology.

Rationale: This amplicon panel provides proof of concept for the disclosed method, where the 51 amplicons have significant overlap to demonstrate the absence of the mini-amplicon dominating the reaction, as well as the evenness of coverage among amplicons that can be achieved using limited multiplex cycle number. In addition, the high percentage of on target reads demonstrates the specificity of priming because primer dimers and non-specific off target amplification products do not appear in the sequenced library.

Materials:
Human HapMap genomic DNA (Coriell Institute, NA12878)
KAPA HiFi HotStart Uracil+ ReadyMix (KAPA Biosystems, cat #KK2802)
102 Target-specific primers (Table 2)
Universal primer containing a 3' adapter oligonucleotide truncated sequence and cleavable bases 14-882 (Table 2)
E. coli DNA ligase buffer (Enzymatics, cat #B6090)
5' adapter oligonucleotide for adapter ligation step (14-571)
5' part of the 3' adapter oligonucleotide for adapter ligation step (14-877)
Linker oligonucleotide for adapter ligation step 14-382 (Table 2)
E. coli DNA ligase (Enzymatics, cat #L6090L)
Uracil-DNA glycosylase (Enzymatics, cat #G5010L)

Endonuclease VIII (Enzymatics, cat #Y9080L)
Taq-B DNA polymerase (Enzymatics, cat #P7250L)
SPRIselect (Beckman coulter, cat #B23419)
20% PEG-8000/2.5M NaCl solution for purification steps Method Human genomic DNA was diluted in DNA suspension buffer (Teknova, cat #T0227) at a concentration of 2 ng/μl. The DNA was slightly sheared by vortexing for 2 minutes. 10 ng of this sheared genomic DNA was used to prepare a library. A first reaction of amplification was assembled in a total volume of 30 μl, comprising a final concentration of 1×KAPA HiFi HotStart Uracil+ ReadyMix, 10 ng of sheared human genomic DNA, 300 pmol of the universal primer and a final concentration of 0.85 uM of a mix of the 102 target-specific primers present in different ratios. The following cycling program was run on this reaction: 3 minutes at 95° C. followed by 4 cycles of 20 seconds at 98° C., 5 minutes at 63° C. and 1 minute at 72° C. to generate target-specific amplicons and terminated by 23 cycles of 20 seconds at 98° C. and 1 minute at 64° C. to produce multiple copies of the target-specific amplicons. After adjusting the volume to 50 μl, the DNA product was purified using 60 μl of SPRIselect beads (ratio 1.2×). The beads were resuspended in 50 μl of a 1× reaction mix containing 1× E. coli ligase buffer, 100 pmol of the linker oligonucleotide, 10 units of E. coli ligase, 10 units of endonuclease VIII, 2 units of uracil-DNA glycosylase, 20 units of Taq-B DNA polymerase, 100 pmol of the 5' adapter oligonucleotide and 100 pmol of the 5' part of the 3' adapter oligonucleotide. The reaction was incubated at 37° C. for 10 minutes and then purified by adding 42.5 μl of a 20% PEG-8000/2.5M NaCl solution (ratio 0.85×). The DNA was eluted in 20 μl, and quantified by qPCR using the Kapa Library Quantification Kit—Illumina/Universal (cat #KK4824). DNA was denatured 5 minutes with a final concentration of 0.1 mM of sodium hydroxide and 600 μl of 10 pM library was loaded on a MiSeq (Illumina).

Results

Figure 45:
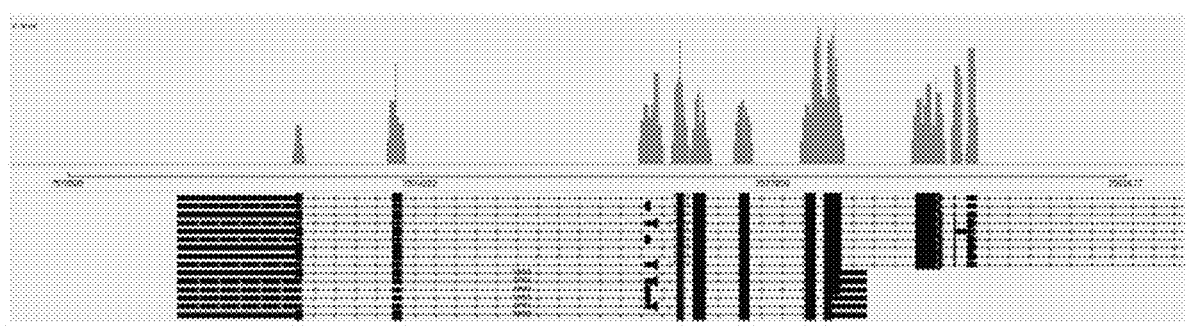
FIG. 45 provides a plot of amplicon coverage over the TP53 coding exons (Example 12).
Figure 46:
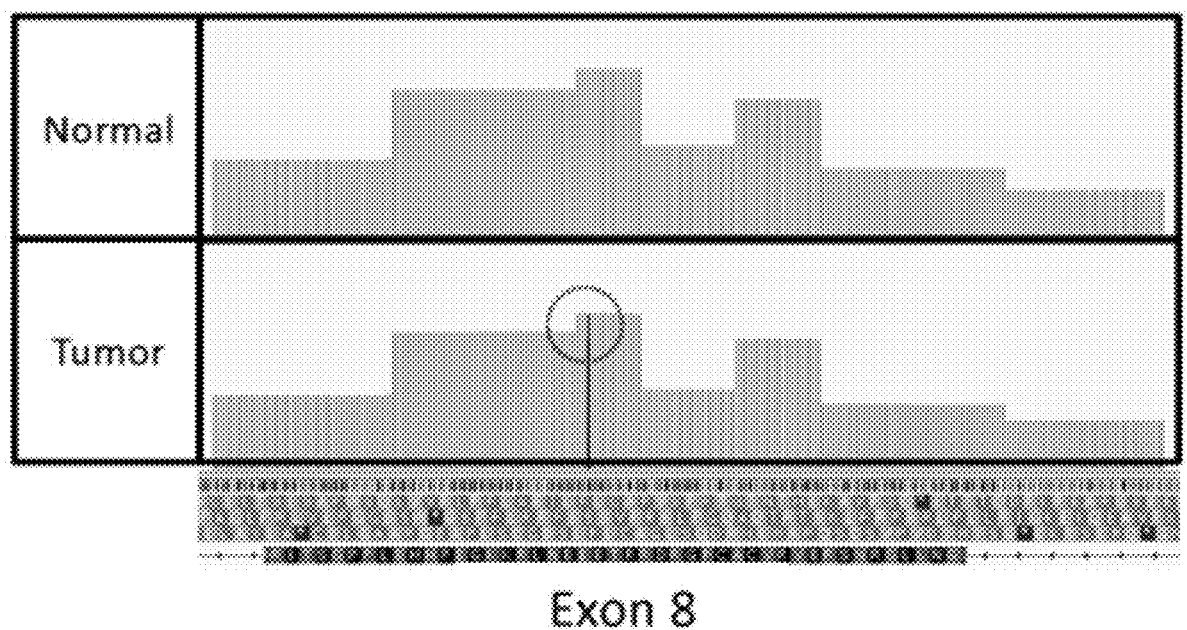
FIG. 46 provides identification of a somatic mutation in exon 8 of TP53 (Example 12).

The library concentration as quantified by qPCR was 19.1 nM. Paired end reads of 101 bases were generated by the v2 chemistry of the Illumina MiSeq. Prior to data analysis, sequence-specific trimming from the 5' end of both read 1 and read 2 is performed to remove synthetic primer sequences using the Cutadapt program. The alignment of the paired reads to the human genome and to the targeted regions using BWA-MEM tool showed exceptional quality data with 98% aligning to targeted regions. Coverage data were also obtained using BEDtools. The coverage uniformity was 100% meaning that each of the 51 amplicons was represented in the final library. The coverage of each individual base in each amplicon was also calculated and was higher than 20% of the mean per base coverage meaning that none of the 51 amplicons were underrepresented in the final product. FIG. 45 depicts the coverage that was obtained for the overlapping amplicons covering the coding exons of the TP53 gene. FIG. 46 depicts a variant call of 18% frequency that was obtained by sequence analysis using VarScan and SAMtools.

Conclusion

A targeted amplicon library was successfully made using human genomic DNA. The sequencing demonstrated high quality data.

TABLE 1

| Sequence name | SEQ ID NO. | Sequence |
|---|---|---|
| 12-900 | 1 | AATGATACGGCGACCACCGAGATCTACACTCTTTCCCTAC ACGACGCTCTTCCGATCT |
| 13-426 | 2 | AGATCGGAAGAGCGTCGTGTAG/3SpC3/ |
| 13-340 | 3 | /5PHOS/AGATCGGAAGAGCGTCGTGTAGGGAAAGAGTGTA GATCTCGGTGGTCGCCGTATCATT/3SpC3/ |
| 13-559 | 4 | ACACGACGCTCTTCCGATCddT |
| 13-558 | 5 | ACACGACGCTCTTCCGATCT/3PHOS/ |
| 13-562 | 6 | /5PHOS/TGTACCTCACTTCTCATCACTGCT/3FAM/ |
| 13-563 | 7 | AGCAGTGATGAGAAGTGAGGTACA |
| 13-561 | 8 | /5PHOS/TGTACCTCACTTCTCATCACTGCT |
| 13-564 | 9 | /5FAM/AGCAGTGATGAGAAGTGAGGTACA |
| 13-560 | 10 | TGTACCTCACTTCTCATCACTGCT |
| 13-144 | 11 | GTGACTGGAGTTCAGACGTGTGCTCTTCCGATCT |
| 13-581 | 12 | TGTACCTCACTTCTCATCACTGCTGTCATCCGAT/3FAM/ |
| 13-582 | 13 | AGCAGTGATGAGAAGTGAGGTACAAGATCGGAAGAGCGT CGTGTAG/3SpC3/ |
| 13-156 | 14 | GACTGGAGTTCAGACGTGTGCTCTTCCGATCTT |
| 13-607 | 15 | CAAGCAGAAGACGGCATACGAGATCGTGATGTGACTGGA GTTCAGACGTGTGCTCTTCCGATCTT |
| 13-596 | 16 | /5SpC3/C*A*AGCAGAAGACGGCATACGAGATCGTGATGTG ACTGGAGTTCAGACGTGTGCTCTTCCGATCTN |

TABLE 1-continued

| Sequence name | SEQ ID NO. | Sequence |
|---|---|---|
| 13-501 | 17 | /5PHOS/AGATCGGAAGAGCACACGTCTGAACTCCAGTCAC ATCACGATCTCGTATGCCGTCTTCTGCT*T*G/3SpC3/ |
| 13-712 | 18 | AGACGUGUGCUCUTCCGATCddT |
| 13-489 | 19 | /5SpC3/A*A*TGATACGGCGACCACCGAGATCTACACTCTTT CCCTACACGACGCTCTTCCGATCT |
| 13-595 | 20 | /5SpC3/A*A*TGATACGGCGACCACCGAGATCTACACTCTTT CCCTACACGACGCTCTTCCGATCTN |
| 13-510 | 21 | /5PHOS/AGATCGGAAGAGCACACGTCTGAACTCCAGTCAC GCCAATATCTCGTATGCCGTCTTCTGCT*T*G/3spC3/ |

*Phosphorothioated DNA bases
/5SpC3/: 5' C3 spacer (IDT)
/3SpC3/: 3' C3 spacer (IDT)
/5PHOS/: 5' Phosphorylation (IDT)
/3PHOS/: 3' Phosphorylation (IDT)
/5FAM/: 5' 6-carboxyfluorescein (IDT)
/3FAM/: 3' 6-carboxyfluorescein (IDT)
ddT: 2',3'-Dideoxythymidine (TriLink)

TABLE 2

Oligonucleotides used in Example 12.

| Sequence name | SEQ ID NO | Sequence (5'-3') | Final concentration in PCR (nM) |
|---|---|---|---|
| 14-758 | 22 | TCAGACGTGTGCTCTTCCGATCTTCTTGCAGCAG CCAGA*C*T | 10 nM |
| 14-759 | 23 | TCAGACGTGTGCTCTTCCGATCTCCTGCCCTTCC AATGGA*T*C | 10 nM |
| 14-760 | 24 | TCAGACGTGTGCTCTTCCGATCTCCCCTAGCAGA GACCT*G*T | 5 nM |
| 14-864 | 25 | TCAGACGTGTGCTCTTCCGATCTGCCCAACCCTT GTCCTT*A*C | 20 nM |
| 14-762 | 26 | TCAGACGTGTGCTCTTCCGATCTCTGACTGCTCT TTTCACCC*A*T | 5 nM |
| 14-763 | 27 | TCAGACGTGTGCTCTTCCGATCTGAGCAGCCTCT GGCATTC*T*G | 5 nM |
| 14-764 | 28 | TCAGACGTGTGCTCTTCCGATCTTGAAGACCCA GGTCCAGAT*G*A | 5 nM |
| 14-765 | 29 | TCAGACGTGTGCTCTTCCGATCTGCTGCCCTGGT AGGTTTTC*T*G | 5 nM |
| 14-766 | 30 | TCAGACGTGTGCTCTTCCGATCTCTGGCCCCTGT CATCTTC*T*G | 15 nM |
| 14-767 | 31 | TCAGACGTGTGCTCTTCCGATCTCAGGCATTGA AGTCTCATG*G*A | 15 nM |
| 14-768 | 32 | TCAGACGTGTGCTCTTCCGATCTTCCTCCCTGCT TCTGTC*T*C | 10 nM |
| 14-769 | 33 | TCAGACGTGTGCTCTTCCGATCTCTGTCAGTGGG GAACAAGA*A*G | 10 nM |
| 14-885 | 34 | TCAGACGTGTGCTCTTCCGATCTGTGCTGTGACT GCTTGTA*G*A | 10 nM |
| 14-886 | 35 | TCAGACGTGTGCTCTTCCGATCTCTCTGTCTCCT TCCTCTTCCT*A*C | 10 nM |
| 14-869 | 36 | TCAGACGTGTGCTCTTCCGATCTCTGTGCAGCTG TGGGTT*G*A | 10 nM |

TABLE 2-continued

Oligonucleotides used in Example 12.

| Sequence name | SEQ ID NO | Sequence (5'-3') | Final concentration in PCR (nM) |
|---|---|---|---|
| 14-773 | 37 | TCAGACGTGTGCTCTTCCGATCTGCTCACCATCG CTATCTG*A*G | 10 nM |
| 14-865 | 38 | TCAGACGTGTGCTCTTCCGATCTCATGACGGAG GTTGTGA*G*G | 5 nM |
| 14-775 | 39 | TCAGACGTGTGCTCTTCCGATCTAGCAATCAGT GAGGAATCAG*A*G | 5 nM |
| 14-776 | 40 | TCAGACGTGTGCTCTTCCGATCTAGCTGGGGCT GGAGA*G*A | 5 nM |
| 14-777 | 41 | TCAGACGTGTGCTCTTCCGATCTGTCATCCAAAT ACTCCACACG*C*A | 5 nM |
| 14-778 | 42 | TCAGACGTGTGCTCTTCCGATCTGCATCTTATCC GAGTGGAA*G*G | 5 nM |
| 14-779 | 43 | TCAGACGTGTGCTCTTCCGATCTCACTGACAACC ACCCTTAA*C*C | 5 nM |
| 14-780 | 44 | TCAGACGTGTGCTCTTCCGATCTCAGGTAGGAC CTGATTTCCTT*A*C | 5 nM |
| 14-781 | 45 | TCAGACGTGTGCTCTTCCGATCTTTCTTGCGGAG ATTCTCTT*C*C | 5 nM |
| 14-782 | 46 | TCAGACGTGTGCTCTTCCGATCTTGGGACGGAA CAGCTTTG*A*G | 5 nM |
| 14-783 | 47 | TCAGACGTGTGCTCTTCCGATCTCCACCGCTTCT TGTCC*T*G | 5 nM |
| 14-784 | 48 | TCAGACGTGTGCTCTTCCGATCTGGGTGCAGTTA TGCCTC*A*G | 5 nM |
| 14-785 | 49 | TCAGACGTGTGCTCTTCCGATCTAGACTTAGTAC CTGAAGGGT*G*A | 5 nM |
| 14-786 | 50 | TCAGACGTGTGCTCTTCCGATCTTAGCACTGCCC AACAACA*C*C | 5 nM |
| 14-787 | 51 | TCAGACGTGTGCTCTTCCGATCTCGGCATTTTGA GTGTTAGACT*G*G | 5 nM |
| 14-788 | 52 | TCAGACGTGTGCTCTTCCGATCTCCTGGTTGTAG CTAACTAACT*T*C | 10 nM |
| 14-789 | 53 | TCAGACGTGTGCTCTTCCGATCTACCATCGTAAG TCAAGTAGCA*T*C | 10 nM |
| 14-790 | 54 | TCAGACGTGTGCTCTTCCGATCTATGGTTCTATG ACTTTGCCT*G*A | 5 nM |
| 14-791 | 55 | TCAGACGTGTGCTCTTCCGATCTAGCAGGCTAG GCTAAGCTA*T*G | 5 nM |
| 14-792 | 56 | TCAGACGTGTGCTCTTCCGATCTCCTGCTGAAAA TGACTGAATATAAACT*T*G | 10 nM |
| 14-793 | 57 | TCAGACGTGTGCTCTTCCGATCTGGTCCTGCACC AGTAATAT*G*C | 10 nM |
| 14-794 | 58 | TCAGACGTGTGCTCTTCCGATCTTGCTTGCTCTG ATAGGAAATG*A*G | 10 nM |
| 14-795 | 59 | TCAGACGTGTGCTCTTCCGATCTGGATCCAGAC AACTGTTCAAAC*T*G | 10 nM |
| 14-796 | 60 | TCAGACGTGTGCTCTTCCGATCTCCAGAAACTG CCTCTTGA*C*C | 3.75 nM |
| 14-797 | 61 | TCAGACGTGTGCTCTTCCGATCTGATGTAAGGG ACAAGCAG*C*C | 3.75 nM |

TABLE 2-continued

Oligonucleotides used in Example 12.

| Sequence name | SEQ ID NO | Sequence (5'-3') | Final concentration in PCR (nM) |
|---|---|---|---|
| 14-798 | 62 | TCAGACGTGTGCTCTTCCGATCTGAACCAATGG ATCGATCTG*C*C | 5 nM |
| 14-799 | 63 | TCAGACGTGTGCTCTTCCGATCTGGGGAACTGA TGTGACTTA*C*C | 5 nM |
| 14-800 | 64 | TCAGACGTGTGCTCTTCCGATCTGAGCAAGA GGCTTTGG*A*G | 5 nM |
| 14-801 | 65 | TCAGACGTGTGCTCTTCCGATCTAACAGTGCAG TGTGGAAT*C*C | 5 nM |
| 14-802 | 66 | TCAGACGTGTGCTCTTCCGATCTCCACAGAAAC CCATGTATGAAG*T*A | 5 nM |
| 14-803 | 67 | TCAGACGTGTGCTCTTCCGATCTGTACCCAAAA AGGTGACATG*G*A | 5 nM |
| 14-804 | 68 | TCAGACGTGTGCTCTTCCGATCTTTTCAGTGTTA CTTACCTGTCTTG*T*C | 10 nM |
| 14-805 | 69 | TCAGACGTGTGCTCTTCCGATCTGGACTCTGAA GATGTACCTATGG*T*C | 10 nM |
| 14-806 | 70 | TCAGACGTGTGCTCTTCCGATCTCTCACCATGTC CTGACTG*T*G | 10 nM |
| 14-807 | 71 | TCAGACGTGTGCTCTTCCGATCTGTGGCACTCTG GAAG*C*A | 10 nM |
| 14-808 | 72 | TCAGACGTGTGCTCTTCCGATCTGTTACTGAAAG CTCAGGGAT*A*G | 10 nM |
| 14-809 | 73 | TCAGACGTGTGCTCTTCCGATCTCCACACTTACA CATCACTTT*G*C | 10 nM |
| 14-810 | 74 | TCAGACGTGTGCTCTTCCGATCTTAGTCTTTCTT TGAAGCAGCA*A*G | 10 nM |
| 14-811 | 75 | TCAGACGTGTGCTCTTCCGATCTCTAGCTGTGAT CCTGAAACTG*A*A | 10 nM |
| 14-812 | 76 | TCAGACGTGTGCTCTTCCGATCTTCCTCCTGCAG GATTCCT*A*C | 20 nM |
| 14-813 | 77 | TCAGACGTGTGCTCTTCCGATCTTGGTGGATGTC CTCAAAAG*A*C | 20 nM |
| 14-814 | 78 | TCAGACGTGTGCTCTTCCGATCTCAGGATTCTTA CAGAAAACAAGTG*G*T | 15 nM |
| 14-815 | 79 | TCAGACGTGTGCTCTTCCGATCTTGATGGCAAAT ACACAGAGGA*A*G | 15 nM |
| 14-816 | 80 | TCAGACGTGTGCTCTTCCGATCTGACGGGTAGA GTGTGCG*T*G | 5 nM |
| 14-817 | 81 | TCAGACGTGTGCTCTTCCGATCTCGCCACAGAG AAGTTGTTG*A*G | 5 nM |
| 14-818 | 82 | TCAGACGTGTGCTCTTCCGATCTCGCACTGGCCT CATCT*T*G | 10 nM |
| 14-819 | 83 | TCAGACGTGTGCTCTTCCGATCTTTCCAGTGTG ATGATGGTG*A*G | 10 nM |
| 14-820 | 84 | TCAGACGTGTGCTCTTCCGATCTCATGTGTAACA GTTCCTGCA*T*G | 5 nM |
| 14-821 | 85 | TCAGACGTGTGCTCTTCCGATCTGGTCAGAGGC AAGCAG*A*G | 5 nM |
| 14-822 | 86 | TCAGACGTGTGCTCTTCCGATCTTACTTCTCCC CCTCCTC*T*G | 10 nM |

TABLE 2-continued

Oligonucleotides used in Example 12.

| Sequence name | SEQ ID NO | Sequence (5'-3') | Final concentration in PCR (nM) |
|---|---|---|---|
| 14-823 | 87 | TCAGACGTGTGCTCTTCCGATCTCTTCCCAGCCTGGGCA*T*C | 10 nM |
| 14-824 | 88 | TCAGACGTGTGCTCTTCCGATCTGCTGAATGAGGCCTTGGA*A*C | 8 nM |
| 14-825 | 89 | TCAGACGTGTGCTCTTCCGATCTCTTTCCAACCTAGGAAGGC*A*G | 8 nM |
| 14-826 | 90 | TCAGACGTGTGCTCTTCCGATCTGCACTGTAATAATCCAGACTGT*G*T | 5 nM |
| 14-827 | 91 | TCAGACGTGTGCTCTTCCGATCTCATGTACTGGTCCCTCATT*G*C | 5 nM |
| 14-828 | 92 | TCAGACGTGTGCTCTTCCGATCTCCTTTCAGGATGGTGGATG*T*G | 20 nM |
| 14-829 | 93 | TCAGACGTGTGCTCTTCCGATCTCGACTCCACCAGGACT*T*G | 20 nM |
| 14-830 | 94 | TCAGACGTGTGCTCTTCCGATCTGTTAACCTTGCAGAATGGTCG*A*T | 5 nM |
| 14-831 | 95 | TCAGACGTGTGCTCTTCCGATCTCCACGAGAACTTGATCATATTC*A*C | 5 nM |
| 14-832 | 96 | TCAGACGTGTGCTCTTCCGATCTCAACAGGTTCTTGCTGGTG*T*G | 5 nM |
| 14-833 | 97 | TCAGACGTGTGCTCTTCCGATCTATGGTGGGATCATATTCATCTA*C*A | 5 nM |
| 14-836 | 98 | TCAGACGTGTGCTCTTCCGATCTAGCTTGTGGAGCCTCTTA*C*A | 5 nM |
| 14-837 | 99 | TCAGACGTGTGCTCTTCCGATCTGGGACCTTACCTTATACACC*G*T | 5 nM |
| 14-838 | 100 | TCAGACGTGTGCTCTTCCGATCTCACCATCTCACAATTGCCA*G*T | 5 nM |
| 14-839 | 101 | TCAGACGTGTGCTCTTCCGATCTGCTTTCGGAGATGTTGCTTC*T*C | 5 nM |
| 14-840 | 102 | TCAGACGTGTGCTCTTCCGATCTGATCCCAGAAGGTGAGAAAG*T*T | 5 nM |
| 14-841 | 103 | TCAGACGTGTGCTCTTCCGATCTTGAGGTTCAGAGCCATG*G*A | 5 nM |
| 14-842 | 104 | TCAGACGTGTGCTCTTCCGATCTCTCCAGGAAGCCTACGT*G*A | 10 nM |
| 14-843 | 105 | TCAGACGTGTGCTCTTCCGATCTGGACATAGTCCAGGAGG*C*A | 10 nM |
| 14-844 | 106 | TCAGACGTGTGCTCTTCCGATCTCACCGCAGCATGTCAAGA*T*C | 10 nM |
| 14-845 | 107 | TCAGACGTGTGCTCTTCCGATCTGACCTAAAGCCACCTCCTT*A*C | 10 nM |
| 14-846 | 108 | TCAGACGTGTGCTCTTCCGATCTTCCACTATACTGACGTCTCCA*A*C | 15 nM |
| 14-847 | 109 | TCAGACGTGTGCTCTTCCGATCTACACACGCAAAATACTCCTTC*A*G | 15 nM |
| 14-850 | 110 | TCAGACGTGTGCTCTTCCGATCTGTCCTCACAGAGTTCAA*G*C | 5 nM |
| 14-851 | 111 | TCAGACGTGTGCTCTTCCGATCTGTTTTGCAGATGATGGGCT*C*C | 5 nM |

TABLE 2-continued

Oligonucleotides used in Example 12.

| Sequence name | SEQ ID NO | Sequence (5'-3') | Final concentration in PCR (nM) |
|---|---|---|---|
| 14-852 | 112 | TCAGACGTGTGCTCTTCCGATCTCTGGACCAAGCCCATC*A*C | 5 nM |
| 14-853 | 113 | TCAGACGTGTGCTCTTCCGATCTTGTGGCCTTGTACTGCA*G*A | 5 nM |
| 14-854 | 114 | TCAGACGTGTGCTCTTCCGATCTCAGTGTGTTCACAGAGACC*T*G | 5 nM |
| 14-855 | 115 | TCAGACGTGTGCTCTTCCGATCTGTAGGAAATAGCAGCCTCAC*A*T | 5 nM |
| 14-856 | 116 | TCAGACGTGTGCTCTTCCGATCTTGTTCCTGATCTCCTTAGACA*A*C | 15 nM |
| 14-857 | 117 | TCAGACGTGTGCTCTTCCGATCTCTTGCTGCACTTCTCACA*C*C | 15 nM |
| 14-858 | 118 | TCAGACGTGTGCTCTTCCGATCTTGAAAATTCCAGTGGCCAT*C*A | 7.5 nM |
| 14-859 | 119 | TCAGACGTGTGCTCTTCCGATCTCAATGAAGAGAGACCAGA*G*C | 7.5 nM |
| 14-860 | 120 | TCAGACGTGTGCTCTTCCGATCTCCCATACCCTCTCAGCGT*A*C | 5 nM |
| 14-861 | 121 | TCAGACGTGTGCTCTTCCGATCTGTGGATGTCAGGCAGAT*G*C | 5 nM |
| 14-862 | 122 | TCAGACGTGTGCTCTTCCGATCTCCCTCCCAGAAGGTCTAC*A*T | 15 nM |
| 14-863 | 123 | TCAGACGTGTGCTCTTCCGATCTTTTTGACATGGTTGGGACTCT*T*G | 15 nM |
| 14-882 | 124 | TCAGACGUGUGCUCUUCCGAU*C*U | 10 µM |
| 14-382 | 125 | GTGACTGGAGTTCAGACGTGT/3PHOS/ | - |
| 14-877 | 126 | AACTCCAGTCACTAATGCGCATCTCGTATGCCGTCTTCTGCTTG/3PHOS/ | - |
| 14-571 | 127 | AATGATACGGCGACCACCGAGATCTACACAGGCGAAGACACTCTTTCCCTACACGACGCTCTTCCGATCT | - |

*Phosphorothioated DNA bases (IDT)
/3PHOS/: 3' Phosphorylation (IDT)

The preceding disclosure is supplemented by the following description of various aspects and embodiments of the disclosure, as provided in the following enumerated paragraphs.

A method of producing a processed substrate molecule, the method comprising: (i) ligating a first polynucleotide to a 3' terminus of a substrate molecule that is at least partially double stranded; (ii) annealing a second polynucleotide to the first polynucleotide under conditions that promote the annealing; (iii) excising at least one nucleotide from the 5' terminus of the substrate molecule; and then (iv) ligating the second polynucleotide to the 5' terminus of the double stranded substrate molecule to produce the processed substrate molecule.

In one embodiment, the method further comprises the step, prior to step (i), of contacting the substrate molecule with a phosphatase enzyme.

In one embodiment, the method further comprises the step of making the substrate molecule blunt-ended by contacting the substrate molecule with a polymerase enzyme possessing 3'-5' exonuclease activity.

In one embodiment, the method further comprises the step of contacting the substrate molecule with a template-independent polymerase to adenylate the 3' end of the substrate molecule.

In one embodiment, the substrate molecule is naturally occurring or the substrate molecule is synthetic.

In one embodiment, the substrate molecule is naturally occurring.

In one embodiment, the substrate molecule is genomic DNA.

In one embodiment, the genomic DNA is eukaryotic or prokaryotic.

In one embodiment, wherein the genomic DNA is fragmented in vitro or in vivo.

In one embodiment, the in vitro fragmenting is performed by a process selected from the group consisting of shearing, cleaving with an endonuclease, sonication, heating, irradiation using an alpha, beta, or gamma source, chemical cleavage in the presence of metal ions, radical cleavage, and a combination thereof.

In one embodiment, the in vivo fragmenting occurs by a process selected from the group consisting of apoptosis, radiation, and exposure to asbestos.

In one embodiment, the substrate molecule is synthetic and is selected from the group consisting of cDNA, DNA produced by whole genome amplification, primer extension products comprising at least one double-stranded terminus, and a PCR amplicon.

The method of any of the preceding embodiments wherein the first polynucleotide is at least partially double stranded and comprises oligonucleotide 1 and oligonucleotide 2.

In one embodiment, the second polynucleotide anneals to oligonucleotide 1.

In one embodiment, the annealing results in a nick, a gap, or an overlapping base between the second polynucleotide and the substrate molecule.

In one embodiment, the second polynucleotide is contacted with a polymerase, resulting in degradation of oligonucleotide 2.

In one embodiment, oligonucleotide 2 comprises a base that is susceptible to degradation.

In one embodiment, oligonucleotide 2 comprises a blocking group at its 3' end that prevents ligation.

The method of any of the preceding embodiments wherein the second polynucleotide comprises a modified base.

In one embodiment, the annealing results in dehybridization of oligonucleotide 1 and oligonucleotide 2.

The method of any of the preceding embodiments, further comprising: (i) ligating a third polynucleotide to a 3' terminus of an additional substrate molecule that is at least partially double stranded; (ii) annealing a fourth polynucleotide to the third polynucleotide under conditions that promote the annealing; (iii) excising at least one nucleotide from the 5' terminus of the additional substrate molecule; and then (iv) ligating the fourth polynucleotide to the 5' terminus of the double stranded additional substrate molecule to produce a processed additional substrate molecule.

In one embodiment, the first polynucleotide and the third polynucleotide are the same.

In one embodiment, the second polynucleotide and the fourth polynucleotide are the same.

What is claimed is:

1. A method of multiplex PCR amplification of a specific target locus on a nucleic acid substrate for preparing a targeted next generation sequencing library comprising the steps of:
(i) combining a plurality of target-specific primers with the nucleic acid substrate to yield a single polymerase chain reaction (PCR) reaction mixture, wherein the plurality of target-specific primers comprise a first forward primer, a second forward primer, a first reverse primer and a second reverse primer, wherein each of the first and second forward and reverse primers comprise a 3' complementary sequence that is fully complementary to a sequence of the specific target locus and a 5' noncomplementary sequence that is not complementary to a sequence of the nucleic acid substrate, wherein the 3' complementary sequence for each of the first and second forward and reverse primers is different, wherein the 3' complementary sequence is between 10 and 40 bases in length, wherein the nucleic acid substrate is human genomic DNA, and wherein the specific target locus is a gene known to have clinical relevance in oncology
(ii) subjecting the PCR reaction mixture to a multiplex polymerase chain reaction thereby generating at least three amplicons within the specific target locus, wherein the at least three amplicons comprise a first amplicon produced by the first forward primer and the first reverse primer, a second amplicon produced by the second forward primer and the second reverse primer, and a third amplicon produced by the second forward primer and the first reverse primer, wherein the third amplicon is shorter in length than the first and second amplicons, wherein at least a portion of the 5' noncomplementary sequence of the second forward primer and the first reverse primer is the same such that each strand of the third amplicon comprises a 3' sequence and a 5' sequence that are complementary to each other, wherein the third amplicon possesses overlapping sequence with the first and second amplicons, wherein the first amplicon possesses overlapping sequence with the second amplicon, wherein when the third amplicon is denatured, each strand of the third amplicon forms a secondary structure as a result of the 3' sequence being complementary to the 5' sequence, wherein the secondary structure is stable during a primer annealing step of the multiplex polymerase chain reaction.

2. The method of claim 1, wherein the 3' complementary sequence is between 16 and 30 bases in length.

3. The method of claim 1, wherein the gene known to have clinical relevance in oncology is selected from the group consisting of ABU, ABL1, ABL2, ACSL3, AF15Q14, AF1Q, AF3p21, AF5q31, AKAP9, AKT1, AKT2, ALDH2, ALK, ALO17, AMER1, APC, ARHGEF12, ARHH, ARID1A, ARID2, ARNT, ASPSCR1, ASXL1, ATF1, ATIC, ATM, ATP1A1, ATP2B3, ATRX, AXIN1, BAP1, BCL10, BCL11A, BCL11B, BCL2, BCL3, BCLS, BCL6, BCL7A, BCL9, BCOR, BCR, BHD, BIRC3, BLM, BMPR1A, BRAF, BRCA1, BRCA2, BRD3, BRD4, BRIP1, BTG1, BUB1B, C12orf9, C15orf21, C15orf55, C16orf75, C2orf44, CACNA1D, CALR, CAMTA1, CANT1, CARD11, CARS, CASP8, CBFA2T1, CBFA2T3, CBFB, CBL, CBLB, CBLC, CCDC6, CCNBHP1, CCND1, CCND2, CCND3, CCNE1, CD273, CD274, CD74, CD79A, CD79B, CDC73, CDH1, CDH11, CDK12, CDK4, CDK6, CDKN2A, CDKN2C, CDKN2a(p14), CDX2, CEBPA, CEP1, CEP89, CHCHD7, CHEK2, CHIC2, CHN1, CIC, CIITA, CLIP1, CLTC, CLTCL1, CMKOR1, CNOT3, COL1A1, COL2A1, COPEB, COX6C, CREB1, CREB3L1, CREB3L2, CREBBP, CRLF2, CRTC3, CSF3R, CTNNB1, CUX1, CYLD, D10S170, DAXX, DCTN1, DDB2, DDIT3, DDX10, DDX5, DDX6, DEK, DICER1, DNM2, DNMT3A, DUX4, EBF1, ECT2L, EGFR, EIF3E, EIF4A2, ELF4, ELK4, ELKS, ELL, ELN, EML4, EP300, EPS15, ERBB2, ERC1, ERCC2, ERCC3, ERCC4, ERCC5, ERG, ETV1, ETV4, ETV5, ETV6, EVI1, EWSR1, EXT1, EXT2, EZH2, EZR, FACL6, FAM46C, FANCA, FANCC, FANCD2, FANCE, FANCF, FANCG, FAS, FBXO11, FBXW7, FCGR2B, FEV, FGFR1, FGFR1OP, FGFR2, FGFR3, FH, FHIT, FIP1L1, FLI1, F1127352, FLT3, FNBP1, FOXA1, FOXL2, FOXO1A, FOXO3A, FOXO4, FOXP1, FSTL3, FUBP1, FUS, FVT1, GAS7, GATA1, GATA2, GATA3, GMPS, GNA11, GNAQ, GNAS, GOLGA5, GOPC, GPC3, GPHN, GRAF, H3F3A, H3F3B, HCMOGT-1, HEAB, HERPUD1, HEY1, HIP1, HIST1H3B, HIST1H4I, HLA-A, HLF, HLXB9, HMGA1, HMGA2, HNRNPA2B1, HOOK3, HOXA11, HOXA13, HOXA9, HOXC11, HOXC13, HOXD11, HOXD13, HRAS, HSPCA, HSPCB, IDH1, IDH2, IGH\, IGK, IGL, IKZFL IL2, IL21R, IL6ST, IL7R, IRF4, IRTA1, ITK, JAKL JAK2, JAK3, JAZFL JUN, KCNJ5, KDM5A, KDM5C, KDM6A, KDR, KIAA1549, KIAA1598, KIF5B, KIT, KLF4, KLK2, KMT2D, KRAS, KTN1, LAF4, LASP1, LCK, LCP1, LCX, LHFP, LIFR, LMNA, LMO1, LMO2, LPP, LRIG3, LSM14A, LYL1, MAF, MAFB, MALAT1, MALT1, MAML2, MAP2K1, MAP2K2, MAP2K4, MAX, MDM2, MDM4, MDS1, MDS2, MECT1, MED12, MEN1, MET, MITF, MKL1, MLF1, MLH1, MLL, MLL3, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYD88, MYH11, MYH9, MYO5A, MYST4, NAB2, NACA, NBS1, NCOA1, NCOA2, NCOA4, NDRG1, NF1, NF2, NFATC2, NFE2L2, NFIB, NFKB2, NIN, NKX2-1, NONO, NOTCH1, NOTCH2, NPM1, NR4A3, NRAS, NRG1, NSD1, NT5C2, NTRK1, NTRK3, NUMA1, NUP214, NUP98, NUTM2A, NUTM2B, OLIG2, OMD, P2RY8, PAFAH1B2, PALB2, PAX3, PAX5, PAX7, PAX8, PBRM1, PBX1, PCM1, PCSK7, PDE4DIP, PDGFB, PDGFRA, PDGFRB, PER1, PHF6, PHOX2B, PICALM, PIK3CA, PIK3R1, PIM1, PLAG1, PLCG1, PML, PMS1, PMS2, PMX1, PNUTL1, POT1, POU2AF1, POU5F1, PPARG, PPFIBP1, PPP2R1A, PRCC, PRDM1, PRDM16, PRF1, PRKAR1A, PSIP1, PTCH1, PTEN, PTPN11, PTPRB, PTPRC, PTPRK, PWWP2A, RAB5EP, RAC1, RAD21, RAD51L1, RAF1, RALGDS, RANBP17, RAP1GD51, RARA, RB1, RBM15, RECQL4, REL, RET, RNF43, ROS1, RPL10, RPL22, RPL5, RPN1, RSPO2, RSPO3, RUNDC2A, RUNX1, RUNXBP2, SBDS, SDC4, SDH5, SDHB, SDHC, SDHD, 42253, SET, SETBP1, SETD2, SF3B1, SFPQ, SFRS3, SH2B3, SH3GL1, SIL, SLC34A2, SLC45A3, SMAD4, SMARCA4, SMARCB1, SMARCE1, SMO, SOCS1, SOX2, SRGAP3, SRSF2, SS18, SS18L1, SSX1, SSX2, SSX4, STAG2, STAT3, STATSB, STAT6, STK11, STL, SUFU, SUZ12, SYK, TAF15, TALL TAL2, TBL1XR1, TCEA1, TCF1, TCF12, TCF3, TCF7L2, TCL1A, TCL6, TERT, TET2, TFE3, TFEB, TFG, TFPT, TFRC, THRAP3, TIF1, TLX1, TLX3, TMPRSS2, TNFAIP3, TNFRSF14, TNFRSF17, TOP1, TP53, TPM3, TPM4, TPR, TRA, TRAF7, TRB, TRD, TRIM27, TRIM33, TRIP11, TRRAP, TSC1, TSC2, TSHR, TTL, U2AF1, UBRS, USP6, VHL, VTI1A, WAS, WHSC1, WHSC1L1, WIF1, WRN, WT1, WWTR1, XPA, XPC, XPO1, YWHAE, ZCCHC8, ZNF145, ZNF198, ZNF278, ZNF331, ZNF384, ZNF521, ZNF9 and ZRSR2.

4. The method of claim 1, wherein the gene known to have clinical relevance in oncology is BRCA1 or BRCA2.

5. The method of claim 1, wherein the gene known to have clinical relevance in oncology is TP53.

6. The method of claim 1, further comprising (iii) incubating a sample comprising the first and second amplicons with a 3' adaptor, a 5' adaptor and a ligase under conditions sufficient to permit ligation of the 3' adaptor to a 3' end of the first and second amplicons and 5' adaptor to a 5' end of the first and second amplicons thereby yielding the targeted next generation sequencing library.

7. The method of claim 6, further comprising (iv) sequencing the targeted next generation sequencing library.

8. The method of claim 1, wherein the melting temperature of the target-specific primers is from about 60.5° C. to about 65.5° C.

9. A method of multiplex PCR amplification of a specific target locus on a nucleic acid substrate for preparing a targeted next generation sequencing library comprising the steps of:

(i) combining a plurality of target-specific primers with the nucleic acid substrate to yield a single polymerase chain reaction (PCR) reaction mixture, wherein the plurality of target-specific primers comprise a first forward primer, a second forward primer, a first reverse primer and a second reverse primer, wherein each of the first and second forward and reverse primers comprise a 3' complementary sequence that is fully complementary to a sequence of the specific target locus and a 5' noncomplementary sequence that is not complementary to a sequence of the nucleic acid substrate, wherein the 3' complementary sequence for each of the first and second forward and reverse primers is different, wherein the 3' complementary sequence is between 16 and 30 bases in length, and wherein the specific target locus is a gene known to have clinical relevance in oncology;
(ii) subjecting the PCR reaction mixture to a multiplex polymerase chain reaction thereby generating at least three amplicons within the specific target locus, wherein the at least three amplicons comprise a first amplicon produced by the first forward primer and the first reverse primer, a second amplicon produced by the second forward primer and the second reverse primer, and a third amplicon produced by the second forward primer and the first reverse primer, wherein the third amplicon is shorter in length than the first and second amplicons, wherein at least a portion of the 5' non-complementary sequence of the second forward primer and the first reverse primer is the same such that each strand of the third amplicon comprises a 3' sequence and a 5' sequence that are complementary to each other, wherein the third amplicon possesses overlapping sequence with the first and second amplicons, wherein the first amplicon possesses overlapping sequence with the second amplicon, wherein when the third amplicon is denatured, each strand of the third amplicon forms a secondary structure as a result of the 3' sequence being complementary to the 5' sequence, wherein at the end of the multiplex polymerase chain reaction, the first and second amplicons are each present at a greater amount than the third amplicon, and wherein the nucleic acid substrate is human genomic DNA.

10. The method of claim 9, wherein the gene known to have clinical relevance in oncology is selected from the group consisting of ABU, ABL1, ABL2, ACSL3, AF15Q14, AF1Q, AF3p21, AF5q31, AKAP9, AKT1, AKT2, ALDH2, ALK, ALO17, AMER1, APC, ARHGEF12, ARHH, ARID1A, ARID2, ARNT, ASPSCR1, ASXL1, ATF1, ATIC, ATM, ATP1A1, ATP2B3, ATRX, AXIN1, BAP1, BCL10, BCL11A, BCL11B, BCL2, BCL3, BCLS, BCL6, BCL7A, BCL9, BCOR, BCR, BHD, BIRC3, BLM, BMPR1A, BRAF, BRCA1, BRCA2, BRD3, BRD4, BRIP1, BTG1, BUB1B, C12orf9, C15orf21, C15orf55, C16orf75, C2orf44, CACNA1D, CALR, CAMTA1, CANT1, CARD11, CARS, CASP8, CBFA2T1, CBFA2T3, CBFB, CBL, CBLB, CBLC, CCDC6, CCNBHP1, CCND1, CCND2, CCND3, CCNE1, CD273, CD274, CD74, CD79A, CD79B, CDC73, CDH1, CDH11, CDK12, CDK4, CDK6, CDKN2A, CDKN2C, CDKN2a(p14), CDX2, CEBPA, CEP1, CEP89, CHCHD7, CHEK2, CHIC2, CHN1, CIC, CIITA, CLIP1, CLTC, CLTCL1, CMKOR1, CNOT3, COL1A1, COL2A1, COPEB, COX6C, CREB1, CREB3L1, CREB3L2, CREBBP, CRLF2, CRTC3, CSF3R, CTNNB1, CUX1, CYLD, D10S170, DAXX, DCTN1, DDB2, DDIT3, DDX10, DDX5, DDX6, DEK, DICER1, DNM2, DNMT3A, DUX4, EBF1, ECT2L, EGFR, EIF3E, EIF4A2, ELF4, ELK4, ELKS, ELL, ELN, EML4, EP300, EPS15, ERBB2, ERC1, ERCC2, ERCC3, ERCC4, ERCC5, ERG, ETV1, ETV4, ETV5, ETV6, EVI1, EWSR1, EXT1, EXT2, EZH2, EZR, FACL6, FAM46C, FANCA, FANCC, FANCD2, FANCE, FANCF, FANCG, FAS, FBXO11, FBXW7, FCGR2B, FEV, FGFR1, FGFR1OP, FGFR2, FGFR3, FH, FHIT, FIP1L1, FLI1, F1127352, FLT3, FNBP1, FOXA1, FOXL2, FOXO1A, FOXO3A, FOXO4, FOXP1, FSTL3, FUBP1, FUS, FVT1, GAS7, GATA1, GATA2, GATA3, GMPS, GNA11, GNAQ, GNAS, GOLGA5, GOPC, GPC3, GPHN, GRAF, H3F3A, H3F3B, HCMOGT-1, HEAB, HERPUD1, HEY1, HIP1, HIST1H3B, HIST1H4I, HLA-A, HLF, HLXB9, HMGA1, HMGA2, HNRNPA2B1, HOOK3, HOXA11, HOXA13, HOXA9, HOXC11, HOXC13, HOXD11, HOXD13, HRAS, HSPCA, HSPCB, IDH1, IDH2, IGH\, IGK, IGL, IKZFL IL2, IL21R, IL6ST, IL7R, IRF4, IRTA1, ITK, JAKL JAK2, JAK3, JAZFL JUN, KCNJ5, KDM5A, KDM5C, KDM6A, KDR, KIAA1549, KIAA1598, KIF5B, KIT, KLF4, KLK2, KMT2D, KRAS, KTN1, LAF4, LASP1, LCK, LCP1, LCX, LHFP, LIFR, LMNA, LMO1, LMO2, LPP, LRIG3, LSM14A, LYL1, MAF, MAFB, MALAT1, MALT1, MAML2, MAP2K1, MAP2K2, MAP2K4, MAX, MDM2, MDM4, MDS1, MDS2, MECT1, MED12, MEN1, MET, MITF, MKL1, MLF1, MLH1, MLL, MLL3, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYD88, MYH11, MYH9, MYO5A, MYST4, NAB2, NACA, NBS1, NCOA1, NCOA2, NCOA4, NDRG1, NF1, NF2, NFATC2, NFE2L2, NFIB, NFKB2, NIN, NKX2-1, NONO, NOTCH1, NOTCH2, NPM1, NR4A3, NRAS, NRG1, NSD1, NT5C2, NTRK1, NTRK3, NUMA1, NUP214, NUP98, NUTM2A, NUTM2B, OLIG2, OMD, P2RY8, PAFAH1B2, PALB2, PAX3, PAX5, PAX7, PAX8, PBRM1, PBX1, PCM1, PCSK7, PDE4DIP, PDGFB, PDGFRA, PDGFRB, PER1, PHF6, PHOX2B, PICALM, PIK3CA, PIK3R1, PIM1, PLAG1, PLCG1, PML, PMS1, PMS2, PMX1, PNUTL1, POT1, POU2AF1, POU5F1, PPARG, PPFIBP1, PPP2R1A, PRCC, PRDM1, PRDM16, PRF1, PRKAR1A, PSIP1, PTCH1, PTEN, PTPN11, PTPRB, PTPRC, PTPRK, PWWP2A, RAB5EP, RAC1, RAD21, RAD51L1, RAF1, RALGDS, RANBP17, RAP1GD51, RARA, RB1, RBM15, RECQL4, REL, RET, RNF43, ROS1, RPL10, RPL22, RPL5, RPN1, RSPO2, RSPO3, RUNDC2A, RUNX1, RUNXBP2, SBDS, SDC4, SDH5, SDHB, SDHC, SDHD, 42253, SET, SETBP1, SETD2, SF3B1, SFPQ, SFRS3, SH2B3, SH3GL1, SIL, SLC34A2, SLC45A3, SMAD4, SMARCA4, SMARCB1, SMARCE1, SMO, SOCS1, SOX2, SRGAP3, SRSF2, SS18, SS18L1, SSX1, SSX2, SSX4, STAG2, STAT3, STATSB, STAT6, STK11, STL, SUFU, SUZ12, SYK, TAF15, TAL1, TAL2, TBL1XR1, TCEA1, TCF1, TCF12, TCF3, TCF7L2, TCL1A, TCL6, TERT, TET2, TFE3, TFEB, TFG, TFPT, TFRC, THRAP3, TIF1, TLX1, TLX3, TMPRSS2, TNFAIP3, TNFRSF14, TNFRSF17, TOP1, TP53, TPM3, TPM4, TPR, TRA, TRAF7, TRB, TRD, TRIM27, TRIM33, TRIP11, TRRAP, TSC1, TSC2, TSHR, TTL, U2AF1, UBRS, USP6, VHL, VTI1A, WAS, WHSC1, WHSC1L1, WIF1, WRN, WT1, WWTR1, XPA, XPC, XPO1, YWHAE, ZCCHC8, ZNF145, ZNF198, ZNF278, ZNF331, ZNF384, ZNF521, ZNF9 and ZRSR2.

11. The method of claim 9, wherein the melting temperature of the target-specific primers is from about 60.5° C. to about 65.5° C.

12. The method of claim 9, wherein the gene known to have clinical relevance in oncology is BRCA1 or BRCA2.

13. The method of claim 9, wherein the gene known to have clinical relevance in oncology is TP53.

14. A method of multiplex PCR amplification of a specific target locus on a nucleic acid substrate for preparing a targeted next generation sequencing library comprising the steps of:
(i) combining a plurality of target-specific primers with the nucleic acid substrate to yield a single polymerase chain reaction (PCR) reaction mixture, wherein the plurality of target-specific primers comprise a first forward primer, a second forward primer, a first reverse primer and a second reverse primer, wherein each of the first and second forward and reverse primers comprise a 3' complementary sequence that is fully complementary to a sequence of the specific target locus and a 5' noncomplementary sequence that is not complementary to a sequence of the nucleic acid substrate, wherein the 3' complementary sequence for each of the first and second forward and reverse primers is different, wherein the 3' complementary sequence is between 16 and 30 bases in length;

(ii) subjecting the PCR reaction mixture to a multiplex polymerase chain reaction thereby generating at least three amplicons within the specific target locus, wherein the at least three amplicons comprise a first amplicon produced by the first forward primer and the first reverse primer, a second amplicon produced by the second forward primer and the second reverse primer, and a third amplicon produced by the second forward primer and the first reverse primer, wherein the third amplicon is shorter in length than the first and second amplicons, wherein at least a portion of the 5' noncomplementary sequence of the second forward primer and the first reverse primer is the same such that each strand of the third amplicon comprises a 3' sequence and a 5' sequence that are complementary to each other, wherein the third amplicon possesses overlapping sequence with the first and second amplicons, wherein the first amplicon possesses overlapping sequence with the second amplicon, wherein when the third amplicon is denatured, each strand of the third amplicon forms a secondary structure as a result of the 3' sequence being complementary to the 5' sequence, wherein the secondary structure is stable during a primer annealing step of the multiplex polymerase chain reaction.

15. The method of claim 14, wherein the specific target locus is selected from the group consisting of a gene known to have relevance in oncology, a gene associated with drug resistance, inherited or infectious disease, a bacterial gene, a viral gene, and a fungal gene.

16. The method of claim 14, wherein the melting temperature of the target-specific primers is from about 60.5° C. to about 65.5° C.

17. The method of claim 14, wherein the specific target locus is a gene known to have clinical relevance in oncology.

18. The method of claim 17, wherein the gene known to have clinical relevance in oncology is selected from the group consisting of ABU, ABL1, ABL2, ACSL3, AF15Q14, AF1Q, AF3p21, AF5q31, AKAP9, AKT1, AKT2, ALDH2, ALK, ALO17, AMER1, APC, ARHGEF12, ARHH, ARID1A, ARID2, ARNT, ASPSCR1, ASXL1, ATF1, ATIC, ATM, ATP1A1, ATP2B3, ATRX, AXIN1, BAP1, BCL10, BCL11A, BCL11B, BCL2, BCL3, BCLS, BCL6, BCL7A, BCL9, BCOR, BCR, BHD, BIRC3, BLM, BMPR1A, BRAF, BRCA1, BRCA2, BRD3, BRD4, BRIP1, BTG1, BUB1B, C12orf9, C15orf21, C15orf55, C16orf75, C2orf44, CACNA1D, CALR, CAMTA1, CANT1, CARD11, CARS, CASP8, CBFA2T1, CBFA2T3, CBFB, CBL, CBLB, CBLC, CCDC6, CCNBHP1, CCND1, CCND2, CCND3, CCNE1, CD273, CD274, CD74, CD79A, CD79B, CDC73, CDH1, CDH11, CDK12, CDK4, CDK6, CDKN2A, CDKN2C, CDKN2a(p14), CDX2, CEBPA, CEP1, CEP89, CHCHD7, CHEK2, CHIC2, CHN1, CIC, CIITA, CLIP1, CLTC, CLTCL1, CMKOR1, CNOT3, COL1A1, COL2A1, COPEB, COX6C, CREB1, CREB3L1, CREB3L2, CREBBP, CRLF2, CRTC3, CSF3R, CTNNB1, CUX1, CYLD, D10S170, DAXX, DCTN1, DDB2, DDIT3, DDX10, DDX5, DDX6, DEK, DICER1, DNM2, DNMT3A, DUX4, EBF1, ECT2L, EGFR, EIF3E, EIF4A2, ELF4, ELK4, ELKS, ELL, ELN, EML4, EP300, EPS15, ERBB2, ERC1, ERCC2, ERCC3, ERCC4, ERCC5, ERG, ETV1, ETV4, ETV5, ETV6, EVIL EWSR1, EXT1, EXT2, EZH2, EZR, FACL6, FAM46C, FANCA, FANCC, FANCD2, FANCE, FANCF, FANCG, FAS, FBXO11, FBXW7, FCGR2B, FEV, FGFR1, FGFR1OP, FGFR2, FGFR3, FH, FHIT, FIP1L1, FLI1, F1127352, FLT3, FNBP1, FOXA1, FOXL2, FOXO1A, FOXO3A, FOXO4, FOXP1, FSTL3, FUBP1, FUS, FVT1, GAS7, GATA1, GATA2, GATA3, GMPS, GNA11, GNAQ, GNAS, GOLGA5, GOPC, GPC3, GPHN, GRAF, H3F3A, H3F3B, HCMOGT-1, HEAB, HERPUD1, HEY1, HIP1, HIST1H3B, HIST1H4I, HLA-A, HLF, HLXB9, HMGA1, HMGA2, HNRNPA2B1, HOOK3, HOXA11, HOXA13, HOXA9, HOXC11, HOXC13, HOXD11, HOXD13, HRAS, HSPCA, HSPCB, IDH1, IDH2, IGH\, IGK, IGL, IKZFL IL2, IL21R, IL6ST, IL7R, IRF4, IRTA1, ITK, JAKL JAK2, JAK3, JAZFL JUN, KCNJ5, KDM5A, KDM5C, KDM6A, KDR, KIAA1549, KIAA1598, KIF5B, KIT, KLF4, KLK2, KMT2D, KRAS, KTN1, LAF4, LASP1, LCK, LCP1, LCX, LHFP, LIFR, LMNA, LMO1, LMO2, LPP, LRIG3, LSM14A, LYL1, MAF, MAFB, MALAT1, MALT1, MAML2, MAP2K1, MAP2K2, MAP2K4, MAX, MDM2, MDM4, MDS1, MDS2, MECT1, MED12, MEN1, MET, MITF, MKL1, MLF1, MLH1, MLL, MLL3, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYD88, MYH11, MYH9, MYO5A, MYST4, NAB2, NACA, NBS1, NCOA1, NCOA2, NCOA4, NDRG1, NF1, NF2, NFATC2, NFE2L2, NFIB, NFKB2, NIN, NKX2-1, NONO, NOTCH1, NOTCH2, NPM1, NR4A3, NRAS, NRG1, NSD1, NT5C2, NTRK1, NTRK3, NUMA1, NUP214, NUP98, NUTM2A, NUTM2B, OLIG2, OMD, P2RY8, PAFAH1B2, PALB2, PAX3, PAX5, PAX7, PAX8, PBRM1, PBX1, PCM1, PCSK7, PDE4DIP, PDGFB, PDGFRA, PDGFRB, PER1, PHF6, PHOX2B, PICALM, PIK3CA, PIK3R1, PIM1, PLAG1, PLCG1, PML, PMS1, PMS2, PMX1, PNUTL1, POT1, POU2AF1, POU5F1, PPARG, PPFIBP1, PPP2R1A, PRCC, PRDM1, PRDM16, PRF1, PRKAR1A, PSIP1, PTCH1, PTEN, PTPN11, PTPRB, PTPRC, PTPRK, PWWP2A, RAB5EP, RAC1, RAD21, RAD51L1, RAF1, RALGDS, RANBP17, RAP1GD51, RARA, RB1, RBM15, RECQL4, REL, RET, RNF43, ROS1, RPL10, RPL22, RPL5, RPN1, RSPO2, RSPO3, RUNDC2A, RUNX1, RUNXBP2, SBDS, SDC4, SDH5, SDHB, SDHC, SDHD, 42253, SET, SETBP1, SETD2, SF3B1, SFPQ, SFRS3, SH2B3, SH3GL1, SIL, SLC34A2, SLC45A3, SMAD4, SMARCA4, SMARCB1, SMARCE1, SMO, SOCS1, SOX2, SRGAP3, SRSF2, SS18, SS18L1, SSX1, SSX2, SSX4, STAG2, STAT3, STATSB, STAT6, STK11, STL, SUFU, SUZ12, SYK, TAF15, TAL1, TAL2, TBL1XR1, TCEA1, TCF1, TCF12, TCF3, TCF7L2, TCL1A, TCL6, TERT, TET2, TFE3, TFEB, TFG, TFPT, TFRC, THRAP3, TIF1, TLX1, TLX3, TMPRSS2, TNFAIP3, TNFRSF14, TNFRSF17, TOP1, TP53, TPM3, TPM4, TPR, TRA, TRAF7, TRB, TRD, TRIM27, TRIM33, TRIP11, TRRAP, TSC1, TSC2, TSHR, TTL, U2AF1, UBRS, USP6, VHL, VTI1A, WAS, WHSC1, WHSC1L1, WIF1, WRN, WT1, WWTR1, XPA, XPC, XPO1, YWHAE, ZCCHC8, ZNF145, ZNF198, ZNF278, ZNF331, ZNF384, ZNF521, ZNF9 and ZRSR2.

19. The method of claim 17, wherein the gene known to have clinical relevance in oncology is BRCA1 or BRCA2.

20. The method of claim 17, wherein the gene known to have clinical relevance in oncology is TP53.

* * * * *

UNITED STATES PATENT AND TRADEMARK OFFICE
CERTIFICATE OF CORRECTION

PATENT NO.       : 11,203,781 B2
APPLICATION NO.  : 17/238016
DATED            : December 21, 2021
INVENTOR(S)      : Makarov et al.

Page 1 of 1

It is certified that error appears in the above-identified patent and that said Letters Patent is hereby corrected as shown below:

In the Claims

Claim 3, Column 135, Line 18, the claim term 'ABU', should read -ABI1-

Claim 10, Column 137, Line 33, the claim term 'ABU', should read -ABI1-

Claim 18, Column 139, Line 45, the claim term 'ABU', should read -ABI1-

Signed and Sealed this
Nineteenth Day of April, 2022

Katherine Kelly Vidal
*Director of the United States Patent and Trademark Office*